US008524735B2

(12) United States Patent
Surber et al.

(10) Patent No.: US 8,524,735 B2
(45) Date of Patent: *Sep. 3, 2013

(54) AEROSOLIZED FLUOROQUINOLONES AND USES THEREOF

(75) Inventors: Mark W. Surber, San Diego, CA (US); Keith A. Bostian, Atherton, CA (US); Michael N. Dudley, San Diego, CA (US); Olga Lomovskaya, Mill Valley, CA (US); David C. Griffith, San Marcos, CA (US)

(73) Assignee: MPEX Pharmaceuticals, Inc., Bridgewater, NJ (US)

( * ) Notice: Subject to any disclaimer, the term of this patent is extended or adjusted under 35 U.S.C. 154(b) by 831 days.

This patent is subject to a terminal disclaimer.

(21) Appl. No.: 12/604,347

(22) Filed: Oct. 22, 2009

(65) Prior Publication Data

US 2010/0037890 A1    Feb. 18, 2010

Related U.S. Application Data

(62) Division of application No. 11/436,875, filed on May 18, 2006, now Pat. No. 7,838,532.

(60) Provisional application No. 60/682,530, filed on May 18, 2005, provisional application No. 60/696,160, filed on Jul. 1, 2005, provisional application No. 60/773,300, filed on Feb. 13, 2006.

(51) Int. Cl.

| A61K 31/00 | (2006.01) |
|---|---|
| A61K 31/44 | (2006.01) |
| A61K 31/4412 | (2006.01) |
| A61K 33/00 | (2006.01) |
| A61K 33/06 | (2006.01) |
| A61K 33/14 | (2006.01) |
| A61K 33/26 | (2006.01) |
| A61K 33/30 | (2006.01) |
| A01N 25/00 | (2006.01) |
| A01N 25/02 | (2006.01) |
| A01N 25/06 | (2006.01) |
| A01N 59/08 | (2006.01) |

(52) U.S. Cl.
USPC ........... 514/294; 424/405; 424/602; 424/641; 424/646; 424/677; 424/681; 424/682; 514/279

(58) Field of Classification Search
USPC ................. 514/279, 294; 424/405, 602, 641, 424/646, 677, 681, 682
See application file for complete search history.

(56) References Cited

U.S. PATENT DOCUMENTS

| 2,587,215 A | 2/1952 | Priestly |
|---|---|---|
| 2,868,691 A | 1/1959 | Porush et al. |
| 3,014,844 A | 12/1961 | Thiel et al. |
| 3,456,644 A | 7/1969 | Thiel |
| 3,456,645 A | 7/1969 | Brock |
| 3,456,646 A | 7/1969 | Phillips et al. |
| 3,507,277 A | 4/1970 | Altounyan et al. |
| 3,565,070 A | 2/1971 | Hanson et al. |
| 3,598,294 A | 8/1971 | Hedrick et al. |
| 3,635,219 A | 1/1972 | Altounyan et al. |
| 3,636,949 A | 1/1972 | Kropp |
| 3,669,113 A | 6/1972 | Altounyan et al. |
| 3,732,864 A | 5/1973 | Thompson et al. |
| 3,789,843 A | 2/1974 | Armstrong et al. |
| 3,807,400 A | 4/1974 | Cocozza |
| 3,826,255 A | 7/1974 | Havstad et al. |
| 3,906,950 A | 9/1975 | Cocozza |
| 3,948,264 A | 4/1976 | Wilke et al. |
| 3,971,377 A | 7/1976 | Damani |
| 3,991,761 A | 11/1976 | Cocozza |
| 4,013,075 A | 3/1977 | Cocozza |
| 4,046,146 A | 9/1977 | Rosskamp et al. |
| 4,147,166 A | 4/1979 | Hansen |
| 4,253,468 A | 3/1981 | Lehmbeck |
| 4,263,907 A | 4/1981 | Lindsey |
| 4,268,460 A | 5/1981 | Boiarski |
| 4,353,365 A | 10/1982 | Hallworth et al. |
| 4,470,412 A | 9/1984 | Nowacki et al. |
| 4,510,929 A | 4/1985 | Bordoni et al. |
| 4,534,345 A | 8/1985 | Wetterlin |
| 4,624,251 A | 11/1986 | Miller |
| 4,648,393 A | 3/1987 | Landis et al. |
| 4,649,911 A | 3/1987 | Knight et al. |
| 4,664,107 A | 5/1987 | Wass |

(Continued)

FOREIGN PATENT DOCUMENTS

| CN | 1312076 | 9/2002 |
|---|---|---|
| EP | 0 211 595 A2 | 2/1987 |

(Continued)

OTHER PUBLICATIONS

English language translation of WO 2006/100875 A1 obtained on Dec. 17, 2012.*
H. Mazurek et al. "Cystic fibrosis lung disease: infection, inflammation, or both?: Helicobacter pylori seroprevalence in patients with cystic fibrosis", #2807, accessed on Apr. 18, 2013 at http://www.ers-education.org/pages/default.aspx?id=816idBrowse=85322&det=1.*
A. Tabaru et al. "Various aspects of respiratory epidemiology: Helicobacter pylori infection in COPD," #4677, accessed on Apr. 18, 2013 at http://www.ers-education.org/pages/default.aspx?id=816&idBrowse=85322&det=1.*
Aggarwal et al., "Predictors of mortality and resource utilization in cirrhotic patients admitted to the medical ICU*", Chest (2001) 119(5):1489-1497.

(Continued)

Primary Examiner — James H. Alstrum-Acevedo
(74) Attorney, Agent, or Firm — Knobbe, Martens, Olson & Bear, LLP

(57) ABSTRACT

Disclosed herein are formulations of fluoroquinolones suitable for aerosolization and use of such formulations for aerosol administration of fluoroquinolone antimicrobials for the treatment of pulmonary bacterial infections. In particular, inhaled levofloxacin specifically formulated and delivered for bacterial infections of the lungs is described. Methods include inhalation protocols and manufacturing procedures for production and use of the compositions described.

16 Claims, 61 Drawing Sheets

(56) References Cited

U.S. PATENT DOCUMENTS

| | | |
|---|---|---|
| 4,667,668 A | 5/1987 | Wetterlin |
| 4,688,218 A | 8/1987 | Blineau et al. |
| 4,730,000 A | 3/1988 | Chu |
| 4,790,305 A | 12/1988 | Zoltan et al. |
| 4,805,811 A | 2/1989 | Wetterlin |
| 4,807,814 A | 2/1989 | Douche et al. |
| 4,809,692 A | 3/1989 | Nowacki et al. |
| 4,811,731 A | 3/1989 | Newell et al. |
| 4,832,015 A | 5/1989 | Nowacki et al. |
| 4,844,902 A | 7/1989 | Grohe |
| 4,857,311 A | 8/1989 | Domb et al. |
| 4,889,144 A | 12/1989 | Tateno et al. |
| 4,907,538 A | 3/1990 | Helmle et al. |
| 4,926,852 A | 5/1990 | Zoltan et al. |
| 4,955,371 A | 9/1990 | Zamba et al. |
| 4,985,557 A | 1/1991 | Hayakawa et al. |
| 5,012,803 A | 5/1991 | Foley et al. |
| 5,012,804 A | 5/1991 | Foley et al. |
| 5,024,467 A | 6/1991 | Truchet |
| 5,027,806 A | 7/1991 | Zoltan et al. |
| 5,033,463 A | 7/1991 | Cocozza |
| 5,040,527 A | 8/1991 | Larson et al. |
| 5,053,407 A | 10/1991 | Hayakawa et al. |
| 5,060,643 A | 10/1991 | Rich et al. |
| 5,113,855 A | 5/1992 | Newhouse |
| 5,119,806 A | 6/1992 | Palson et al. |
| 5,142,046 A | 8/1992 | Hayakawa et al. |
| 5,164,740 A | 11/1992 | Ivri |
| 5,217,004 A | 6/1993 | Blasnik et al. |
| 5,284,133 A | 2/1994 | Burns et al. |
| 5,304,559 A | 4/1994 | Rozier |
| 5,334,589 A | 8/1994 | Al-Razzak et al. |
| 5,347,998 A | 9/1994 | Hodson et al. |
| 5,364,838 A | 11/1994 | Rubsamen |
| 5,385,140 A | 1/1995 | Smith |
| 5,388,572 A | 2/1995 | Mulhauser et al. |
| 5,404,871 A | 4/1995 | Goodman et al. |
| 5,427,089 A | 6/1995 | Kraemer |
| 5,437,270 A | 8/1995 | Braithwaite |
| 5,478,578 A | 12/1995 | Arnold et al. |
| 5,508,269 A | 4/1996 | Smith et al. |
| 5,549,102 A | 8/1996 | Lintl et al. |
| 5,563,155 A | 10/1996 | Domagala et al. |
| 5,586,550 A | 12/1996 | Ivri et al. |
| 5,642,730 A | 7/1997 | Baran |
| 5,645,049 A | 7/1997 | Foley et al. |
| 5,694,920 A | 12/1997 | Abrams et al. |
| 5,709,202 A | 1/1998 | Loyd et al. |
| 5,740,794 A | 4/1998 | Smith et al. |
| 5,756,506 A | 5/1998 | Copeland et al. |
| 5,758,637 A | 6/1998 | Ivri et al. |
| 5,775,320 A | 7/1998 | Patton et al. |
| 5,785,049 A | 7/1998 | Smith et al. |
| 5,816,240 A | 10/1998 | Komesaroff |
| 5,820,873 A | 10/1998 | Choi et al. |
| 5,823,179 A | 10/1998 | Grychowski et al. |
| 5,829,434 A | 11/1998 | Ambrosio et al. |
| 5,840,279 A | 11/1998 | Narodylo et al. |
| 5,906,202 A | 5/1999 | Schuster et al. |
| 5,918,594 A | 7/1999 | Asking et al. |
| 5,934,272 A | 8/1999 | Lloyd et al. |
| 5,960,792 A | 10/1999 | Lloyd et al. |
| 5,971,951 A | 10/1999 | Ruskewicz |
| 5,988,160 A | 11/1999 | Foley et al. |
| 6,003,512 A | 12/1999 | Gerde |
| 6,006,747 A | 12/1999 | Eisele et al. |
| 6,026,807 A | 2/2000 | Puderbaugh et al. |
| 6,026,809 A | 2/2000 | Abrams et al. |
| 6,029,662 A | 2/2000 | Marcom |
| 6,070,575 A | 6/2000 | Gonda et al. |
| 6,083,922 A | 7/2000 | Montgomery |
| 6,161,536 A | 12/2000 | Redmon et al. |
| 6,192,876 B1 | 2/2001 | Denyer et al. |
| 6,196,219 B1 | 3/2001 | Hess et al. |
| 6,223,746 B1 | 5/2001 | Jewett et al. |
| 6,230,706 B1 | 5/2001 | Gonda et al. |
| 6,264,922 B1 | 7/2001 | Wood et al. |
| 6,288,080 B1 | 9/2001 | Barsuhn et al. |
| 6,294,178 B1 | 9/2001 | Weinstein et al. |
| 6,333,044 B1 | 12/2001 | Santus et al. |
| 6,333,045 B1 | 12/2001 | Yasueda et al. |
| 6,338,443 B1 | 1/2002 | Piper |
| 6,349,719 B2 | 2/2002 | Gonda |
| 6,350,199 B1 | 2/2002 | Williams et al. |
| 6,367,470 B1 | 4/2002 | Denyer et al. |
| 6,406,880 B1 | 6/2002 | Thornton |
| 6,427,682 B1 | 8/2002 | Klimowicz et al. |
| 6,435,177 B1 | 8/2002 | Schmidt et al. |
| 6,468,967 B1 | 10/2002 | Oleson, Jr. et al. |
| 6,492,328 B2 | 12/2002 | Lehrer et al. |
| 6,503,953 B2 | 1/2003 | Vyden |
| 6,518,239 B1 | 2/2003 | Kuo et al. |
| 6,523,536 B2 | 2/2003 | Fugelsang et al. |
| 6,543,442 B2 | 4/2003 | Gonda et al. |
| 6,544,555 B2 | 4/2003 | Rudnic et al. |
| 6,557,549 B2 | 5/2003 | Schmidt et al. |
| 6,561,186 B2 | 5/2003 | Casper et al. |
| 6,576,224 B1 | 6/2003 | Osbakken et al. |
| 6,579,854 B1 | 6/2003 | Mitchell et al. |
| 6,584,971 B1 | 7/2003 | Denyer et al. |
| 6,585,958 B1 | 7/2003 | Keller et al. |
| 6,586,008 B1 | 7/2003 | Batycky et al. |
| 6,601,581 B1 | 8/2003 | Babaev |
| 6,605,609 B2 | 8/2003 | Barbachyn et al. |
| 6,608,078 B2 | 8/2003 | De Souza et al. |
| 6,612,303 B1 | 9/2003 | Grychowski et al. |
| 6,626,173 B2 | 9/2003 | Genova et al. |
| 6,644,304 B2 | 11/2003 | Grychowski et al. |
| 6,663,890 B2 | 12/2003 | Rudnic et al. |
| 6,663,891 B2 | 12/2003 | Rudnic et al. |
| 6,664,239 B2 | 12/2003 | Mitchell et al. |
| 6,667,042 B2 | 12/2003 | Rudnic et al. |
| 6,667,057 B2 | 12/2003 | Rudnic et al. |
| 6,669,948 B2 | 12/2003 | Rudnic et al. |
| 6,672,304 B1 | 1/2004 | Casper et al. |
| 6,681,768 B2 | 1/2004 | Haaije de Boer et al. |
| 6,689,769 B2 | 2/2004 | Gordeev et al. |
| 6,716,819 B2 | 4/2004 | Welsh et al. |
| 6,723,341 B2 | 4/2004 | Rudnic et al. |
| 6,730,320 B2 | 5/2004 | Rudnic et al. |
| 6,756,369 B2 | 6/2004 | Mitchell et al. |
| 6,806,256 B2 | 10/2004 | Ulrich et al. |
| 6,835,372 B2 | 12/2004 | Kuo et al. |
| 6,838,552 B1 | 1/2005 | Mitchell et al. |
| 6,869,965 B2 | 3/2005 | Gordeev et al. |
| 6,878,713 B2 | 4/2005 | De Souza et al. |
| 6,884,784 B1 | 4/2005 | Mitchell et al. |
| 6,890,526 B2 | 5/2005 | Stratton et al. |
| 6,962,151 B1 | 11/2005 | Knoch et al. |
| 6,987,094 B2 | 1/2006 | Malvolti et al. |
| 7,148,404 B2 | 12/2006 | Hogenhaug et al. |
| 2001/0049366 A1 | 12/2001 | Singh et al. |
| 2002/0061281 A1 | 5/2002 | Osbakken et al. |
| 2002/0086867 A1 | 7/2002 | Dubois et al. |
| 2002/0142050 A1 | 10/2002 | Straub et al. |
| 2002/0197212 A1 | 12/2002 | Osbakken et al. |
| 2003/0012814 A1 | 1/2003 | Rudnic et al. |
| 2003/0028025 A1 | 2/2003 | Raghavan |
| 2003/0032600 A1 | 2/2003 | Ulrich et al. |
| 2003/0078517 A1 | 4/2003 | Kensey |
| 2003/0138403 A1 | 7/2003 | Drustrup |
| 2003/0171340 A1 | 9/2003 | Isbister |
| 2003/0186894 A1 | 10/2003 | Kuo et al. |
| 2004/0009126 A1 | 1/2004 | Pilkiewicz et al. |
| 2004/0009989 A1 | 1/2004 | Niddam-Hildesheim et al. |
| 2004/0014750 A1 | 1/2004 | Michaelis et al. |
| 2004/0045546 A1 | 3/2004 | Hirsh et al. |
| 2004/0152701 A1 | 8/2004 | Reddy et al. |
| 2005/0036951 A1 | 2/2005 | Henderson |
| 2005/0106151 A1 | 5/2005 | Shapiro |
| 2005/0139211 A1 | 6/2005 | Alston et al. |
| 2005/0147567 A1 | 7/2005 | Kuo et al. |
| 2005/0235987 A1 | 10/2005 | Smaldone et al. |
| 2005/0260099 A1 | 11/2005 | Xia et al. |

| | | | |
|---|---|---|---|
| 2005/0288302 A1 | 12/2005 | Niddam-Hildesheim et al. | |
| 2006/0003944 A1 | 1/2006 | Glinka et al. | |
| 2006/0025355 A1 | 2/2006 | Duddu et al. | |
| 2006/0223751 A1 | 10/2006 | Mygind et al. | |
| 2006/0258677 A1 | 11/2006 | Amir et al. | |
| 2006/0276416 A1 | 12/2006 | Sinclair et al. | |
| 2006/0276463 A1 | 12/2006 | Sharma et al. | |
| 2006/0276473 A1 | 12/2006 | Bostion et al. | |
| 2006/0276483 A1 | 12/2006 | Surber et al. | |
| 2006/0286574 A1 | 12/2006 | Romesberg et al. | |
| 2007/0003753 A1 | 1/2007 | Asgari | |
| 2007/0071686 A1 | 3/2007 | Lintz et al. | |
| 2007/0155715 A1 | 7/2007 | van Duzer et al. | |
| 2007/0197548 A1 | 8/2007 | Murthy | |
| 2009/0025713 A1 | 1/2009 | Keller et al. | |
| 2010/0204470 A1 | 8/2010 | Wieser et al. | |

FOREIGN PATENT DOCUMENTS

| | | | |
|---|---|---|---|
| EP | 0 455 463 A1 | | 11/1991 |
| EP | 0 467 172 A1 | | 1/1992 |
| EP | 0 470 667 A1 | | 2/1992 |
| EP | 0 347 779 | | 5/1994 |
| EP | 0 855 183 A2 | | 7/1998 |
| EP | 1 092 430 A1 | | 4/2001 |
| EP | 1 223 915 B1 | | 12/2005 |
| GB | 901107 A | | 7/1962 |
| SU | 628930 | | 10/1978 |
| WO | WO 87/05213 | | 9/1987 |
| WO | WO 90/07351 | | 7/1990 |
| WO | WO 90/13327 | | 11/1990 |
| WO | WO 92/09322 | | 6/1992 |
| WO | WO 93/12831 | | 7/1993 |
| WO | WO 93/24165 | | 12/1993 |
| WO | WO 95/11666 | | 5/1995 |
| WO | WO 96/23485 | | 8/1996 |
| WO | WO 97/03649 | | 2/1997 |
| WO | WO 98/03217 | | 1/1998 |
| WO | WO 99/59566 | | 11/1999 |
| WO | WO 99/62495 | | 12/1999 |
| WO | WO 00/18388 A1 | | 4/2000 |
| WO | WO 01/02024 | | 1/2001 |
| WO | WO 02/18345 | | 3/2002 |
| WO | WO 02/072102 | | 9/2002 |
| WO | WO 03/035030 A1 | | 5/2003 |
| WO | WO 03/066064 A2 | | 8/2003 |
| WO | WO 03/075889 A1 | | 9/2003 |
| WO | WO 2004/019912 | | 3/2004 |
| WO | WO 2005/037256 A2 | | 4/2005 |
| WO | WO 2005/089738 | | 9/2005 |
| WO | WO 2006/011051 A1 | | 2/2006 |
| WO | WO 2006/033713 | | 3/2006 |
| WO | WO 2006/078925 A2 | | 7/2006 |
| WO | WO 2006/100875 | | 9/2006 |
| WO | WO 2006/125132 A2 | | 11/2006 |
| WO | WO 2007/085057 | | 8/2007 |
| WO | WO 2007/090123 | | 8/2007 |
| WO | WO 2007/090646 | | 8/2007 |
| WO | WO 2007/095156 | | 8/2007 |
| WO | WO 2007/095187 | | 8/2007 |
| WO | WO 2008/025560 A1 | | 3/2008 |

OTHER PUBLICATIONS

Ambrose, Paul G.et al., "Pharmacokinetics—Pharmacodynamics of Antimicrobial Therapy: It's Not Just for Mice Anymore", Antimicrobial Resistance (2007) 44:79-86.

Amsden, "Anti-inflammatory effects of macrolides—an underappreciated benefit in the treatment of community-acquired respiratory tract infections and chronic inflammatory pulmonary conditions?", Journal of Antimicrobial Chemotherapy (2005) 55:10-21.

Anonymous, "MPEX Pharmaceuticals Initiates Multi-Dose Clinical Trial in the U.S. with MP-376 in Patients with Cystic Fibrosis" Science Letter (2007) 2 pages.

Anonymous, Mpex Candidate, MP-376, Granted US Orphan Drug Status for the Treatment of Cystic Fibrosis, Medical News Today, www.medicalnewstoday.com (retrieved online Dec. 11, 2009), Mar. 5, 2008, XP002560239.

Araujo et al., "Effect of moxifloxacin on secretion of cytokines by human monocytes stimulated with lipopolysaccharide", Clin. Microbiol. Infect. (2002) 8:26-30.

Araujo et al., "Gemifloxacin inhibits cytokine secretion by lipopolysaccharide stimulated human monocytes at the post-transcriptional level", Clin. Microbiol. Infect. (2004) 10:213-219.

Arzte, Zeitung De, www.aerztezeitunq.de/extras/druckansicht/?sid=347342&pid=351267 (retrieved online Dec. 11, 2009), Mar. 14, 2005, XP002560241. (Machine Translation Provided).

Atkins et al., "The Design and Development of Inhalation Drug Delivery Systems", Pharmaceutical Inhalation Aerosol Technology, Marcel Dekker, Inc., New York, NY (1992) 6: p. 155-185.

Baker et al., "A Prodrug Approach Toward the Development of Water Soluble Fluoroquinolones and Structure-Activity Relationships of Quinoline-3-Carboxylic Acids"J. Med. Chem. (2004) 47: 4693-4709.

Banerjee et al., "The treatment of respiratory *Pseudomonas* infection in cystic fibrosis: what drug and which way?" Drugs (2000) 60(5):1053-64. (Abstract Only).

Barry et al., "Novel agents in the management of *Mycobacterium tuberculosis* disease" Current medicinal chemistry (Netherlands) (2007) 14(18):2000-8. (Abstract Only).

Battram et al., "In vitro and in vivo pharmacological characterization of 5-[®-2-(5,6-diethyl-indan-2-ylamino)-1-hydroxy-ethyl]-8-hydroxy-1H-quinolin-2-one (indacaterol), a novel inhaled beta(2) adrenoceptor agonist with a 24-h duration of action", J Pharmacol Exp Ther. (2006) 317(2):762-70. (Abstract Only).

Beasley et al., "Adverse reactions to the non-drug constituents of nebuliser solutions", Br. J. clin. Pharmac., (1988) 25: p. 283-287.

Benko et al., "Pharmacokinetics and pharmacodynamics of levofloxacin in critically ill patients with ventilator-associated pneumonia" International journal of antimicrobial agents (Netherlands) (2007) 30(2):162-8. (Abstract Only).

Berg, "Combination products are spotlighted at Drug/Device Summit" The BBI Newsletter (2005). (Abstract Only).

Blaser et al., "Influence of Medium and Method on the In Vitro Susceptibility of *Pseudomonas aeruginos* and Other Bacteria to Ciprofloxacin and Enoxacin, Antimicrobial Agents and Chemotherapy", American Society for Microbiology (1986) 29(5):927-929.

Blau et al., "Moxifloxacin but not Ciprofloxacin or Azithromycin Selectively Inhibits IL-8, IL-6, ERK1/2, JNK, and NF-kB Activation in a Cystic Fibrosis Epithelial Cell Line", Am. J. Physiol. Lung Cell Mol. Physiol. (2007) 292:L343-L352.

Blitz et al., "Aerosolized Magnesium Sulfate for Acute Asthma: A Systematic Review", Chest The Cardiopulmonary and Critical Care Journal, (2005) 128: p. 337-344.

Brouillard et al., "Antibiotic selection and resistance issues with fluoroquinolones and doxycycline against bioterrorism agents" Pharmacotherapy (United States) (2006) 26(1):3-14. (Abstract Only).

Bryskier, "*Bacillus anthracis* and antibacterial agents" Clinical microbiology and infection—the official publication of the European Society of Clinical Microbiology and Infectious Diseases (France) (2002) 8(8):467-78. (Abstract Only).

Calbo et al., "Systemic expression of cytokine production in patients with severe pneumococcal pneumonia: effects of treatment with a beta-lactam versus a fluoroquinolone, antimicrobial agents and chemotherapy", American Society for Microbiology (2008) 52(7):2395-2402.

Carratala et al., "Clinical experience in the management of community-acquired pneumonia: lessons from the use of fluoroquinolones" Clinical microbiology and infection—the official publication of the European Society of Clinical Microbiology and Infectious Diseases (France) (2006) 12(3):2-11. (Abstract Only).

Celli et al., "The body-mass index, airflow obstruction, dyspnea, and exercise capacity index in chronic obstructive pulmonary disease", N Engl J Med. (2004) 350(10):1005-1012.

Chang et al., Properties of the Drug Molecule in Nasal Systemic Drug Delivery, 1989, pp. 49-51, Chapter 3, Marcel Dekker, Inc.

Chien et al., "Properties of the Drug Molecule in Nasal Systemic Drug Delivery", (1989) pp. 63-68, Chapter 3, Marcel Dekker, Inc.

Chodosh S., "Clinical significance of the infection-free interval in the management of acute bacterial exacerbations of chronic bronchitis", Chest (2005) 127(6):2231-2236.

Choi et al., "Effect of moxifloxacin on production of proinflammatory cytokines from human peripheral blood mononuclear cells", Antimicrobial Agents and Chemotherapy (2003) 47(12):3704-3707.

Cigana et al., "Azithromycin selectively reduces tumor necrosis factor alpha levels in cystic fibrosis airway epithelial cells", Antimicrob. Agents Chemother. (2007) 51(3):975-981.

Conrad, "Mpex 204 Phase 2", Stanford School of Medicine (retrieved online Dec. 11, 2009), Sep. 3, 2008, pp. 1-7 (PCT ISR/WO provided a partial reference, and the full reference is no longer available.).

Conte et al., "intrapulmonary pharmacodynamics of high-dose levofloxacin in subjects with chronic bronchitis or chronic obstructive pulmonary disease", International Journal of Antimicrobial Agents, Elsevier Science, Amsterdam, NL (2007) 30(5):422-427.

Dalhoff et al., "Immunomodulatory effects of quinolones", The Lancet Infectious Diseases (2003) 3:359-71.

Dalhoff, "Immunomodulatory activities of fluoroquinolones", Infection (2005) 33(Suppl 2):55-70.

Derbacher et al., "Physical Properties of Nebulized Solutions", Poster (1994) 381-382 (English Translation included).

DeRyke et al., "Pharmacodynamic target attainment of six beta-lactams and two fluoroquinolones against *Pseudomonas aeruginosa, Acinetobacter baumannii, Escherichia coli,* and *Klebsiella* species collected from United States intensive care units in 2004" Pharmacotherapy (United States) (2007) 27(3):333-42. (Abstract Only).

Diakov et al., "The chemotherapeutic efficacy of ciprofloxacin and lomefloxacin in the inhalation method of infecting white mice with tularemia., Khimioterapevticheskaia effektivnost' tsiprofloksatsina i lomefloksatsina pri ingaliatsionnom sposobe zarazheniia tuliaremiei belykh myshei" Antibiotiki i khimioterapii a = Antibiotics and chemoterapy sic / Ministerstvo meditsinskoi i mikrobiologicheskoi promyshlennosti SSSR (Russia) (2000) 45(6):17-20. (Abstract Only).

Doring et al., "Antibiotic therapy against *Pseudomonas aeruginosa* in cystic fibrosis: a European consensus" [comment in Eur Respir J. 2000 16(4):585-7], Euro Respir J. (2000) 16(4):749-67. (Abstract Only).

Drevensek et al., "Influence of Copper(II) and Magnesium(II) ions on the Ciprofloxacin Binding to DNA", J.Inorg. Biochem. (2003) 96:407-415.

Drevensek et al., "X-Ray Crystallographic, NMR and Antimicrobial Activity Studies of Magnesium Complexes of Fluoroquinolones—Racemic Ofloxacin and its S-form, Levofloxacin" J. Inorg. Biochem. (2006) 100:1755-1763.

Drusano et al., "Pharmacodynamics of a Fluoroquinolone Antimicrobial Agent in a Neutropenic Rat Model of *Pseudomonas* Sepsis" Antimicrob. Agents & Chemother. (1993) 37(3):483-490.

Elizur et al., "Airway inflammation in cystic fibrosis," CHEST (2008) 133:489-495.

File, "A New Dosing Paradigm: High-Dose, Short-Course Fluoroquinolone Therapy for Community-Acquired Pneumonia" Clinical Cornerstone (2003) 3:S21-S28.

Gavilanes et al., "Azithromycin fails to reduce increased expression of neutrophil-related cytokines in primary-cultured epithelial cells from cystic fibrosis mice", J. Cyst. Fibros. (2009) 10(1016):1-8.

Goh et al., "Current Status of Topical Nasal Antimicrobial Agents" The Laryngoscope (2000) 110:875-880.

Griese et al., "Amphotericin B and Pulmonary Surfactant", European Journal of Medical Research, I. Holzapfel Publishers (1998) 3:383-386.

Griffith et al., "Efficacy of fluoroquinolones against *Leptospira interrogans* in a hamster model" Antimicrobial agents and chemotherapy (United States) (2007) 51(7):2615-7. (Abstract only).

Griffith et al., "Pharmacokinetics and Safety of MP-376 (Levofloxacin Solution for Inhalation) in Normal Healthy Volunteers and Cystic Fibrosis Patients", Pediatr. Pulmonol., (2007) 42(S30):303.

Guina et al., "Quantitative proteomic analysis indicates increased synthesis of a quinolone by *Pseudomonas aeruginosa* isolates from cystic fibrosis airways", PNAS (2003) 100(5):2771-2776.

Hart et al., "Cross-over assessment of serum bactericidal activity of moxifloxacin and levofloxacin versus penicillin-susceptible and penicillin-resistant *Streptococcus pneumoniae* in healthy volunteers", Diagnostic microbiology and infectious disease (United States) (2007) 58(3):375-8. (Abstract Only).

Hashimoto et al., "Grepafloxacin Inhibits Tumor Necrosis Factor-alpha-induced Interleukin-8 Expression in Human Airway Epithelial Cells", Life Sci (2000) 66(5):PL 77-82.

Hecht et al., "In vitro activities of 15 antimicrobial agents against 110 toxigenic *Clostridium difficile* clinical isolates collected from 1983 to 2004" Antimicrobial agents and chemotherapy (United States) (2007) 51(8):2716-9. (Abstract Only).

Heine et al., "Comparison of 2 antibiotics that inhibit protein synthesis for the treatment of infection with *Yersinia pestis* delivered by aerosol in a mouse model of pneumonic plague", Journal of Infectious Diseases (United States) (2007) 196(5):782-7. (Abstract Only).
Hoffmann, et al., "Novel mouse model of chronic *Pseudomonas aeruginosa* lung infection mimicking cystic fibrosis", Infect. Immun. (2005) 73(4):2504-2514.
Honeybourne, "Antibiotic penetration in the respiratory tract and implications for the selection of antimicrobial therapy" Curr Opin Pulm Med. (1997) 3(2):170-4. (Abstract Only).
Horiguchi et al., "Usefulness of sparfloxacin against *Chlamydia pneumoniae* infection in patients with bronchial asthma" Journal of international medical research (England) Nov.-Dec. 2005 (2005) 33(6):668-76. (Abstract Only).
Hrkach et al., "Synthesis of poly(l-lactic acid-co-L-lysine) graft copolymers", Macromolecules (1995) 28: 4736-4739.
Huang et al., "Oxidation of fluoroquinolone antibacterials and structurally related amines with manganese oxide" National Meeting—American Chemical Society Division of Environmental Chemistry (2003) 43(2)(5):1257-1260.
Hung et al., "Evaluation of two commercial jet nebulisers and three compressors for the nebulisation of antibiotics", Archives of Disease in Childhood (1994) 71(4):335-338.
Hutschala et al., "In vivo measurement of levofloxacin penetration into lung tissue: CPB versus OPCAB" European Journal of Anaesthesiology (2005) 49(12) 5107-11.
Jacquot et al., "Airway epithelial cell inflammatory signalling in cystic fibrosis," The International Journal of Biochemistry & Cell Biology (2008) 40:1703-15.
Jarraud et al., "Legionnaires disease (Legionellose)" Presse medicale (Paris, France—1983) (France) (2007) 36(2 Pt 2):279-87. (Abstract Only).
Jones et al., "Quantifying of severity of exacerbations in chronic obstructive pulmonary disease: adaptations to the definition to allow quantification", Proc Am Thorac Soc. (2007) 4(8):597-601.
Jumbe et al., "Application of a mathematical model to prevent in vivo amplification of antibiotic-resistant bacterial populations during therapy", J Clin Invest. (2003) 112(2):275-85.
Khan et al., "Effect of trovafloxacin on production of cytokines by human monocytes", Antimicrobial Agents and Chemotherapy (1998) 42(7):1713-7.
Khan et al., "Protection against lipopolysaccharide-induced death by fluoroquinolones," Antimicrobial Agents and Chemotherapy, (2000) 44(11): 3169-73.
Kitazawa et al., "Biphasic regulation of levofloxacin on lipopolysaccharide-induced IL-1B production", Life Sciences, (2007) 80:1572-1577.
Kobayashi et al., "Antibacterial activity of tosufloxacin against major organisms detected from patients with respiratory infections" Japanese journal of antibiotics (Japan) (2007) 60(2):98-106. (Abstract Only).
Kohyama et al., "Fourteen-member macrolides inhibit interleukin-8 release by human eosinophils from atopic donors", Antimicrobial Agents and Chemotherapy (1999) 43(4):907-911.
Kuhn, "Formulation of aerosolized therapeutics", Chest, The Cardiopulmonary and Critical Care Journal (2001) 120(3):94S-98S. (Abstract Only).
Kurosaka et al., "DX-619, a novel des-F(6)-quinolone: pharmacodynamics (PD) activity and thereapeutic efficacy in animal infection models", Interscience Conference on Antimicrobial Agents and Chemotherapy (2003) $43^{rd}$:Chicago.
LaPlante et al., "Fluoroquinolone resistance in *Streptococcus pneumoniae*: area under the concentration-time curve/MIC ratio and resistance development with gatifloxacin, gemifloxacin, levofloxacin, and moxifloxacin" Antimicrobial agents and chemotherapy (United States) (2007) 51(4):1315-20. (Abstract Only).

Le Conte et al., "Lung Distribution and Pharmacokinetics of Aerosolized Tobramycin", American Review of Respiratory Disease, (1993) vol. 147, p. 1279-1282.

Lee et al., "Levofloxacin pharmacokinetics in adult cystic fibrosis", Chest (2007) 131(3):796-802.

Legssyer et al., "Azithromycin reduces spontaneous and induced inflammation in F508 cystic fibrosis mice", Respiratory Research (2006) 7(134):1-13.

Leiva et al., "Effects of telithromycin in in vitro and in vivo models of lipopolysaccharide-induced airway inflammation", Chest (2008) 134:20-29.

Leonard et al., "Topical Antibiotic Therapy for Recalcitrant Sinusitis" The Laryngoscope (1999) 109(4): 668-670.

Louie et al., "Impact of resistance selection and mutant growth fitness on the relative efficacies of streptomycin and levofloxacin for plague therapy", Antimicrob Agents Chemother. (2007) 51(8):2661-2667. Epub May 21, 2007. (Abstract Only).

Martin Physical Pharmacy (4th Edition), pp. 261-263, 265, 1993.

Martinez et al., "Appropriate outpatient treatment of acute bacterial exacerbations of chronic bronchitis", American Journal of Medicine, Elsevier Science, Amsterdam, NL (2005) 118(7A): 39S-44S.

Matthys, "Inhalation delivery of asthma drugs" Lung. (1990) 168:645-52. (Abstract Only).

Mohammed et al., "Intravenous and nebulised magnesium sulphate for acute asthma: systematic review and meta-analysis", Emergency Medicine Journal (2007) 24: p. 823-830.

Moss, "Administration of aerosolized antibiotics in cystic fibrosis patients" Chest (2001) 120(3):107S-113S. (Abstract Only).

Murphy et al., "*Pseudomonas aeruginosa* in chronic obstructive pulmonary disease", Am J Respir Crit Care Med. (2008) 177(8):853-60. Epub Jan. 17, 2008.

Nakanishi et al., "A case of cystic fibrosis in a Japanese student" Nihon Kyobu Shikkan Gakkai zasshi (Japan) (1995) 33(7):771-4. (Abstract Only).

Neu, "The Effects of Cations Upon the Activity of Quinolone Agents", Quinolones Bulletin, Reports on Gyrase Inhibitors (1985).

Neu et al., "In Vitro Activity of S-Ofloxacin, Antimicrobial Agents and Chemotherapy", American Society for Microbiology (1989) 33 (7):1105-1107.

Newman, "Aerosols and the Lung: Clinical and Experimental Aspects", Butterworth & Co. Ltd., London, England (1984) 197-224.

Nouira et al., "Once daily oral ofloxacin in chronic obstructive pulmonary disease exacerbation requiring mechanical ventilation: a randomised placebo-controlled trial", Lancet (North American Edition) (2001) 358(9298): 2020-2025.

Ono et al., "Effect of grepafloxacin on cytokine production in vitro", Journal of Antimicrobial Chemotherapy, (2000) 46:91-94.

Ortho-McNeil Pharmaceutical, Inc., OMP Division, Text of Proposed Labeling for Levaquin® (2004) 1-52.

Ortho-McNeil Pharmaceutical, Inc., Package Insert for Levaquin®, (2006) 15 pages.

Perez et al., "CFTR inhibition mimics the cystic fibrosis inflammatory profile", Am J. Physiol. Lung Cell Mol Physiol, (2007) 292(2):L383-395. Epub Aug. 18, 2006.

Preston et al., "Pharmacodynamics of levofloxacin: a new paradigm for early clinical trials," JAMA. (1998) 279(2):125-129.

Querol-Ribelles et al., "Discrepancy between antibiotics administered in acute exacerbations of chronic bronchitis and susceptibility of isolated pathogens in respiratory samples: multicentre study in the primary care setting" International journal of antimicrobial agents (Netherlands) (2006) 28(5):472-6. (Abstract Only).

Ratcliffe et al., "Effects of Magnesium on the Activity of 4-Quinolone Antibacterial Agents", Journal of Pharmacy and Pharmacology, 1983, p. 61, vol. 35, Supplement Dec. 1983, The Pharmaceutical Society of Great Britain.

Reato et al., "Immunomodulating effect on antimicrobial agents on cytokine production by human polymorphonuclear neutrophils", International Journal of Antimicrobial Agents (2004) 23:150-154.

Rennard, "COPD: overview of definitions, epidemiology, and factors influencing its development", Chest (1998) 113(Suppl 4):235:41s).

Romano et al., "[The use of ofloxacin in cystic fibrosis patients.] Uso dell'ofloxacin nei pazienti con fibrosi cistica", Minerva Pediatr. (1992) 44(3):79-86. (Abstract Only).

Rosell et al., 2005. Microbiologic determinants of exacerbation in chronic obstructive pulmonary disease. Arch Intern Med 165: 891-897.

Rosenfeld et al., "Defining a pulmonary exacerbation in cystic fibrosis ", J Pediatr. (2001) 139(3):359-365.

Ross et al., Physicochemical properties of the fluoroquinolone antimicrobials V. effect of fluoroquinolone structure and pH on the complexation of various fluoroquinolones with magnesium and calcium ions, International Journal of Pharmaceutics (1993) 93:121-129.

Sabet et al., "Efficacy of Aerosol MP-376, a levofloxacin inhalation solution, in models of mouse lung infection due to *Pseudomonas aeruginosa*, Antimicrobial Agents and Chemotherapy", (2009) 53(9):3923-3928.

Sabet et al., "In-Vivo Antibacterial Activity of Aerosol MP-376 in Mouse Models of Pulmonary Infection", Pediatr. Pulmonol., (2007) 42(S30):304.

Sagel et al., "Sputum biomarkers of inflammation in cystic fibrosis lung disease", Proc. Am. Thorac. Soc. (2007) 4:406-417.

Sato, et al., "Antimicrobial activity of DU-6859, a new potent fluoroquinolone, against clinical isolates", Antimicrob Agents Chemother. (1992) 36(7):1491-1498.

Scheinberg et al., "Nebulized Antibiotics for the Treatment of Acute Exacerbations of Chronic Rhinosinusitis", Ear, Nose & Throat J. (2002) 81:648-652. (Best Available Copy).

Seemungal et al., "Long-term erythromycin therapy is associated with decreased chronic obstructive pulmonary disease exacerbations", Am J Respir Crit Care Med (2008) 178:1139-1147.

Shalit et al., "Immunomodulatory and protective effects of moxifloxacin against *Candida albicans*-induced bronchopneumonia in mice Injected with cyclophosphamide", Antimicrobial Agents and Chemotherapy (2002) 46(8):2442-2449.

Shalit et al.,"Anti-inflammatory effects of moxifloxacin on IL-8, IL-1B and TNF-a secretion and NFkB and MAP-kinase activation in human moncytes stimulated with *Aspergillus fumigatus*", Journal of Antimicrobial Chemotherapy (2006) 57:230-235.

Shinkai et al., "Clarithromycin has an immunomodulatory effect on ERK-mediated inflammation induced by *Pseudomonas aeruginosa* flagellin", Journal of Antimicrobial Chemotherapy (2007) 59:1096-1101.

Shinkai et al., "Macrolide antibiotics as immunomodulatory medications: Proposed mechanisms of action, Pharmacology & Therapeutics" (2008) 117:393-405.

Skauge et al., "Interaction Between Ciprofloxacin and DNA Mediated by Mg2+-ions", Inorganica Chimica Acta (2002) 339: 239-247.

Smith et al., "Chemistry and Mechanisms of Action of the Quinolone Antibacterials", The Quinolones, Academic Press Limited, Harcourt Brace Janovich, Publishers (1988) pp. 23-82.

Smith, "Interactions Between 4-Quinolone Antibacterials and Multivalent Metal Ions", Journal of Chemotherapy, 134-135.

Stephenson, "Applications of x-ray powder diffraction in the pharmaceutical industry", The Rigaku Journal (2005) 22(1):2-15.

Suman et al., "Comparison of nasal deposition and clearance of aerosol generated by a nebulizer and an aqueous spray pump" Pharma Res. (1999) 16:1648-1652.

Suman et al., "Validity of in vitro tests on aqueous spray pumps as surrogates for nasal deposition", Pharmaceutical Research (2002) 19(1):1-6.

Suzuki et al., "Histopathological Study of the Effects of a Single Intratracheal Instillation of Surface Active Agents on Lung in Rats", The Journal of Toxicological Sciences (2000) 25(1):49-55.

Takeyama et al., "The 6-Fluoro-8-Methoxy Quinolone Gatifloxacin Down-Regulates Interleukin-8 Production in Prostate Cell Line PC-3", Antimicrobial Agents and Chemotherapy (2007) 51(1):162-168.

Takizawa et al., "Erythromycin Modulates IL-8 expression in normal and inflamed human bronchial epithelial cells", Am. J. Respir. Crit. Care Med. (1997) 156:266-271.

Tsai et al., "Azitromycin blocks neutrophil recruitment in *Pseudomonas endobronchial* infection", Am. J. respir Crit. Care Med. (2004) 170, pp. 1331-1339.
Tsapis et al., "Direct lung delivery of para-aminosalicylic acid by aerosol particles" Tuberculosis (Edinburgh, Scotland) (England) (2003) 83(6):379-85. (Abstract Only).
Turel et al., "Biological activity of some magnesium(II) complexes of quinolones", (2000) 7(2):101-104.
Vaughan et al., "Use of nebulized antibiotics for acute infections in chronic sinusitis", Otolaryngology—Head & Neck Surgery (2002) 127:558-68.
Vaughan, "Nebulization of antibiotics in management of sinusitis", Curr. Infect. Dis. Reports. (2004) 6:187-190.
Villeneuve et al., "Nebulized Magnesium Sulfate in the Management of Acute Exacerbations of Asthma", The Annals of Pharmacotherapy (2006) 40:1118.
Wada et al., "Immunomodulatory effect of gatifloxacin on mouse peritoneal macrophages in vitro and in models of endotoxin-induced rat conjunctivitis and rabbit bacterial keratitis", Opthalmic Res. (2008) 40:54-60.
Wahl et al. "New Medical Management Techniques for Acute Exacerbations of Chronic Rhinosinusitis", Curr Opin Otolaryngol Head Neck Surg. (2003) 11:27-32.
Wang et al. "Synthesis and crystal structure of a new copper (II) complex containing fluoroquinolone", Inter'l Symposium on Solid State Chemistry in China; Frontiers of Solid State Chemistry, World Scientific (2002) 327-332.
Weber et al., "Nebulizer Delivery of Tobramycin to the Lower Respiratory Tract", Pediatric Pulmonology, Wiley-Liss, Inc. (1994) 17: p. 331-339.
Weber et al. "Effect of nebulizer type and antibiotic concentration on device performance", Pediatric Pulmonology (1997) 23(4):249-260.
Weiss et al., "Anti-inflammatory effects of moxifloxacin on activated human monocytic cells: inhibition of NF-kB and mitogen-activated protein kinase activation and of synthesis of proinflammatory cytokines, " Antimicrobial Agents and Chemotherapy, (2004) 48(6):1974-1982.
Werber et al., "Moxifloxacin inhibits cytokine-induced MAP kinase and NF-KB activation as well as nitric oxide synthesis in a human respiratory epithelial cell line", Journal of Antimicrobial Chemotherapy (2005) 55:293-300.
Wilkinson et al., "Effect of interactions between lower airway bacterial and rhinoviral infection in exacerbations of COPD", Chest (2006) 129: 317-324.
Williams, "Fluoroquinolones for respiratory infections: too valuable to overuse", Chest (2001) 120:1771-1775.
Yamamoto et al., "Treatment of respiratory and urinary tract infections in elderly inmates at a nursing home by selective antimicrobial agents based on the sensitivity of the isolated bacteria" Nippon Ronen Igakkai zasshi. Japanese journal of geriatrics (Japan) (2007) 44(3):359-66. (Abstract Only).
Zach, M., "Discussion", Chest (1988) 94:160S-162S.
Zhang et al., "Besifloxacin, a novel fluoroquinolone antimicrobial agent, exhibits potent inhibition of pro-inflammatory cytokines in human THP-1 monocytes", Journal of Antimicrobial Chemotherapy (2008) 61:111-116.
Zhao et al., "Description and Clinical Treatment of an Early Outbreak of Severe Acute Respiratory Syndrome (SARS) in Guangzhou, PR China" Journal of Medical Microbio. (2003) 52(8):715-720.
Zheng et al., "Pulmonary delivery of a dopamine D-1 agonist, ABT-431, in dogs and humans" Int J Pharm. (1999) 191(2):131-40. (Abstract Only).
Zimmermann et al., "Anti-inflammatory effects of antibacterials on human bronchial epithelial cells," Respiratory Research (2009) 10(89):1-8.
International Preliminary Report on Patentability dated Nov. 29, 2007 for International Patent Application No. PCT/US2006/019351, filed May 18, 2006.
International Search Report and Written Opinion dated Oct. 20, 2006 for International Patent Application No. PCT/US2006/019351, filed May 18, 2006.
International Preliminary Report on Patentability dated Aug. 28, 2008 for International Patent Application No. PCT/US2007/003649, filed Feb. 12, 2007.
International Search Report and Written Opinion dated Oct. 25, 2007 for International Patent Application No. PCT/US2007/003649, filed Feb. 12, 2007.
International Search Report and Written Opinion dated Jan. 21, 2010, for International Patent Application No. PCT/US2009/059740, filed Oct. 6, 2009.
IPOS Search Report, Written Opinion and Invitation to Response to Written Opinion, dated Aug. 12, 2010 for Singapore Patent Application No. 200717702-5.
"Cystic Fibrosis," Medline Plus Medical Encyclopedia—accessed at www.nlm.nih.gov/medlineplus/ency/article/000107.htm on Jul. 11, 2008.
"Dynamic, absolute, kinematic viscosity" accessed online at www.engineeringtoolbox.com/dynamic-absolute-kinematicviscosity-d_412.html on Apr. 11, 2011.
Seddon, "Pseudopolymorph: a polemic", Crystal Growth & Design (2004) 4(6):1087, web release date Oct. 19, 2004.
"Surface Tension," The Engineering Toolbox—accessed at www.engineeringitoolbox.com/surface-tensiond_962.html on Jun. 21, 2011.
Vippagunta et al., "Crystalline Solids", Adv Drug Deliv Rev. (2001) 48(1):3-26.
Navarro, et al., "Oral Absorption of Ofloxacin Administered Together with Aluminum", Antimicrobial Agents and Chemotherapy, 1994, vol. 3 8, No. 10, p. 2510-2512.
Sabet, et al. "In Vivo Antibacterial Activity of Aerosol MP-376 in Mouse Model of Pulmonary Infection, " $21^{st}$ Annual North American Cystic Fibrosis Conference, 2007, pp. 304.
"Fungal Lung Disease," In Breathing in America: Diseases, Progress, and Hope, chapter 9, pp. 92 and 95, published online in 2010 by the American Thoracic Society, accessed on Jan. 2, 2013 at http://www.thoracic.org/education/breaething-in-america/resources/chapter-9-fungal-lung-disease.pdf.
"Influenza," Merck Manual Home Edition article accessed on Feb. 22, 2010 at www.merck.com/print/sec17/ch198/ch198.html.
"Overview of Pneumonia" Merck Manual Home Edition article accessed on Jan. 2, 2012 at www.merckmanuals.com/home/print/lung_and_airway_disorders/pneumonia/overview_of_pneumoni.
Turel, Izto; The interactions of metal ions with quinolone antibacterial agents, Coordination Chemistry Reviews; Oct. 2002; pp. 27-47(21); vol. 232, Elseveir.
MP-376 safe and effective for treatment of P. aeruginosa in CF patients. May 16, 2010 at http://www.eurekalert.org/pub_releases/2010-05/ats-msa051010.php.
King et al., "Effect of oxygen limitation of the in vitro activity of levofloxacin and other antibiotics administered by the aerosol route against Pseudomonas aeruginosa from cystic fibrosis patients," Diagnostic Microbiology and infectious Disease 66 (2010) 181-186.
King et al., "In Vitro PharmaCodynamics of Levofloxacin and other Aerosolized Antibiotics under Multiple Conditions Relevant tot Chronic Pulmonary Infection in Cystic Fibrosis," Antimicrobial Agents and Chemotherapy, Jan. 2010, pp. 143-148.
S. Sethi, et al. "Poster No. 27964: A Phase 2 Study to Evaluate the Safety, Tolerability, and Efficacy of Levofloxacin Inhalation Solution (MP-376) Administered for 5 Days Every 28 Days to Prevent Acute Exacerbations in High Risk COPD Patients" American Thoracic Society 2012 International Conference, May 18-23, 2012.
G.L. Kearns et al., "Poster No. 88: Levofloxacin Pharmacokinetics (PK) after Administration of MP-376 (Levofloxacin Inhalation Solution; Aeroquin®) in Children with Cystic Fibrosis (CF)" 34th European Cystic Fibrosis Conference Jun. 8-11, 2011.

* cited by examiner

AEROSOLIZED FLUOROQUINOLONES AND USES THEREOF

RELATED APPLICATIONS

This application is a Divisional of U.S. application Ser. No. 11/436,875 filed on May 18, 2006 which claims priority to U.S. Provisional Application No. 60/682,530 filed on May 18, 2005, U.S. Provisional Application No. 60/696,160 filed on Jul. 1, 2005, and U.S. Provisional Application No. 60/773,300 filed on Feb. 13, 2006, all of which are incorporated herein by reference in their entireties.

BACKGROUND OF THE INVENTION

Description of the Related Art

Antibiotics have been effective tools in the treatment of infectious diseases during the last half-century. From the development of antimicrobial therapy to the late 1980s, most bacterial infections occurring in patients in developed countries could be controlled unless the infection occurred in an organ or environment where antibiotics were difficult to deliver or were ineffective, such as bacterial infections of the circulatory system in sepsis patients, or bacterial infections of the lungs in cystic fibrosis. However, even in ordinary infections, in response to the pressure of antimicrobial usage, multiple resistance mechanisms have become widespread and are threatening the clinical utility of even the most aggressive antibacterial therapy. The increase in antimicrobial resistant strains has been particularly common in major hospitals and care centers. The consequences of the increase in resistant strains include higher morbidity and mortality, longer patient hospitalization, and an increase in treatment costs.

Bacteria have developed several different mechanisms to overcome the action of antimicrobials. These mechanisms of resistance can be specific for a molecule or a family of antimicrobials, or can be non-specific and be involved in resistance to unrelated antimicrobials. Several mechanisms of resistance can exist in a single bacterial strain, and those mechanisms may act independently or they may act synergistically to overcome the action of an antimicrobial or a combination of antimicrobials. Specific mechanisms include degradation of the drug, inactivation of the drug by enzymatic Modification, and alteration of the drug target. There are, however, more general mechanisms of drug resistance, in which access of the antimicrobial to the target is prevented or reduced by decreasing the transport of the antimicrobial into the cell or by increasing the efflux of the drug from the cell to the outside medium. Both mechanisms can lower the concentration of drug at the target site and allow bacterial survival in the presence of one or more antimicrobials that would otherwise inhibit or kill the bacterial cells. Some bacteria utilize both mechanisms, combining a low permeability of the cell wall (including membranes) with an active efflux of antimicrobials.

SUMMARY OF THE INVENTION

Various embodiments provide compositions and methods for optimal antimicrobial activity for the treatment of respiratory tract and pulmonary infections in human and/or veterinary subjects using short-term, rapid aerosol administration, and through the delivery of high-concentration drug exposure directly to the affected tissue. Specifically, in some embodiments, concentrated doses of agents from the fluoroquinolone class of antibiotic are delivered to produce maximum concentrations of active drug to the respiratory, pulmonary, and other non-oral topical compartments including, but not limited to the skin, rectum, vagina, urethra, urinary bladder, eye, and ear. Because different drug products are known to produce different antimicrobial effects depending on the dose, form, concentration and delivery profile, some embodiments provide specific formulation and delivery parameters that produce antimicrobial results that are therapeutically significant. The invention includes, but is not limited to, specific fluoroquinolone antibiotics, such as levofloxacin, formulated to enable aerosol administration meeting specific concentrations and antimicrobial criteria necessary to treat patients with distinct bacterial infections. These formulations and methods are useful with commercially available inhalation devices for one or more aerosol therapeutic product opportunities.

Aerosol administration directly to the nasal, sinus, respiratory tract and pulmonary compartments through intra-nasal or oral inhalation enables high concentration drug delivery to a site of respiratory infection with decreased risk of extra-respiratory toxicity associated with non-respiratory routes of drug delivery. Furthermore, direct administration to the site of infection permits very high local drug levels, a property that enables "rapid administration, high concentration, local exposure" killing effect special to this class of antibiotic. Accordingly, because the microbial killing effect of a particular antibiotic compound and therapeutic composition varies depending on the formulation and delivery parameters, newer compositions and delivery methods can be developed for existing drug compounds that are re-formulated and administered through novel delivery techniques. Other topical infections may also benefit from this discovery through high concentration, direct exposure of fluoroquinolone to infected skin, rectum, vagina, urethra, urinary bladder, eye, and ear.

Members of the fluoroquinolone drug class exhibit unique pharmacologic properties, including bioavailability (F), mean absorption time (MAT) from the lung, maximal drug concentrations in the epithelial lining fluid, bronchial lavage fluid, sputum and/or lung tissue (Cmax) following aerosol administration, pulmonary retention time, area under the curve (AUC), minimal inhibitory concentrations (MIC) of the antibiotic required for antibacterial activity, AUC/MIC ratio, and local and systemic safety. Specific to the invention is the use short-term, rapid aerosol administration, delivering high concentration drug exposure directly to the affected tissue (ELF, sputum, BAL, tissue) via aerosol delivery for treatment of bacterial infection in animals and humans.

In addition to the clinical and pharmacological requirements present in any composition intended for therapeutic administration, many physicochemical factors unique to a drug compound must also be considered. These include, but are not limited to aqueous solubility, viscosity, partitioning coefficient (Log P), predicted stability in various formulations, osmolality, surface tension, pH, pKa, pKb, dissolution rate, sputum permeability, sputum binding/inactivation, taste, throat irritability and acute tolerability.

Other factors to consider when designing the product form include fluoroquinolone physical chemistry and antibacterial activity, disease indication, clinical acceptance, and patient compliance. By non-limiting example, if desired the aerosol fluoroquinolone product may be in the form of a simple liquid (e.g. soluble fluoroquinolone with non-encapsulating soluble excipients/salts), complex liquid (e.g. fluoroquinolone encapsulated or complexed with soluble excipients such as lipids, liposomes, cyclodextrins, microencapsulations, and emulsions), complex suspension (e.g. fluoroquinolone as a low-solubility, stable nanosuspension alone, co-crystal/co-precipitate complexes, and mixtures with low solubility lipids such as solid-lipid nanoparticles), or dry powder (dry powder fluoroquinolone alone or in co-crystal/co-precipitate/spray-dried complex or mixture with low solubility excipients/salts or readily soluble blends such as lactose).

Combined with product form is a packaging consideration. By non-limiting example, considerations for packaging include intrinsic product stability, the need for stability-providing lyophilization, device selection (e.g. liquid nebulizer, dry-powder inhaler, meter-dose inhaler), and packaging form (e.g. simple liquid or complex liquid formulation in a vial as liquid or lyophilisate to be dissolved prior to or upon insertion into the device; complex suspension formulations in a vial as a liquid or lyophilisate with or without a soluble salt/excipient component to be dissolved prior to or upon insertion into the device, or separate packaging of liquid and solid components; dry powder formulations in a vial, capsule or blister pack; and other formulations packaged as readily soluble or low-solubility solid agents in separate containers alone or together with readily soluble or low-solubility solid agents. Any separately packaged agent will be manufactured to be mixed prior to or upon insertion into the delivery device).

In some aspects, the present invention relates to the aerosol and topical delivery of fluoroquinolone antimicrobials, such as levofloxacin. Levofloxacin has favorable solubility characteristics enabling dosing of clinically-desirable fluoroquinolone levels by aerosol (e.g. through liquid nebulization, dry powder dispersion or meter-dose administration) or topically (e.g. aqueous suspension, oily preparation or the like or as a drip, spray, suppository, salve, or an ointment or the like) and can be used in methods for acute or prophylactic treatment of an infected vertebrate, e.g. a bacterial infection, or a subject at risk of an infection.

Others include: ofloxacin, lomefloxacin, pefloxacin, ciprofloxacin, gatifloxacin, gemifloxacin, moxifloxacin, tosufloxacin, pazufloxacin, rufloxacin, fleroxacin, balofloxacin, sparfloxacin, trovafloxacin, enoxacin, norfloxacin, clinafloxacin, grepafloxacin, sitafloxacin, marbofloxacin, orbifloxacin, sarafloxacin, danofloxacin, difloxacin, enrofloxacin, garenoxacin, prulifloxacin, olamufloxacin, DX-619, TG-873870 and DW-276.

In a preferred embodiment, the method treats a bacterial infection in a subject using concentrated aerosol levofloxacin administered to a subject infected with a pathogenic bacteria in the lungs.

The therapeutic method may also include a diagnostic step, such as identifying a patient infected with a particular pathogenic bacteria, or a resistant bacteria. In some embodiments, the method further includes identifying a patient as colonized with a bacteria that is capable of developing resistance to fluoroquinolone antimicrobials. In some embodiments, the delivered amount of aerosol levofloxacin is sufficient to overcome resistance or prevent resistance development to levofloxacin. In one embodiment, the MIC of the fluoroquinolone antibacterial compound for the microbe is greater than about 2 ug/ml.

In another embodiment, the delivered amount of aerosol levofloxacin is sufficient to overcome resistance or prevent further resistance of an organism exhibiting an MIC of the fluoroquinolone antibacterial compound that is greater than about 4 ug/ml.

In another embodiment, the delivered amount of aerosol fluoroquinolone is sufficient to overcome resistance or prevent further resistance of an organism exhibiting an MIC of the fluoroquinolone antibacterial compound that is greater than about 8 ug/ml.

In another embodiment, the delivered amount of aerosol fluoroquinolone is sufficient to overcome resistance or prevent further resistance of an organism exhibiting an MIC of the fluoroquinolone antibacterial compound that is greater than about 16 ug/ml.

In another embodiment, the delivered amount of aerosol fluoroquinolone is sufficient to overcome resistance or prevent further resistance of an organism exhibiting an MIC of the fluoroquinolone antibacterial compound that is greater than about 32 ug/ml.

In another embodiment, a method is provided for prophylactic treatment of a subject, including administering to a subject, susceptible to microbial infection or a chronic carrier of an asymptomatic or low symptomatic microbial infection, a fluoroquinolone antimicrobial to achieve a minimal inhibitory concentration of antimicrobial at a site of potential or current infection. In one embodiment, the method further comprising identifying a subject as a subject at risk of a bacterial infection or at risk for an exacerbation of an infection.

In another embodiment, a method is provided for acute or prophylactic treatment of a patient through aerosol administration of fluoroquinolone to produce and maintain threshold drug concentrations in the lung, which may be measured as drug levels in epithelial lining fluid (ELF), sputum, lung tissue or bronchial lavage fluid (BAL). One embodiment includes the use of short-term, rapid aerosol administration, delivering high concentration drug exposure directly to the affected tissue for treatment of bacterial infections in animals and humans.

In another embodiment, a method is provided for treating a microbial infection in a subject, including administering to a subject infected with a microbe a fluoroquinolone antimicrobial to achieve a minimal inhibitory concentration of antimicrobial at a site of infection. In one embodiment, the method further comprising identifying the subject as infected with a microbe that is resistant to an antimicrobial agent.

In another embodiment, a method is provided for acute or prophylactic treatment of a patient through non-oral or non-nasal topical administration of fluoroquinolone to produce and maintain threshold drug concentrations at the site of infection or at risk of infection. One embodiment includes the use of short-term, rapid aerosol administration, delivering high concentration drug exposure directly to the affected tissue for treatment or prevention of bacterial infections in skin, rectal, vaginal, urethral, ocular, and auricular tissues.

In another embodiment, a method is provided for administering a fluoroquinolone antimicrobial by inhalation, wherein the inhaled liquid or dry powder aerosol has a mean particle size from about 1 micron to 10 microns mass median aerodynamic diameter and a particle size geometric standard deviation of less than or equal to about 3 microns. In another embodiment, the particle size is 2 microns to about 5 microns mass median aerodynamic diameter and a particle size geometric standard deviation of less than or equal to about 2 microns. In one embodiment, the particle size geometric standard deviation is less than or equal to about 1.8 microns.

In some embodiments of the methods described above, fluoroquinolone antimicrobial minimal inhibitory concentration remains at the site of infection for at least about a 5 minute period, at least about a 10 min period, at least about a 20 min period, at least about a 30 min period, at least about a 1 hour period, 2 hour period, at least about a 4 hour period or other time values on the quarter hour interval. The effective fluoroquinolone antimicrobial minimal inhibitory concentration (MIC) is sufficient to cause a therapeutic effect and the effect may be localized to the site of infection. In some embodiments, one or more levofloxacin administrations achieve an ELF, BAL, and/or sputum fluoroquinolone concentration of at least 1-fold to 5000-fold the infecting or potentially infecting organisms MIC, including all integral values therein such as 2-fold, 4-fold, 8-fold, 16-fold, 32-fold, 64-fold, 128-fold, 256-fold, 512-fold, 1028-fold, 2056-fold, and 4112-fold the microbials MIC.

In some embodiments, such as a pulmonary site, the fluoroquinolone antimicrobial is administered in one or more administrations so as to achieve a respirable delivered dose daily of at least about 5 mg to about 50 mg, including all integral values therein such as 10, 15, 20, 25, 30, 35, 40 and 45 milligrams. Similarly, the fluoroquinolone antimicrobial is administered in one or more administrations so as to achieve a respirable delivered dose daily of at least about 50 to about 100 mg including all integral values therein, such as 55, 60, 65, 70, 75, 80, 85, 90, and 95 mg. In some embodiments of the methods described above, the fluoroquinolone antimicrobial is administered in one or more administrations so as to achieve a respirable delivered daily dose of up to 150 mg including all integral values therein such as 105, 110, 115, 120, 125, 130, 135, 140 and 145 mg. The fluoroquinolone antimicrobial is administered in the described respirable delivered dose in less than 20 minutes, less than 10 minutes, less than 7 minutes, less than 5 minutes, in less than 3 minutes and in less than 2 minutes. In some embodiments of the methods described above, the antimicrobial agent is selected from the group consisting of ofloxacin, lomefloxacin, pefloxacin, ciprofloxacin, gatifloxacin, gemifloxacin, moxifloxacin, tosufloxacin, pazufloxacin, rufloxacin, fleroxacin, balofloxacin, sparfloxacin, trovafloxacin, enoxacin, norfloxacin, clinafloxacin, grepafloxacin, sitafloxacin, marbofloxacin, orbifloxacin, sarafloxacin, danofloxacin, difloxacin, enrofloxacin, garenoxacin, prulifloxacin, olamufloxacin, DX-619, TG-873870 and DW-276, although levofloxacin is preferred.

In some embodiments of the methods described above, the bacteria is a gram-negative bacteria such as *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus.* In some embodiments of the methods described above, the bacteria is a gram-negative anaerobic bacteria, by non-limiting example these include *Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus.* In some embodiments of the methods described above, the bacteria is a gram-positive bacteria, by non-limiting example these include: *Corynebacterium diphtheriae, Corynebacterium ulcerans, Streptococcus pneumoniae, Streptococcus agalactiae, Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus.* In some embodiments of the methods described above, the bacteria is a gram-positive anaerobic bacteria, by non-limiting example these include *Clostridium difficile, Clostridium perfringens, Clostridium tetini,* and *Clostridium botulinum.* In some embodiments of the methods described above, the bacteria is a acid-fast bacteria, by non-limiting example these include *Mycobacterium tuberculosis, Mycobacterium avium, Mycobacterium intracellulare,* and *Mycobacterium leprae.* In some embodiments of the methods described above, the bacteria is a atypical bacteria, by non-limiting example these include *Chlamydia pneumoniae* and *Mycoplasma pneumoniae.*

In some embodiments of the methods described above, the subject is a human. In some embodiments of the methods described above, the subject is a human with cystic fibrosis. In some embodiments of the methods described above, the subject is a human with pneumonia, a chronic obstructive pulmonary disease, or sinusitis, or a human being mechanically ventilated.

In another embodiment, a pharmaceutical composition is provided that includes a simple liquid fluoroquinolone antimicrobial formulation (e.g. soluble fluoroquinolone with non-encapsulating water soluble excipients) as described above having an osmolality from about 200 mOsmol/kg to about 1250 mOsmol/kg. In one such embodiment, the solution has a permeant ion concentration from about 30 mM to about 300 mM. In one embodiment, the osmolality is from about 250 mOsmol/kg to about 1050 mOsmol/kg. In one embodiment, the osmolality is from preferably from about 350 mOsmol/kg and about 750 mOsmol/kg and most preferably approximately 300 mOsmol/kg.

In another embodiment, a pharmaceutical composition is provided that includes a simple liquid fluoroquinolone antimicrobial formulation having a permeant ion concentration between from about 30 mM to about 300 mM and preferably between from about 50 mM to 200 mM. In one such embodiment, one or more permeant ions in the composition are selected from the group consisting of chloride and bromide.

In another embodiment, a pharmaceutical composition is provided that includes a complex liquid fluoroquinolone antimicrobial formulation (e.g. fluoroquinolone encapsulated or complexed with water soluble excipients such as lipids, liposomes, cyclodextrins, microencapsulations, and emulsions) as described above having a solution osmolality from about 200 mOsmol/kg to about 1250 mOsmol/kg. In one such embodiment, the solution has a permeant ion concentration from about 30 mM to about 300 mM. In one embodiment, the osmolality is from about 250 mOsmol/kg to about 1050 mOsmol/kg. In one embodiment, the osmolality is from preferably from about 350 mOsmol/kg and about 750 mOsmol/kg and most preferably approximately 300 mOsmol/kg.

In another embodiment, a pharmaceutical composition is provided that includes a complex liquid fluoroquinolone antimicrobial formulation having a permeant ion concentration from about 30 mM to about 300 mM. In one such embodiment, one or more permeant ions in the composition are selected from the group consisting of chloride and bromide.

In another embodiment, a pharmaceutical composition is provided that includes a complex liquid fluoroquinolone antimicrobial formulation having a permeant ion concentration from about 50 mM to about 200 mM. In one such embodiment, one or more permeant ions in the composition are selected from the group consisting of chloride and bromide.

In another embodiment, a pharmaceutical composition is provided that includes a complex liquid fluoroquinolone antimicrobial formulation (e.g. fluoroquinolone as a low water soluble stable nanosuspension alone or in co-crystal/co-precipitate complexes, or mixtures with low solubility lipids, such as lipid nanosuspensions) as described above having a solution osmolality from about 200 mOsmol/kg to about 1250 mOsmol/kg. In one such embodiment, the solution has a permeant ion concentration from about 30 mM to about 300 mM. In one embodiment, the osmolality is from about 250 mOsmol/kg to about 1050 mOsmol/kg. In one embodiment, the osmolality is from prefereably from about 350 mOsmol/kg and about 750 mOsmol/kg and most preferably approximately 300 mOsmol/kg.

In another embodiment, a pharmaceutical composition is provided that includes a complex suspension fluoroquinolone antimicrobial formulation having a permeant ion concentration from about 30 mM to about 300 mM. In one such embodiment, one or more permeant ions in the composition are selected from the group consisting of chloride and bromide.

In another embodiment, a pharmaceutical composition is provided that includes a complex suspension fluoroquinolone antimicrobial formulation having a permeant ion concentration from about 50 mM to about 200 mM. In one such embodiment, one or more permeant ions in the composition are selected from the group consisting of chloride and bromide.

In another embodiment, a pharmaceutical composition is provided that includes a taste-masking agent. By non-limiting example a taste-masking agent may include a sugar, a divalent or trivalent cation that complexes with a fluoroquinolone, optimized osmolality, and/or an optimized permeant ion concentration.

In another embodiment, a pharmaceutical composition is provided that includes a simple dry powder fluoroquinolone antimicrobial compound (e.g. fluoroquinolone alone in dry powder form with or without a blending agent such as lactose).

In another embodiment, a pharmaceutical composition is provided that includes a complex dry powder fluoroquinolone antimicrobial formulation (e.g. fluoroquinolone in co-crystal/co-precipitate/spray dried complex or mixture with low water soluble excipients/salts in dry powder form with or without a blending agent such as lactose).

In another embodiment, a system is provided for administering a fluoroquinolone antimicrobial that includes a container comprising a solution of a fluoroquinolone antimicrobial and a nebulizer physically coupled or co-packaged with the container and adapted to produce an aerosol of the solution having a particle size from about 2 microns to about 5 microns mean mass aerodynamic diameter and a particle size geometric standard deviation of less than or equal to about 2.5 microns mean mass aerodynamic diameter. In one embodiment, the particle size geometric standard deviation is less than or equal to about 2.0 microns. In one embodiment, the particle size geometric standard deviation is less than or equal to about 1.8 microns.

In another embodiment, a system is provided for administering a fluoroquinolone antimicrobial that includes a container comprising a dry powder of a fluoroquinolone antimicrobial and a dry powder inhaler coupled to the container and adapted to produce a dispersed dry powder aerosol having a particle size from about 2 microns to about 5 microns mean mass aerodynamic and a particle size standard deviation of less than or equal to about 3.0 microns. In one embodiment, the particle size standard deviation is less than or equal to about 2.5 microns. In one embodiment, the particle size standard deviation is less than or equal to about 2.0 microns.

In another embodiment, a kit is provided that includes a container comprising a pharmaceutical formulation comprising a quinolone antimicrobial agent and an aerosolizer adapted to aerosolize the pharmaceutical formulation and deliver it to the lower respiratory tract and pulmonary compartment following intraoral administration. The formulation may also be delivered as a dry powder or through a metered-dose inhaler.

In another embodiment, a kit is provided that includes a container comprising a pharmaceutical formulation comprising a quinolone antimicrobial agent and an aerosolizer adapted to aerosolize the pharmaceutical formulation and deliver it to nasal cavity following intranasal administration. The formulation may also be delivered as a dry powder or through a metered-dose inhaler.

It is to be understood that both the foregoing general description and the following detailed description are exemplary and explanatory only and are not restrictive of the invention, as claimed.

DETAILED DESCRIPTION

Figure 1:
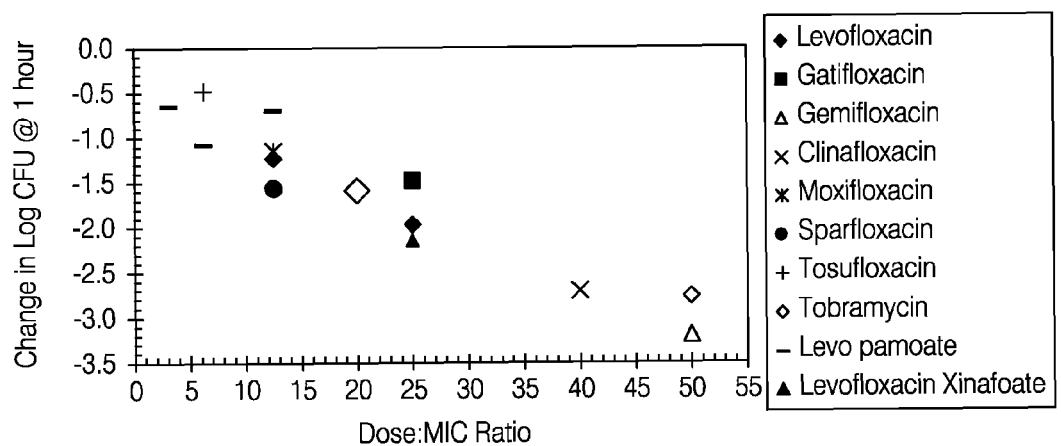
FIG. 1 is a graph showing the dose:MIC relationship of fluoroquinolones and other antibiotics to bacterial killing.
Figure 2:
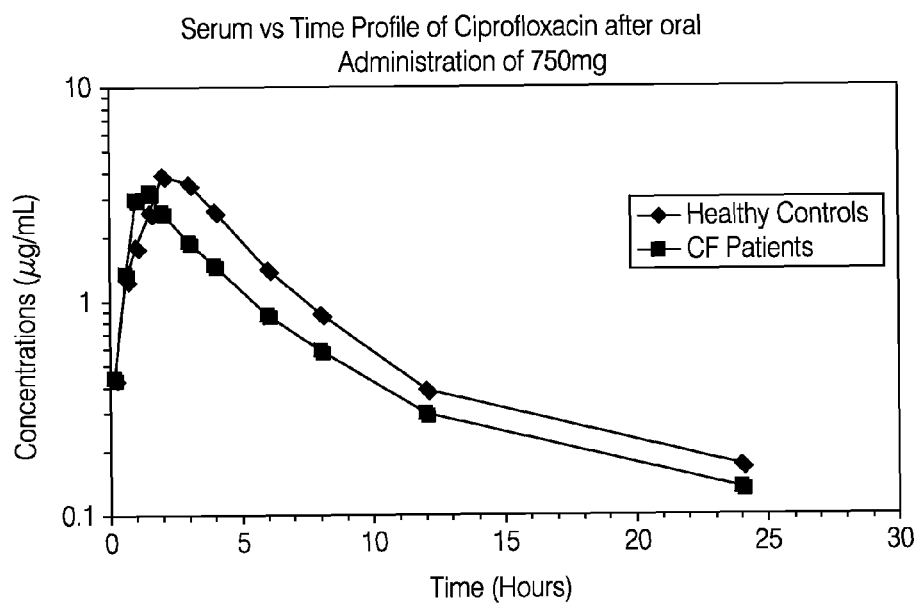
FIG. 2 is a graph showing ciprofloxacin serum concentrations following oral dosing in both CF patients vs healthy controls.

Many of the problems associated with antimicrobial-resistant pathogens could be alleviated if the concentration of the antimicrobial could be safely increased at the site of infection. For example, pulmonary infections may be treated by administration of the antimicrobial agent directly, at high concentrations directly to the site of infection without incurring large systemic concentrations of the antimicrobial. Accordingly, some embodiments disclosed herein are improved methods for delivering drug compositions to treat pulmonary bacterial infections. More specifically, as described herein, it has been discovered that aerosol levofloxacin and other fluoroquinolones can be safely delivered by inhalation at levels sufficient to kill susceptible bacterial infections, to decrease the frequency of antimicrobial resistance and to increase efficacy against resistant pulmonary infections.

DEFINITIONS

The term "administration" or "administering" refers to a method of giving a dosage of an antimicrobial pharmaceutical composition to a vertebrate. The preferred method of administration can vary depending on various factors, e.g., the components of the pharmaceutical composition, the site of the potential or actual bacterial infection, the microbe involved, and the severity of an actual microbial infection.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8*th Ed., Pergamon Press.*

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "microbial infection" refers to the undesired proliferation or presence of invasion of pathogenic microbes in a host organism. This includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, naphthoic acid, oleic acid, palmitic acid, pamoic (embonic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobionic acid, tartaric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsulfuric acid, naphthalene-1,5-disulfonic acid, naphthalene-2-sulfonic acid, and saccharin.

"Solvate" refers to the compound formed by the interaction of a solvent and fluoroquinolone antimicrobial, a metabolite, or salt thereof. Suitable solvates are pharmaceutically acceptable solvates including hydrates.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant a fluoroquinolone antimicrobial agent, as disclosed for this invention, which has a therapeutic effect. The doses of fluoroquinolone antimicrobial agent which are useful in treatment are therapeutically effective amounts. Thus, as used herein, a therapeutically effective amount means those amounts of fluoroquinolone antimicrobial agent which produce the desired therapeutic effect as judged by clinical trial results and/or model animal infection studies. In particular embodiments, the fluoroquinolone antimicrobial agent are administered in a pre-determined dose, and thus a therapeutically effective amount would be an amount of the dose administered. This amount and the amount of the fluoroquinolone antimicrobial agent can be routinely determined by one of skill in the art, and will vary, depending on several factors, such as the particular microbial strain involved. This amount can further depend upon the patient's height, weight, sex, age and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the total or substantial elimination of excessive members of viable microbe of those involved in the infection to a point at or below the threshold of detection by traditional measurements. However, certain long-term or permanent effects of the infection may exist even after a cure is obtained (such as extensive tissue damage). As used herein, a "therapeutic effect" is defined as a statistically significant reduction in bacterial load in a host, emergence of resistance, or improvement in infection symptoms as measured by human clinical results or animal studies.

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a fluoroquinolone antimicrobial agent.

Pharmacokinetics (PK) is concerned with the time course of antimicrobial concentration in the body. Pharmacodynamics (PD) is concerned with the relationship between pharmacokinetics and the antimicrobial efficacy in vivo. PK/PD parameters correlate antimicrobial exposure with antimicrobial activity. The rate of killing by antimicrobial is dependent on antimicrobial mode of action and is determined by either the length of time necessary to kill (time-dependent) or the effect of increasing concentrations (concentration-dependent). Accordingly, to predict the therapeutic efficacy of antimicrobials with diverse mechanisms of action different PK/PD parameters may be used.

"AUC/MIC ratio" is one example of a PK/PD parameter. AUC is defined as the area under the plasma or site-of-infection concentration-time curve of an antimicrobial agent in vivo (in animal or human). AUC/MIC ratio is determined by dividing the 24-hour-AUC for an individual antimicrobial by the MIC for the same antimicrobial determined in vitro. Activity of antimicrobials with the dose-dependent killing (such as fluoroquinolones) is well predicted by the magnitude of the AUC/MIC ratio.

"Cmax:MIC" ratio is another PK:PD parameter. It describes the maximum drug concentration in plasma or tissue relative to the MIC. Fluoroquinolones and aminoglycosides are examples where Cmax:MIC may predict in vivo bacterial killing where resistance can be suppressed.

"Time above MIC" (T>MIC) is another PK/PD parameter. It is expressed a percentage of a dosage interval in which the plasma or site-of-infection level exceeds the MIC. Activity of antimicrobials with the time-dependent killing (such as beta-lactams or oxazolidinones) is well predicted by the magnitude of the T>MIC ratio.

The term "dosing interval" refers to the time between administrations of the two sequential doses of a pharmaceutical's during multiple dosing regimens. For example, in the case of ciprofloxacin, which is administered twice daily (traditional regimen of 400 mg b.i.d) and levofloxacin, which is administered once a day (500 mg or 750 mg q.d.), the dosing intervals are 12 hours and 24 hours, respectively.

As used herein, the "peak period" of a pharmaceutical's in vivo concentration is defined as that time of the pharmaceutical dosing interval when the pharmaceutical concentration is not less than 50% of its maximum plasma or site-of-infection concentration. In some embodiments, "peak period" is used to describe an interval of antimicrobial dosing.

The "respirable delivered dose" is the amount of drug inhaled during the inspiratory phase of the breath simulator that is equal to or less than 5 microns using a simulator programmed to the European Standard pattern of 15 breaths per minute, with an inspiration to expiration ratio of 1:1.

Advantages of Inhaled Aerosol and Topical (Non-Oral) Fluoroquinolone Delivery

The antibiotic rate of killing is dependent upon antibiotic mode of action and is determined by either the length of time necessary for the antibiotic to kill (time-dependent) or the effect of increasing the antibiotic concentration (concentration-dependent). Fluoroquinolones are characterized by concentration-dependent, time-kill activity where a therapeutic effect requires a high local peak concentration above the MICs of the infecting pathogen.

Fluoroquinolone efficacy in humans, animals and in vitro models of infection is linked to AUC:MIC ratio and Cmax:MIC ratio. Given the prior uncertainty of the pharmacokinetics of fluoroquinolones in pulmonary tissue, a number of in vitro studies have been conducted to determine if high doses of levofloxacin with extremely short half-lives (as predicted from a rat and human PK model) result in bacterial killing superior to that seen under conditions with more prolonged residence times. In these studies, levofloxacin concentrations that were 0.018-fold-1024-fold the MIC were evaluated in a standard kill-curve and in vitro hollow fiber assay. In both of these assays, high concentrations of levofloxacin were rapidly bactericidal and reached their maximum level of killing in 10-20 minutes. This level of killing was sustained whether levofloxacin was maintained at that level or given a half-life of 10 minutes. Accordingly, high doses and rapid delivery of specially formulated levofloxacin, such as a rapidly delivered 20-50 mg respirable deposited aerosol levofloxacin dose (which will produce initial ELF concentrations of 800-1600 ug/mL) is rapidly bactericidal for susceptible organisms and resistant organisms with MICs up to 32 ug/ml. It is expected that these unique antimicrobial properties of fluoroquinolones will also translate to topical administrations, including, but not limited to infections or prophylaxis of the skin, eye, ear, rectum, vagina, or urinary tract.

To measure the efficacy of different delivery models, AUC shape-enhancing levofloxacin formulations were prepared and measured in vivo in comparison to non-AUC shape-enhancing levofloxacin formulations and other antibiotics using both rat PK and mouse efficacy following intratracheal administration. As was previously shown in a rat system, there were differences among drugs in pulmonary pharmacokinetics, with some agents showing lower AUCs (e.g., levofloxacin), while others such as gemifloxacin or tobramycin show higher concentrations resulting from slower pulmonary clearance. Studies in a single dose mouse model of infection with aerosol doses have shown variable efficacy among the compounds. Referring to FIG. 1, analysis of the data by dividing the aerosolized dose by the MIC indicated a strong correlation between Dose:MIC ratio and bactericidal activity ($R2=0.89$). These data suggest that the initial bactericidal activity in this model is not affected by the pulmonary clearance of the drug. Although pulmonary clearances have not been estimated in mice, transformation of dose to AUC using scaled rat values would be expected to degrade the relationship. Therefore, this data suggests that optimizing the AUC shape for levofloxacin may not be necessary for aerosol levofloxacin to be effective in treating respiratory tract and pulmonary infections.

Recent investigations with fluoroquinolones resulted in development of the concept of a "mutant selection window" (MSW) for bacterial resistance arising during therapy. This concept assists in identifying a concentration range where mutants are selected more frequently in vitro and in vivo. The lower boundary of the window is the lowest concentration that kills the majority of infecting cells (approximated by the MIC), while the upper boundary of the window is the drug concentration that blocks the growth of the least susceptible first-step mutant. Above the upper boundary concentration the growth of the infecting bacteria requires the presence of at least two resistance mutations. This upper boundary is designated the mutant prevention concentration (MPC). The values of MPC vary depending on bacteria and fluoroquinolone, and may be 10- to 20-fold higher than the MIC. Several modeling studies have demonstrated that the longer the drug concentration exceeds the MPC at the site of infection, the more effectively the treatment will prevent resistance development. Conversely, the longer the antibiotic concentration stays within the MSW, the higher the probability to select resistant mutants. Importantly, the currently approved dosing regimen for oral or intravenous levofloxacin has placed this antibiotic within the MSW for more than 20% of the dosing interval for such pathogens as *P. aeruginosa* (Pa) and *S. pneumonia*. Accordingly, a high level of levofloxacin resistance is reported for both of these pathogens.

Therefore, in one embodiment, the concentration of levofloxacin at the site of infection is increased by delivering it directly to the lung using inhalation therapy, thereby decreasing the amount of time levofloxacin is in the MSW. Such a therapeutic approach achieves broader coverage of pathogens (including levofloxacin resistant strains), prevents further resistance development, and results in shorter courses of levofloxacin therapy.

macokinetic properties of the 2 components are similar. In comparative studies with ciprofloxacin, ofloxacin had a longer half-life and higher distribution into sputum (79% vs 21%) than ciprofloxacin.

Lung Epithelial Lining Fluid

More recent emphasis on the use and development of fluoroquinolones in community acquired gram-positive infections has focused on intrapulmonary pharmacokinetic studies in lung epithelial lining fluid (ELF). Although the relevance of drug distribution into this fluid is not clear in the setting of cystic fibrosis, insights in the drug pharmacology can be obtained from these studies. Levofloxacin penetrates well into lung tissues. Lung tissue concentrations are generally 2- to 5-fold higher than plasma concentrations. Several recent studies (summarized in Table 1) demonstrated that ELF concentrations of levofloxacin in healthy subjects following an oral dose of 750 mg reach a maximum concentration around 20 μg/mL. Similar peak concentrations are expected in the sputum of CF patients after oral or IV administration of 750 mg of levofloxacin. In contrast, ciprofloxacin penetrates lung tissues much less efficiently than levofloxacin. Based upon studies of the mutant selection window (MSW), these ELF fluoroquinolone drug levels are insufficient to achieve the required mutant prevention concentration of 10- to 20-fold the MIC for the infecting organism.

TABLE 1

Concentration of Levofloxacin in Epithelial Lining Fluid in Man.

| | | | ELF Drug Concentration (μg/ml) | | | | | | |
|---|---|---|---|---|---|---|---|---|---|
| Drug | Dose | Route | 0.5 hr | 1 hr | 2 hr | 4 hr | 6 hr | 12 hr | 24 hr |
| levofloxacin | 500 mg | IV | | | | 11 | | 2.5 | 1.24 |
| levofloxacin | 500 mg | oral | | | | 9.9 | | 6.5 | 0.7 |
| levofloxacin | 500 mg | oral | | | | 9.94 | | 6.46 | 0.7 |
| levofloxacin | 500 mg | oral | 4.74 | 10.8 | 9 | 10.9 | 9.6 | | |
| levofloxacin | 750 mg | IV | | | | 12.94 | | 6.04 | 1.73 |
| levofloxacin | 750 mg | oral | | | | 22.1 | | 9.2 | 1.5 |
| levofloxacin | 750 mg | oral | | | | 22.13 | | 9.19 | 1.55 |
| ciprofloxacin | 500 mg | oral | | | | 1.9 | | 0.4 | |

Pharmacokinetics of Orally Administered Fluoroquinolones in Non-CF and CF Populations Sputum Concentrations in CF Patients The pharmacokinetics of ciprofloxacin has been extensively studied in CF patients after oral administration. In fact, it has been demonstrated that the serum PK profile of ciprofloxacin is very similar in CF patients to healthy volunteers (FIG. 2).

Moreover, the sputum vs time profile of ciprofloxacin is very similar to its serum profile after oral administration (FIG. 3). After a 750 mg oral dose, peak concentrations of ~4.2 μg/ml and ~3.5 μg/ml were achieved for serum and sputum, respectively. Serum and sputum drug concentrations peaked at 1.5 and 4 hours, respectively. While the total amount of ciprofloxacin into sputum is high relative to serum concentrations, the absolute concentrations are low relative to MICs of target organisms such as Pa. This data is consistent with poor clinical outcome due to resistance development to these low drug concentrations.

While data for levofloxacin intrapulmonary pharmacokinetics in cystic fibrosis are not available, data on the closely-related ofloxacin were published in the 1980's and 1990s. Ofloxacin is comprised of a racemic mixture of the dextro- (microbiologically inactive) and levo-rotatory (levofloxacin-microbiologically active). Studies have shown that the phar- Quinolones Non-limiting examples of quinolones for use as described herein include amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; garenoxacin; olamufloxacin, clinofloxacin, trovafloxacin, balofloxacin, prulifloxacin, moxifloxacin, gemifloxacin, rufloxacin, sitafloxacin (Sato, K, et al., 1992, Antimicrob Agents Chemother. 37:1491-98, which is incorporated herein by reference in its entirety), marbofloxacin, orbifloxacin, sarafloxacin, danofloxacin, difloxacin, enrofloxacin, TG-873870, DX-619, DW-276, ABT-492, DV-7751a (Tanaka, M, et al., 1992, Antimicrob. Agents Chemother. 37:2212-18), and F-1061 (Kurosaka et al., Interscience Conference on Antimicrobial Agents and Chemotherapy, 2003, 43rd: Chicago, which is incorporated herein by reference in its entirety).

Methods of Treatment or Prophylaxis

In some embodiments, a method is provided for treating a microbial infection in an animal, specifically including in a mammal, by treating an animal suffering from such an infection with a fluoroquinolone antimicrobial. In some embodiments, fluoroquinolone antimicrobials may be administered following aerosol formation and inhalation. Thus, this method of treatment is especially appropriate for the treatment of pulmonary infections involving microbial strains that are difficult to treat using an antimicrobial agent delivered parenterally due to the need for high parenteral dose levels (which can cause undesirable side effects), or due to lack of any clinically effective antimicrobial agents. In one such embodiment, this method may be used to administer a fluoroquinolone antimicrobial directly to the site of infection. Such a method may reduce systemic exposure and maximizes the amount of antimicrobial agent to the site of microbial infection. This method is also appropriate for treating infections involving microbes that are susceptible to fluoroquinolone antimicrobials as a way of reducing the frequency of selection of resistant microbes. This method is also appropriate for treating infections involving microbes that are otherwise resistant to fluoroquinolone antimicrobials as a way of increasing the amount of antimicrobial at the site of microbial infection. A subject may be identified as infected with bacteria that are capable of developing resistance by diagnosing the subject as having symptoms that are characteristic of a bacterial infection with a bacteria species known to have resistant strains or a with a bacteria that is a member of group that are known to have resistant strains. Alternatively, the bacteria may be cultured and identified as a species known to have resistant strains or a bacteria that is a member of group that are known to have resistant strains.

In some embodiments, the aerosol fluoroquinolone antimicrobial agent is administered at a level sufficient to overcome the emergence resistance in bacteria or increase killing efficiency such that resistance does not have the opportunity to develop.

In some embodiments, the aerosol fluoroquinolone therapy may be administered as a treatment or prophylaxis in combination or alternating therapeutic sequence with other aerosol, oral or parenteral antibiotics. By non-limiting example this may include aerosol tobramycin and/or other aminoglycoside, aerosol aztreonam and/or other beta or mono-bactam, aerosol ciprofloxacin and/or other fluoroquinolones, aerosol azithromycin and/or other macrolides or ketolides, tetracycline and/or other tetracyclines, quinupristin and/or other streptogramins, linezolid and/or other oxazolidinones, vancomycin and/or other glycopeptides, and chloramphenicol and/or other phenicols, and colisitin and/or other polymyxins.

Pharmaceutical Compositions

For purposes of the method described herein, a fluoroquinolone antimicrobial agent may be administered using an inhaler. In some embodiments, a fluoroquinolone antimicrobial disclosed herein is produced as a pharmaceutical composition suitable for aerosol formation, good taste, storage stability, and patient safety and tolerability.

In some embodiments, the isoform content of the manufactured fluoroquinolone may be optimized for tolerability, antimicrobial activity and stability.

Administration

The fluoroquinolone antimicrobials disclosed herein can be administered at a therapeutically effective dosage, e.g., a dosage sufficient to provide treatment for the disease states previously described. While optimum human dosage levels have yet to be determined for aerosol delivery, generally a daily aerosol dose of levofloxacin (and for most fluoroquinolone antimicrobial agents described herein) is from about 0.1 to 10 mg/kg of body weight, preferably about 0.20 to 5.0 mg/kg of body weight, and most preferably about 0.4 to 4.0 mg/kg of body weight. Thus, for administration to a 70 kg person, the dosage range would be about 7.0 to 700.0 mg per day, preferably about 14.0 to 350.0 mg per day, and most preferably about 28.0 to 280.0 mg per day. The amount of active compound administered will, of course, be dependent on the subject and disease state being treated, the severity of the affliction, the manner and schedule of administration, and the judgment of the prescribing physician; for example, a likely dose range for aerosol administration of levofloxacin would be about 20 to 400 mg per day.

Administration of the fluoroquinolone antimicrobial agents disclosed herein or the pharmaceutically acceptable salts thereof can be via any of the accepted modes of administration for agents that serve similar utilities including, but not limited to, aerosol inhalation.

Pharmaceutically acceptable compositions include solid, semi-solid, liquid and aerosol dosage forms, such as, e.g., powders, liquids, suspensions, complexations, liposomes, particulates, or the like. Preferably, the compositions are provided in unit dosage forms suitable for single administration of a precise dose. The unit dosage form can also be assembled and packaged together to provide a patient with a weekly or monthly supply and can also incorporate other compounds such as saline, taste masking agents, pharmaceutical excipients, and other active ingredients or carriers.

The fluoroquinolone antimicrobial agent can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, magnesium chloride, magnesium sulfate, calcium chloride, lactose, sucrose, glucose and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrin derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In one preferred embodiment, the compositions will take the form of a unit dosage form such as vial containing a liquid, solid to be suspended, dry powder, lyophilisate, or other composition and thus the composition may contain, along with the active ingredient, a diluent such as lactose, sucrose, dicalcium phosphate, or the like; a lubricant such as magnesium stearate or the like; and a binder such as starch, gum acacia, polyvinylpyrroldine, gelatin, cellulose, cellulose derivatives or the like.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. However, percentages of active ingredient of 0.01% to 90% in solution are employable, and will be higher if the composition is a solid, which will be subsequently diluted to the above percentages. In some embodiments, the composition will comprise 1.0%-50.0% of the active agent in solution.

Fluoroquinolone formulations can be separated into two groups; those of simple formulation and complex formulations providing taste-masking properties, improved tolerability and/or an AUC shape-enhancing formulation. Simple formulations can be further separated into three groups. 1. Simple formulations may include water-based liquid formulations for nebulization. By non-limiting example water-based liquid formulations may consist of fluoroquinolone alone or with non-encapsulating water soluble excipients. 2. Simple formulations may also include organic-based liquid formulations for nebulization or meter-dose inhaler. By non-limiting example organic-based liquid formulations may consist of fluoroquinolone or with non-encapsulating organic soluble excipients. 3. Simple formulations may also include dry powder formulations for administration with a dry powder inhaler. By non-limiting example dry powder formulations may consist of fluoroquinolone alone or with either water soluble or organic soluble non-encapsulating excipients with or without a blending agent such as lactose. Complex formulations can be further separated into five groups. 1. Complex formulations may include water-based liquid formulations for nebulization. By non-limiting example water-based liquid complex formulations may consist of fluoroquinolone encapsulated or complexed with water-soluble excipients such as lipids, liposomes, cyclodextrins, microencapsulations, and emulsions. 2. Complex formulations may also include organic-based liquid formulations for nebulization or meter-dose inhaler. By non-limiting example organic-based liquid complex formulations may consist of fluoroquinolone encapsulated or complexed with organic-soluble excipients such as lipids, microencapsulations, and reverse-phase water-based emulsions. 3. Complex formulations may also include low-solubility, water-based liquid formulations for nebulization. By non-limiting example low-solubility, water-based liquid complex formulations may consist of fluoroquinolone as a low-water soluble, stable nanosuspension alone or in co-crystal/co-precipitate excipient complexes, or mixtures with low solubility lipids, such as lipid nanosuspensions. 4. Complex formulations may also include low-solubility, organic-based liquid formulations for nebulization or meter-dose inhaler. By non-limiting example low-solubility, organic-based liquid complex formulations may consist of fluoroquinolone as a low-organic soluble, stable nanosuspension alone or in co-crystal/co-precipitate excipient complexes, or mixtures with low solubility lipids, such as lipid nanosuspensions. 5. Complex formulations may also include dry powder formulations for administration using a dry powder inhaler. By non-limiting example, complex dry powder formulations may consist of fluoroquinolone in co-crystal/co-precipitate/spray dried complex or mixture with low-water soluble excipients/salts in dry powder form with or without a blending agent such as lactose. Specific methods for simple and complex formulation preparation are described herein.

Aerosol Delivery

Fluoroquinolone antimicrobial agents as described herein, are preferably directly administered as an aerosol to a site of infection in the respiratory tract. In some embodiments, aerosol delivery is used to treat an infection in the lungs, such as a *Pseudomonas* lung infection.

Several device technologies exist to deliver either dry powder or liquid aerosolized products. Dry powder formulations generally require less time for drug administration, yet longer and more expensive development efforts. Conversely, liquid formulations have historically suffered from longer administration times, yet have the advantage of shorter and less expensive development efforts. The fluoroquinolone antimicrobial agents disclosed herein range in solubility, are generally stable and have a range of tastes. In one such embodiment, the fluoroquinolone antimicrobial levofloxacin is water soluble at neutral pH, is stable in aqueous solution and has limited to no taste.

Accordingly, in one embodiment, a particular formulation of fluoroquinolone antimicrobial agent disclosed herein is combined with a particular aerosolizing device to provide an aerosol for inhalation that is optimized for maximum drug deposition at a site of infection and maximal tolerability. Factors that can be optimized include solution or solid particle formulation, rate of delivery, and particle size and distribution produced by the aerosolizing device.

Particle Size and Distribution

Generally, inhaled particles are subject to deposition by one of two mechanisms: impaction, which usually predominates for larger particles, and sedimentation, which is prevalent for smaller particles. Impaction occurs when the momentum of an inhaled particle is large enough that the particle does not follow the air stream and encounters a physiological surface. In contrast, sedimentation occurs primarily in the deep lung when very small particles which have traveled with the inhaled air stream encounter physiological surfaces as a result of random diffusion within the air stream.

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled. Measures of particle size can be referred to as volumetric mean diameter (VMD), mass median diameter (MMD), or MMAD. These measurements may be made by impaction (MMD and MMAD) or by laser (VMD). For liquid particles, VMD, MND and MMAD may be the same if environmental conditions are maintained, e.g. standard humidity. However, if humidity is not maintained, MMD and MMAD determinations will be smaller than VMD due to dehydration during impator measurements. For the purposes of this description, VMD, MMD and MMAD measurements are considered to be under standard conditions such that descriptions of VMD, MND and MMAD will be comparable. Similarly, dry powder particle size determinations in MMD, and MMAD are also considered comparable.

In some embodiments, the particle size of the aerosol is optimized to maximize fluoroquinolone antimicrobial agent deposition at the site of infection and to maximize tolerability. Aerosol particle size may be expressed in terms of the mass median aerodynamic diameter (MMAD). Large particles (e.g., MMAD>5 μm) may deposit in the upper airway because they are too large to navigate the curvature of the upper airway. Small particles (e.g., MMAD<2 μm) may be poorly deposited in the lower airways and thus become exhaled, providing additional opportunity for upper airway deposition. Hence, intolerability (e.g., cough and bronchospasm) may occur from upper airway deposition from both inhalation impaction of large particles and settling of small particles during repeated inhalation and expiration. Thus, in one embodiment, an optimum particle size is used (e.g., MMAD=2-5 µm) in order to maximize deposition at a mid-lung site of infection and to minimize intolerability associated with upper airway deposition. Moreover, generation of a defined particle size with limited geometric standard deviation (GSD) may optimize deposition and tolerability. Narrow GSD limits the number of particles outside the desired MMAD size range. In one embodiment, an aerosol containing one or more compounds disclosed herein is provided having a MMAD from about 2 microns to about 5 microns with a GSD of less than or equal to about 2.5 microns. In another embodiment, an aerosol having an MMAD from about 2.8 microns to about 4.3 microns with a GSD less than or equal to 2 microns is provided. In another embodiment, an aerosol having an MMAD from about 2.5 microns to about 4.5 microns with a GSD less than or equal to 1.8 microns is provided.

Fluoroquinolone antimicrobial agents disclosed herein intended for respiratory delivery (for either systemic or local distribution) can be administered as aqueous formulations, as suspensions or solutions in halogenated hydrocarbon propellants, or as dry powders. Aqueous formulations may be aerosolized by liquid nebulizers employing either hydraulic or ultrasonic atomization. Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

Liquid Nebulizer

In one embodiment, a nebulizer is selected on the basis of allowing the formation of an aerosol of a fluoroquinolone antimicrobial agent disclosed herein having an MMAD predominantly between about 2 to about 5 microns. In one embodiment, the delivered amount of fluoroquinolone antimicrobial agent provides a therapeutic effect for respiratory infections.

Previously, two types of nebulizers, jet and ultrasonic, have been shown to be able to produce and deliver aerosol particles having sizes between 2 and 4 um. These particle sizes have been shown as being optimal for treatment of pulmonary bacterial infection cause by gram-negative bacteria such as *Pseudomonas aeruginosa, Escherichia coli, Enterobacter species, Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans*, and multidrug resistant *Pseudomonas aeruginosa*. However, unless a specially formulated solution is used, these nebulizers typically need larger volumes to administer sufficient amount of drug to obtain a therapeutic effect. A jet nebulizer utilizes air pressure breakage of an aqueous solution into aerosol droplets. An ultrasonic nebulizer utilizes shearing of the aqueous solution by a piezoelectric crystal. Typically, however, the jet nebulizers are only about 10% efficient under clinical conditions, while the ultrasonic nebulizer is only about 5% efficient. The amount of pharmaceutical deposited and absorbed in the lungs is thus a fraction of the 10% in spite of the large amounts of the drug placed in the nebulizer.

Accordingly, in one embodiment, a vibrating mesh nebulizer is used to deliver an aerosol of the fluoroquinolone antimicrobial agent disclosed herein. A vibrating mesh nebulizer consists of a liquid storage container in fluid contact with a diaphragm and inhalation and exhalation valves. In one embodiment, about 1 to about 5 ml of the fluoroquinolone antimicrobial agent is placed in the storage container and the aerosol generator is engaged producing atomized aerosol of particle sizes selectively between about 1 and about 5 um.

By non-limiting example, a fluoroquinolone antimicrobial agent disclosed herein is placed in a liquid nebulization inhaler and prepared in dosages to deliver from about 7 to about 700 mg from a dosing solution of about 1 to about 5 ml, preferably from about 14 to about 350 mg in about 1 to about 5 ml, and most preferably from about 28 to about 280 mg in about 1 to about 5 ml with MMAD particles sizes between about 2 to about 5 um being produced.

By non-limiting example, a nebulized fluoroquinolone antimicrobial may be administered in the described respirable delivered dose in less than about 20 min, preferably less than about 10 min, more preferably less than about 7 min, more preferably less than about 5 min, more preferably less than about 3 min, and in some cases most preferable if less than about 2 min.

By non-limiting example, in other circumstances, a nebulized fluoroquinolone antimicrobial may achieve improved tolerability and/or exhibit an AUC shape-enhancing characteristic when administered over longer periods of time. Under these conditions, the described respirable delivered dose in more than about 2 min, preferably more than about 3 min, more preferably more than about 5 min, more preferably more than about 7 min, more preferably more than about 10 min, and in some cases most preferable from about 10 to about 20 min.

For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; PARI Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Heathcare, Inc. and DeVilbiss Health Care, Inc. Vibrating mesh nebulizers rely upon either piezoelectric or mechanical pulses to respirable liquid droplets generate. Other examples of nebulizers for use with fluoroquinolone antimicrobial agents described herein are described in U.S. Pat. Nos. 4,268,460; 4,253,468; 4,046,146; 3,826,255; 4,649,911; 4,510,929; 4,624,251; 5,164,740; 5,586,550; 5,758,637; 6,644,304; 6,338,443; 5,906,202; 5,934,272; 5,960,792; 5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303 all of which are hereby incorporated by reference in their entirety. Commercial examples of nebulizers that can be used with the fluoroquinolone antimicrobial agents described herein include Respirgard II®, Aeroneb®, Aeroneb® Pro, and Aeroneb® Go produced by Aerogen; AERx® and AERx Essence™ produced by Aradigm; Porta-Neb®, Freeway Freedom™, Sidestream, Ventstream and I-neb produced by Respironics, Inc.; and PARI LC-Plus®, PARI LC-Star®, and e-Flow$^{7m}$ produced by PARI, GmbH. By further non-limiting example, U.S. Pat. No. 6,196,219, is hereby incorporated by reference in its entirety.

In some embodiments, the drug solution is formed prior to use of the nebulizer by a patient. In other embodiments, the drug is stored in the nebulizer in solid form. In this case, the solution is mixed upon activation of the nebulizer, such as described in U.S. Pat. No. 6,427,682 and PCT Publication No. WO 03/035030, both of which are hereby incorporated by reference in their entirety. In these nebulizers, the solid drug, optionally combined with excipients to form a solid composition, is stored in a separate compartment from a liquid solvent.

The liquid solvent is capable of dissolving the solid composition to form a liquid composition, which can be aerosolized and inhaled. Such capability is, among other factors, a function of the selected amount and, potentially, the composition of the liquid. To allow easy handling and reproducible dosing, the sterile aqueous liquid may be able to dissolve the solid composition within a short period of time, possibly under gentle shaking. In some embodiments, the final liquid is ready to use after no longer than about 30 seconds. In some cases, the solid composition is dissolved within about 20 seconds, and advantageously, within about 10 seconds. As used herein, the terms "dissolve(d)", "dissolving", and "dissolution" refer to the disintegration of the solid composition and the release, i.e. the dissolution, of the active compound. As a result of dissolving the solid composition with the liquid solvent a liquid composition is formed in which the active compound is contained in the dissolved state. As used herein, the active compound is in the dissolved state when at least about 90 wt.-% are dissolved, and more preferably when at least about 95 wt.-% are dissolved.

With regard to basic separated-compartment nebulizer design, it primarily depends on the specific application whether it is more useful to accommodate the aqueous liquid and the solid composition within separate chambers of the same container or primary package, or whether they should be provided in separate containers. If separate containers are used, these are provided as a set within the same secondary package. The use of separate containers is especially preferred for nebulizers containing two or more doses of the active compound. There is no limit to the total number of containers provided in a multi-dose kit. In one embodiment, the solid composition is provided as unit doses within multiple containers or within multiple chambers of a container, whereas the liquid solvent is provided within one chamber or container. In this case, a favorable design provides the liquid in a metered-dose dispenser, which may consist of a glass or plastic bottle closed with a dispensing device, such as a mechanical pump for metering the liquid. For instance, one actuation of the pumping mechanism may dispense the exact amount of liquid for dissolving one dose unit of the solid composition.

In another embodiment for multiple-dose separated-compartment nebulizers, both the solid composition and the liquid solvent are provided as matched unit doses within multiple containers or within multiple chambers of a container. For instance, two-chambered containers can be used to hold one unit of the solid composition in one of the chambers and one unit of liquid in the other. As used herein, one unit is defined by the amount of drug present in the solid composition, which is one unit dose. Such two-chambered containers may, however, also be used advantageously for nebulizers containing only one single drug dose.

In one embodiment of a separated-compartment nebulizer, a blister pack having two blisters is used, the blisters representing the chambers for containing the solid composition and the liquid solvent in matched quantities for preparing a dose unit of the final liquid composition. As used herein, a blister pack represents a thermoformed or pressure-formed primary packaging unit, most likely comprising a polymeric packaging material that optionally includes a metal foil, such as aluminum. The blister pack may be shaped to allow easy dispensing of the contents. For instance, one side of the pack may be tapered or have a tapered portion or region through which the content is dispensable into another vessel upon opening the blister pack at the tapered end. The tapered end may represent a tip.

In some embodiments, the two chambers of the blister pack are connected by a channel, the channel being adapted to direct fluid from the blister containing the liquid solvent to the blister containing the solid composition. During storage, the channel is closed with a seal. In this sense, a seal is any structure that prevents the liquid solvent from contacting the solid composition. The seal is preferably breakable or removable; breaking or removing the seal when the nebulizer is to be used will allow the liquid solvent to enter the other chamber and dissolve the solid composition. The dissolution process may be improved by shaking the blister pack. Thus, the final liquid composition for inhalation is obtained, the liquid being present in one or both of the chambers of the pack connected by the channel, depending on how the pack is held.

According to another embodiment, one of the chambers, preferably the one that is closer to the tapered portion of the blister pack, communicates with a second channel, the channel extending from the chamber to a distal position of the tapered portion. During storage, this second channel does not communicate with the outside of the pack but is closed in an air-tight fashion. Optionally, the distal end of the second channel is closed by a breakable or removable cap or closure, which may e.g. be a twist-off cap, a break-off cap, or a cut-off cap.

In one embodiment, a vial or container having two compartments is used, the compartment representing the chambers for containing the solid composition and the liquid solvent in matched quantities for preparing a dose unit of the final liquid composition. The liquid composition and a second liquid solvent may be contained in matched quantities for preparing a dose unit of the final liquid composition (by non-limiting example in cases where two soluble excipients or the fluoroquinolone and excipient are unstable for storage, yet desired in the same mixture for administration.

In some embodiments, the two compartments are physically separated but in fluid communication such as when so the vial or container are connected by a channel or breakable barrier, the channel or breakable barrier being adapted to direct fluid between the two compartments to enable mixing prior to administration. During storage, the channel is closed with a seal or the breakable barrier intact. In this sense, a seal is any structure that prevents mixing of contents in the two compartments. The seal is preferably breakable or removable; breaking or removing the seal when the nebulizer is to be used will allow the liquid solvent to enter the other chamber and dissolve the solid composition or in the case of two liquids permit mixing. The dissolution or mixing process may be improved by shaking the container. Thus, the final liquid composition for inhalation is obtained, the liquid being present in one or both of the chambers of the pack connected by the channel or breakable barrier, depending on how the pack is held.

The solid composition itself can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

In another embodiment, the solid composition resembles a coating layer that is coated on multiple units made of insoluble material. Examples of insoluble units include beads made of glass, polymers, metals, and mineral salts. Again, the desired effect is primarily rapid disintegration of the coating layer and quick drug dissolution, which is achieved by providing the solid composition in a physical form that has a particularly high surface-to-volume ratio. Typically, the coating composition will, in addition to the drug and the water-soluble low molecular weight excipient, comprise one or more excipients, such as those mentioned above for coating soluble particles, or any other excipient known to be useful in pharmaceutical coating compositions.

To achieve the desired effects, it may be useful to incorporate more than one water-soluble low molecular weight excipient into the solid composition. For instance, one excipient may be selected for its drug carrier and diluent capability, while another excipient may be selected to adjust the pH. If the final liquid composition needs to be buffered, two excipients that together form a buffer system may be selected.

In one embodiment, the liquid to be used in a separated-compartment nebulizer is an aqueous liquid, which is herein defined as a liquid whose major component is water. The liquid does not necessarily consist of water only; however, in one embodiment it is purified water. In another embodiment, the liquid contains other components or substances, preferably other liquid components, but possibly also dissolved solids. Liquid components other than water which may be useful include propylene glycol, glycerol, and polyethylene glycol. One of the reasons to incorporate a solid compound as a solute is that such a compound is desirable in the final liquid composition, but is incompatible with the solid composition or with a component thereof, such as the active ingredient.

Another desirable characteristic for the liquid solvent is that it is sterile. An aqueous liquid would be subject to the risk of considerable microbiological contamination and growth if no measures were taken to ensure sterility. In order to provide a substantially sterile liquid, an effective amount of an acceptable antimicrobial agent or preservative can be incorporated or the liquid can be sterilized prior to providing it and to seal it with an air-tight seal. In one embodiment, the liquid is a sterilized liquid free of preservatives and provided in an appropriate air-tight container. However, according to another embodiment in which the nebulizer contains multiple doses of the active compound, the liquid may be supplied in a multiple-dose container, such as a metered-dose dispenser, and may require a preservative to prevent microbial contamination after the first use.

Meter Dose Inhaler (MDI)

A propellant driven inhaler (pMDI) releases a metered dose of medicine upon each actuation. The medicine is formulated as a suspension or solution of a drug substance in a suitable propellant such as a halogenated hydrocarbon. pMDIs are described in, for example, Newman, S. P., Aerosols and the Lung, Clarke et al., eds., pp. 197-224 (Butterworths, London, England, 1984).

In some embodiments, the particle size of the drug substance in an MDI may be optimally chosen. In some embodiments, the particles of active ingredient have diameters of less than about 50 microns. In some embodiments, the particles have diameters of less than about 10 microns. In some embodiments, the particles have diameters of from about 1 micron to about 5 microns. In some embodiments, the particles have diameters of less than about 1 micron. In one advantageous embodiment, the particles have diameters of from about 2 microns to about 5 microns.

The propellants for use with the MDIs may be any propellants known in the art. Examples of propellants include chlorofluorocarbons (CFCs) such as dichlorodifluoromethane, trichlorofluoromethane, and dichlorotetrafluoroethane; hydrofluoroalkanes (HFAs); and carbon dioxide. It may be advantageous to use HFAs instead of CFCs due to the environmental concerns associated with the use of CFCs. Examples of medicinal aerosol preparations containing HFAs are presented in U.S. Pat. Nos. 6,585,958; 2,868,691 and 3,014,844, all of which are hereby incorporated by reference in their entirety. In some embodiments, a co-solvent is mixed with the propellant to facilitate dissolution or suspension of the drug substance.

In some embodiments, the propellant and active ingredient are contained in separate containers, such as described in U.S. Pat. No. 4,534,345, which is hereby incorporated by reference in its entirety.

In some embodiments, the MDI used herein is activated by a patient pushing a lever, button, or other actuator. In other embodiments, the release of the aerosol is breath activated such that, after initially arming the unit, the active compound aerosol is released once the patient begins to inhale, such as described in U.S. Pat. Nos. 6,672,304; 5,404,871; 5,347,998; 5,284,133; 5,217,004; 5,119,806; 5,060,643; 4,664,107; 4,648,393; 3,789,843; 3,732,864; 3,636,949; 3,598,294; 3,565,070; 3,456,646; 3,456,645; and 3,456,644, each of which is hereby incorporated by reference in its entirety. Such a system enables more of the active compound to get into the lungs of the patient. Another mechanism to help a patient get adequate dosage with the active ingredient may include a valve mechanism that allows a patient to use more than one breath to inhale the drug, such as described in U.S. Pat. Nos. 4,470,412 and 5,385,140, both of which are hereby incorporated by reference in their entirety.

Additional examples of MDIs known in the art and suitable for use herein include U.S. Pat. Nos. 6,435,177; 6,585,958;

5,642,730; 6,223,746; 4,955,371; 5,404,871; 5,364,838; and 6,523,536, all of which are hereby incorporated by reference in their entirety.

Dry Powder Inhaler (DPI)

There are two major designs of dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of drug into small particles of mass median diameters from about 1 to about 5 um, and usually involve co-formulation with larger excipient particles (typically 100 um diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

As with liquid nebulization and MDIs, particle size of the fluoroquinolone antimicrobial agent aerosol formulation may be optimized. If the particle size is larger than about 5 um MMAD then the particles are deposited in upper airways. If the particle size of the aerosol is smaller than about 1 um then it is delivered into the alveoli and may get transferred into the systemic blood circulation.

By non-limiting example, in dry powder inhalers, the fluoroquinolone antimicrobial agents disclosed herein are prepared in dosages to deliver from about 7 to about 700 mg from a dosing solution of about 1 to about 5 ml, preferably from about 14 to about 350 mg in about 1 to about 5 ml, and most preferably from about 28 to about 280 mg in about 1 to about 5 ml with MMAD particles sizes between about 2 to about 5 um being produced.

In some embodiments, a dry powder inhaler (DPI) is used to dispense the fluoroquinolone antimicrobial agents described herein. DPIs contain the drug substance in fine dry particle form. Typically, inhalation by a patient causes the dry particles to form an aerosol cloud that is drawn into the patient's lungs. The fine dry drug particles may be produced by any technique known in the art. Some well-known techniques include use of a jet mill or other comminution equipment, precipitation from saturated or super saturated solutions, spray drying, in situ micronization (Hovione), or supercritical fluid methods. Typical powder formulations include production of spherical pellets or adhesive mixtures. In adhesive mixtures, the drug particles are attached to larger carrier particles, such as lactose monohydrate of size about 50 to about 100 microns in diameter. The larger carrier particles increase the aerodynamic forces on the carrier/drug agglomerates to improve aerosol formation. Turbulence and/or mechanical devices break the agglomerates into their constituent parts. The smaller drug particles are then drawn into the lungs while the larger carrier particles deposit in the mouth or throat. Some examples of adhesive mixtures are described in U.S. Pat. No. 5,478,578 and PCT Publication Nos. WO 95/11666, WO 87/05213, WO 96/23485, and WO 97/03649, all of which are incorporated by reference in their entirety. Additional excipients may also be included with the drug substance.

There are three common types of DPIs, all of which may be used with the fluoroquinolone antimicrobial agents described herein. In a single-dose DPI, a capsule containing one dose of dry drug substance/excipients is loaded into the inhaler. Upon activation, the capsule is breached, allowing the dry powder to be dispersed and inhaled using a dry powder inhaler. To dispense additional doses, the old capsule must be removed and an additional capsule loaded. Examples of single-dose DPIs are described in U.S. Pat. Nos. 3,807,400; 3,906,950; 3,991,761; and 4,013,075, all of which are hereby incorporated by reference in their entirety. In a multiple unit dose DPI, a package containing multiple single dose compartments is provided. For example, the package may comprise a blister pack, where each blister compartment contains one dose. Each dose can be dispensed upon breach of a blister compartment. Any of several arrangements of compartments in the package can be used. For example, rotary or strip arrangements are common. Examples of multiple unit does DPIs are described in EPO Patent Application Publication Nos. 0211595A2, 0455463A1, and 0467172A1, all of which are hereby incorporated by reference in their entirety. In a multi-dose DPI, a single reservoir of dry powder is used. Mechanisms are provided that measure out single dose amounts from the reservoir to be aerosolized and inhaled, such as described in U.S. Pat. Nos. 5,829,434; 5,437,270; 2,587,215; 5,113,855; 5,840,279; 4,688,218; 4,667,668; 5,033,463; and 4,805,811 and PCT Publication No. WO 92/09322, all of which are hereby incorporated by reference in their entirety.

In some embodiments, auxiliary energy in addition to or other than a patient's inhalation may be provided to facilitate operation of a DPI. For example, pressurized air may be provided to aid in powder de-agglomeration, such as described in U.S. Pat. Nos. 3,906,950; 5,113,855; 5,388,572; 6,029,662 and PCT Publication Nos. WO 93/12831, WO 90/07351, and WO 99/62495, all of which are hereby incorporated by reference in their entirety. Electrically driven impellers may also be provided, such as described in U.S. Pat. Nos. 3,948,264; 3,971,377; 4,147,166; 6,006,747 and PCT Publication No. WO 98/03217, all of which are hereby incorporated by reference in their entirety. Another mechanism is an electrically powered tapping piston, such as described in PCT Publication No. WO 90/13327, which is hereby incorporated by reference in its entirety. Other DPIs use a vibrator, such as described in U.S. Pat. Nos. 5,694,920 and 6,026,809, both of which are hereby incorporated by reference in their entirety. Finally, a scraper system may be employed, such as described in PCT Publication No. WO 93/24165, which is hereby incorporated by reference in its entirety.

Additional examples of DPIs for use herein are described in U.S. Pat. Nos. 4,811,731; 5,113,855; 5,840,279; 3,507,277; 3,669,113; 3,635,219; 3,991,761; 4,353,365; 4,889,144, 4,907,538; 5,829,434; 6,681,768; 6,561,186; 5,918,594; 6,003,512; 5,775,320; 5,740,794; and 6,626,173, all of which are hereby incorporated by reference in their entirety.

In some embodiments, a spacer or chamber may be used with any of the inhalers described herein to increase the amount of drug substance that gets absorbed by the patient, such as is described in U.S. Pat. Nos. 4,470,412; 4,790,305; 4,926,852; 5,012,803; 5,040,527; 5,024,467; 5,816,240; 5,027,806; and 6,026,807, all of which are hereby incorporated by reference in their entirety. For example, a spacer may delay the time from aerosol production to the time when the aerosol enters a patient's mouth. Such a delay may improve synchronization between the patient's inhalation and the aerosol production. A mask may also be incorporated for infants or other patients that have difficulty using the traditional mouthpiece, such as is described in U.S. Pat. Nos. 4,809,692; 4,832,015; 5,012,804; 5,427,089; 5,645,049; and 5,988,160, all of which are hereby incorporated by reference in their entirety.

Dry powder inhalers (DPIs), which involve deaggregation and aerosolization of dry powders, normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage; SU 628930 (Abstract), describing a hand-held powder disperser having an axial air flow tube; Fox et al., Powder and Bulk Engineering, pages 33-36 (March 1988), describing a venturi eductor having an axial air inlet tube upstream of a venturi restriction; EP 347 779, describing a hand-held powder disperser having a collapsible expansion chamber, and U.S. Pat. No. 5,785,049, directed to dry powder delivery devices for drugs.

Solution/Dispersion Formulations

In one embodiment, aqueous formulations containing soluble or nanoparticulate drug particles are provided. For aqueous aerosol formulations, the drug may be present at a concentration of about 1 mg/mL up to about 700 mg/mL. Such formulations provide effective delivery to appropriate areas of the lung, with the more concentrated aerosol formulations having the additional advantage of enabling large quantities of drug substance to be delivered to the lung in a very short period of time. In one embodiment, a formulation is optimized to provide a well tolerated formulation. Accordingly, in one embodiment, fluoroquinolone antimicrobial agents disclosed herein are formulated to have good taste, pH from about 5.5 to about 7, osmolarity from about 200 to about 1250 mOsmol/kg, permeant ion concentration from about 30 to about 300 mM.

In one embodiment, the solution or diluent used for preparation of aerosol formulations has a pH range from about 4.5 to about 7.5, preferably from about 5.5 to about 7.0. This pH range improves tolerability. When the aerosol is either acidic or basic, it can cause bronchospasm and cough. Although the safe range of pH is relative and some patients may tolerate a mildly acidic aerosol, while others will experience bronchospasm. Any aerosol with a pH of less than about 4.5 typically induces bronchospasm. Aerosols with a pH from about 4.5 to about 5.5 will cause bronchospasm occasionally. Any aerosol having pH greater than about 7.5 may have low tolerability because body tissues are generally unable to buffer alkaline aerosols. Aerosols with controlled pH below about 4.5 and over about 7.5 typically result in lung irritation accompanied by severe bronchospasm cough and inflammatory reactions. For these reasons as well as for the avoidance of bronchospasm, cough or inflammation in patients, the optimum pH for the aerosol formulation was determined to be between about pH5.5 to about pH 7.0. Consequently, in one embodiment, aerosol formulations for use as described herein are adjusted to pH between about 4.5 and about 7.5 with preferred pH range from about 5.5 to about 7.5. Most preferred pH range is from about 5.5 to about 7.5.

By non-limiting example, compositions may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine, hydrochloride, or phosphate buffers.

Many patients have increased sensitivity to various chemical tastes, including bitter, salt, sweet, metallic sensations. To create well-tolerated drug products, by non-limiting example taste masking may be accomplished through the addition of taste-masking excipients, adjusted osmolality, and sweeteners.

Many patients have increased sensitivity to various chemical agents and have high incidence of bronchospastic, asthmatic or other coughing incidents. Their airways are particularly sensitive to hypotonic or hypertonic and acidic or alkaline conditions and to the presence of any permanent ion, such as chloride. Any imbalance in these conditions or a presence of chloride above certain value leads to bronchospastic or inflammatory events and/or cough which greatly impair treatment with inhalable formulations. Both these conditions prevent efficient delivery of aerosolized drugs into the endobronchial space.

In some embodiments, the osmolality of aqueous solutions of the fluoroquinolone antimicrobial agent disclosed herein are adjusted by providing excipients. In some cases, a certain amount of chloride or another anion is needed for successful and efficacious delivery of aerosolized antibiotic. However, it has been discovered that such amounts are lower than amounts provided and typically used for aerosols of other compounds.

Bronchospasm or cough reflexes do not respond to the same osmolality of the diluent for aerosolization. However, they can be sufficiently controlled and/or suppressed when the osmolality of the diluent is in a certain range. A preferred solution for aerosolization of therapeutic compounds which is safe and tolerated has a total osmolality from about 200 to about 1250 mOsmol/kg with a range of chloride concentration of from about 30 mM to about 300 mM and preferably from about 50 mM to about 150 mM. This osmolality controls bronchospasm, the chloride concentration, as a permeant anion, controls cough. Because they are both permeant ions, both bromine or iodine anions may be substituted for chloride. In addition, bicarbonate may substituted for chloride ion.

By non-limiting example, the formulation for an aerosol fluoroquinolone antimicrobial agent may comprise from about 7 to about 700 mg, preferably from about 14 to about 300 mg, or most preferably from about 28 to about 280 mg fluoroquinolone antimicrobial agent per about 1 to about 5 ml of dilute saline (between 1/10 to 1/1 normal saline). Accordingly, the concentration of a levofloxacin solution may be greater than about 25 mg/ml, greater than about 35 mg/ml and is preferably greater than about 40 mg/ml, and is as high or greater than 50/ml.

In one embodiment, solution osmolality is from about 100 mOsmol/kg to about 600 mOsmol/kg. In various other embodiments, the solution osmolality is from about 2000 mOsmol/kg to about 1250 mOsmol/kg; from about 250 mOsmol/kg to about 1050 mOsmol/kg; and from about 350 mOsmol/kg to about 750 mOsmol/kg.

In one embodiments, permeant ion concentration is from about 25 mM to about 400 mM. In various other embodiments, permeant ion concentration is from about 30 mM to about 300 mM; from about 40 mM to about 200 mM; and from about 50 mM to about 150 mM.

Solid Particle Formulations

In some embodiments, solid drug nanoparticles are provided for use in generating dry aerosols or for generating nanoparticles in liquid suspension. Powders comprising nanoparticulate drug can be made by spray-drying aqueous dispersions of a nanoparticulate drug and a surface modifier to form a dry powder which consists of aggregated drug nanoparticles. In one embodiment, the aggregates can have a size of about 1 to about 2 microns which is suitable for deep lung delivery. The aggregate particle size can be increased to target alternative delivery sites, such as the upper bronchial region or nasal mucosa by increasing the concentration of drug in the spray-dried dispersion or by increasing the droplet size generated by the spray dryer.

Alternatively, an aqueous dispersion of drug and surface modifier can contain a dissolved diluent such as lactose or mannitol which, when spray dried, forms respirable diluent particles, each of which contains at least one embedded drug nanoparticle and surface modifier. The diluent particles with embedded drug can have a particle size of about 1 to about 2 microns, suitable for deep lung delivery. In addition, the diluent particle size can be increased to target alternate delivery sites, such as the upper bronchial region or nasal mucosa by increasing the concentration of dissolved diluent in the aqueous dispersion prior to spray drying, or by increasing the droplet size generated by the spray dryer.

Spray-dried powders can be used in DPIs or pMDIs, either alone or combined with freeze-dried nanoparticulate powder. In addition, spray-dried powders containing drug nanoparticles can be reconstituted and used in either jet or ultrasonic nebulizers to generate aqueous dispersions having respirable droplet sizes, where each droplet contains at least one drug nanoparticle. Concentrated nanoparticulate dispersions may also be used in these aspects of the invention.

Nanoparticulate drug dispersions can also be freeze-dried to obtain powders suitable for nasal or pulmonary delivery. Such powders may contain aggregated nanoparticulate drug particles having a surface modifier. Such aggregates may have sizes within a respirable range, e.g., about 2 to about 5 microns MMAD.

Freeze dried powders of the appropriate particle size can also be obtained by freeze drying aqueous dispersions of drug and surface modifier, which additionally contain a dissolved diluent such as lactose or mannitol. In these instances the freeze dried powders consist of respirable particles of diluent, each of which contains at least one embedded drug nanoparticle.

Freeze-dried powders can be used in DPIs or pMDIs, either alone or combined with spray-dried nanoparticulate powder. In addition, freeze-dried powders containing drug nanoparticles can be reconstituted and used in either jet or ultrasonic nebulizers to generate aqueous dispersions that have respirable droplet sizes, where each droplet contains at least one drug nanoparticle.

One embodiment of the invention is directed to a process and composition for propellant-based systems comprising nanoparticulate drug particles and a surface modifier. Such formulations may be prepared by wet milling the coarse drug substance and surface modifier in liquid propellant, either at ambient pressure or under high pressure conditions. Alternatively, dry powders containing drug nanoparticles may be prepared by spray-drying or freeze-drying aqueous dispersions of drug nanoparticles and the resultant powders dispersed into suitable propellants for use in conventional pMDIs. Such nanoparticulate pMDI formulations can be used for either nasal or pulmonary delivery. For pulmonary administration, such formulations afford increased delivery to the deep lung regions because of the small (e.g., about 1 to about 2 microns MMAD) particle sizes available from these methods. Concentrated aerosol formulations can also be employed in pMDIs.

Another embodiment is directed to dry powders which contain nanoparticulate compositions for pulmonary or nasal delivery. The powders may consist of respirable aggregates of nanoparticulate drug particles, or of respirable particles of a diluent which contains at least one embedded drug nanoparticle. Powders containing nanoparticulate drug particles can be prepared from aqueous dispersions of nanoparticles by removing the water via spray-drying or lyophilization (freeze drying). Spray-drying is less time consuming and less expensive than freeze-drying, and therefore more cost-effective. However, certain drugs, such as biologicals benefit from lyophilization rather than spray-drying in making dry powder formulations.

Conventional micronized drug particles used in dry powder aerosol delivery having particle diameters of from about 2 to about 5 microns MMAD are often difficult to meter and disperse in small quantities because of the electrostatic cohesive forces inherent in such powders. These difficulties can lead to loss of drug substance to the delivery device as well as incomplete powder dispersion and sub-optimal delivery to the lung. Many drug compounds, particularly proteins and peptides, are intended for deep lung delivery and systemic absorption. Since the average particle sizes of conventionally prepared dry powders are usually in the range of from about 2 to about 5 microns MMAD, the fraction of material which actually reaches the alveolar region may be quite small. Thus, delivery of micronized dry powders to the lung, especially the alveolar region, is generally very inefficient because of the properties of the powders themselves.

The dry powder aerosols which contain nanoparticulate drugs can be made smaller than comparable micronized drug substance and, therefore, are appropriate for efficient delivery to the deep lung. Moreover, aggregates of nanoparticulate drugs are spherical in geometry and have good flow properties, thereby aiding in dose metering and deposition of the administered composition in the lung or nasal cavities.

Dry nanoparticulate compositions can be used in both DPIs and pMDIs. As used herein, "dry" refers to a composition having less than about 5% water.

In one embodiment, compositions are provided containing nanoparticles which have an effective average particle size of less than about 1000 nm, more preferably less than about 400 nm, less than about 300 nm, less than about 250 nm, or less than about 200 nm, as measured by light-scattering methods. By "an effective average particle size of less than about 1000 nm" it is meant that at least 50% of the drug particles have a weight average particle size of less than about 1000 nm when measured by light scattering techniques. Preferably, at least 70% of the drug particles have an average particle size of less than about 1000 nm, more preferably at least 90% of the drug particles have an average particle size of less than about 1000 nm, and even more preferably at least about 95% of the particles have a weight average particle size of less than about 1000 nm.

For aqueous aerosol formulations, the nanoparticulate agent may be present at a concentration of about 5.0 mg/mL up to about 700 mg/mL. For dry powder aerosol formulations, the nanoparticulate agent may be present at a concentration of about 5.0 mg/g up to about 1000 mg/g, depending on the desired drug dosage. Concentrated nanoparticulate aerosols, defined as containing a nanoparticulate drug at a concentration of about 5.0 mg/mL up to about 700 mg/mL for aqueous aerosol formulations, and about 5.0 mg/g up to about 1000 mg/g for dry powder aerosol formulations, are specifically provided. Such formulations provide effective delivery to appropriate areas of the lung or nasal cavities in short administration times, ie., less than about 3-15 seconds per dose as compared to administration times of up to 4 to 20 minutes as found in conventional pulmonary nebulizer therapies.

Nanoparticulate drug compositions for aerosol administration can be made by, for example, (1) nebulizing a dispersion of a nanoparticulate drug, obtained by either grinding or precipitation; (2) aerosolizing a dry powder of aggregates of nanoparticulate drug and surface modifier (the aerosolized composition may additionally contain a diluent); or (3) aerosolizing a suspension of nanoparticulate drug or drug aggregates in a non-aqueous propellant. The aggregates of nanoparticulate drug and surface modifier, which may additionally contain a diluent, can be made in a non-pressurized or a pressurized non-aqueous system. Concentrated aerosol formulations may also be made via such methods.

Milling of aqueous drug to obtain nanoparticulate drug may be performed by dispersing drug particles in a liquid dispersion medium and applying mechanical means in the presence of grinding media to reduce the particle size of the drug to the desired effective average particle size. The particles can be reduced in size in the presence of one or more surface modifiers. Alternatively, the particles can be contacted with one or more surface modifiers after attrition. Other compounds, such as a diluent, can be added to the drug/surface modifier composition during the size reduction process. Dispersions can be manufactured continuously or in a batch mode.

Another method of forming nanoparticle dispersion is by microprecipitation. This is a method of preparing stable dispersions of drugs in the presence of one or more surface modifiers and one or more colloid stability enhancing surface active agents free of any trace toxic solvents or solubilized heavy metal impurities. Such a method comprises, for example, (1) dissolving the drug in a suitable solvent with mixing; (2) adding the formulation from step (1) with mixing to a solution comprising at least one surface modifier to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate drug dispersion can be utilized in liquid nebulizers or processed to form a dry powder for use in a DPI or pMDI.

In a non-aqueous, non-pressurized milling system, a non-aqueous liquid having a vapor pressure of about 1 atm or less at room temperature and in which the drug substance is essentially insoluble may be used as a wet milling medium to make a nanoparticulate drug composition. In such a process, a slurry of drug and surface modifier may be milled in the non-aqueous medium to generate nanoparticulate drug particles. Examples of suitable non-aqueous media include ethanol, trichloromonofluormethane, (CFC-11), and dichlorotetrafluoroethane (CFC-114). An advantage of using CFC-11 is that it can be handled at only marginally cool room temperatures, whereas CFC-114 requires more controlled conditions to avoid evaporation. Upon completion of milling the liquid medium may be removed and recovered under vacuum or heating, resulting in a dry nanoparticulate composition. The dry composition may then be filled into a suitable container and charged with a final propellant. Exemplary final product propellants, which ideally do not contain chlorinated hydrocarbons, include HFA-134a (tetrafluoroethane) and HFA-227 (heptafluoropropane). While non-chlorinated propellants may be preferred for environmental reasons, chlorinated propellants may also be used in this aspect of the invention.

In a non-aqueous, pressurized milling system, a non-aqueous liquid medium having a vapor pressure significantly greater than 1 atm at room temperature may be used in the milling process to make nanoparticulate drug compositions. If the milling medium is a suitable halogenated hydrocarbon propellant, the resultant dispersion may be filled directly into a suitable pMDI container. Alternately, the milling medium can be removed and recovered under vacuum or heating to yield a dry nanoparticulate composition. This composition can then be filled into an appropriate container and charged with a suitable propellant for use in a pMDI.

Spray drying is a process used to obtain a powder containing nanoparticulate drug particles following particle size reduction of the drug in a liquid medium. In general, spray-drying may be used when the liquid medium has a vapor pressure of less than about 1 atm at room temperature. A spray-dryer is a device which allows for liquid evaporation and drug powder collection. A liquid sample, either a solution or suspension, is fed into a spray nozzle. The nozzle generates droplets of the sample within a range of about 20 to about 100 μm in diameter which are then transported by a carrier gas into a drying chamber. The carrier gas temperature is typically from about 80 to about 200° C. The droplets are subjected to rapid liquid evaporation, leaving behind dry particles which are collected in a special reservoir beneath a cyclone apparatus.

If the liquid sample consists of an aqueous dispersion of nanoparticles and surface modifier, the collected product will consist of spherical aggregates of the nanoparticulate drug particles. If the liquid sample consists of an aqueous dispersion of nanoparticles in which an inert diluent material was dissolved (such as lactose or mannitol), the collected product will consist of diluent (e.g., lactose or mannitol) particles which contain embedded nanoparticulate drug particles. The final size of the collected product can be controlled and depends on the concentration of nanoparticulate drug and/or diluent in the liquid sample, as well as the droplet size produced by the spray-dryer nozzle. Collected products may be used in conventional DPIs for pulmonary or nasal delivery, dispersed in propellants for use in pMDIs, or the particles may be reconstituted in water for use in nebulizers.

In some instances it may be desirable to add an inert carrier to the spray-dried material to improve the metering properties of the final product. This may especially be the case when the spray dried powder is very small (less than about 5 μm) or when the intended dose is extremely small, whereby dose metering becomes difficult. In general, such carrier particles (also known as bulking agents) are too large to be delivered to the lung and simply impact the mouth and throat and are swallowed. Such carriers typically consist of sugars such as lactose, mannitol, or trehalose. Other inert materials, including polysaccharides and cellulosics, may also be useful as carriers.

Spray-dried powders containing nanoparticulate drug particles may used in conventional DPIs, dispersed in propellants for use in pMDIs, or reconstituted in a liquid medium for use with nebulizers.

For compounds that are denatured or destabilized by heat, such as compounds having a low melting point (i.e., about 70 to about 150° C.), or for example, biologics, sublimation is preferred over evaporation to obtain a dry powder nanoparticulate drug composition. This is because sublimation avoids the high process temperatures associated with spray-drying. In addition, sublimation, also known as freeze-drying or lyophilization, can increase the shelf stability of drug compounds, particularly for biological products. Freeze-dried particles can also be reconstituted and used in nebulizers. Aggregates of freeze-dried nanoparticulate drug particles can be blended with either dry powder intermediates or used alone in DPIs and pMDIs for either nasal or pulmonary delivery.

Sublimation involves freezing the product and subjecting the sample to strong vacuum conditions. This allows for the formed ice to be transformed directly from a solid state to a vapor state. Such a process is highly efficient and, therefore, provides greater yields than spray-drying. The resultant freeze-dried product contains drug and modifier(s). The drug is typically present in an aggregated state and can be used for inhalation alone (either pulmonary or nasal), in conjunction with diluent materials (lactose, mannitol, etc.), in DPIs or pMDIs, or reconstituted for use in a nebulizer.

Liposomal Compositions

In some embodiments, fluoroquinolone antimicrobial agents disclosed herein may be formulated into liposome particles, which can then be aerosolized for inhaled delivery. Lipids which are useful in the present invention can be any of a variety of lipids including both neutral lipids and charged lipids. Carrier systems having desirable properties can be prepared using appropriate combinations of lipids, targeting groups and circulation enhancers. Additionally, the compositions provided herein can be in the form of liposomes or lipid particles, preferably lipid particles. As used herein, the term "lipid particle" refers to a lipid bilayer carrier which "coats" a nucleic acid and has little or no aqueous interior. More particularly, the term is used to describe a self-assembling lipid bilayer carrier in which a portion of the interior layer comprises cationic lipids which form ionic bonds or ion-pairs with negative charges on the nucleic acid (e.g., a plasmid phosphodiester backbone). The interior layer can also comprise neutral or fusogenic lipids and, in some embodiments, negatively charged lipids. The outer layer of the particle will typically comprise mixtures of lipids oriented in a tail-to-tail fashion (as in liposomes) with the hydrophobic tails of the interior layer. The polar head groups present on the lipids of the outer layer will form the external surface of the particle.

Liposomal bioactive agents can be designed to have a sustained therapeutic effect or lower toxicity allowing less frequent administration and an enhanced therapeutic index. Liposomes are composed of bilayers that entrap the desired pharmaceutical. These can be configured as multilamellar vesicles of concentric bilayers with the pharmaceutical trapped within either the lipid of the different layers or the aqueous space between the layers.

By non-limiting example, lipids used in the compositions may be synthetic, semi-synthetic or naturally-occurring lipids, including phospholipids, tocopherols, steroids, fatty acids, glycoproteins such as albumin, negatively-charged lipids and cationic lipids. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC) and dioleoylphosphatidylglycerol (DOPG). Other examples include dimyristoylphosphatidycholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), and single acylated phospholipids like mono-oleoyl-phosphatidylethanolamine (MOPE).

In a preferred embodiment, PEG-modified lipids are incorporated into the compositions of the present invention as the aggregation-preventing agent. The use of a PEG-modified lipid positions bulky PEG groups on the surface of the liposome or lipid carrier and prevents binding of DNA to the outside of the carrier (thereby inhibiting cross-linking and aggregation of the lipid carrier). The use of a PEG-ceramide is often preferred and has the additional advantages of stabilizing membrane bilayers and lengthening circulation lifetimes. Additionally, PEG-ceramides can be prepared with different lipid tail lengths to control the lifetime of the PEG-ceramide in the lipid bilayer. In this manner, "programmable" release can be accomplished which results in the control of lipid carrier fusion. For example, PEG-ceramides having $C_{20}$-acyl groups attached to the ceramide moiety will diffuse out of a lipid bilayer carrier with a half-life of 22 hours. PEG-ceramides having $C_{14}$- and $C_8$-acyl groups will diffuse out of the same carrier with half-lives of 10 minutes and less than 1 minute, respectively. As a result, selection of lipid tail length provides a composition in which the bilayer becomes destabilized (and thus fusogenic) at a known rate. Though less preferred, other PEG-lipids or lipid-polyoxyethylene conjugates are useful in the present compositions. Examples of suitable PEG-modified lipids include PEG-modified phosphatidylethanolamine and phosphatidic acid, PEG-modified diacylglycerols and dialkylglycerols, PEG-modified dialkylamines and PEG-modified 1,2-diacyloxypropan-3-amines. Particularly preferred are PEG-ceramide conjugates (e.g., PEG-Cer-$C_8$, PEG-Cer-$C_{14}$ or PEG-Cer-$C_{20}$) which are described in U.S. Pat. No. 5,820,873, incorporated herein by reference.

The compositions of the present invention can be prepared to provide liposome compositions which are about 50 nm to about 400 nm in diameter. One with skill in the art will understand that the size of the compositions can be larger or smaller depending upon the volume which is encapsulated. Thus, for larger volumes, the size distribution will typically be from about 80 nm to about 300 nm.

Surface Modifiers

Fluoroquinolone antimicrobial agents disclosed herein may be prepared in a pharmaceutical composition with suitable surface modifiers which may be selected from known organic and inorganic pharmaceutical excipients. Such excipients include low molecular weight oligomers, polymers, surfactants and natural products. Preferred surface modifiers include nonionic and ionic surfactants. Two or more surface modifiers can be used in combination.

Representative examples of surface modifiers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens®, such as e.g., Tween 20®, and Tween 80®, (ICI Specialty Chemicals)); polyethylene glycols (e.g., Carbowaxs 3350®, and 1450®., and Carbopol 934®, (Union Carbide)), dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68®, and F108®., which are block copolymers of ethylene oxide and propylene oxide); poloxamines (e.g., Tetronic 908®., also known as Poloxamine 908®., which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508®; (T-1508) (BASF Wyandotte Corporation), dialkylesters of sodium sulfosuccinic acid (e.g., Aerosol OT®., which is a dioctyl ester of sodium sulfosuccinic acid (American Cyanamid)); Duponol P®., which is a sodium lauryl sulfate (DuPont); Tritons X-200®., which is an alkyl aryl polyether sulfonate (Rohm and Haas); Crodestas F-110®., which is a mixture of sucrose stearate and sucrose distearate (Croda Inc.); p-isononylphenoxypoly-(glycidol), also known as Olin-log®, or Surfactant 10-G®, (Olin Chemicals, Stamford, Conn.); Crodestas SL-40®, (Croda, Inc.); and SA9OHCO, which is $C_{18}H_{37}CH_2$ (CON($CH_3$)-$CH_2$ (CHOH)$_4$ ($CH_{20}H)_2$ (Eastman Kodak Co.); decanoyl-N-methylglucamide; n-decyl beta.-D-glucopyranoside; n-decyl .beta.-D-maltopyranoside; n-dodecyl .beta.-D-glucopyranoside; n-dodecyl .beta.-D-maltoside; heptanoyl-N-methylglucamide; n-heptyl-.beta.-D-glucopyranoside; n-heptyl .beta.-D-thioglucoside; n-hexyl beta.-D-glucopyranoside; nonanoyl-N-methylglucamide; n-noyl .beta.-D-glucopyranoside; octanoyl-N-methylglucamide; n-octyl-.beta.-D-glucopyranoside; octyl .beta.-D-thioglucopyranoside; and the like. Tyloxapol is a particularly preferred surface modifier for the pulmonary or intranasal delivery of steroids, even more so for nebulization therapies.

Examples of surfactants for use in the solutions disclosed herein include, but are not limited to, ammonium laureth sulfate, cetamine oxide, cetrimonium chloride, cetyl alcohol, cetyl myristate, cetyl palmitate, cocamide DEA, cocamidopropyl betaine, cocamidopropylamine oxide, cocamide MEA, DEA lauryl sulfate, di-stearyl phthalic acid amide, dicetyl dimethyl ammonium chloride, dipalmitoylethyl hydroxyethylmonium, disodium laureth sulfosuccinate, di(hydrogenated) tallow phthalic acid, glyceryl dilaurate, glyceryl distearate, glyceryl oleate, glyceryl stearate, isopropyl myristate nf, isopropyl palmitate nf, lauramide DEA, lauramide MEA, lauramide oxide, myristamine oxide, octyl isononanoate, octyl palmitate, octyldodecyl neopentanoate, olealkonium chloride, PEG-2 stearate, PEG-32 glyceryl caprylate/caprate, PEG-32 glyceryl stearate, PEG-4 and PEG-150 stearate & distearate, PEG-4 to PEG-150 laurate & dilaurate, PEG-4 to PEG-150 oleate & dioleate, PEG-7 glyceryl cocoate, PEG-8 beeswax, propylene glycol stearate, sodium C14-16 olefin sulfonate, sodium lauryl sulfoacetate, sodium lauryl sulphate, sodium trideceth sulfate, stearalkonium chloride, stearamide oxide, TEA-dodecylbenzene sulfonate, TEA lauryl sulfate Most of these surface modifiers are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference. The surface modifiers are commercially available and/or can be prepared by techniques known in the art. The relative amount of drug and surface modifier can vary widely and the optimal amount of the surface modifier can depend upon, for example, the particular drug and surface modifier selected, the critical micelle concentration of the surface modifier if it forms micelles, the hydrophilic-lipophilic-balance (HLB) of the surface modifier, the melting point of the surface modifier, the water solubility of the surface modifier and/or drug, the surface tension of water solutions of the surface modifier, etc.

In the present invention, the optimal ratio of drug to surface modifier is ~0.1% to ~99.9% fluoroquinolone antimicrobial agent, more preferably about 10% to about 90%.

Microspheres

Microspheres can be used for pulmonary delivery of fluoroquinolones by first adding an appropriate amount of drug compound to be solubilzed in water. For example, an aqueous levofloxacin solution may be dispersed in methylene chloride containing a predetermined amount (0.1-1% w/v) of poly (DL-lactide-co-glycolide) (PLGA) by probe sonication for 1-3 min on an ice bath. Separately, levofloxacin will be solubilized in methylene chloride containing PLGA (0.1-1% w/v). The resulting water-in-oil primary emulsion or the polymer/drug solution will be dispersed in an aqueous continuous phase consisting of 1-2% polyvinyl alcohol (previously cooled to 4° C.) by probe sonication for 3-5 min on an ice bath. The resulting emulsion will be stirred continuously for 2-4 hours at room temperature to evaporate methylene chloride. Microparticles thus formed will be separated from the continuous phase by centrifuging at 8000-10000 rpm for 5-10 min. Sedimented particles will be washed thrice with distilled water and freeze dried. Freeze-dried levofloxacin microparticles will be stored at −20° C.

By non-limiting example, a spray drying approach will be employed to prepare levofloxacin microspheres. An appropriate amount of levofloxacin will be solubilized in methylene chloride containing PLGA (0.1-1%). This solution will be spray dried to obtain the microspheres.

By non-limiting example, levofloxacin microparticles will be characterized for size distribution (requirement: 90%<5 µm, 95%<10 µm), shape, drug loading efficiency and drug release using appropriate techniques and methods.

By non-limiting example, this approach may also be used to sequester and improve the water solubility of solid, AUC shape-enhancing formulations, such as low-solubility levofloxacin salt forms for nanoparticle-based formulations.

A certain amount of fluoroquinolone can be first dissolved in the minimal quantity of ethanol 96% necessary to maintain the fluoroquinolone in solution when diluted with water from 96 to 75%. This solution can then be diluted with water to obtain a 75% ethanol solution and then a certain amount of paracetamol can be added to obtain the following w/w drug/polymer ratios: 1:2, 1:1, 2:1, 3:1, 4:1, 6:1, 9:1, and 19:1. These final solutions are spray-dried under the following conditions: feed rate, 15 mL/min; inlet temperature, 110° C.; outlet temperature, 85° C.; pressure 4 bar and throughput of drying air, 35 m3/hr. Powder is then collected and stored under vacuum in a dessicator.

Solid Lipid Particles

Preparation of Fluoroquinolone Solid Lipid Particles May Involve dissolving the drug in a lipid melt (phospholipids such as phophatidyl choline and phosphatidyl serine) maintained at least at the melting temperature of the lipid, followed by dispersion of the drug-containing melt in a hot aqueous surfactant solution (typically 1-5% w/v) maintained at least at the melting temperature of the lipid. The coarse dispersion will be homogenized for 1-10 min using a Microfluidizer® to obtain a nanoemulsion. Cooling the nanoemulsion to a temperature between 4-25° C. will re-solidify the lipid, leading to formation of solid lipid nanoparticles. Optimization of formulation parameters (type of lipid matrix, surfactant concentration and production parameters) will be performed so as to achieve a prolonged drug delivery. By non-limiting example, this approach may also be used to sequester and improve the water solubility of solid, AUC shape-enhancing formulations, such as low-solubility levofloxacin salt forms for nanoparticle-based formulations.

Melt-Extrusion AUC Shape-Enhancing Formulation

Melt-Extrusion AUC shape-enhancing fluoroquinolone formulations may be preparation by dissolving the drugs in micelles by adding surfactants or preparing micro-emulsion, forming inclusion complexes with other molecules such as cyclodextrins, forming nanoparticles of the drugs, or embedding the amorphous drugs in a polymer matrix. Embedding the drug homogeneously in a polymer matrix produces a solid dispersion. Solid dispersions can be prepared in two ways: the solvent method and the hot melt method. The solvent method uses an organic solvent wherein the drug and appropriate polymer are dissolved and then (spray) dried. The major drawbacks of this method are the use of organic solvents and the batch mode production process. The hot melt method uses heat in order to disperse or dissolve the drug in an appropriate polymer. The melt-extrusion process is an optimized version of the hot melt method. The advantage of the melt-extrusion approach is lack of organic solvent and continuous production process. As the melt-extrusion is a novel pharmaceutical technique, the literature dealing with it is limited. The technical set-up involves a mixture and extrusion of fluoroquinolone, hydroxypropyl-b-cyclodextrin (HP-b-CD), and hydroxypropylmethylcellulose (HPMC), in order to, by non-limiting example create a AUC shape-enhancing formulation of levofloxacin or other fluoroquinolone. Cyclodextrin is a toroidal-shaped molecule with hydroxyl groups on the outer surface and a cavity in the center. Cyclodextrin sequesters the drug by forming an inclusion complex. The complex formation between cyclodextrins and drugs has been investigated extensively. It is known that water-soluble polymer interacts with cyclodextrin and drug in the course of complex formation to form a stabilized complex of drug and cyclodextrin co-complexed with the polymer. This complex is more stable than the classic cyclodextrin-drug complex. As one example, HPMC is water soluble; hence using this polymer with HP-b-CD in the melt is expected to create an aqueous soluble AUC shape-enhancing formulation. By non-limiting example, this approach may also be used to sequester and improve the water solubility of solid, AUC shape-enhancing formulations, such as low-solubility levofloxacin salt forms for nanoparticle-based formulations.

Co-Precipitates

Co-precipitate fluoroquinolone formulations may be prepared by formation of co-precipitates with pharmacologically inert, polymeric materials. It has been demonstrated that the formation of molecular solid dispersions or co-precipitates to create an AUC shape-enhancing formulations with various water-soluble polymers can significantly slow their in vitro dissolution rates and/or in vivo absorption. In preparing powdered products, grinding is generally used for reducing particle size, since the dissolution rate is strongly affected by particle size. Moreover, a strong force (such as grinding) may increase the surface energy and cause distortion of the crystal lattice as well as reducing particle size. Co-grinding drug with hydroxypropylmethylcellulose, b-cyclodextrin, chitin and chitosan, crystalline cellulose, and gelatine, may enhance the dissolution properties such that AUC shape-enhancement is obtained for otherwise readily bioavialble fluoroquinolones. By non-limiting example, this approach may also be used to sequester and improve the water solubility of solid, AUC shape-enhancing formulations, such as low-solubility levofloxacin salt forms for nanoparticle-based formulations.

Dispersion-Enhancing Peptides

Compositions may include one or more di- or tripeptides containing two or more leucine residues. By further non-limiting example, U.S. Pat. No. 6,835,372 disclosing dispersion-enhancing peptides, is hereby incorporated by reference in its entirety. This patent describes the discovery that di-leucyl-containing dipeptides (e.g., dileucine) and tripeptides are superior in their ability to increase the dispersibility of powdered composition.

In another embodiment, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include—OH, halogen (—Br, —Cl, —I and —F)—O (aliphatic, substituted aliphatic, benzyl, substituted benzyl, aryl or substituted aryl group), —CN, —NO.sub.2, —COOH, —NH.sub.2, —NH(aliphatic group, substituted aliphatic, benzyl, substituted benzyl, aryl or substituted aryl group), —N(aliphatic group, substituted aliphatic, benzyl, substituted benzyl, aryl or substituted aryl group).sub.2, —COO(aliphatic group, substituted aliphatic, benzyl, substituted benzyl, aryl or substituted aryl group), —CONH.sub.2, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C (.dbd.NH)—NH.sub.2. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm.sup.3.

Methods of forming and delivering particles which include an amino acid are described in U.S. Pat. No. 6,586,008, entitled Use of Simple Amino Acids to Form Porous Particles During Spray Drying, the teachings of which are incorporated herein by reference in their entirety.

Proteins/Amino Acids

Protein excipients may include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility—enhancing peptide excipients include dimers, trimers, tetramers, and pentamers comprising one or more hydrophobic amino acid components such as those described above.

Carbohydrates

By non-limiting example, carbohydrate excipients may include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol, isomalt, trehalose and the like.

Polymers

By non-limiting example, compositions may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), polyethylene glycols, and pectin may also be used.

Highly dispersible particles administered comprise a bioactive agent and a biocompatible, and preferably biodegradable polymer, copolymer, or blend. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(DL-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., Macromolecules, 28: 4736-4739 (1995); and Hrkach et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M, Ottenbrite et al., Eds., American Chemical Society, Chapter 8, pp. 93-101, 1996.

In a preferred embodiment of the invention, highly dispersible particles including a bioactive agent and a phospholipid are administered. Examples of suitable phospholipids include, among others, phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidyicholine (DSPC), dipalmitoyl phosphatidyl glycerol (DPPG) or any combination thereof. Other phospholipids are known to those skilled in the art. In a preferred embodiment, the phospholipids are endogenous to the lung.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, around or above the physiological body temperature of a patient. Preferred phase transition temperatures range from 30 degrees C. to 50 degrees C. (e.g., within +/−10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures.

Taste Masking, Flavor, Other

By non-limiting example, compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80"), sorbitan esters, saccharin, cyclodextrins, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998).

By non-limiting example, classes of taste-masking agents for fluoroquinolone formulation include the addition of flavorings, sweeteners, and other various coating strategies. By non-limiting examples these may be chosen from sugars such as sucrose, dextrose, and lactose), carboxylic acids, salts such as magnesium and calcium (non-specific or chelation-based fluoroquinolone taste masking), menthol, amino acids or amino acid derivatives such as arginine, lysine, and monosodioum glutamate, and synthetic flavor oils and flavoring aromatics and/or natural oils, extracts from plants, leaves, flowers, fruits, etc. and combinations thereof. These may include cinnamon oils, oil of wintergreen, peppermint oils, clover oil, bay oil, anise oil, eucalyptus, vanilla, citrus oil such as lemon oil, orange oil, grape and grapefruit oil, fruit essences including apple, peach, pear, strawberry, raspberry, cherry, plum, pineapple, apricot, etc. Additional sweeteners include sucrose, dextrose, aspartame (Nutrasweet®), acesulfame-K, sucrolose and saccharin, organic acids (by non-limiting example citric acid and aspartic acid). Such flavors may be present at about 0.05 to about 4 percent. Another approach to improve or mask the taste of unpleasant inhaled drugs is to decrease the drugs solubility, e.g. drugs must dissolve to interact with taste receptors. Hence, to deliver solid forms of the drug may avoid the taste response and acquire the desired improved taste affect. Non-limiting methods to decrease fluoroquinolone solubility are described in this document, e.g. salt forms of levofloxacin or gemifloxacin with xinafoic acid, oleic acid, stearic acid and pamoic acid. Additional co-precipitating agents include dihydropyridines and a polymer such as polyvinyl pyrrolidone. Moreover, taste-masking may be accomplished by creation of lipopilic vesicles. Additional coating or capping agents include dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), modified celluloses such as ethyl cellulose, methyl cellulose, hydroxypropyl cellulose, hydroxyl propyl methyl cellulose, polyalkylene glycols, polyalkylene oxides, sugars and sugar alcohols, waxes, shellacs, acrylics and mixtures thereof. By non-limiting example, other methods to deliver non-dissolved forms of fluoroquinolones are to administer the drug alone or in simple, non-solubilty affecting formulation as a crystalline micronized, dry powder, spray-dried, and nanosuspension formulation. However, an alternative method is to include taste-modifying agents. These include taste-masking substance that is mixed with, coated onto or otherwise combined with the fluoroquinolone active medicament. However, this addition may also serve to improve the taste of another chosen drug product addition, e.g. a mucolytic agent. Non-limiting examples of such substances include acid phospholipids, lysophospholipid, tocopherol polyethyleneglycol succinate, and embonic acid (pamoate). Many of these agents can be used alone or in combination with fluoroquinolones for aerosol administration.

Mucolytic Agents

Methods to produce formulations that combine agents to reduce sputum viscosity during aerosol treatment with a fluoroquinolone include the following. These agents can be prepared in fixed combination or be administered in succession with aerosol fluoroquinolone therapy.

The most commonly prescribed agent is N-acetylcysteine (NAC), which depolymerizes mucus in vitro by breaking disulphide bridges between macromolecules. It is assumed that such reduction of sputum tenacity facilitates its removal from the respiratory tract. In addition, NAC may act as an oxygen radical scavenger. NAC can be taken either orally or by inhalation. Differences between these two methods of administration have not been formally studied. After oral administration, NAC is reduced to cysteine, a precursor of the antioxidant glutathione, in the liver and intestine. The antioxidant properties could be useful in preventing decline of lung function in cystic fibrosis (CF). Nebulized NAC is commonly prescribed to patients with CF, in particular in continental Europe, in order to improve expectoration of sputum by reducing its tenacity. The ultimate goal of this is to slow down the decline of lung function in CF.

L-lysine-N-acetylcysteinate (ACC) or Nacystelyn (NAL) is a novel mucoactive agent possessing mucolytic, antioxidant, and anti-inflammatory properties. Chemically, it is a salt of ACC. This drug appears to present an activity superior to its parent molecule ACC because of a synergistic mucolytic activity of L-lysine and ACC. Furthermore, its almost neutral pH (6.2) allows its administration in the lungs with a very low incidence of bronchospasm, which is not the case for the acidic ACC (pH 2.2). NAL is difficult to formulate in an inhaled form because the required lung dose is very high (approximately 2 mg) and the micronized drug is sticky and cohesive and it is thus problematic to produce a redispersible formulation. NAL was first developed as a chlorofluorocarbon (CFC) containing metered-dose inhaler (MDI) because this form was the easiest and the fastest to develop to begin the preclinical and the first clinical studies. NAL MDI delivered 2 mg per puff, from which approximately 10% was able to reach the lungs in healthy volunteers. One major inconvenience of this formulation was patient compliance because as many as 12 puffs were necessary to obtain the required dose. Furthermore, the progressive removal of CFC gases from medicinal products combined with the problems of coordination met in a large proportion of the patient population (12) have led to the development of a new galenical form of NAL. A dry powder inhaler (DPI) formulation was chosen to resolve the problems of compliance with MDIs and to combine it with an optimal, reproducible, and comfortable way to administer the drug to the widest possible patient population, including young children.

The DPI formulation of NAL involved the use of a non-conventional lactose (usually reserved for direct compression of tablets), namely, a roller-dried (RD) anhydrous β-lactose. When tested in vitro with a monodose DPI device, this powder formulation produces a fine particle fraction (FPF) of at least 30% of the nominal dose, namely three times higher than that with MDIs. This approach may be used in combination with a fluoroquinolone antibiotic for either co-administration or fixed combination administration antibiotic therapy.

In addition to mucolytic activity, excessive neutrophil elastase activity within airways of cystic fibrosis (CF) patients results in progressive lung damage. Disruption of disulfide bonds on elastase by reducing agents may modify its enzymatic activity. Three naturally occurring dithiol reducing systems were examined for their effects on elastase activity: 1) *Escherichia coli* thioredoxin (Trx) system, 2) recombinant human thioredoxin (rhTrx) system, and 3) dihydrolipoic acid (DKLA). The Trx systems consisted of Trx, Trx reductase, and NADPH. As shown by spectrophotometric assay of elastase activity, the two Trx systems and DHLA inhibited purified human neutrophil elastase as well as the elastolytic activity present in the soluble phase (sol) of CF sputum. Removal of any of the three Trx system constituents prevented inhibition. Compared with the monothiols N-acetylcysteine and reduced glutathione, the dithiols displayed greater elastase inhibition. To streamline Trx as an investigational tool, a stable reduced form of rhTrx was synthesized and used as a single component. Reduced rhTrx inhibited purified elastase and CF sputum sol elastase without NADPH or Trx reductase. Because Trx and DHLA have mucolytic effects, we investigated changes in elastase activity after mucolytic treatment. Unprocessed CF sputum was directly treated with reduced rhTrx, the Trx system, DHLA, or DNase. The Trx system and DHLA did not increase elastase activity, whereas reduced rhTrx treatment increased sol elastase activity by 60%. By contrast, the elastase activity after DNase treatment increased by 190%. The ability of Trx and DHLA to limit elastase activity combined with their mucolytic effects makes these compounds potential therapies for CF.

In addition, bundles of F-actin and DNA present in the sputum of cystic fibrosis (CF) patients but absent from normal airway fluid contribute to the altered viscoelastic properties of sputum that inhibit clearance of infected airway fluid and exacerbate the pathology of CF. One approach to alter these adverse properties is to remove these filamentous aggregates using DNase to enzymatically depolymerize DNA to constituent monomers and gelsolin to sever F-actin to small fragments. The high densities of negative surface charge on DNA and F-actin suggest that the bundles of these filaments, which alone exhibit a strong electrostatic repulsion, may be stabilized by multivalent cations such as histones, antimicrobial peptides, and other positively charged molecules prevalent in airway fluid. Furthermore, As a matter-a-fact, it has been observed that bundles of DNA or F-actin formed after addition of histone H1 or lysozyme are efficiently dissolved by soluble multivalent anions such as polymeric aspartate or glutamate. Addition of poly-aspartate or poly-glutamate also disperses DNA and actin-containing bundles in CF sputum and lowers the elastic moduli of these samples to levels comparable to those obtained after treatment with DNase I or gelsolin. Addition of poly-aspartic acid also increased DNase activity when added to samples containing DNA bundles formed with histone H1. When added to CF sputum, poly-aspartic acid significantly reduced the growth of bacteria, suggesting activation of endogenous antibacterial factors. These findings suggest that soluble multivalent anions have potential alone or in combination with other mucolytic agents to selectively dissociate the large bundles of charged biopolymers that form in CF sputum.

Hence, NAC, unfractionated heparin, reduced glutathione, dithiols, Trx, DHLA, other monothiols, DNAse, dornase alfa, hypertonic formulations (e.g. osmolalities greater than about 350 mOsmol/kg), multivalent anions such as polymeric aspartate or glutamate, glycosidases and other examples listed above can be combined with fluoroquinolone antibiotics and other mucolytic agents for aerosol administration to improve antibacterial activity through better distribution from reduced sputum viscosity, and improved clinical outcome through improved pulmonary function (from improved sputum mobility and mucociliary clearance) and decreased lung tissue damage from the immune inflammatory response.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

High Local Concentration with Short Duration Aerosol Fluoroquinolone Exposure

Aerosol administration of fluoroquinolones such as levofloxacin produces high concentrations in the epithelial lining fluid (ELF) of rats and humans. However, this dose has been observed to rapidly decline following administration.

In order to determine if short duration, high concentrations of levofloxacin could be effective in treatment of *P. aeruginosa* (PA), studies were conducted to measure their bactericidal activity on various strains of this organism which were grown at different conditions. Those were chosen based on what is known about conditions and growth of PA in a cystic fibrosis (CF) lung. Four isogenic strains of *P. aeruginosa* were used for these experiments (Table 2).

TABLE 2

Strains of PA Used in Time-Kill Experiments.

| Strain | Genotype | Levofloxacin MIC (ug/ml) |
|---|---|---|
| PAM1020 | wt | 0.25 |
| PAM1032 | nalB | 1 |

PAM1020 is the parent wild-type strain, PAM1032 contains nalB mutation which results in increased levofloxacin resistance due to overexpression of the MexAB-OprM efflux pump which can extrude levofloxacin out of cells.

Experiment 1

Activity of Levofloxacin Against Exponentially Grown Cells

Methods

Inoculum Preparation

Strains were grown aerobically overnight in Mueller-Hinton Broth (MHB) at 35° C. Next, cultures were diluted 1:1000 into 100 ml of fresh MHB and grown to $OD_{600}$~0.3 to reach CFU/ml ~$10^8$. 10 ml of this culture was moved to 50 ml flasks, each containing 10 ml of pre-warmed MHB broth with appropriate concentrations of levofloxacin (2× as compared to the exposure concentrations).

Exposure

All strains were treated for 10 min., 20 min., 40 min., 80 min. and 160 minutes. The following concentrations of levofloxacin (ug/ml) were used for the exposure of PAM1020 and PAM1032: 16, 32, 64, 128 and 256. All strains were treated at each concentration for 10 min., 20 min., 40 min., 80 min. and 160 minutes.

Determination of Viable Cell Numbers

At appropriate times, 1 ml of each exposure culture was centrifuged for 2 minutes, the pellet was washed twice with 1 ml of drug-free MHB, and re-suspended in 1 ml of MHB. The viable cell numbers were enumerated by plating serially diluted samples (in duplicates) on MHB plates by the drop (10 ul) plating method. The limit of detection was 100 CFU/ml. Killing is reported as the log reduction calculated relative to cell count at the time of initiation of antibiotic exposure. Relative antibiotic concentrations (relative to MIC of the corresponding strains) are used. Cell numbers at initiation of antibiotic exposure are shown in Table 3.

TABLE 3

Bacterial Numbers at Time of Initial Bacterial Exposure.

| Strain | CFU/ml |
|---|---|
| PAM1020 | 4.03E+07 |
| PAM1032 | 5.60E+07 |

Results

Figure 4A:
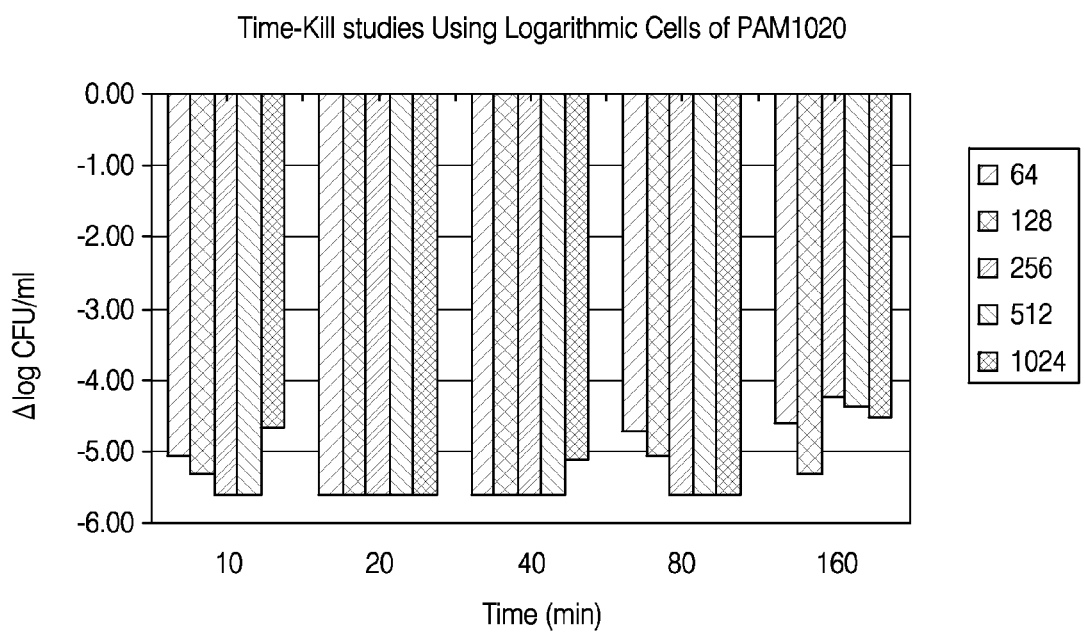
FIG. 4A is a graph showing Levofloxacin time-kill affects on logarithmic PAM1020 cells.
Figure 4B:
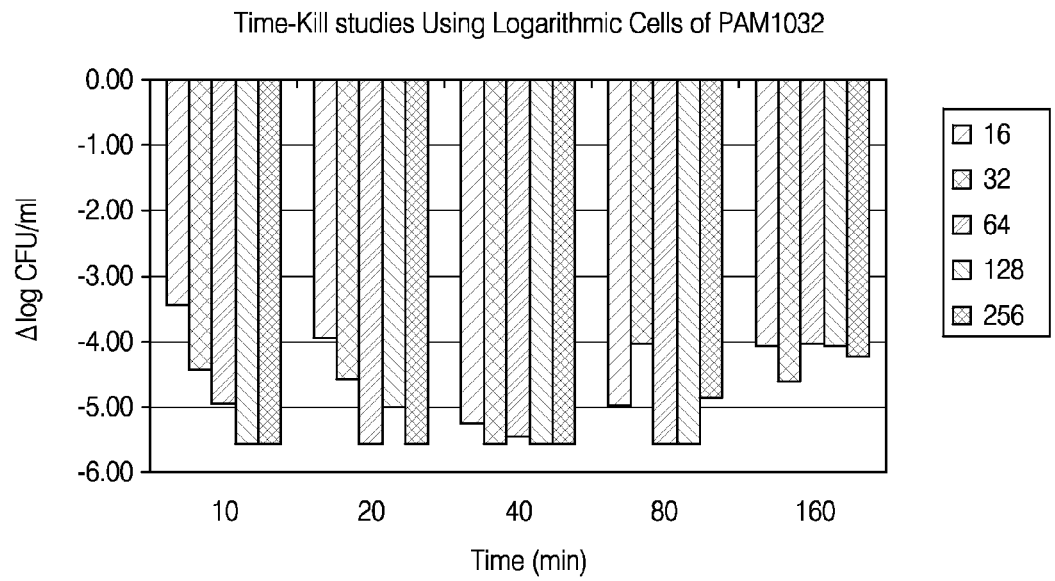
FIG. 4B is a graph showing Levofloxacin time-kill affects on logarithmic PAM1032 cells.

For the most susceptible strain, PAM1020, maximum killing (5.5 log decrease in viable cell counts) was achieved after incubation for 10 minutes with the concentration of levofloxacin corresponding to 256-fold MIC (64 ug/ml tested). 5-logs of killing were achieved already with the lowest concentration tested (16 ug/ml or 64-fold MIC) (FIG. 4A). For the strain PAM1032, as long as the concentration above 128-fold the MIC (128 ug/ml) was reached, 10 minute of exposure was sufficient to result in maximum killing (more than 5 logs). At short duration exposures (10 or 20 minutes), less killing was observed at concentrations below 128-fold of MICs. At longer exposure times, concentration corresponding to 16-fold MICs and above resulted in similar maximum killing (FIG. 4B). These results indicate that logarithmic cells of P. aeruginosa are efficiently killed after short duration exposures to high concentrations of levofloxacin.

Experiment 2

Activity of Levofloxacin Against Stationary Phase Cells

Methods

Inoculum Preparation

Strains were grown aerobically overnight in Mueller-Hinton Broth (MHB) at 35° C. (350 ml total). The spent medium was obtained after centrifugation of overnight cultures and filtering the supernatant. Cultures were diluted to OD=0.3 into spent medium. The same medium was also used to prepare antibiotic concentrations (the same as in Experiment 1).

Exposure

Antibiotic concentrations, time of exposure as determination of viable cell counts were the same as in Experiment 1.

Results

Cell numbers at initiation of antibiotic exposure are shown in Table 4.

TABLE 4

Bacterial Numbers at Time of Initial Bacterial Exposure.

| Strain | CFU/ml |
|---|---|
| PAM1020 | 8.0E+08 |
| PAM1032 | 8.50E+08 |

Figure 5A:
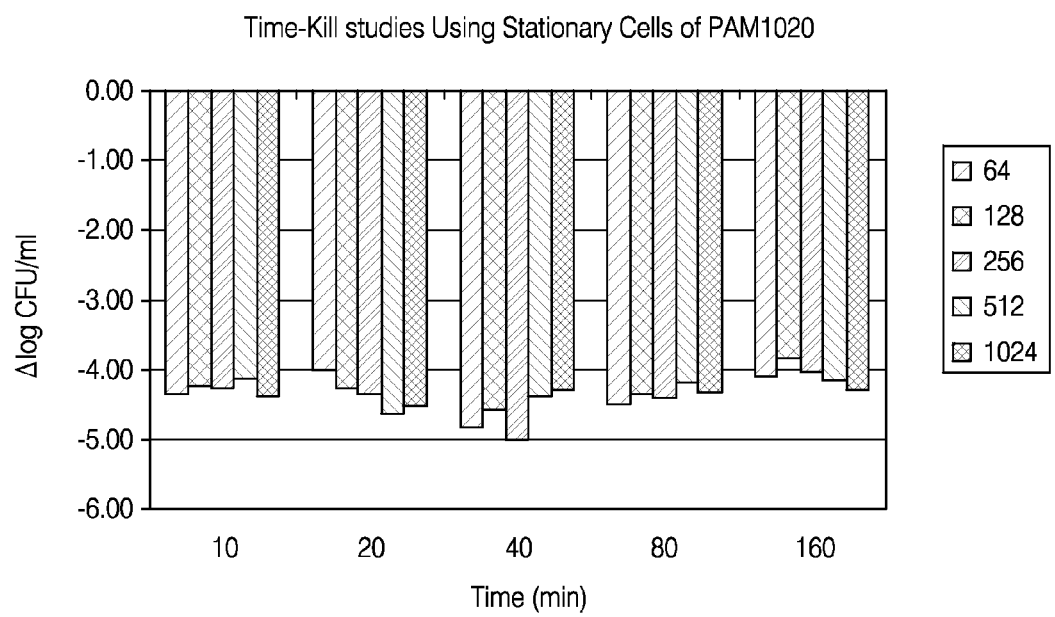
FIG. 5A is a graph showing Levofloxacin time-kill affects on stationary phase PAM1020 cells.
Figure 5B:
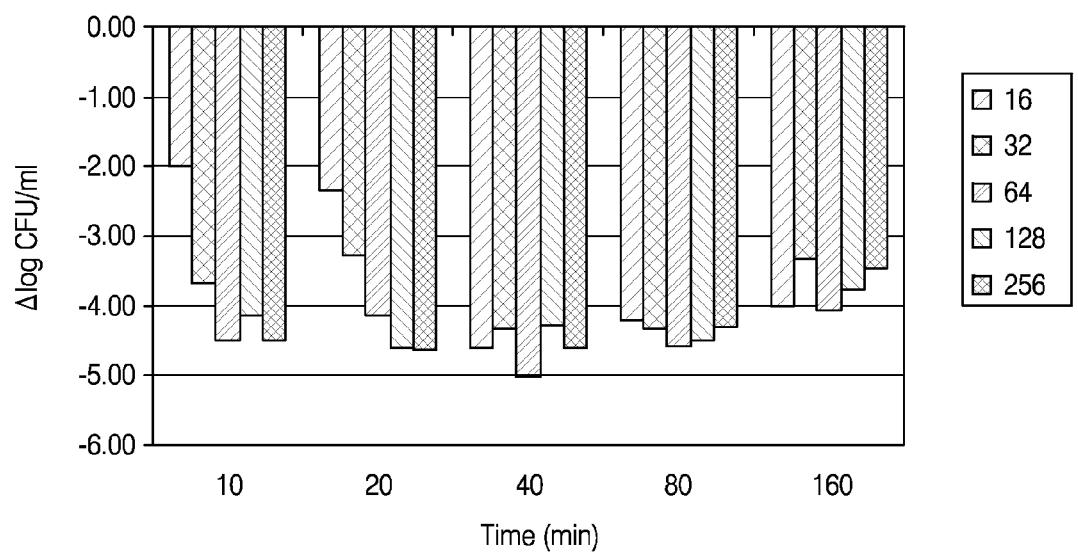
FIG. 5B is a graph showing Levofloxacin time-kill affects on stationary phase PAM1032 cells.
Figure 6A:
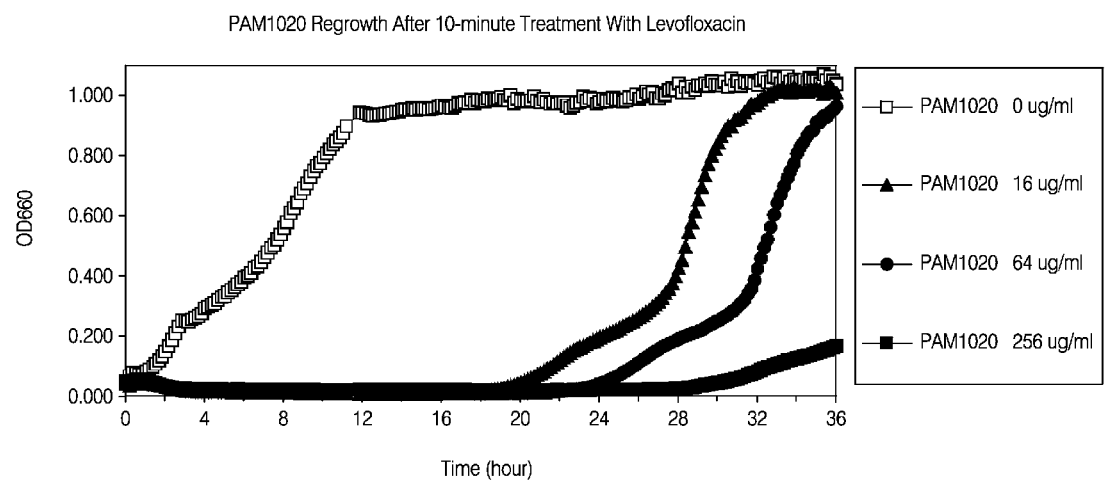
FIG. 6A is a graph showing PAM 1020 re-growth following a 10 minute Levofloxacin exposure.
Figure 6B:
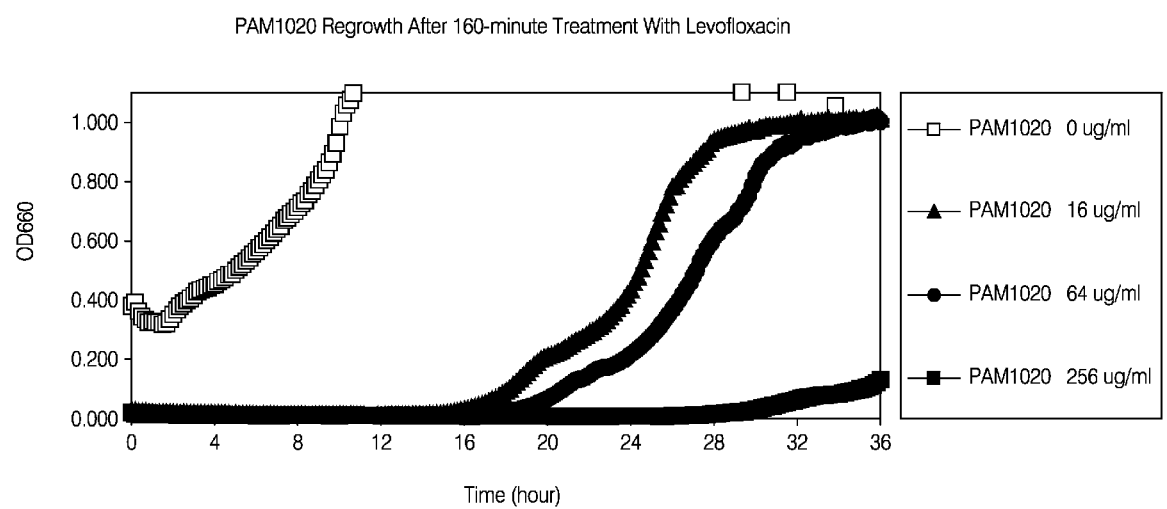
FIG. 6B is a graph showing PAM 1020 re-growth following a 160 minute Levofloxacin exposure.
Figure 6C:
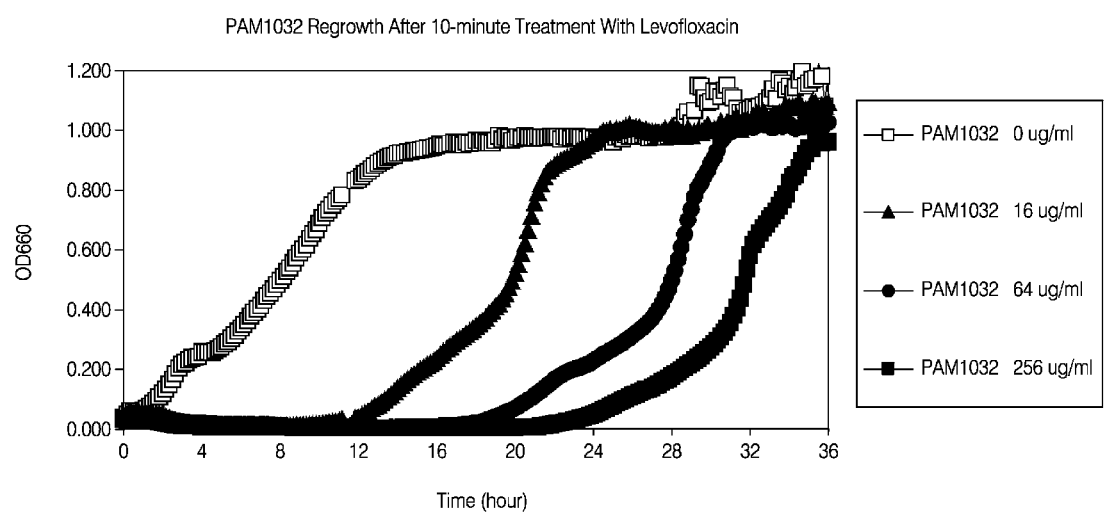
FIG. 6C is a graph showing PAM 1032 re-growth following a 10 minute Levofloxacin exposure.
Figure 6D:
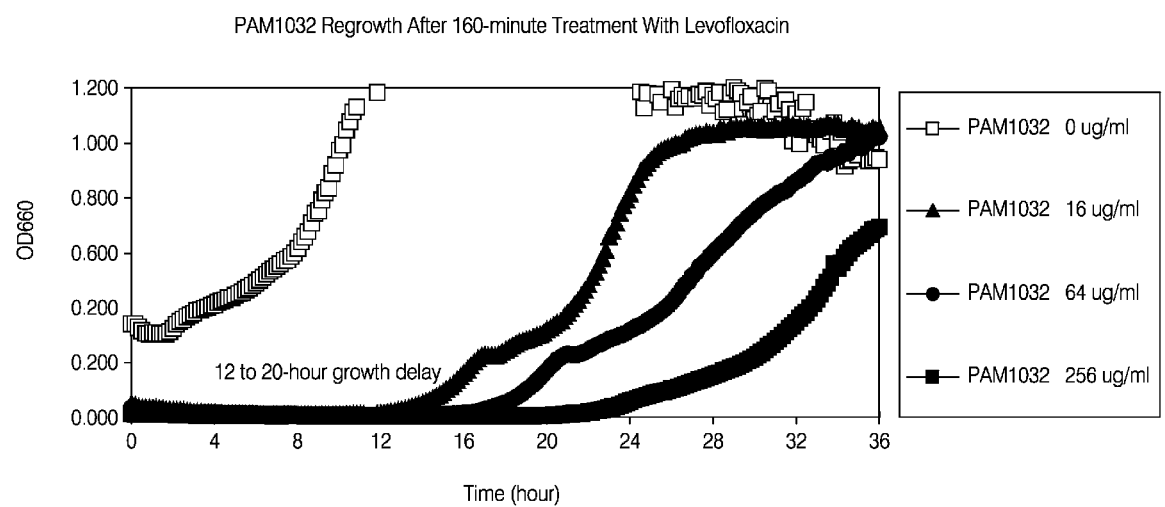
FIG. 6D is a graph showing PAM 1032 re-growth following a 160 minute Levofloxacin exposure.

For stationary phase cells of PAM1020, maximum killing was observed at the lowest concentration corresponding to 64-fold above MIC (16 ug/ml) and the shortest duration of exposure, 10 minutes (FIG. 5A). However, PAM1032 demonstrated clear dose-dependent killing with the maximum killing (4 logs) at concentrations 64 the MIC at a short exposure time. Extending the exposure times did not result in larger extent of killing. However, lower concentrations of drug were required to achieve the same killing at longer exposure times (FIG. 5B).

Next, we have compared the re-growth of PAM1020 and PAM1032 after either 10 minutes or 160 minutes of treatment with various concentrations of levofloxacin. After the corresponding treatments, cells were washed twice with antibiotic-free medium. 150 µl of cells was placed into 96-well plate and the growth was continuously monitored at $A_{660}$ using SpectraMax (Molecular Devices). The results are shown in FIG. 6A-6D.

The results demonstrate that the re-growth of both strains was observed at approximately the same time whether cells were treated with high concentrations of levofloxacin for 10 minutes or 160 minutes. These results further support the efficiency of short duration treatment with high concentrations of levofloxacin.

Experiment 3

Activity of Levofloxacin Against Cells Grown Under Oxygen-Limiting Conditions

Methods

Inoculum Preparation

Overnight cultures were grown aerobically overnight in Mueller-Hinton Broth and next diluted 1:10000 in MHB which filled growth flasks to the very top. Cultures were grown without shaking to OD~0.3 at 37° C. Under these conditions an average of ~20 hours was required to reach an OD=0.3 as compared to ~5 hours under aerated conditions (50 ml of medium in 250 ml flasks, vigorous shaking). Upon analysis, it appeared that an OD=0.3 corresponded to a late-logarithmic phase of growth. Other than decreased aeration, antibiotic concentration, time of exposure, and determination of viable cell counts were the same as in Experiments 1 and 2.

Results

Cell numbers at initiation of antibiotic exposure are shown in Table 5.

TABLE 5

Bacterial Numbers at Time of Initial Bacterial Exposure.

| Strain | CFU/ml |
| --- | --- |
| PAM1020 | 7.5E+07 |
| PAM1032 | 8.5E+07 |

Figure 7A:
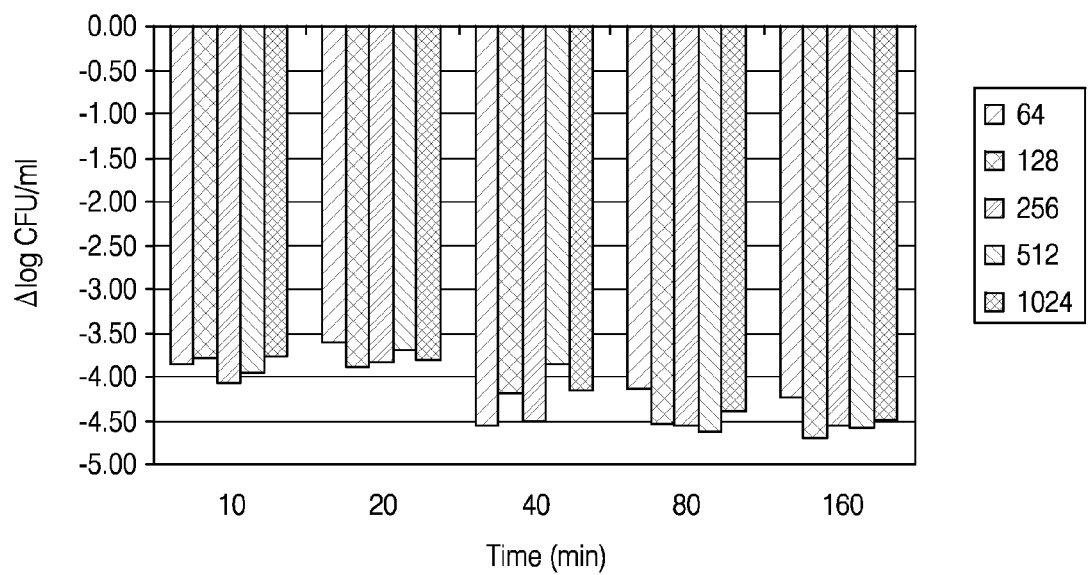
FIG. 7A is a graph showing Levofloxacin time-kill affects on late-logarithmic PAM 1020 cells under oxygen limiting conditions.
Figure 7B:
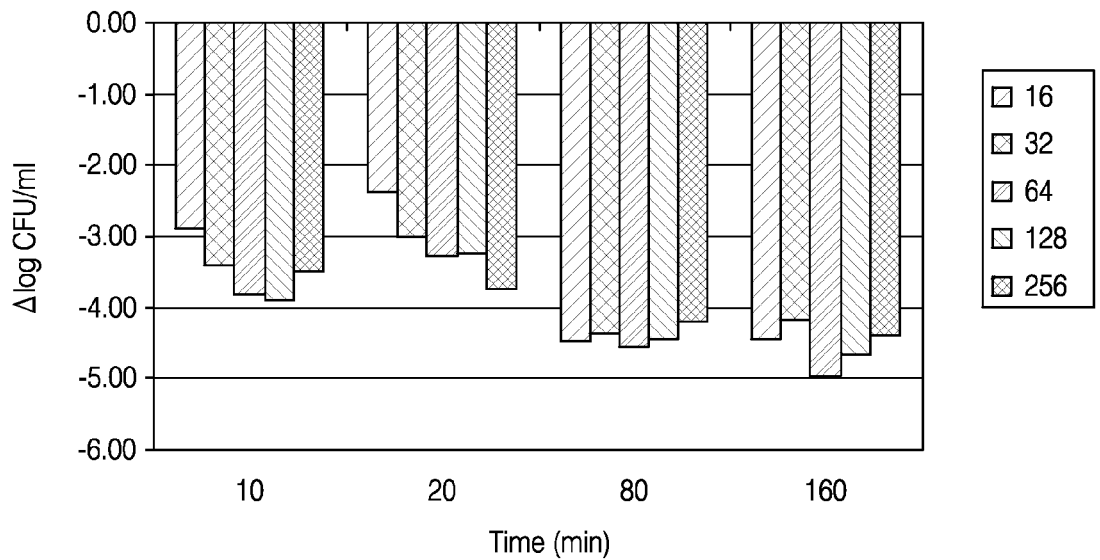
FIG. 7B is a graph showing Levofloxacin time-kill affects on late-logarithmic PAM 1032 cells under oxygen limiting conditions.

In the case of PAM1020 near maximum killing (4 logs vs 4.5 logs observed under normal aeration) was achieved after exposure with the lowest concentration of levofloxacin for the shortest duration of time (10 minutes) (FIG. 7A). In the case of PAM1032 dose-dependent killing was observed for 10 minutes or 20 minutes of exposure with the highest killing observed at concentrations corresponding to 128 to 256-fold the MIC. Slightly stronger (less than 1 log difference) killing was observed for longer exposure intervals (FIG. 7B). These data indicate that under conditions of oxygen limitation cells which are at the late logarithmic phase of growth are efficiently killed after short duration of exposure with high concentrations of levofloxacin.

Experiment 4

Activity of Levofloxacin Against PAM1032 in CF Sputum

Methods

Figure 8A:
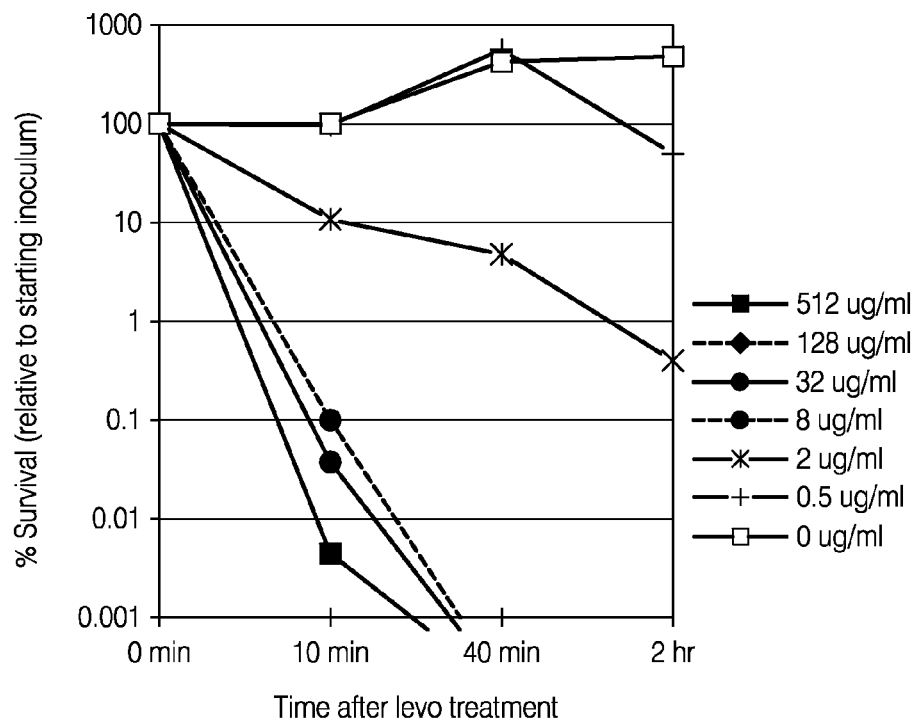
FIG. 8A is a graph showing Levofloxacin killing kinetics of PAM1032 in Meuller-Hinton broth (MHB).
Figure 8B:
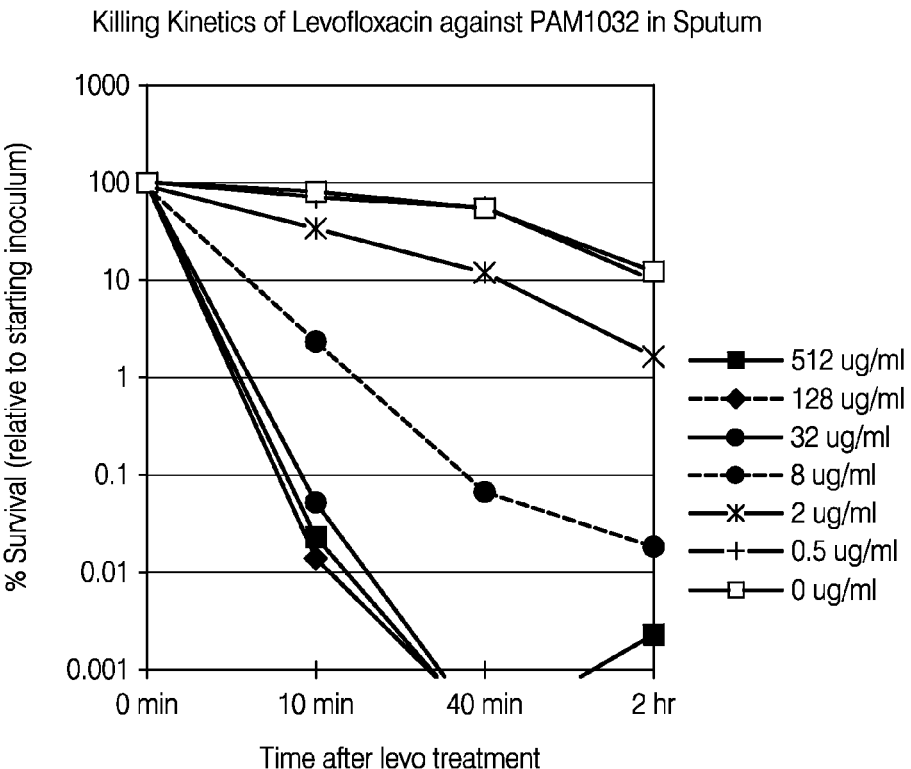
FIG. 8B is a graph showing Levofloxacin killing kinetics of PAM1032 in cystic fibrosis sputum.

Cells of strain PAM1032 (MIC=1 ug/ml) were grown to OD=1 (late-exponential/early stationary phase of growth) in MHB and next concentrated 10-fold in 10-fold concentrated MHB. 10 ul of cells were then added to 90 ul of sputum or water in 96-well round bottom plates, restoring MHB to its original concentration. Quantitation plates were pre-warmed for 5 minutes at 37° C. and different concentrations of levofloxacin (512 ug/ml, 128 ug/ml, 32 ug/ml, 8 ug/ml, 2 ug/ml, and 0.5 ug/ml) were added. At appropriate times, 10 ul of each treatment culture was diluted 100-fold in MHB to minimize the carryover of levofloxacin. Viable cell numbers were enumerated by plating serially diluted samples on MHB plates by the drop (10 ul) plating method. The limit of detection was $10^4$ CFU/ml. Killing is reported as the percentage of the starting inoculum survived after the levofloxacin treatment. Results are shown in FIGS. 8A and 8B.

Results

The results indicate that while sputum slightly affected the degree of killing by levofloxacin, rapid and extensive (up to five orders of magnitude) killing by levofloxacin in sputum was still observed after short duration of treatment at high concentrations of antibiotic.

Experiment 4

Activity of Levofloxacin Against Colony Biofilms of PAM1032

Methods

Biofilm Preparation

Colony biofilms were grown on polycarbonate membrane filters (diameter, 25 mm; Poretics, Livermore, Calif.) resting on MHB plates. Overnight culture of PAM1032 was diluted to OD=0.3, and then diluted 1:100 in fresh MHB. 5 ul of this culture was spotted on the membrane filter. Bacteria were incubated at 37° C. for 48 hours (mature biofilms).

Exposure

Figure 9:
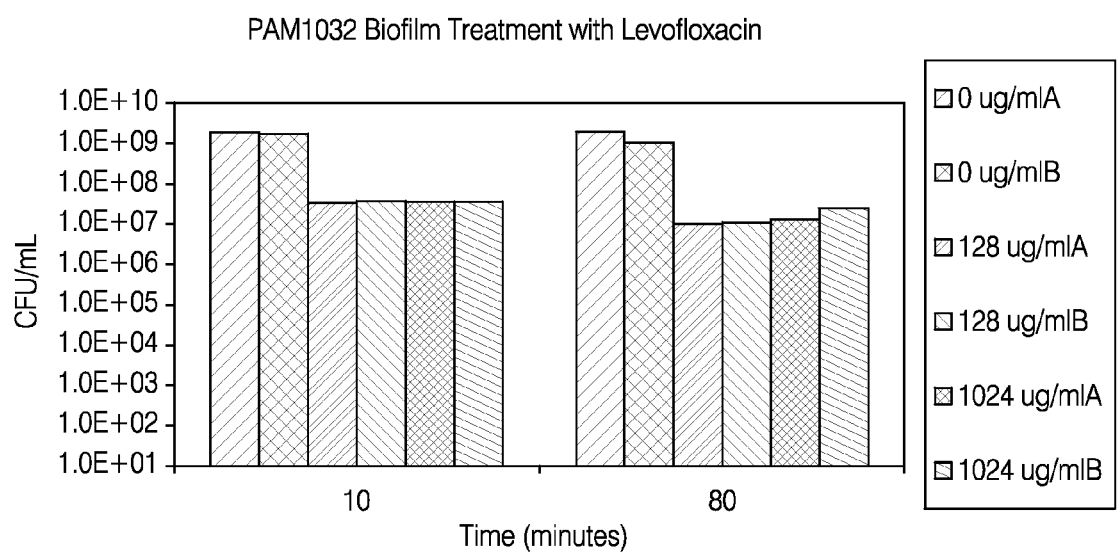
FIG. 9 is a graph showing levofloxacin killing affects on *Pseudomonas* biofilms.

After growth filters were placed into tubes containing 3 ml saline or saline and levofloxacin at 128 ug/ml and 1024 ug/ml. Each tube was treated for 10 minutes and 80 minutes. At about 5 min. before incubation time elapsed, tubes were vigorously vortexed (A) or sonicated and vortexed (B) to detach cells. 1 ml of each exposure culture was centrifuged for 2 minutes, the pellet was washed twice with 1 ml of drug-free MHB, and re-suspended in 1 ml of MHB. The viable cell numbers were enumerated by plating serially diluted samples (in duplicates) on MHB plates by the drop (10 ul) plating method. Results are shown in FIG. 9.

Results

The data demonstrate that maximum killing (~2 logs) is obtained after 10 min with the lowest concentration of levofloxacin tested (128-fold MIC). No additional killing was observed at the higher levofloxacin concentration. These data indicate that colony biofilms are more resistant to killing as compared to logarithmic or stationary phase cells. However, the maximum observed bactericidal activity against biofilms (99% under these conditions) was achieved after 10 minutes of levofloxacin exposure.

Experiment 5

Simulated Short-Term, Rapid Aerosol Administration, Delivering High Concentration Drug Exposure in In Vitro Pharmacodynamic Model In vitro pharmacodynamic models of infection allow for exposure of a growing bacterial inoculum to changing concentrations of drug as would occur in vivo. The strength of this approach is that the serum concentration vs. time profile of a drug in man can be simulated in the laboratory in vitro to determine the optimal exposure profile (i.e., dose and dosing interval) for a drug and target pathogen.

The following report describes experiments designed to determine the Cmax and AUC that will provide maximum bactericidal effects after an aerosol dose of a fluoroquinolone.

Material and Methods

In Vitro Pharmacodynamic Model of Infection

The in vitro pharmacodynamic model consists of a central (analogous "serum" compartment) and peripheral ("extravascular") compartment. The peripheral compartments consist of artificial capillary units (Unisyn, Hopkinton, Mass.) arranged in series with the central compartment. Each capillary unit has a bundle of small semi-permeable fibers with a molecular size retention of ca. 10,000 MW to allow passage of nutrients but not bacteria. The entire system is set up in a dry heat incubator adjusted to 37° C.

Both the central and peripheral compartments were filled with Mueller-Hinton broth. Each peripheral compartment (capillary unit and tubing) contained ca. 23 ml of growth medium.

Bacteria were introduced into the peripheral chamber of the model and allowed to grow for 2 hours prior to the first "dose" of drug. Drug doses were administered into the central compartment and pumped to peripheral chambers by a peristaltic pump. Concentrations in the model declined according to first order elimination (half-life) by dilution of the central compartment with drug free medium introduced by an additional peristaltic pump adjusted to the desired clearance.

Samples (0.3 ml) were collected from peripheral compartments at various intervals for determination of drug and bacterial concentrations. Samples were collected from the peripheral compartments and assayed for drug concentrations by HPLC.

Bacterial Test Strains

*Pseudomonas aeruginosa* PAM1032 and PAM1582. The MICs of these strains to levofloxacin were 1.0 and 32 ug/ml, respectively.

Inoculum Preparation

Strains were grown aerobically overnight in Mueller-Hinton Broth (MHB) at 35° C. and subcultured to fresh MHB and preincubated at 35° C. for 2 hours. After 2 hours, the inoculum was further diluted 1:1000 to a final concentration of approx. 1.0×106 CFU/ml. Of the resulting dilution, 2.3 ml was injected into each peripheral chamber of the hollow-fiber bioreactors (Unisyn, Hopkinton, Mass.).

Pharmacokinetics

The half-life of levofloxacin was adjusted to be 10 minutes to be equivalent to that observed following aerosol delivery of levofloxacin to the pulmonary compartment of man. The targeted Cmax was 1000 and 600 ug/ml over two experiments.

Results

As targeted, the model exhibited a levofloxacin half-life of 10 minutes and the Cmax of 1000 ug/ml for Experiment 5. By comparison, Experiment 6 was modified to achieve the same half-life as Experiment 5, but with a targeted Cmax of 600 μg/ml.

Figure 10:
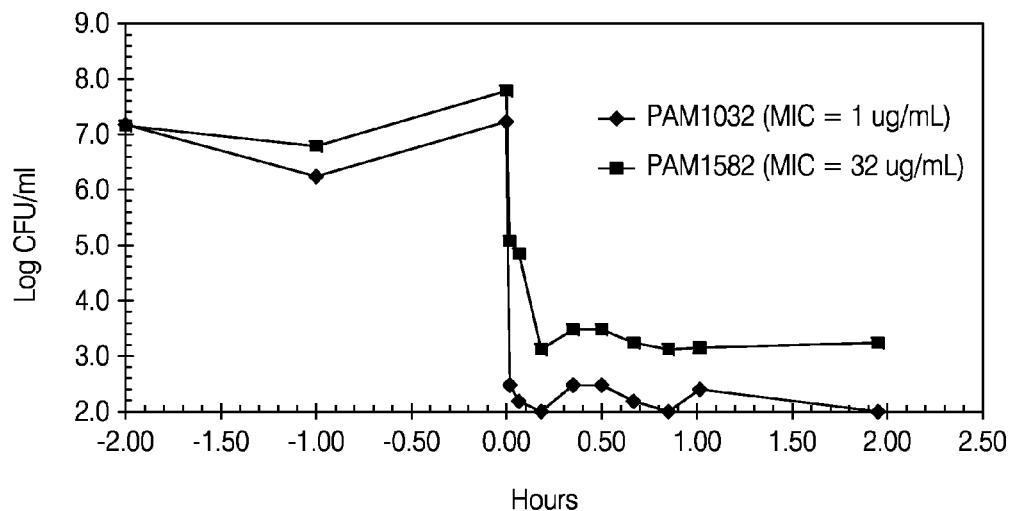
FIG. 10 is a graph showing the bactericidal effects of levofloxacin with a Cmax of 1000 μg/ml and a 10 minute half-life in a hollow fiber model.
Figure 11:
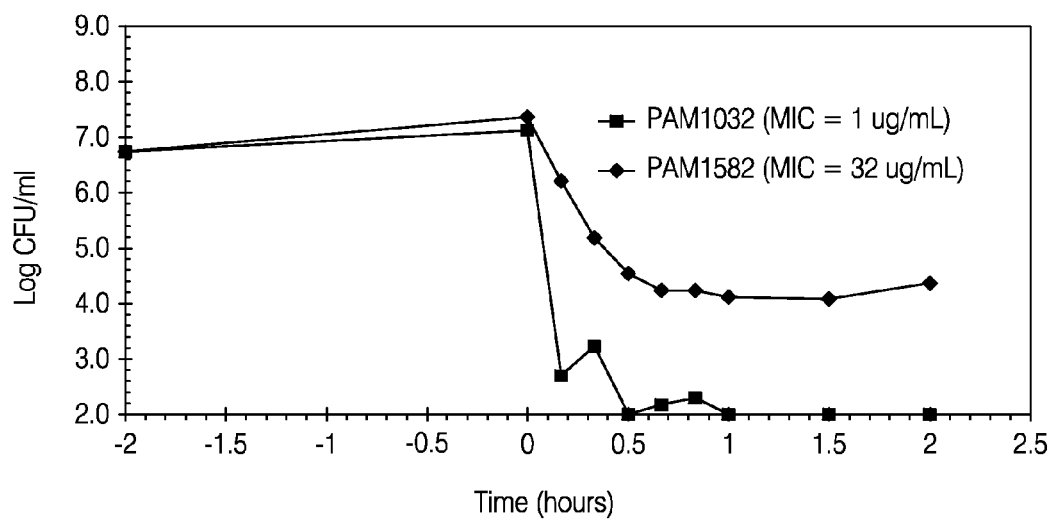
FIG. 11 is a graph showing the bactericidal effects of levofloxacin with a Cmax of 600 μg/ml and a 10 minute half-life in a hollow fiber model.

The bactericidal effects of these two regimens correlated with the Cmax. In Experiment 5 with a Cmax of 1000 ug/ml, the maximum bactericidal effect was observed as a 5 log reduction in bacterial counts within 10 minutes with PAM1032 and a 4 log reduction in bacterial counts within 20 minutes with PAM1582 and no re-growth observed over the remaining 2 hours of the experiment (FIG. 10). In contrast, while the Cmax of 600 ug/ml used in Experiment 6 maintained the 5-log reduction in bacterial counts for PAM1032, albeit taking 30 min instead of 10 min observed in Experiment 1, only a 3-log reduction in bacterial counts was observed for PAM1582 after 45 min (FIG. 11). Moreover, PAM1582 exhibited initial re-growth before the end of the 2 hour experimental window.

Conclusions

Levofloxacin can produce up to a 99.9999% bacterial reduction with a Cmax of both 600 and 1000 ug/ml against a strain with an MIC of 1 ug/ml. However, maximal bactericidal activity requires 3× more time at a Cmax of 600 ug/ml. Levofloxacin can also produce up to 99.99% bacterial reduction with a Cmax of both 600 ug/ml against a strain with an MIC of 32 ug/ml. However, the time to reach the maximum effect is 45 minutes. In contrast, levofloxacin can produce up to 99.999% bacterial reduction of this resistant strain with a Cmax of 1000 ug/ml and the time to maximum effect is reduced to 20 minutes. From these results, extremely high, but short duration exposures of levofloxacin produce rapid and sustained bacterial killing in both flask and hollow fiber models. Taken together, the above results indicate that achieving an initial 800 ug/ml levofloxacin or other fluoroquinolone human ELF or sputum concentration is sufficient to achieve the above antibiotic affects for the MIC99 population as represented by PAM1582 (MIC of 32 ug/ml).

Example 2

Determination of the Aerosol Properties of Antibacterial Fluoroquinolones

Introduction

Objective. The purpose of these studies was to evaluate the ability to formulate and deliver by nebulization a variety of fluoroquinolones for treatment of pulmonary bacterial infections by aerosol administration. The fluoroquinolones evaluated are shown in Table 6.

TABLE 6

Fluoroquinolones Tested.

| Fluoroquinolone | Sp $MIC_{90}$ (ug/mL) | MSSA $MIC_{90}$ (ug/mL) | MRSA $MIC_{90}$ (ug/mL) | Pa $MIC_{90}$ (ug/mL) | Approval Status |
|---|---|---|---|---|---|
| Ciprofloxacin | 2 | 1 | 64 | 8 | Approved |
| Gemifloxacin | 0.06 | 0.06 | 2 | 8 | Approved |
| Levofloxacin | 2 | 0.5 | 16 | 8 | Approved |
| Marbofloxacin | 2 | 2 | ND | 8 | Veterinary |
| Gatifloxacin | 0.5 | 0.125 | 4 | 16 | Approved |
| Ofloxacin | 2 | 1 | >32 | 16 | Approved |
| Tosufloxacin | 0.5 | 0.125 | >16 | 16 | Japan |
| Lomefloxacin | 16 | 2 | >32 | 32 | Approved |
| Moxifloxacin | 0.25 | 0.125 | 2 | 32 | Approved |
| Sparfloxacin | 0.5 | 0.125 | 16 | 32 | Withdrawn |
| Orbifloxacin | 2 | 2 | ND | >32 | Veterinary |
| Pefloxacin | 32 | 2 | >32 | >32 | Europe |
| Trovafloxacin | 0.25 | 0.06 | 8 | >32 | Withdrawn |

These fluoroquinolones were chosen based on their availability, approval status and antimicrobial properties. All tested fluoroquinolones are either currently approved in the United States or have been approved but later withdrawn due to various adverse reactions. In addition, several fluoroquinolones, which are in use for veterinary applications, have also been evaluated. Among bacterial pathogens responsible for respiratory tract infections, *Pseudomonas aeruginosa* (Pa) and methicillin resistant *Staphylococcus aureus* (MRSA) are the most refractory to treatment with fluoroquinolones. *Streptococcus pneumonia* (Sp) is probably the most important pathogen responsible for respiratory tract infections and numerous reports demonstrate high rates of fluoroquinolone resistance in these bacteria. $MIC_{90}$ for Pa ranges from 4 ug/ml to 32 ug/ml and from 2 ug/ml to >32 ug/ml for Pa and MRSA, respectively. Ciprofloxacin, levofloxacin, gemifloxacin and gatifloxacin vs gemifloxacin and moxifloxacin are the most potent against Pa and MRSA, respectively.

Table 7 contains a list of additional fluoroquinolones for potential evaluation. The most microbiologically interesting compounds in the list are clinafloxacin and olamufloxacin, which were discontinued due to adverse reactions, and sitafloxacin, which is in Phase III clinical trials.

TABLE 7

Fluoroquinolones For Potential Evaluation.

| Fluoroquinolone | Sp $MIC_{90}$ (ug/mL) | Sa $MIC_{90}$ (ug/mL) | MRSA $MIC_{90}$ (ug/mL) | Pa $MIC_{90}$ (ug/mL) | Market Status |
|---|---|---|---|---|---|
| Clinafloxacin | 0.06 | 0.06 | 2 | 4 | Discontinued |
| Sitafloxacin | 0.06 | 0.125 | 4 | 8 | Phase III |
| Olamufloxacin | 0.06 | 1 | 2 | 16 | Discontinued |
| Norfloxacin | 16 | 1 | >4 | 16 | Approved |
| Prulifloxacin | 1 | 0.25 | 32 | 16 | Phase III |
| Danofloxacin | NA | 0.125 | NA | >16 | Veterinary |
| Enrofloxacin | 1 | 0.125 | 8 | >16 | Veterinary |
| Sarafloxacin | NA | 0.25 | >16 | >16 | Veterinary |
| Balofloxacin | 0.5 | 0.25 | 8 | 32 | Korea |
| Fleroxacin | 8 | 1 | >4 | 32 | Europe |
| Difloxacin | 2 | 0.5 | NA | 32 | Veterinary |
| Rufloxacin | 32 | 2 | 64 | 32 | Europe, China |
| Enoxacin | 16 | 1 | >4 | >32 | Withdrawn |
| Garenoxacin | 0.06 | 0.06 | 8 | >32 | Phase III |

TABLE 7-continued

Fluoroquinolones For Potential Evaluation.

| Fluoroquinolone | Sp MIC$_{90}$ (ug/mL) | Sa MIC$_{90}$ (ug/mL) | MRSA MIC$_{90}$ (ug/mL) | Pa MIC$_{90}$ (ug/mL) | Market Status |
|---|---|---|---|---|---|
| Grepafloxacin | 0.5 | 0.125 | 32 | >32 | Withdrawn |
| Pazufloxacin | 4 | 0.5 | >16 | >32 | Japan |

The fluoroquinolones in these two tables represent one field of options for an aerosol fluoroquinolone candidate. Several potent fluoroquinolones such as DX-619 and DW-286, which are at the early stage of clinical development, might also be of interest for future studies.

Specific physico-chemical considerations for nebulization include aqueous solubility, viscosity and surface tension. The aqueous solubility of the drug should advantageously be sufficient to meet or exceed the minimal dosing requirement. The loading drug concentration also affects delivery time. Longer delivery times may be commercially unacceptable or lead to poor patient compliance. Although longer delivery times may in effect modify the AUC shape, by non-limiting example, the PARI eFlow device has been discovered to administer 4 ml of aqueous levofloxacin in less than 5 min. Moreover, using such an efficient device, high concentration levofloxacin may be able to deliver the effective doses described herein in a timeframe further enabling the rapid administration, high concentration drug requirements needed for optimal fluoroquinolone therapy.

In the case of fluoroquinolones, pH directly affects solubility. In general, solubility decreases significantly with increase in pH in the range 1.5 to 6.5. Because pH also affects patient tolerability (see below), the optimal choice of fluoroquinolone for pulmonary delivery via aerosol has certain solubility and pH levels.

For the purpose of this feasibility study, the target solubility was set at 10 mg/mL or higher at a pH of 4.5 or greater, based on calculations of therapeutic dose and the delivery metrics for available nebulizers. In order to be above the mutant prevention concentration (MPC), peak concentration of fluoroquinolone after aerosol administration advantageously reaches about 100 ug/ml to about 1000 ug/ml at the site of infection, pending the MIC of the infecting organism. Based on these considerations, the minimal dose to be in this therapeutically relevant range was projected to be at least about 30-40 mg Respirable Delivered Dose (RDD). Given the relative half-life of levofloxacin in the human lung, the practical achievement of this dose by nebulization may be obtained with a loading dose of at least about 100 mg in a volume of about 2 mL (about 50 mg/mL) in a high-efficiency vibrating-mesh device operating at its maximum performance efficiency delivering this dose in less than 4 min. A standard ultrasonic or jet nebulizer may require a loading dose of at least about 400 mg in a volume of about 5 mL (about 80 mg/mL). However, the rate of administration by these less efficient devices may not be sufficient to achieve high local concentration with short duration exposure. Similar efficacious doses may also be achieved by administration of levofloxacin as a dry powder, where the rapid solubility properties of levofloxacin may permit a quick dissolution resulting in these desired soluble drug concentrations. However, alternative concentrations or alteration of the fluoroquinolone AUC shape profile may be desirable.

Alternatively, although aqueous solubility is important, it is reasonable to predict a formulation utilizing particle or complexation technology to enable nebulization of less soluble fluoroquinolones. Unfortunately, more intricate formulations increase both the complexity and cost of drug development, and in the case of jet and ultrasonic nebulizers, a significant reduction in efficiency of delivery, and limit the ability to introduce other design elements into a final drug product.

In addition to drug solubility, for vibrating mesh devices nebulization is also sensitive to the surface tension of the drug formulation. Therefore, in one embodiment, the surface tension is adjusted during formulation by modifying drug concentration, excipient concentration and/or the addition of surfactant.

In addition to factors that affect efficient nebulization, other factors may be considered for patient tolerability and compliance. By non-limiting example, these factors may include osmolality, pH and taste. Osmolality affects acute tolerability in the respiratory tract and can be optimized for most drugs during formulation. Similarly, the pH of an aerosol also contributes to tolerability, yet only negatively when the formulation pH is less than 4.5. Therefore, because pH directly contributes to fluoroquinolone solubility, fluoroquinolones that require a pH less than 4.5 for solubility are likely to be poorly tolerated. Finally, fluoroquinolone taste can affect good patient compliance. Fluoroquinolones are known generally to be associated with an unpleasant, sometimes very intense taste. While there are technologies available that may mask poor drug taste, these technologies increase development complexity and cost, and may not be totally effective in the case of fluoroquinolones. Thus, similar to pH, taste may be considered in identifying a fluoroquinolone suitable for nebulization.

Preparation and Characterization of the Test Solutions

Antibiotics were purchased from one of several sources as shown in Table 8.

TABLE 8

| Preparation of Fluoroquinolone Test Solutions. | | | | | | |
|---|---|---|---|---|---|---|
| No. | Fluoroquinolone | Source[a] | Purity[b] | Amount | Volume $H_2O$ | Final Conc. |
| 1 | Gatifloxacin | LKT | 99.6 | 8.7 mg | 0.87 mL | 10 mg/mL |
| 2 | Gemifloxacin | LG | 99.6 | 9.5 mg | 0.95 mL | 10 mg/mL |
| 3 | Levofloxacin | LKT | 99.2 | 10.3 mg | 1.03 mL | 10 mg/mL |
| 4 | Moxifloxacin | LKT | 99.5 | 12.5 mg | 1.25 mL | 10 mg/mL |
| 5 | Ciprofloxacin | LKT | 99.3 | 19.5 mg | 1.95 mL | 10 mg/mL |
| 6 | Ofloxacin | LKT | 99.1 | 11.7 mg | 1.17 mL | 10 mg/mL |
| 7 | Lomefloxacin | MPI | NA | 17.0 mg | 1.70 mL | 10 mg/mL |
| 8 | Marbofloxacin | Vetoquino | NA | 4.8 mg | 0.48 mL | 10 mg/mL |
| 9 | Orbifloxacin | MPI | NA | 4.2 mg | 0.42 mL | 10 mg/mL |
| 10 | Pefloxacin | MPI | NA | 15.0 mg | 1.50 mL | 10 mg/mL |
| 11 | Sparfloxacin | MPI | NA | 14.5 mg | 1.45 mL | 10 mg/mL |

TABLE 8-continued

Preparation of Fluoroquinolone Test Solutions.

| No. | Fluoroquinolone | Source[a] | Purity[b] | Amount | Volume H$_2$O | Final Conc. |
|---|---|---|---|---|---|---|
| 12 | Tosufloxacin | MPI | NA | 15.2 mg | 1.52 mL | 10 mg/mL |
| 13 | Trovafloxacin | MPI | NA | 2.0 mg | 0.20 mL | 10 mg/mL |

[a]LKT: LKT Laboratories. LG: LG Chem. NA. Source unavailable.
[b]Purity of material tested. Described as GMP or in percent API.
[c]25 mg/ml solution.

A 2 to 20 mg sample of each antibiotic was weighed into sterile plastic tubes and brought up with a volume of sterile water to make a 10 mg/mL solution or suspension of the antibiotic. Samples were incubated for approximately 10 minutes at room temperature with occasional mixing, prior to further handling.

Following the incubation period, the antibiotic solutions were observed for their visible appearance, with results as shown in Table 9.

Five of the fluoroquinolones tested were visibly soluble, and either colorless, or a shade of yellow. Eight were visibly insoluble, appearing either cloudy (fine particulate), opaque (dense fine to medium particulate), or turbid (thick, large particulate slurry), in all cases with a visible sediment. The pH of these initial solutions were determined, and ranged from 3.5 to 7.0. The insoluble solutions were titrated with 1N HCl to the point of visible solubility, and the pH of the solubilized solution determined. In three cases, marbofloxacin, sparfloxacin and tosufloxacin, solubility was not reached by pH 1.5, and further addition of acid was stopped. With the exception of ofloxacin, the pH of these titrated solutions was in the range of 1.5 to 3.0.

After the pH adjustment, and following a further 10 minute incubation period with occasional mixing, the final appearance of the solutions was determined, just prior to the aerosol tolerability and taste test. Results are shown in Table 10.

TABLE 10

Appearance of Fluoroquinolone Final Solution.

| No. | Fluoroquinolone | pH | Solubility | Color | Sediment | Opaqueness |
|---|---|---|---|---|---|---|
| 1 | Gatifloxacin | 3.0 | + | C | none | none to very slight |
| 2 | Gemifloxacin | | + | C | none | none to very slight |
| 3 | Levofloxacin | 4.7 | + | VLY | none | none |
| 4 | Moxifloxacin | 4.7 | + | Y | +/− | none |
| 5 | Ciprofloxacin | 2.0 | + | C | none | none |
| 6 | Ofloxacin | 5.2 | + | LY | +/− | none |
| 7 | Lomefloxacin | 4.2 | + | C | +/− | none to very slight |
| 8 | Marbofloxacin | 1.5 | −− | W | ++ | ++ |
| 9 | Orbifloxacin | 1.7 | + | C | none | slight |

TABLE 9

Flouroquinolone Solution Characteristics.

| | | Initial Solution | | After pH Adjustment | | |
|---|---|---|---|---|---|---|
| | | | | 1N HCl | | |
| No. | Fluoroquinolone | Appearance | pH | (uL) | Appearance[a] | pH |
| 1 | Gatifloxacin | white, cloudy, visible sediment | 7.0 | 5 | slight yellow color, transparent, no sediment | 3.0 |
| 2 | Gemifloxacin | colorless, transparent, no sediment | 4.7 | | NR | — |
| 3 | Levofloxacin | slight yellow color, transparent, no sediment | 4.7 | | NR | — |
| 4 | Moxifloxacin | bright yellow color, transparent, no sediment | 4.7 | | NR | — |
| 5 | Ciprofloxacin | white, opaque (very dense), visible sediment | 5.5 | 60 | colorless, transparent, no sediment | 2.0 |
| 6 | Ofloxacin | cloudy, visible sediment | 6.5 | 10 | slightly yellow color, transparent, no sediment | 5.2 |
| 7 | Lomefloxacin | cloudy, visible sediment | 4.2 | — | transparent, no sediment, after 10 min. at rm. temp. | — |
| 8 | Marbofloxacin | white, very turbid, visible sediment | 6.5 | 40 | white, turbid, visible sediment | 1.5 |
| 9 | Orbifloxacin | white, cloudy, visible sediment | | 20 | colorless, transparent, no sediment | 1.7 |
| 10 | Pefloxacin | colorless, transparent, no precipitate | 4.5 | | NR | — |
| 11 | Sparfloxacin | bright yellow, turbid, visible sediment | 5.0 | 20 | bright yellow, densely turbid, visible sediment | 1.5 |
| 12 | Tosufloxacin | white, turbid, visible sediment | 3.5 | 20 | white, cloudy, less turbid, visible sediment | 1.5 |
| 13 | Trovafloxacin | colorless, slightly cloudy, no sediment | 4.2 | | NR | — |

[a]NR: pH adjustment not required. Fluoroquinolone was soluble at a pH ≧ 4 in the initial solution.

TABLE 10-continued

Appearance of Fluoroquinolone Final Solution.

| No. | Fluoro-quinolone | pH | Solubility | Color | Sediment | Opaqueness |
|---|---|---|---|---|---|---|
| 10 | Pefloxacin | 4.5 | + | C | none | slight |
| 11 | Sparfloxacin | 1.5 | --- | DY | +++ | ++++ |
| 12 | Tosufloxacin | 1.5 | -- | W | ++ | +++ |
| 13 | Trovafloxacin | 4.2 | + | C | + | slight |

Y = yellow;
LY = light yellow;
VLY = very light yellow;
DY = dark yellow;
C = colorless;
W = white.

The compounds exhibiting preferred solubility for solutions suitable for delivery by inhalation (10 mg/mL at a pH of 4.5 or above), were levofloxacin, gemifloxacin, moxifloxacin, ofloxacin and pefloxacin. Levofloxacin, ofloxacin and moxifloxacin exhibited the best solubility/pH characteristics.

Taste and Tolerability Evaluation

Two evaluations were done to determine the suitability of the fluoroquinolone solutions with respect to taste and tolerability.

First, in an oral taste test the taste of a 20 uL portion of test sample was determined in a single, healthy human volunteer by placing the material directly onto the center front part of the tongue. Taste was then monitored over a 1 minute period. This test was performed on the initial solutions prepared as well as the final solutions following pH adjustment. Data are shown in Table 11.

TABLE 11

Oral Fluoroquinolone Taste Test.

| No. | Fluoro-quinolone | Initial Solution | Final Solution |
|---|---|---|---|
| 1 | Gatifloxacin | moderate bitter unpleasant taste, slightly aromatic | strong bitter unpleasant almond-like taste, strong aftertaste |
| 2 | Gemifloxacin | very bitter unpleasant taste with strong aftertaste, all the way into throat | not performed |
| 3 | Levofloxacin | slight chemical taste, slightly bitter, slight almond-like taste | not performed |
| 4 | Moxifloxacin | moderate bitter-sweet unpleasant taste, slightly aromatic | not performed |
| 5 | Ciprofloxacin | sweet almond-like taste | very strong bitter taste all the way into the throat |
| 6 | Ofloxacin | bitter unpleasant, almond-like taste | moderate bitter unpleasant, almond-like taste |
| 7 | Lomefloxacin | moderate to strong almond-like taste, not very unpleasant | not performed |
| 8 | Marbofloxacin | bitter unpleasant almond-like taste | moderate to strong bitter unpleasant almond-like taste |
| 9 | Orbifloxacin | strong unpleasant taste | very strong, very unpleasant bitter taste |
| 10 | Pefloxacin | strong bitter unpleasant almond-like taste | not performed |
| 11 | Sparfloxacin | slight taste | strong almond-like taste |
| 12 | Tosufloxacin | mild to moderate almond-like taste | strong almond-like taste |
| 13 | Trovafloxacin | very strong bitter unpleasant almond-like taste, strong aftertaste | not done |

Lowering of the pH generally had the effect of enhancing the taste properties of the solution. Gatifloxacin, gemifloxacin, ciprofloxacin, orbifloxacin and trovafloxacin were the least desirable in taste testing. Of the fluoroquinolones tested, Levofloxacin was the only fluoroquinolone that was tolerable with respect to taste, at the concentration tested. Lomefloxacin had a moderately strong almond-like taste, and the taste was slightly unpleasant.

In the second test, the tolerability and taste of a small aerosol sample from a 0.5 ml aliquot of the test formulation was determined in a single healthy human volunteer, following nebulization in a PARI eFlow nebulizer (Table 12).

TABLE 12

Aerosol Fluoroquinolone Tolerability and Taste Test.

| No. | Fluoro-quinolone | Aerosol Tolerability and Taste |
|---|---|---|
| 1 | Gatifloxacin | moderate bitter unpleasant taste, mild cough sensation |
| 2 | Gemifloxacin | strong unpleasant bitter taste, strong aftertaste, mild cough sensation |
| 3 | Levofloxacin | chemical taste, somewhat bitter, mild cough sensation |
| 4 | Moxifloxacin | moderate bitter unpleasant taste, some cough, strong bitter aftertaste |

TABLE 12-continued Aerosol Fluoroquinolone Tolerability and Taste Test.

| No. | Fluoro-quinolone | Aerosol Tolerability and Taste |
|---|---|---|
| 5 | Ciprofloxacin | very strong, bitter unpleasant taste, immediate coughing |
| 6 | Ofloxacin | bitter chemical taste, mild cough sensation |
| 7 | Lomefloxacin | chemical taste, somewhat bitter, mild cough sensation |
| 8 | Marbofloxacin | too insoluble to test |
| 9 | Orbifloxacin | very acidic, strong bitter unpleasant taste, strong cough |
| 10 | Pefloxacin | chemical taste, some cough |
| 11 | Sparfloxacin | too insoluble to test |
| 12 | Tosufloxacin | too insoluble to test |
| 13 | Trovafloxacin | bitter unpleasant taste, no cough or cough sensation, no aftertaste |

In the case of orbifloxacin, marbofloxacin and trovafloxacin, smaller portions were tested, due to solubility limitations. In a calibration experiment, the inhaler produced an aerosol output of 4.1 microns VMD, with a geometric standard deviation (GSD) of 1.64 micron VMD. In addition to these measurements, the inhaler produced a fine particle dose (FPD) of 54.9% (percent of emitted dose in particles less than 5 microns). The tolerability and taste of the drug during a very brief administration period and for a period of 10 minutes post administration were monitored. Tolerability parameters were of the following types: (i) cough, cough sensation, or sneezing (ii) irritation, burning or tightness of throat, (ii) irritation or Funniness in nasal passages or eyes, (iii) irritation, burning or tightness of the lungs or shortness of breadth, and (iv) dizziness, headache, nausea or other systemic effects.

Marbofloxacin, sparfloxacin and tosufloxacin were too insoluble to evaluate in this test. For the remaining fluoroquinolones tested, no tolerability effects were observed during or after aerosol exposure in categories ii, iii or iv (above). Gatifloxacin, moxifloxacin ciprofloxacin, orbifloxacin and pefloxacin were all associated with cough. In the case of ciprofloxacin and orbifloxacin this may have been associated with the low-pH of the solution. Of the fluoroquinolones tested, Levofloxacin at 10 mg/ml had the best taste characteristics. Ofloxacin, lomefloxacin and pefloxacin had a more discernible taste than levofloxacin, which were also acceptable during the short course of administration.

Summary and Conclusions from the Fluoroquinolone Taste Test

Of the thirteen fluoroquinolones tested in this study, levofloxacin had preferred physical-chemical properties for aerosol administration and a demonstration of best acute tolerability of the fluoroquinolones tested (Table 13). Levofloxacin is also recognized as having one of the best antimicrobial profiles for respiratory pathogens and has the highest in vivo efficacy, comparable to ciprofloxacin, for treatment of *Pseudomonas aeruginosa* infections.

TABLE 13

| Overall Suitability for Nebulization. | | | | |
|---|---|---|---|---|
| No. | Fluoro-quinolone | Assessment | Overall Score | Limitation |
| 1 | Gatifloxacin | poor solubility and pH, moderately strong bitter aerosol taste | −− | Solubility, Taste |
| 2 | Gemifloxacin | sufficient solubility and pH, strong bitter aerosol taste, strong aftertaste | −−− | Taste |
| 3 | Levofloxacin | excellent solubility and pH, chemical aerosol taste, somewhat bitter | + | Taste |
| 4 | Moxifloxacin | sufficient solubility and pH, moderately strong bitter aerosol taste, strong aftertaste | −− | Taste, Pa Activity |
| 5 | Ciprofloxacin | poor solubility and pH, very strong bitter aerosol taste, coughing | −−− | Solubility, Taste |
| 6 | Ofloxacin | minimally acceptable solubility and pH, bitter chemical aerosol taste | −/+ | Taste |
| 7 | Lomefloxacin | minimally acceptable solubility and pH, chemical aerosol taste, strong liquid taste | −/+ | Pa Activity |
| 8 | Marbofloxacin | very poor solubility even at low pH, unable to test | −−− | Solubility |
| 9 | Orbifloxacin | very poor solubility even at low pH, strong bitter unpleasant aerosol taste, strong cough | −−− | Solubility, Taste, Pa Activity |
| 10 | Pefloxacin | sufficient solubility and pH, aerosol chemical taste, strong unpleasant liquid taste | −/+ | Pa Activity |
| 11 | Sparfloxacin | very poor solubility even at low pH, unable to test | −−− | Solubility, Pa Activity |
| 12 | Tosufloxacin | very poor solubility even at low pH, unable to test | −−− | Solubility |
| 13 | Trovafloxacin | moderate solubility and pH, bitter aerosol taste | −− | Taste, Pa Activity |

Ofloxacin, lomefloxacin and pefloxacin exhibited lower solubility and stronger taste at 10 mg/mL than levofloxacin. Ofloxacin is 2-fold less potent that levofloxacin, and lomefloxacin and pefloxacin are 4-fold less potent. Higher concentrations of these antibiotics have the preferred potency and administration times under 15 minutes.

In a separate study, conducted in a similar manner, norfloxacin was tested and found to have a solubility, taste and potency profile very similar to gatifloxacin, with the exception of significantly less activity against the gram-positive pathogens.

Taste Testing of Aerosol Salt Formulations of Levofloxacin and Gemifloxacin

Based on the results of the above studies, levofloxacin, and its racemate ofloxacin, as well as gemifloxacin, and to a lesser extent gatifloxacin and norfloxacin are amenable to aerosol administration for pulmonary antibacterial treatment. To further test the taste and acute tolerability (cough sensation and cough) properties of levofloxacin and gemifloxacin, several formulations were prepared with different organic and inorganic acids and tested in the manner described above. Solutions were prepared by first adding 500 mg levofloxacin to 10 ml of water or adding 500 mg of gemifloxacin to 20 ml of saline (due to solubility limitations), titrating the pH to ~6.5 with HCl or organic acid, then adjusting the osmolality of levofloxacin containing solutions to 300 mOsmol/kg with sodium chloride. The formulations tested are shown in Table 14.

These formulations were tested by a total of three healthy human volunteers in the same manner as described above, at a levofloxacin concentration of 50 mg/mL, and a gemifloxacin concentration of 25 mg/mL, in a carefully controlled, head-to-head, fully blinded test. Results are shown in Table 15 and 16.

These results demonstrate that hydrochloric acid, citric acid and ascorbic acid formulations of levofloxacin have superior taste and tolerability compared to the acetic acid, lactic acid and tartaric acid formulations of levofloxacin. Furthermore, these levofloxacin formulations have superior taste and tolerability over the equivalent gemifloxacin formulations. With respect to gemifloxacin, the citric acid formulation had superior taste and tolerability compared to the HCl and ascorbic acid formulations of gemifloxacin, and with further formulation refinement, would be amenable to aerosol administration.

TABLE 14

Levofloxacin and Gemifloxacin Formulations.

| Fluoroquinolone | Acid | Conc (mg/mL) | pH | Osmolality (mOsm/kg) |
|---|---|---|---|---|
| Levofloxacin | HCl | 50 | 6.5 | 181 |
| Levofloxacin | Acetic | 50 | 6.41 | 273 |
| Levofloxacin | Citric | 50 | 6.45 | 286 |
| Levofloxacin | Lactic | 50 | 6.42 | 286 |
| Levofloxacin | Ascorbic | 50 | 6.50 | 278 |
| Levofloxacin | Tartaric | 50 | 6.35 | 286 |
| Gemifloxacin | HCl | 25 | 5.6 | 330 |
| Gemifloxacin | Citric | 25 | 5.7 | 363 |
| Gemifloxacin | Ascorbic | 25 | 5.9 | 347 |

TABLE 15

Aerosol Taste and Tolerability of Levofloxacin Formulations at 50 mg/mL.

| | Taster | | |
|---|---|---|---|
| Acid | 1 | 2 | 3 |
| HCl | Moderate bitter taste | Bitter taste, cough sensation | Bitter taste |
| Acetic Acid | Very acidic taste | Strong acidic taste, cough sensation | Acidic taste, after taste |
| Citric Acid | Mild after taste, slightly sweet | Mild taste, sweet | Mild after taste |
| Lactic Acid | Strong bitter taste, aftertaste | Mild taste, after taste, slight cough | Bitter, mild after taste |
| Ascorbic Acid | Mild taste, slight acidity | Mild taste | Little taste or after-taste |
| Tartaric Acid | Very bitter, strong after taste | Strong bitter taste, bitter after taste | Bitter taste |

TABLE 16

Taste and Tolerability of Gemifloxacin Formulations at 25 mg/mL.

| | Taster | | |
|---|---|---|---|
| Acid | 1 | 2 | 3 |
| Hydrochloric Acid | Metallic taste, strong after taste | Slight bitter taste | Bitter taste, slightly metallic |
| Citric Acid | Slightly sweet | Mild cough, slightly bitter | Very mild taste, no after taste |
| Ascorbic Acid | Mild taste | Cough, mild bitter after taste | Slightly bitter, mild after taste |

Taste Testing of Additional Aerosol Levofloxacin Formulations

To further test the taste and tolerability properties of additional levofloxacin excipient combinations in a systematic manner, a series of formulations were prepared and tested. The formulations are listed in Table 17. They included sugars, salts, sweeteners and other excipients prepared by mixing levofloxacin with water, adding the excipients listed in Table 17, and titrating if necessary to the desired pH with dilute HCl, Osmolality was not optimized for these studies. However, osmolality was determined using an Advanced Instruments Model 3250 Osmometer. This measurement, made on 250 μL of sample, relies on freezing point depression to determine osmolality.

These formulations were tested in a total of three healthy human volunteers in a series of tests (A-G) in the same manner as described above, in a carefully controlled, head-to-head, fully blinded manner. All tests were performed in a fully blinded fashion. Results of the tests (Tables 19-25) are described below. The following scoring system was used (Table 18).

Test A: Taste Testing of Sweeteners Divalent Metal Salts, and Surface Active Agents.

This test included sweeteners, calcium and magnesium salts, and surface active agents (i.e., glycerin and PS-80). As shown in Table 17, formulations containing the sweeteners shown are mildly bitter and have metallic taste. The artificial sweeteners appeared to produce a bitter taste that is distinct from the bitterness otherwise observed. Most significantly, the formulation containing $CaCl_2$ had the most improved taste relative to control ($MgCl_2$ was not tested in this experiment) (Table 19).

Test B: Taste Testing of Mono- and Disaccharides in the Presence of Calcium Chloride.

All of the formulations screened in this experiment were well tolerated and tasted better than the control sample. Formulations containing both the calcium salt and sugar performed better than either one alone, suggesting that these compounds improve taste through different mechanisms. Of these formulations, 5% $CaCl_2$+7.5% glucose performed best. Note that the lactose is present at a lower concentration than the other sugars (Table 20).

TABLE 17

Levofloxacin Formulations Containing Various Excipients.

| Fluoroquinolone | Conc (mg/mL) | Excipients | pH | Osmolality (mOsm/kg) |
|---|---|---|---|---|
| Levofloxacin | 50 | Control A (0.225% NaCl) | 6.50 | 180 |
| Levofloxacin | 50 | Aspartame (0.1%) | 6.49 | 175 |
| Levofloxacin | 50 | Sucralose (0.1%) | 6.49 | 178 |
| Levofloxacin | 50 | Glucose (5%) | 6.5 | 380 |
| Levofloxacin | 50 | Sucrose (7.5%); NaCl (0.225%) | 6.51 | 329 |
| Levofloxacin | 50 | Glycerin (5%) | 6.48 | 880 |
| Levofloxacin | 50 | PS-80 (0.1%) | 6.51 | 189 |
| Levofloxacin | 50 | $CaCl_2$ (5%) | 6.10 | 784 |
| Levofloxacin | 50 | $MgSO_4$ (5%) | 6.41 | 73 |
| Levofloxacin | 50 | Control - B-E (0.225% NaCl) | 6.51 | 182 |
| Levofloxacin | 50 | $CaCl_2$ (5%) | 6.1 | 735 |
| Levofloxacin | 50 | $CaCl_2$ (5%), Sucrose (7.5%) | 6.10 | 958 |
| Levofloxacin | 50 | $CaCl_2$ (5%), Glucose (7.5%) | 6.10 | 1174 |
| Levofloxacin | 50 | $CaCl_2$ (5%), Glucose (7.5%) | 5.25 | 1246 |
| Levofloxacin | 50 | $CaCl_2$ (5%), Lactose (5%) | 6.07 | 864 |
| Levofloxacin | 50 | $MgCl_2$ (5%) | 5.90 | 600 |
| Levofloxacin | 50 | $MgCl_2$ (5%), Sucrose (7.5%) | 5.98 | 815 |
| Levofloxacin | 50 | $MgCl_2$ (5%), Glucose (7.5%) | 5.98 | 999 |
| Levofloxacin | 50 | $MgCl_2$ (5%), Glucose (7.5%) | 5.04 | 1035 |
| Levofloxacin | 50 | $MgCl_2$ (5%), Lactose (5%) | 5.96 | 697 |
| Levofloxacin | 50 | $MgSO_4$ (5%), Sucrose (7.5%) | 6.20 | 433 |
| Levofloxacin | 50 | $MgSO_4$ (5%), Glucose (7.5%) | 6.21 | 625 |
| Levofloxacin | 50 | $MgSO_4$ (5%), Glucose (7.5%) | 5.40 | 660 |
| Levofloxacin | 50 | $MgSO_4$ (5%), Lactose (5%) | 6.18 | 387 |
| Levofloxacin | 50 | Control F-G (0.45% NaCl) | 6.5 | 221 |
| Levofloxacin | 50 | Glucose (5%) | 6.5 | 376 |
| Levofloxacin | 50 | Sucrose (5%) | 6.5 | 240 |
| Levofloxacin | 50 | Lactose (5%) | 6.62 | 241 |
| Levofloxacin | 50 | Lactose (2.5%) | 6.55 | 170 |
| Levofloxacin | 50 | $CaCl_2$ (5%) | 6.10 | 735 |
| Levofloxacin | 50 | $CaCl_2$ (5%), Lactose (5%) | 6.21 | 1037 |
| Levofloxacin | 50 | $CaCl_2$ (2.5%), Lactose (5%) | 6.36 | 565 |
| Levofloxacin | 50 | $CaCl_2$ (2.5%), Lactose (2.5%) | 6.41 | 370 |
| Levofloxacin | 50 | $CaCl_2$ (1.25%), Lactose (2.5%) | 6.64 | 227 |
| Levofloxacin | 50 | $CaCl_2$ (0.625%), Lactose (2.5%) | 6.06 | 163 |

TABLE 18

Taste Test Scoring System.

| Score | Taste | Tolerability |
|---|---|---|
| 1 | Comparable to saline | No cough sensation, no cough |
| 1.25 | Slightly more taste than saline | Slight cough sensation, no cough |
| 1.5 | Mild bitter/metallic taste | Cough sensation, slight cough |
| 1.75 | Between 1.5 and 2 | — |
| 2 | Moderate bitter/metallic taste | Cough sensation, moderate cough |
| 2.25 | Between 2 and 2.5 | — |
| 2.5 | Strong bitter/metallic taste | — |
| 2.75 | Between 2.5 and 3 | — |
| 3 | Very strong bitter/metallic taste | Cough sensation and strong cough |
| 4 | Very strong bitter/metallic taste and other unacceptable taste | Cough sensation, strong cough and other irritation |

TABLE 19

Taste and Tolerability of Levofloxacin Formulations Containing Sweeteners, Divalent Metal Salts, and Surface Active Agent.

| | Taster | | | | | | | |
|---|---|---|---|---|---|---|---|---|
| | 1 | | 2 | | 3 | | Median | |
| Excipients | Taste | Tol. | Taste | Tol. | Taste | Tol. | Taste | Tol. |
| Aspartame (0.1%) | 2 | 1.25 | 2 | 1 | 2 | 1 | 2 | 1 |
| Sucralose (0.1%) | 2 | 1 | 1.75 | 1 | 2 | 1 | 2 | 1 |
| Sucrose (7.5%); NaCl (0.225%) | 2 | 1 | 2.25 | 1 | 2 | 1 | 2 | 1 |
| Glucose (5%) | 1.5 | 2 | 2.5 | 1 | 2 | 1 | 2 | 1 |
| Glycerin (5%) | 2.25 | 1 | 2.25 | 1 | 2.5 | 1 | 2.3 | 1 |
| PS-80 (0.1%) | 1.75 | 1 | 2.25 | 1 | 2.5 | 1 | 2.3 | 1 |
| $CaCl_2$ (5%) | 1.25 | 1 | 1.5 | 1 | 2 | 1 | 1.5 | 1 |
| $MgSO_4$ (5%) | 1.5 | 1.5 | 2.5 | 2.5 | 2.5 | 1 | 2.5 | 1.5 |
| Control - A (0.225% NaCl) | 3 | 1 | 3 | 1 | 2.5 | 1 | 3 | 1 |

TABLE 20

Taste and Tolerability of Levofloxacin CaCl₂ Formulations.

| | Taster | | | | | | | |
| | 1 | | 2 | | 3 | | Median | |
| Excipients | Taste | Tol. | Taste | Tol. | Taste | Tol. | Taste | Tol. |
|---|---|---|---|---|---|---|---|---|
| CaCl₂ (5%) | 1.75 | 1 | 2 | 1 | 2.75 | 1 | 2 | 1 |
| Sucrose (5%) | 2 | 1 | 2 | 1 | 2 | 1 | 2 | 1 |
| CaCl2 (5%)₂, Sucrose (7.5%) | 1.75 | 1 | 1.75 | 1 | 1.5 | 1 | 1.8 | 1 |
| CaCl₂ (5%), Glucose (7.5%) | 1.5 | 1 | 1.5 | 1 | 2 | 1 | 1.5 | 1 |
| CaCl₂ (5%), Lactose (5%) | 1 | 1 | 1.75 | 1 | 2 | 1 | 1.8 | 1 |
| Control B-E (0.225% NaCl) | 3 | 1 | 2.5 | 1 | 3 | 1 | 3 | 1 |

Test C: Taste Testing of Mono- and Disaccharides in the Presence of Magnesium Chloride.

As above, all of the formulations screened in this experiment were well tolerated and tasted better than the control sample. Formulations containing both the magnesium salt and lactose appeared to perform slightly better than either one alone. This experiment confirms that combining divalent metal salts and simple sugars are effective at improving taste (Table 21).

TABLE 21

Taste and Tolerability of Levofloxacin MgCl₂ Formulations.

| | Taster | | | | | | | |
| | 1 | | 2 | | 3 | | Median | |
| Excipients | Taste | Tol. | Taste | Tol. | Taste | Tol. | Taste | Tol. |
|---|---|---|---|---|---|---|---|---|
| MgCl₂ (5%) | 1.5 | 1 | — | — | 1.75 | 1 | 1.6 | 1 |
| MgCl₂ (5%), Sucrose (7.5%) | 1.5 | 1 | 1.75 | 1 | 2 | 1 | 1.8 | 1 |
| MgCl₂ (5%), Glucose (7.5%) | 1.25 | 1 | 2.25 | 1 | 2 | 1 | 2 | 1 |
| MgCl₂ (5%), Lactose (5%) | 1 | 1 | 1.5 | 1 | 1.5 | 1 | 1.5 | 1 |
| Control B-E (0.225% NaCl) | 2.25 | 1 | — | — | 2.75 | 1 | 2.5 | 1 |

Test D: Taste Testing of Mono- and Disaccharides in the Presence of Magnesium Sulfate.

As with calcium and magnesium chloride, formulations containing magnesium sulfate and glucose, sucrose or lactose tasted better than the control sample. This experiment reconfirms that combining divalent metal salts and simple sugars improve taste (Table 22).

TABLE 22

Taste and Tolerability of Levofloxacin MgSO₄ Formulations.

| | Taster | | | | | | | |
| | 1 | | 2 | | 3 | | Median | |
| Excipients | Taste | Tol. | Taste | Tol. | Taste | Tol. | Taste | Tol. |
|---|---|---|---|---|---|---|---|---|
| MgSO₄, Sucrose | 1.5 | 2 | 1.5 | 1.25 | 1.5 | 1 | 1.5 | 1.3 |
| MgSO₄, Glucose | 1.5 | 2.75 | 2 | 2.5 | 1.5 | 1.5 | 1.5 | 2.5 |
| MgSO₄, Lactose | 1.25 | 2.25 | 1.75 | 1.25 | 1.75 | 1 | 1.8 | 1.3 |
| Control B-E (0.225% NaCl) | 2.25 | 1 | — | — | 3 | 1 | 2.6 | 1 |

Test E: Taste Testing of Divalent Metal Salts in the Presence of Glucose at Low and High pH.

In this experiment, the effect of glucose in combination with each of the three divalent cation salts on taste and tolerability was tested at low ($\leq 5.5$) and high ($\geq 6.0$) pH. Small but consistent improvements in taste were observed at the higher pH (Table 23).

TABLE 23

Taste and Tolerability of Levofloxacin CaCl$_2$ Formulations at Low Versus High pH.

| | Taster | | | | | | | |
|---|---|---|---|---|---|---|---|---|
| | 1 | | 2 | | 3 | | Median | |
| Excipients | Taste | Tol. | Taste | Tol. | Taste | Tol. | Taste | Tol. |
| CaCl$_2$ (5%), Glucose (7.5%), pH 6.1 | 1 | 1 | 1.5 | 1 | 2 | 1 | 1.5 | 1 |
| CaCl$_2$ (5%), Glucose (7.5%), pH 5.5 | 1.25 | 1 | 1.75 | 1 | 2.5 | 1 | 1.8 | 1 |
| MgCl$_2$ (5%), Glucose (7.5%), pH 6.0 | 1.25 | 1 | 2 | 1 | 2 | 1 | 2 | 1 |
| MgCl$_2$ (5%), Glucose (7.5%), pH 5.0 | 1.75 | 1 | 1.75 | 1 | 1.5 | 1 | 1.8 | 1 |
| MgSO$_4$ (5%), Glucose (7.5%), pH 6.2 | 1.25 | 2.25 | 2.25 | 1.75 | 1.5 | 1 | 1.5 | 1.8 |
| MgSO$_4$ (5%), Glucose (7.5%), pH 5.4 | 1.5 | 1.75 | 1.75 | 1.5 | 2 | 1 | 1.8 | 1.5 |
| Control B-E (0.225% NaCl) | 2 | 1 | — | — | — | — | — | — |

Test F. Taste Testing of Mono- and Disaccharides.

All of the formulations screened in this experiment were well tolerated and tasted better than the control sample. All three sugars at 5% were better than the control, lactose at 2.5% tasted better than the control, but not as good as at 5%. This experiment reconfirms that simple sugars improve taste (Table 24).

TABLE 24

Taste and Tolerability of Levofloxacin Sugar Formulations.

| | Taster | | | | | |
|---|---|---|---|---|---|---|
| | 1 | | 3 | | Median | |
| Excipients | Taste | Tol. | Taste | Tol. | Taste | Tol. |
| Glucose (5%) | 1.5 | 1.5 | 2 | 1 | 1.8 | 1.3 |
| Sucrose (5%) | 1.5 | 1.5 | 1.5 | 1 | 1.5 | 1.3 |
| Lactose (5%) | 1.75 | 1.25 | 2 | 1 | 1.9 | 1.1 |
| Lactose (2.5%) | 2.25 | 1.5 | 2 | 1 | 2.1 | 1.3 |
| Control F-G (0.45% NaCl) | 2.5 | 1 | 2.5 | 1 | 2.5 | 1 |

Test G. Taste and Tolerability of Levofloxacin CaCl$_2$ Formulations in the Presence of Lactose.

In this experiment, levofloxacin was formulated with varying concentrations of calcium chloride and lactose (Table 25). As noted through this series of experiments, all formulations containing divalent metal salts and sugar were improved with respect to taste and tolerability relative to the control formulation. Most importantly, 5% calcium chloride or 2.5% calcium chloride in the presence of 5% lactose were most effective at decreasing levofloxacin bitterness. Further decreases in the concentration of these excipients were less effective.

TABLE 25

Taste and Tolerability of Levofloxacin CaCl$_2$ Formulations in the Presence of Lactose.

| | Taster | | | | | |
|---|---|---|---|---|---|---|
| | 1 | | 3 | | Median | |
| Excipients | Taste | Tol. | Taste | Tol. | Taste | Tol. |
| CaCl$_2$ (5%) | 1.25 | 1 | 1.5 | 1 | 1.4 | 1 |
| CaCl$_2$ (5%), Lactose (5%) | 1.25 | 1 | 2 | 1 | 1.6 | 1 |
| CaCl$_2$ (2.5%), Lactose (5%) | 1.25 | 1 | 2 | 1 | 1.6 | 1 |
| CaCl$_2$ (2.5%), Lactose (2.5%) | 1.5 | 1 | 2.5 | 1 | 2 | 1 |
| CaCl$_2$ (1.25%), Lactose (2.5%) | 1.75 | 1 | 2 | 1 | 1.9 | 1 |
| CaCl$_2$ (0.625%), Lactose (2.5%) | 1.75 | 1.25 | 2 | 1 | 1.9 | 1.1 |
| Control F-G (0.45% NaCl) | 3 | 1 | 2.5 | 1 | 2.8 | 1 |

Example 3

Aerosol Levofloxacin Characterization in PARI LC Plus Jet Nebulizer

The following studies describe the potential for aerosolized delivery of levofloxacin to be administered to a patient via a jet nebulizer. To accomplish this task, a simple levofloxacin formulation was prepared and the aerosol was characterized in a jet nebulizer. The results of these studies are shown in the summary below.

Levofloxacin inhalation solution (55 mg/ml) was evaluated using a PARI LC Plus Air Jet Nebulizer with ProNeb Compressor. The emitted dose, particle size distribution and fine particle fraction were measured by cascade impaction using a Marple Miller Impactor. The above-mentioned parameters were used for evaluating the in vitro performance of aerosolized medications.

Marple Miller Study

Objective.

To determine the particle size distribution and estimate the amount of drug that a patient is likely to inhale (respirable fraction). A secondary objective was to estimate emitted dose, which is the amount of levofloxacin that exited the nebulizer.

Methods.

Formulation: 55 mg/ml levofloxacin, 120 mM chloride, 70 mM sodium, pH 6.7. Formulation established from maximum solubility permitting a 300 mg dosage in 6 ml and neutral pH. 5.5 ml of levofloxacin formulation was added to a PARI LC Plus Air-Jet Nebulizer with ProNeb Compressor. The nebulizer cup contained a total of 302 mg of levofloxacin. The nebulizer was connected inline with a Marple Miller Impactor (MMI), which was run with an airflow rate of 60 l/min. Each nebulizer (n=2) was run to dryness (no aerosol produced as judged by visual inspection for 15 minutes. Following aerosolization, the MMI was disassembled and levofloxacin was quantitatively extracted with mobile phase (90/10 ACN:water) from the USP entry port, each of the impactor collection cups (stages) and the glass fiber filter. Any remaining formulation in the nebulizer after aerosolization (cup and mouthpiece) was also quantified.

Results

As shown in Table 26, the total average amount recovered from the MMI experiments was 170.2 mg. The expected recovery was 302 mg. This represents a total recovery of ~57%, which does not meet the generally accepted specifications for impaction-based studies (85%-115% total recovery). This difference was found to be due to non-specific adherence of levofloxacin to the LC Plus nebulizer device. The average percent of drug exiting the nebulizer in fine particles was ~72%. Thus, the respirable emitted dose was 89.7 mg. Assuming that ~50% is not inhaled during normal tidal breathing, a total of ~40 mg may be deposited in the lung with this 300 mg dose. However, given the slow administration time with this device, competition with pulmonary clearance would likely prevent the accumulation of sufficient levofloxacin to meet the required minimal concentration for "rapid administration, high concentration" dosing needed for maximum fluoroquinolone antimicrobial activity and resistance prevention.

TABLE 26

Marple Miller Impactor Data Set.

| Sample ID | A Emitted Dose (mg) | B Amount of Drug Remaining in Nebulizer Cup (mg) | A + B Amount of Drug Recovered (mg) | Percent of Total Drug Exiting Nebulizer in Fine Particle Fraction (% <5 um) |
|---|---|---|---|---|
| Levo Run 1 | 134.70 | 45.00 | 179.70 | 73.5 |
| Levo Run 2 | 114.40 | 46.30 | 160.70 | 70.4 |
| Average | 124.6 | 45.7 | 170.2 | 72.0 |

Example 4

Animal Models and Evaluation of Fluoroquinolones and Fluoroquinolone Formulations Pharmacokinetic Model Six rats per study are given a single slow bolus intravenous dose of 10 mg/kg via the lateral tail vein or are given a single microspray aerosol dose of 10 mg/kg using a microspray aerosol generation device (PennCentury, Philadelphia, Pa.). Blood samples are taken at various times over 3 hours to determine the plasma pharmacokinetic parameters. Two rats are sacrificed at 0.5, 1.5 and 3 hours after dosing to determine lung, broncheoalveolar lavage (BAL), and epithelial lining fluid (ELF) levels. The plasma and tissue concentrations are determined by an HPLC method and the data are then fit using WinNonlin. Data are shown in Table 27.

Efficacy Model

P. aeruginosa strain PAM 1723 is grown in Mueller-Hinton Broth (MHB) at 35° C. under constant aeration, after 16 hours, the inoculum is sub-cultured into fresh MHB and allowed to regrow at 35° C., under constant aeration, for 4 hours. The inoculum is adjusted to ca. $5 \times 10^6$ CFU/ml by correlation of absorbance at 600 nm with predetermined plate counts. Male CFW mice (4-6 weeks old, N=4/group) are made neutropenic by the intraperitoneal injection of 150 mg/kg cyclophosphamide (Cytoxan, Mead Johnson, Princeton, N.J.) on days 1 and 4. On day 5, mice are infected by an intratracheal instillation of 0.05 ml of inoculum while under isoflurane anesthesia (5% isoflurane in oxygen running at 4 L/min). Two hours after infection, mice are given either intraperitoneal or intratracheal doses of each fluoroquinolone at a dose of 25 mg/kg. Mice are sacrificed 1 and 4 hours after treatment, their lungs removed, homogenized and plated to determine colony counts. Data are shown in Table 28.

TABLE 27

Pharmacokinetic Modeling.

| Drug | Route | Dose (mg/kg) | Serum AUC (0-inf) | Serum t½ | ELF AUC (0.5-3 h) | F, % from Lung vs. IV |
|---|---|---|---|---|---|---|
| Levofloxacin | IV | 10 | 3.8 | 0.5 | 10.5 | NA |
| Levofloxacin | IT | 10 | 3.28 | 0.4 | 12.07 | 86% |
| Ciprofloxacin | IV | 10 | 2.56 | 0.53 | ND | NA |
| Ciprofloxacin | IT | 3.3 | 0.8 | 0.93 | 194 | 82% |
| Clinafloxacin | IT | 10 | 3.2 | 0.74 | 30.8 | |
| Gatifloxacin | IV | 10 | 5.31 | 1.06 | 5.32 | |
| Gatifloxacin | IT | 10 | 5.83 | 1.13 | 54.7 | 100% |
| Norfloxacin | IV | 10 | 4.65 | 1.21 | 3.27 | |
| Norfloxacin | IT | 10 | 4.46 | 1.13 | 41.7 | 100% |
| Gemifloxacin | IV | 8 | 4.54 | 1.04 | 3.72 | |
| Gemifloxacin | IT | 10 | 5.86 | 1.68 | 536.5 | 86% |
| Tobramycin | IV | 10 | 15.7 | 0.5 | 27.6 | NA |
| Tobramycin | IT | 10 | 13.82 | 1.0 | 5152.0 | 81% |

In rat pharmacokinetic studies, aerosol administration of fluoroquinolones results in increased ELF AUCs from 0.5-3 hours for all fluoroquinolones tested, as well as tobramycin, suggesting that the aerosol route of administration will produce increased efficacy against lung infections.

In a mouse lung infection model, the increased efficacy, suggested by the pharmacokinetic studies rats, was confirmed. For all fluoroquinolones tested, the aerosol route of administration (intratracheal, or IT), produced larger reductions in bacterial counts than the intraperitoneal (IP) route of administration, suggesting that observed increased efficacy was due to high local concentrations produced by direct aerosol administration.

TABLE 28

Efficacy Modeling.

| Drug | Route[a] | Dose (mg/kg) | DeltaLOG CFU 1 hr[b] | DeltaLOG CFU 4 hr[b] |
|---|---|---|---|---|
| Levofloxacin | IP | 25 | −1.00 | −0.52 |
| Levofloxacin | IT | 25 | −1.97 | −1.28 |
| Gemifloxacin | IP | 25 | −0.28 | −0.32 |
| Gemifloxacin | IT | 25 | −2.45 | −1.81 |
| Levofloxacin | IP | 25 | −1.40 | −1.14 |
| Levofloxacin | IT | 25 | −2.48 | −1.45 |
| Gemifloxacin | IP | 25 | −0.74 | −0.71 |
| Gemifloxacin | IT | 25 | −3.20 | −2.28 |
| Clinafloxacin | IP | 25 | −1.32 | −1.33 |
| Clinafloxacin | IT | 25 | −2.86 | −2.47 |
| Tobramycin | IP | 5 | −0.70 | 0.29 |
| Tobramycin | IT | 5 | −1.59 | −0.94 |
| Ciprofloxacin | IP | 25 | −1.59 | −0.41 |
| Ciprofloxacin | IT | 25 | −2.32 | −1.45 |
| Gatifloxacin | IP | 25 | −0.34 | −0.02 |
| Gatifloxacin | IT | 25 | −1.48 | −2.11 |
| Clinafloxacin | IP | 10 | −0.96 | −1.39 |
| Clinafloxacin | IT | 10 | −2.71 | −2.40 |
| Sparfloxacin | IP | 25 | −0.85 | 0.09 |
| Sparfloxacin | IT | 25 | −1.56 | −0.81 |
| Tosufloxacin | IP | 25 | 0.00 | 1.33 |
| Tosufloxacin | IT | 25 | −0.48 | −0.24 |

[a]Route of drug administration.
[b]Time post-drug administration.

Example 5

Aerosol Levofloxacin Characterization in the PARI eFlow Nebulizer

Laser Particle Sizing

Device performance was characterized by measuring the size of the particles emitted. By non-limiting example, particle sizing of emitted aerosol of Levofloxacin solution may be conducted with a Malvern Spraytec particle sizer under the following conditions. Ambient conditions are controlled to maintain a room temperature of between 23.0° C. and 24.0° C. and relative humidity of 42% to 45%. Levofloxacin at 25 mg/ml was loaded into 2 PARI eFlow Nebulizers fitted with the "40" nebulizing heads. Software for the Malvern Spraytec particle sizer is programmed to calculate the following information. A) Volume Mean Diameter (VMD), the volume mean of the particles passing across the beam of the laser. B) Geometric Standard Deviation (GSD), diameter 84th percentile/diameter 50th percentile. C) % of particles≦5 microns, the percent of the number of particles less than 5 microns or % of particle>1 micron and <7 microns, the percent of the number of particles between 1 and 7 microns.

The device was loaded with 2 ml Levofloxacin at 25 mg/ml. The mouthpiece of the device was positioned with the tip of the mouthpiece 2 cm from the center of the beam on the x axis and as close to the optical lens of the laser as possible on the y axis. Ambient conditioned, bias flow was provided through the nebulizer in an amount to obtain a total nebulizer flow of 20 LPM. Ambient conditioned, bias flow was provided through the nebulizer in an amount to obtain a total nebulizer flow of 20 LPM. The nebulizer was turned on and allowed to run continuously for 1 minute prior to measuring. The measurement sequence was begun after 1 minute and measurements are made continuously for 1 minute in 1 second intervals. At the end of the measurement phase, these 60 records are averaged for VMD, GSD and %≦5 micron and %>1 and <7 micron. Finally, the nebulizer was weighed for determination of output rate.

Breath Simulation Studies

Device performance was measured under conditions similar to natural inhalation by using a breath simulator PARI Compas breath Simulator programmed to use the European Standard pattern of 15 breaths per minute with an inspiration to expiration ratio of 1:1. Such measurements was performed under ambient conditions that can be controlled to maintain a room temperature of between 23.0° C. and 24.0° C. and relative humidity of 42% to 45%. For this experiment, the PARI eFlow device was loaded with 4 ml Levofloxacin solution at 25 mg/ml.

Breathing simulation was commenced, and the nebulizers begun. The devices were allowed to run continuously until nebulization ceases. The duration is timed from the beginning of nebulization. Following nebulization, the inspiratory and expiratory filters were individually washed in a known amount of solvent (dH$_2$O). The nebulizer cup is also washed individually. For quantitation, the individual washings were assayed via spectrophotometry at a wavelength of 290 nanometers and the resultant concentration converted to content. Using this quantitative data, the following analysis was made. A) Inspired dose (ID), the total amount of drug assayed from the inspiratory filter. B) Residual dose (RD), the amount of drug assayed from the nebulizer at the end of nebulization. C) Fine Particle Dose (FPD), the ID multiplied by the respirable fraction (for example, % particles≦5 microns VMD depending on the method used to determine the size of the particles emitted from the selected device). D) Duration, time from the beginning to the end of nebulization. E) Respirable Delivered Dose (RDD), % ID that is, for example, ≦5 microns VMD.

The results in Table 29 indicate that a 100 mg dose of levofloxacin likely deposits ~34 mg fluoroquinolone in the pulmonary compartment in ~4 min using the PARI eFlow device (Table 29) compared to the 300 mg dose from the PAR LC Plus device delivering an equivalent dose in >15 min. From the "rapid administration, high concentration" dosing and delivery model described herein, while the 15 min delivery time from the LC Plus will likely fail, a 4 min administration time for 35-40 mg levofloxacin may meet the criteria for maximum fluoroquinolone activity. However, increasing the drug concentration to enable more rapid administration (e.g. 50 mg/ml in a 2 ml dosing delivering 35-40 mg levofloxacin in ~2 min) will more likely meet these minimal requirements. Moreover, shorter administration times will improve patient dosing compliance. In addition, it should be noted that hypotonic solutions of levofloxacin at concentrations greater than 10 mg/ml are poorly tolerated for inhalation.

TABLE 29

| Levofloxacin Aerosol Properties (100 mg Loading Dose). | | | | | | | | |
|---|---|---|---|---|---|---|---|---|
| Duration | Residual | Inspired | FPD (%) | | RDD (mg) | | VMD | GSD | Osmo |
| (minutes) | Dose | Dose | ≤5u | 1-7u | ≤5u | 1-7u | um | um | mOs/kg |
| 3.9 ± 0.1 | 24.8 ± 3.4 | 61.1 ± 1.6 | 54.9 | 73.8 | 33.5 | 45.1 | 4.7 | 1.6 | 67 ± 1.0 |

Example 6

Tolerability of Aerosol Levofloxacin in a Healthy Human Subject

Methods

In a single subject, healthy volunteer the feasibility of delivering levofloxacin as an aerosol was established using either an Aerogen Clinical vibrating mesh device creating a 3.4 micron volumetric mean diameter (VMD) particle, or ~2 micron MMAD (hereinafter "Aerogen Small"), or using a PARI eFlow nebulizer producing a ~4.7 micron VMD particle (hereinafter "PARI Large"). Levofloxacin was tested at a concentration of 4.25 mg/mL or 18.75 mg/mL at doses of 10 mg, 35 mg and 55 mg, in isotonic solution.

Results

In the first test, 6 mL of the 4.25 mg/mL solution was inhaled using the Aerogen Small nebulizer. The estimated RDD based on separate in vitro device characterization studies using breath simulation was estimated to be 10 mg. Delivery time was 22 minutes. No discernable adverse effects were observed in the throat, airway or lungs, during or after administration, including cough sensation or cough, and there was only a slight chemical taste during and after administration. No adverse effects or taste were observed over a 30 minute monitoring period following drug administration. At this low concentration and dose, and slow rate of administration, levofloxacin was well tolerated.

In the second test, 4 ml of the 18.75 mg/mL solution was inhaled using the Aerogen Small nebulizer. The estimated RDD based on separate in vitro device characterization studies using a breath simulator was 35 mg. Delivery time for administration of the drug was 14 minutes. Despite the increased dose, the acute tolerability was very comparable to the first test both during and after administration. The taste, which was stronger, was the solution had a more the bitter/metallic chemical taste characteristic of levofloxacin. The taste was most discernible for a period of a few minutes after the end of administration, again a characteristic of levofloxacin.

In the third test, 4 mL of the 18.75 mg/mL solution was inhaled using the PARI Large device. The estimated RDD based on separate in vitro device characterization studies was ~55 mg (using the <5 microns FPD definition). Delivery time for administration of the drug was ~5 minutes. Despite the significantly increased particle size and delivery rate for drug compared to test 2, no adverse effects in the throat, airway or lungs, other than the acute effects of taste noted above, were experienced, including cough sensation or coughing, throughout the dosing period and for a 30 minute observation period following delivery of the dose. Urinary recovery of the drug, which is an accurate measure of exposure, confirms that the projected respirable dose of approximately 55 mg was successfully delivered.

These results demonstrate the feasibility of aerosol delivery of levofloxacin in a human subject at the intermediate concentrations tested, and suggest that higher concentrations and doses, properly formulated for tolerability and taste are achievable.

Example 7

Levofloxacin Micronization

Levofloxacin Micronization

Dry powder levofloxacin base may be micronized for high local concentration exposure therapy, taste-masking or AUC shape-enhanced delivery of levofloxacin using dry powder pulmonary administration. Other approaches currently being investigated include spray-dry and in situ micronization techniques. This approach may also be used with other fluoroquinolone antibiotics including, without limitation ofloxacin, lomefloxacin, pefloxacin, ciprofloxacin, gatifloxacin, gemifloxacin, moxifloxacin, tosufloxacin, pazufloxacin, rufloxacin, fleroxacin, balofloxacin, sparfloxacin, trovafloxacin, enoxacin, norfloxacin, clinafloxacin, grepafloxacin, sitafloxacin, marbofloxacin, orbifloxacin, sarafloxacin, danofloxacin, difloxacin, enrofloxacin, garenoxacin, prulifloxacin, olamufloxacin, DX-619, TG-873870 and DW-276.

Description

To characterize the feasibility of micronizing levofloxacin base, the following studies were performed.

Micronization

Levofloxacin drug powder was micronized using a jet mill. Following micronization the drug powder was collected in two fractions, one between 5-6 micron and a finer fraction.

Powder Characterization

The drug was characterized for particle size and particle size distribution, before and after milling using laser diffraction technology. Any changes in the physical form of the drug were evaluated by Differential Scanning Calorimetery (DSC) and X-Ray diffraction (XRD). Particle morphology was studied using Scanning Electron Microscopy (SEM). The equilibrium moisture content of the drug powder before and after micronization was determined by Thermogravimetric Analysis (TGA) or Karl Fischer. Any degradation of the drug substance during micronization was evaluated by HPLC. The separation conditions were used to determine if any new peaks are formed after micronization.

Micronization

Experimental Methodology

Two batches of Levofloxacin were micronized using a jet mill (Glen Mills). Method development was performed to determine the micronization pressure required to achieve the required size fractions between a) 5-6 micron and b) 2-3 micron. The particle size of levofloxacin was determined by Sympatec HELOS laser diffraction particle size analyzer.

Results

Figure 12:
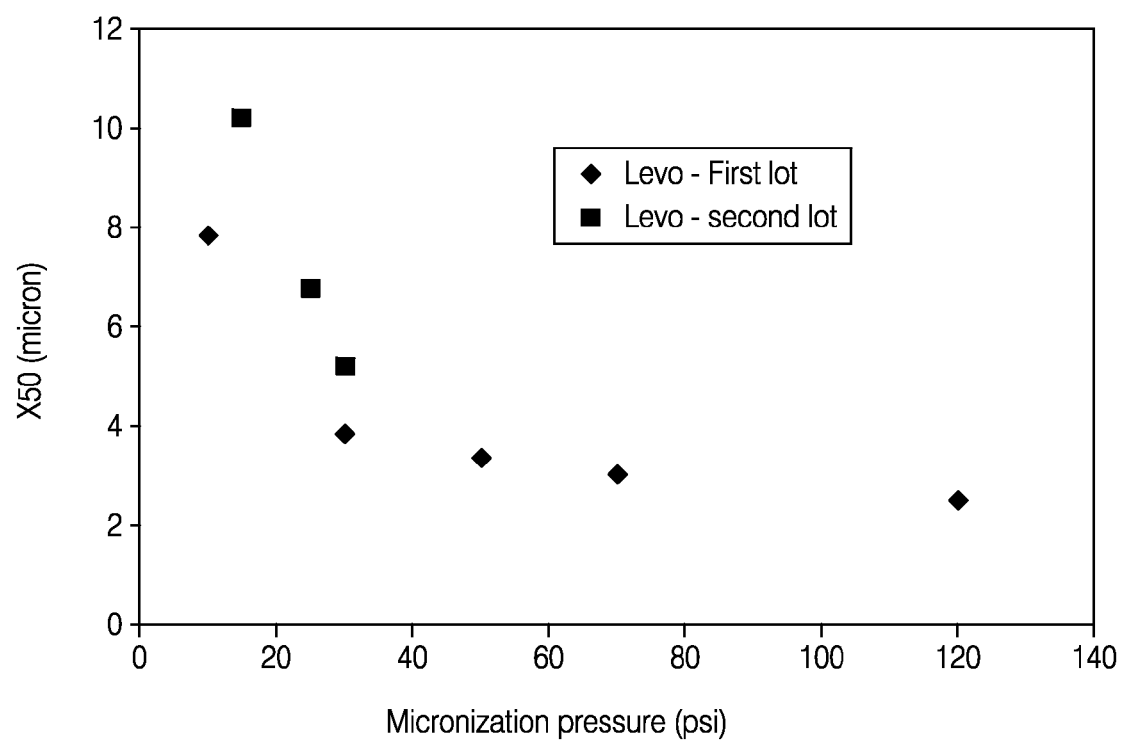
FIG. 12 is a graph relating the micronization pressure used to micronized dry powder levofloxacin vs. mean Levofloxacin dry powder particle size.

FIG. 12 shows the plot of mean particle diameter (×50) Vs micronization pressure. The first batch of Levofloxacin showed a mean particle diameter of 10.6 micron before micronization. From the plot it is seen that particle size decreased as the micronization pressure increased. A pressure of about 120 psi was required to achieve a size of 2.5 micron. With the second batch of levofloxacin, having a mean particle size of 12.99 micron before micronization, a pressure of 30 psi was required to achieve a particle size of 5.2 micron.

Powder Characterization
Differential Scanning Calorimetry
Experimental Methodology Differential Scanning Calorimetry of pre-micronized as well as micronized levofloxacin (mean particle size 2.5 micron) was performed using TA Instrument DSC Q1000. 1-2 mg of each sample was weighed into pan, sealed and heated at 10° C./min from 25° C. to 300° C. under nitrogen.

Results

Figure 13A:
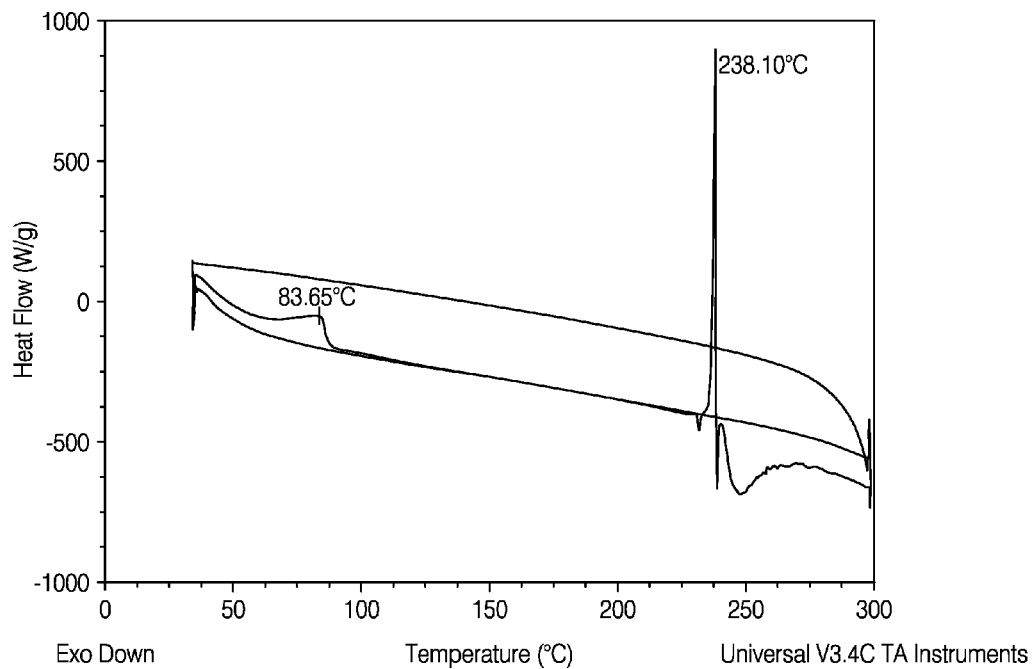
FIG. 13 is a graph showing the DSC profile of pre-micronized and micronized dry powder Levofloxacin.
Figure 13B:
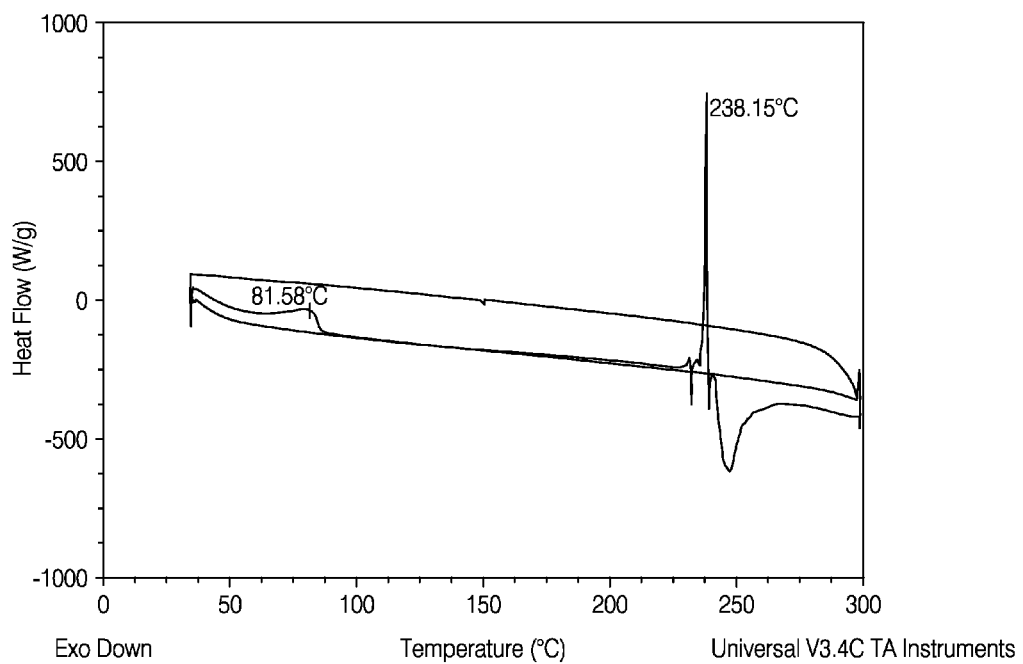

The DSC profiles of the pre-micronized and micronized levofloxacin are shown as FIG. 13. There was no difference in the DSC profiles of micronized compared to pre-micronized levofloxacin.

Experimental Methodology

The powders (micronized and pre-micronized) were adhered to double-sided carbon tabs on aluminum stubs, which were then coated with gold-palladium. Photomicrographs were taken of several different areas of the powder on the stub using a Scanning electron microscope.

Results

Figure 14A:
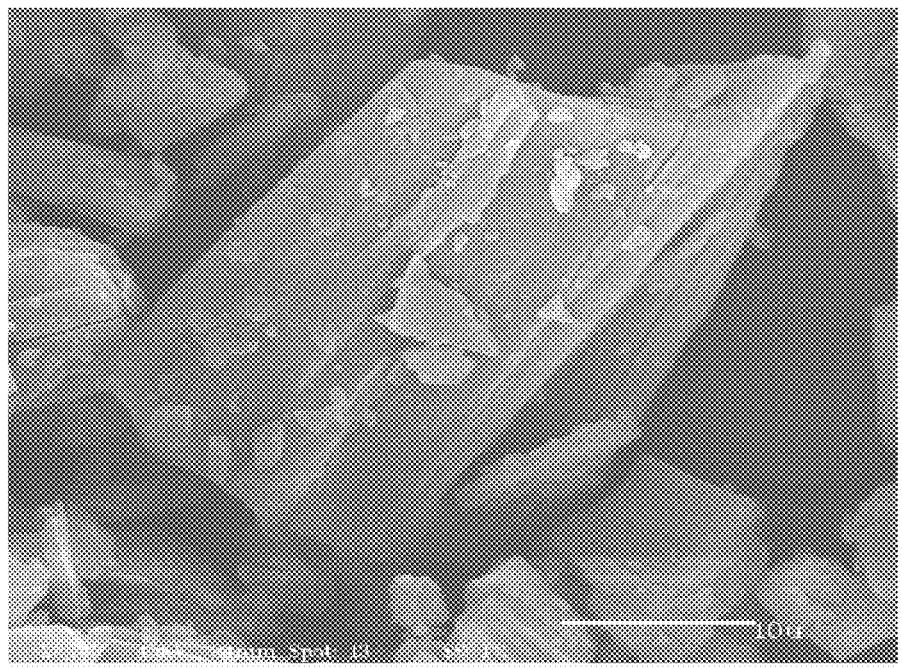
FIG. 14A is a graph showing SEM photomicrographs of pre-micronized dry powder Levofloxacin.
Figure 14B:
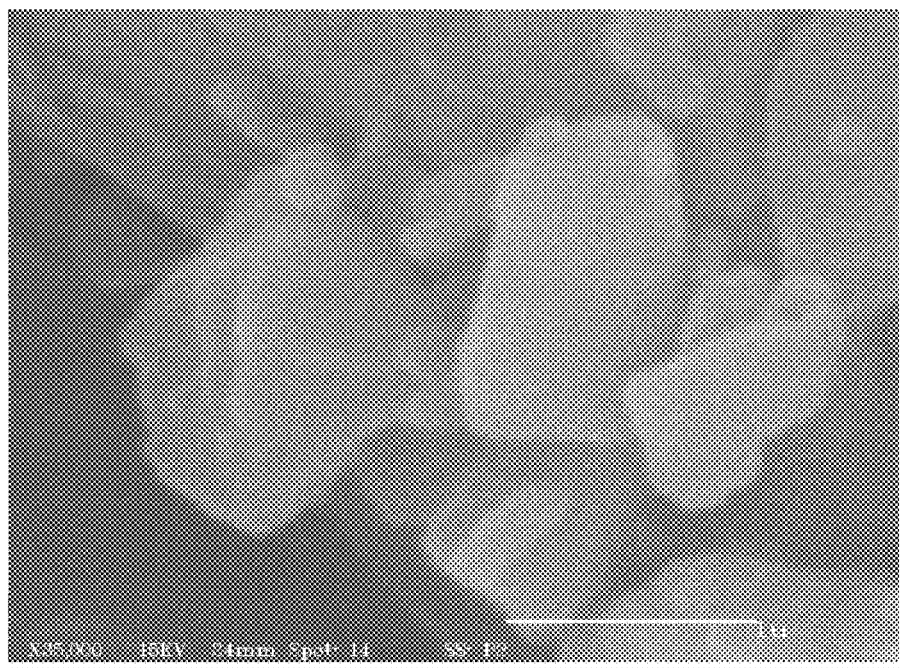
FIG. 14B is a graph showing SEM photomicrographs of micronized dry powder Levofloxacin.

Representative Scanning electron micrographs of the pre-micronized and micronized levofloxacin are shown in FIGS. 14A and 14B. Crystals of levofloxacin are plate like before micronization. This shape is retained after micronization.

Experimental Methodology

A thin layer of powder sample was mounted on a zero background plate in an XRD sample holder. Each sample was analyzed using a Scintag XDS 2000 Diffractometer under the following conditions:

Excitation source: Copper K α X-rays; Scan rate: 1° per minute
Voltage: 40 KV; Current: 35 mA.

Results

Figure 15A:
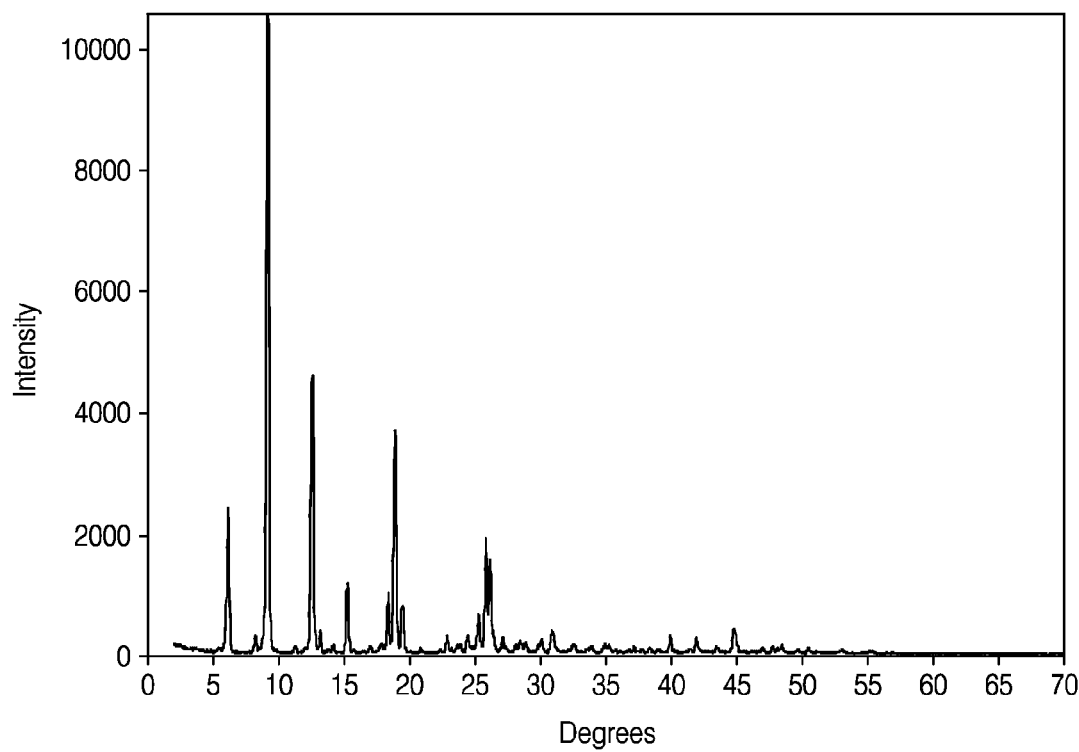
FIG. 15 is a graph showing X-ray diffraction of pre-micronized and micronized dry powder Levofloxacin.
Figure 15B:
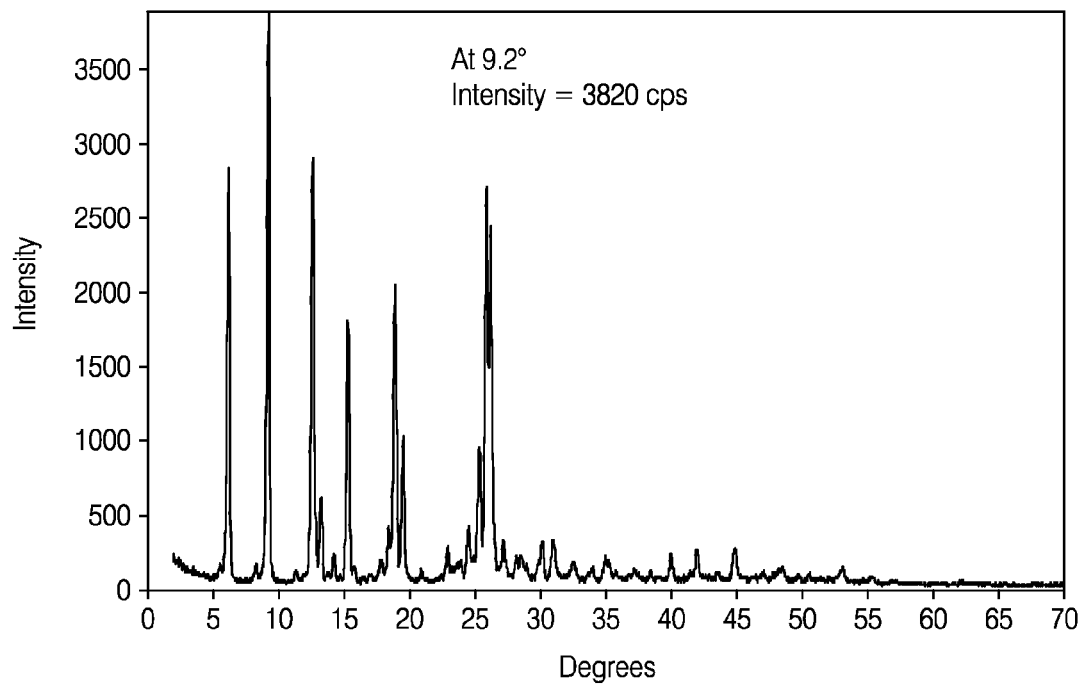

The X-ray diffraction plots of pre-micronized and micronized Levofloxacin are shown as FIG. 15. Intensity of diffracted peak at 9° is reduced after micronization. These results are in accordance to those reported in the literature for micronization of olanzapine (Stephenson G, A. The Rigaku Journal, 22 (2005): 2-15). The reduction in the relative intensities of the diffracted peaks might be due to formation of new faces to a crystal. The most developed face after micronization would be the one for which the intensity is maximally reduced.

Experimental Methodology 15-25 mg of micronized and pre-micronized levofloxacin samples were dissolved in methanol (having predetermined moisture content) and the moisture content in the samples were determined by Aquastar 3000 Coulometric Karl Fisher Titrator.

Results

The results of Karl Fisher analysis are shown in Table 30.

TABLE 30

Moisture Content of Pre and Post Micronized Levofloxacin.

| | Moisture content (%) |
|---|---|
| Pre-micronized | 6.16 |
| Post-micronized | 5.42 |

Example 8

Preformulation of Levofloxacin Base

The goal of this study was to characterize levofloxacin base to understand the physico-chemical capabilities and restrictions of levofloxacin base for various formulation approaches. The purpose of this study was to characterize the physicochemical properties of levofloxacin base.

Preformulation
pH-Solubility Studies

The solubility of levofloxacin was determined as a function of pH. Buffers were first prepared in the pH range 2-10. Small aliquots of each buffer (~200-250 µL) were saturated with drug and agitated to achieve equilibrium solubility. The samples were then becentrifuged and the supernatant analyzed for dissolved drug by UV or HPLC. The buffers used in this study were shown to affect the solubility result (because different buffer counter-ions can form different levo salt forms in solution). Hence, pH-solubility will also be assessed in the absence of buffers (via titration).

pKa Determination

The pKa of levofloxacin was determined by titrimetry. Obtained pKa values were confirmed by UV spectrophotometry. This information was used to aid in salt selection for levofloxacin and to determine the charge on levofloxacin under the pH conditions in the lung.

Preformulation for Liquid System

The feasibility of a liquid formulation was investigated using (a) solubility and (b) surface tension as baseline parameters for formulation in saline alone.

Preformulation Studies on Levofloxacin
HPLC Method Transfer
Experimental Methodology A HPLC method was used to evaluate the linearity, accuracy and precision of the levofloxacin assay. The column used was a 50×4.6 mm, Onyx Monolithic C18 (Phenomenex) at 30° C. The mobile phase consisted of 85% of 0.1% TFA in water and 15% 0.1% TFA acetonitrile. The flow rate was adjusted to 3 ml/min. Samples were injected into the chromatographic system and the effluent monitored at 277 nm.

Results

The retention time for levofloxacin was approximately 0.82 min. The assay was found to be linear over a range of 5-15 µg/ml, with a correlation coefficient of 1.000. RSD (relative standard deviation) was less than 0.5% and accuracy was within 98-102%.

pH-Solubility Studies
By Titration
Experimental Methodology

A saturated solution of levofloxacin in 0.1 N HCl was titrated with NaOH. After each addition of the base, the solution was shaken by vortexing. An aliquot of the sample solution was removed, centrifuged and the supernatant analyzed by UV spectroscopy at 288 nm. The same solution was back titrated with HCl.

Results

Figure 16:
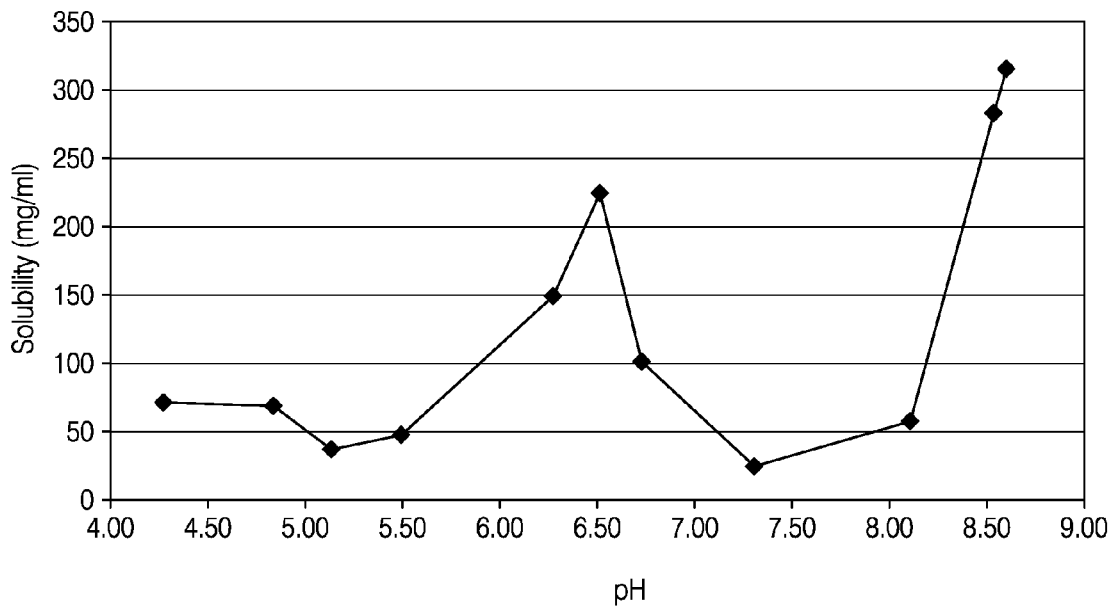
FIG. 16 is a graph showing the pH solubility profile of Levofloxacin by acid titration.

The pH-solubility profile of levofloxacin is shown in FIG. 16. By titrimetery levofloxacin exhibited a solubility of 25.4 mg/ml at pH 7.3. However contrary to the results of the shaking experiments, the solubility by titrimetry decreased below pH 6.5 which can be attributed to the common ion effect. Since a solution of levofloxacin was prepared in HCl, a hydrochloride salt of levofloxacin would have formed in solution. Further addition of chloride ions in the form of hydrochloric acid would suppress the solubility of the hydrochloride salt.

pKa Determination
By Titrimetery
Experimental Methodology

A solution of levofloxacin (18 mg/g) was prepared in water (18.45 mg/g). The initial pH of the solution was 7.36. This solution was titrated with 1 N HCl. Measured aliquots of HCl were added and the pH recorded after each addition. Titration was continued till a pH of 1.

In order to determine the acidic pKa, a solution of levofloxacin (18.38 mg/g) was prepared in 0.1 N HCl. The initial pH of the solution was 1.32. The solution was titrated with 1 N NaOH. Titration was continued till a pH of 6.55.

Results

Figure 17:
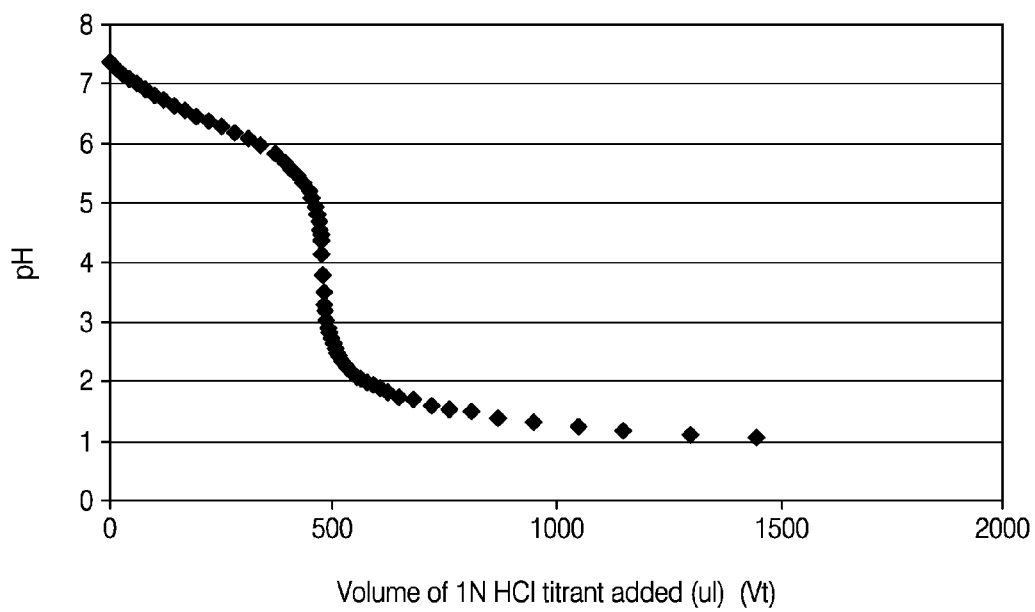
FIG. 17 is a graph measuring pH while titrating Levofloxacin with HCl.
Figure 18:
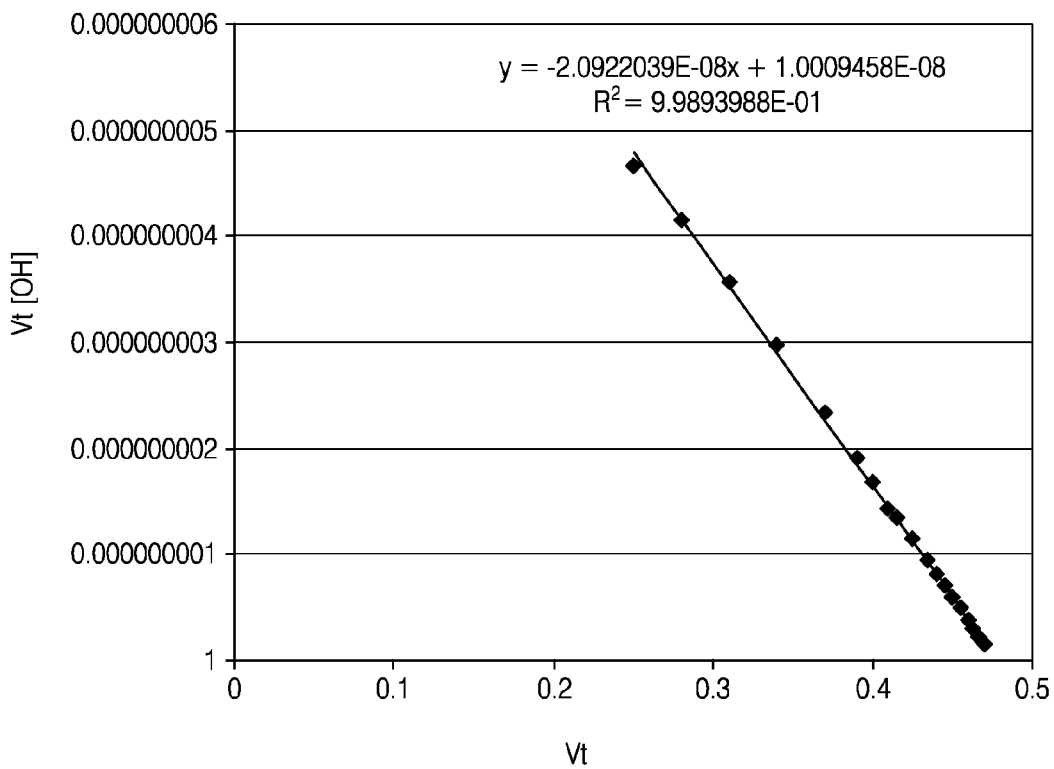
FIG. 18 is a graph showing the Vt[OH] vs. Vt of Levofloxacin.

FIG. 17 shows a plot of pH Vs volume of titrant added for the titration of levofloxacin with HCL. This data was fit into the following equation:

$$V_t[OH^-] = K_b \cdot V_{ep} - K_b \cdot V_t$$

where,
$V_t$=Volume of titrant added
$V_{ep}$=volume of titrant added till the equivalence point
$[OH^-]$=hydroxide ion concentration=$K_w/[H^+]$
$[H^+]$=hydronium ion concentration=$10^{-pH}$ A plot of $V_t[OH^-]$ Vs $V_t$ gave a straight line (FIG. 18). Data shown is from the pre-equivalence point region. From the slope we get Slope: $K_b$=2.09×10$^{-8}$ $pK_b$=−log $K_b$=7.7

$pK_a$=14−$pK_b$=6.3

Figure 19:
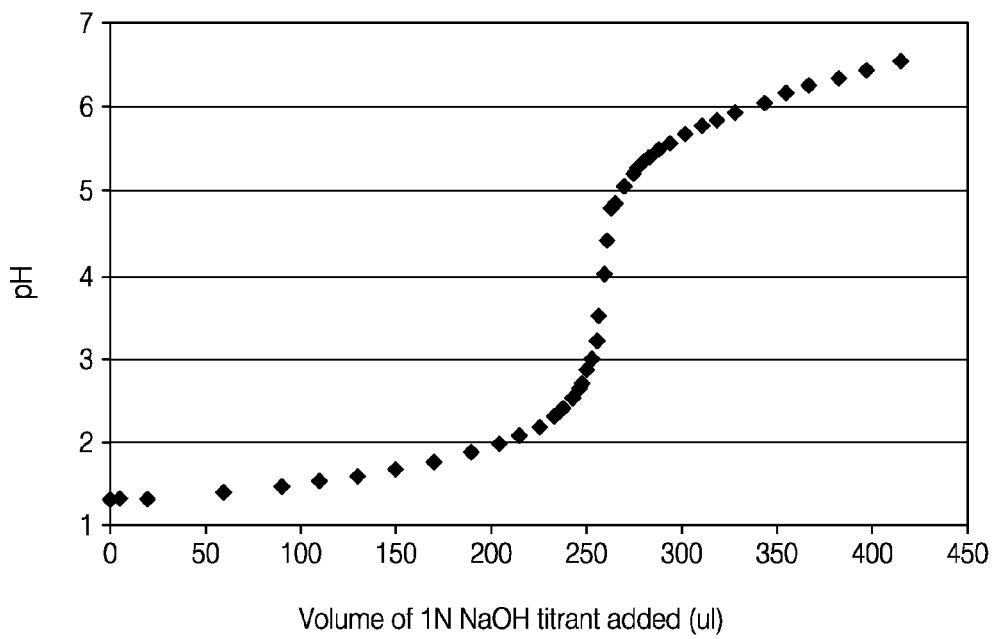
FIG. 19 is a graph measuring pH while titrating Levofloxacin with NaOH.
Figure 20:
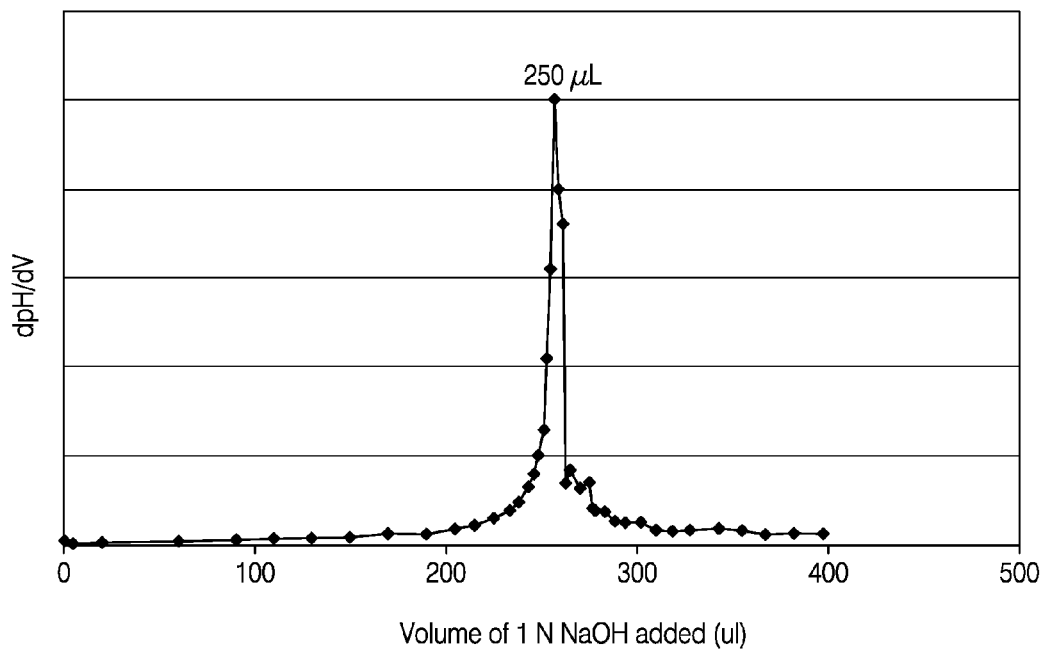
FIG. 20 is a graph measuring dpH/dV vs volume of NaOH titrant (Vt) for titration of Levofloxacin.

FIG. 19 shows a plot of pH Vs volume of titrant added for the titration of levofloxacin with NaOH. Acidic pKa was difficult to calculate because it was quite low (<2.0). However, a rough approximation of pKa can be made as the pH at half the equivalence point. From the plot dpH/dV vs volume of titrant ($V_t$) (FIG. 20), the equivalence point is at 250 μl. The pH at half the equivalence point (i.e. when $V_t$=125 μl) is 1.6. So the acidic pKa~1.6.

By UV Spectroscopy
Experimental Methodology

Dilute solutions of levofloxacin (0.013 mg/ml) were prepared in several buffers. The buffers used were HCL (pH 1,2), acetate (pH 4,5), phosphate (pH 6,7,8) and borate (9,10). The levofloxacin solutions were analyzed by UV spectroscopy at 257 nm.

Results

Figure 21:
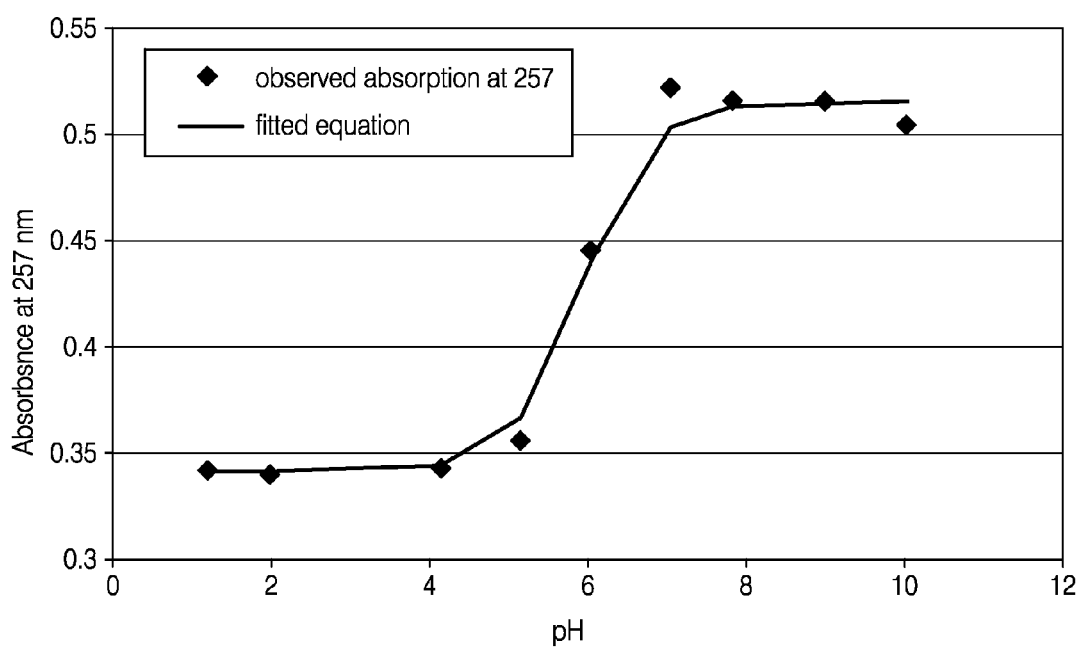
FIG. 21 is a graph measuring the absorbance of a Levofloxacin solution at 257 nm vs pH.
Figure 22A:
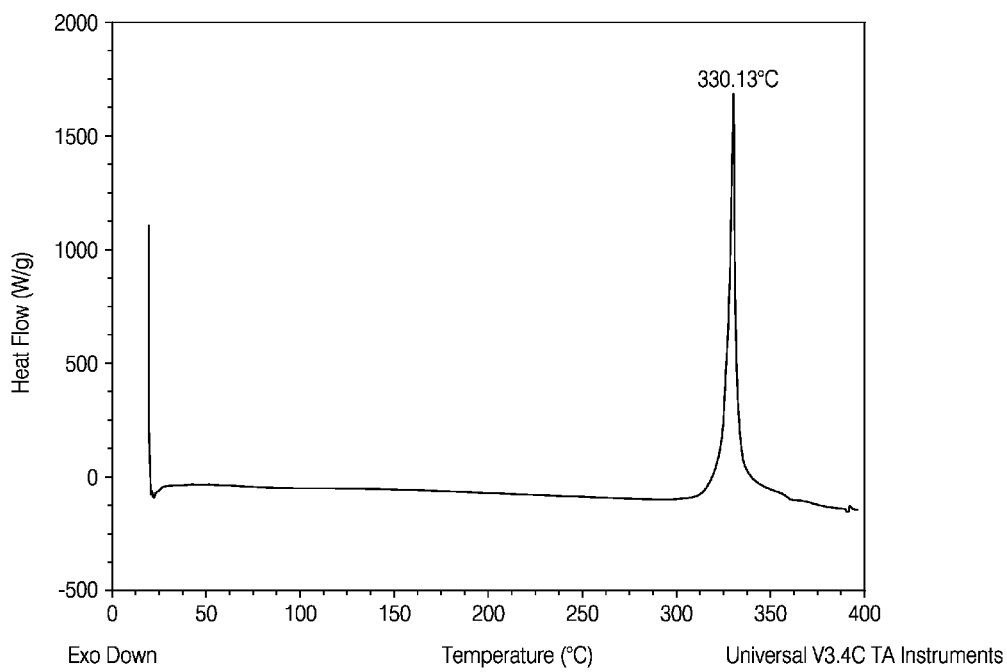
FIG. 22 depicts graphs showing DSC scans of pamoic acid, Levofloxacin, Levofloxacin pamoic acid co-crystallized precipitate, and Levofloxacin-pamoic acid physical mixture.
Figure 22B:
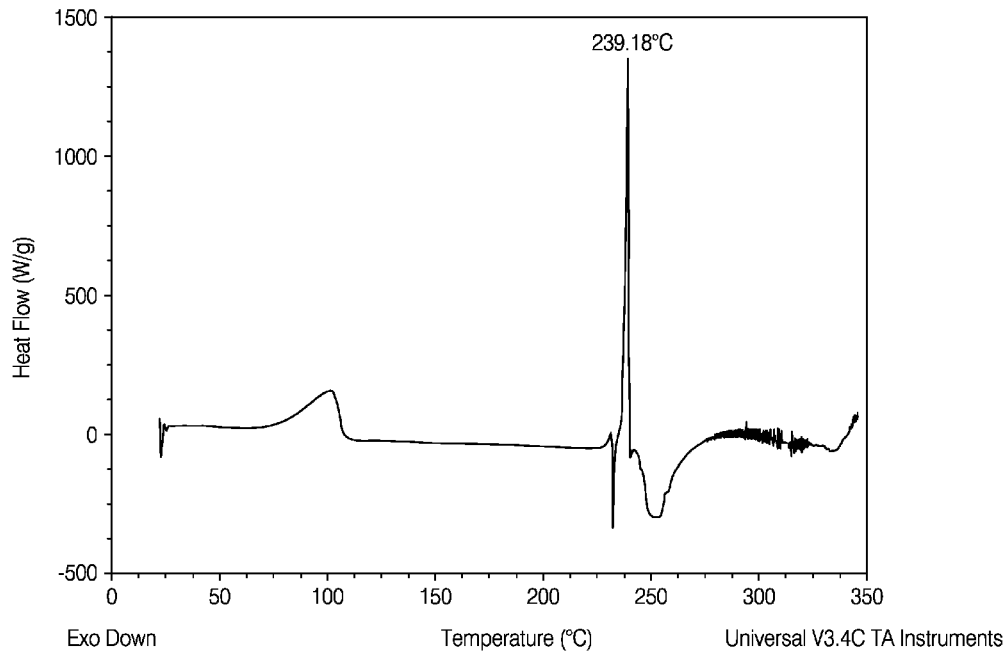
Figure 22C:
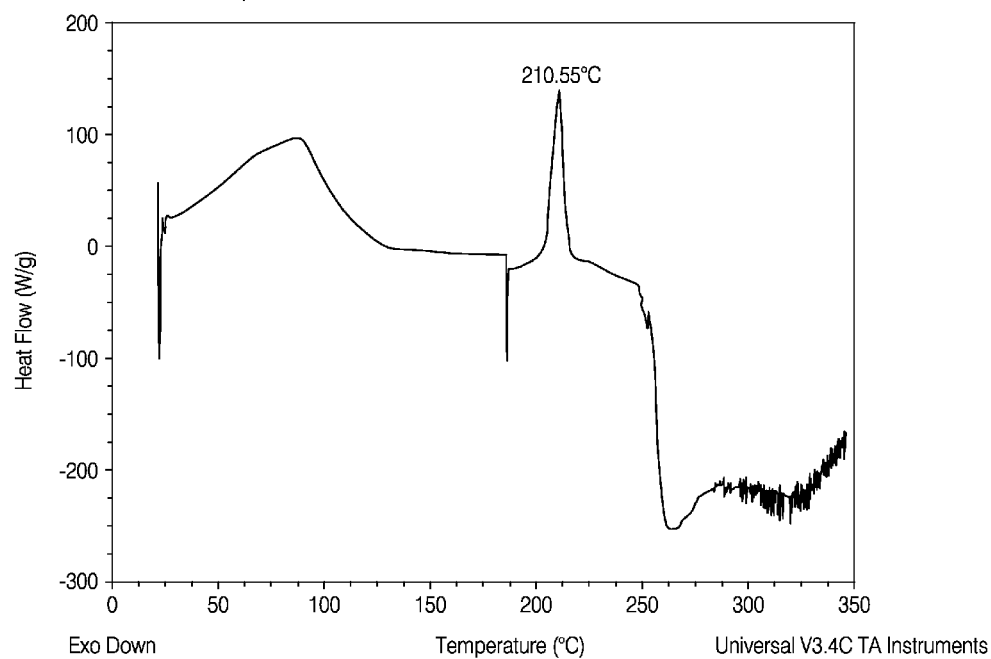
Figure 22D:
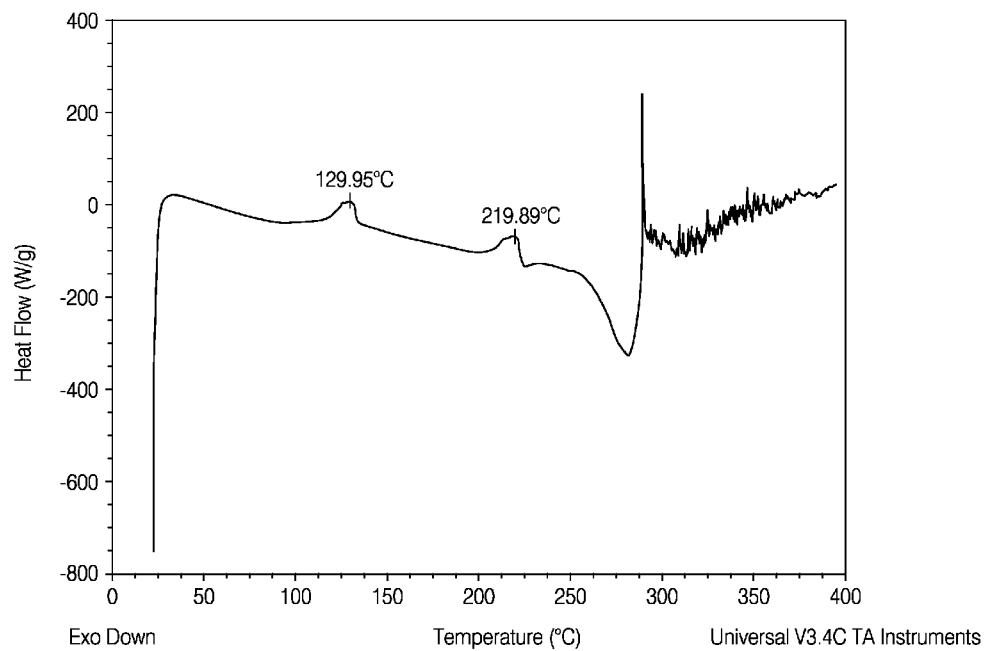
Figure 23A:
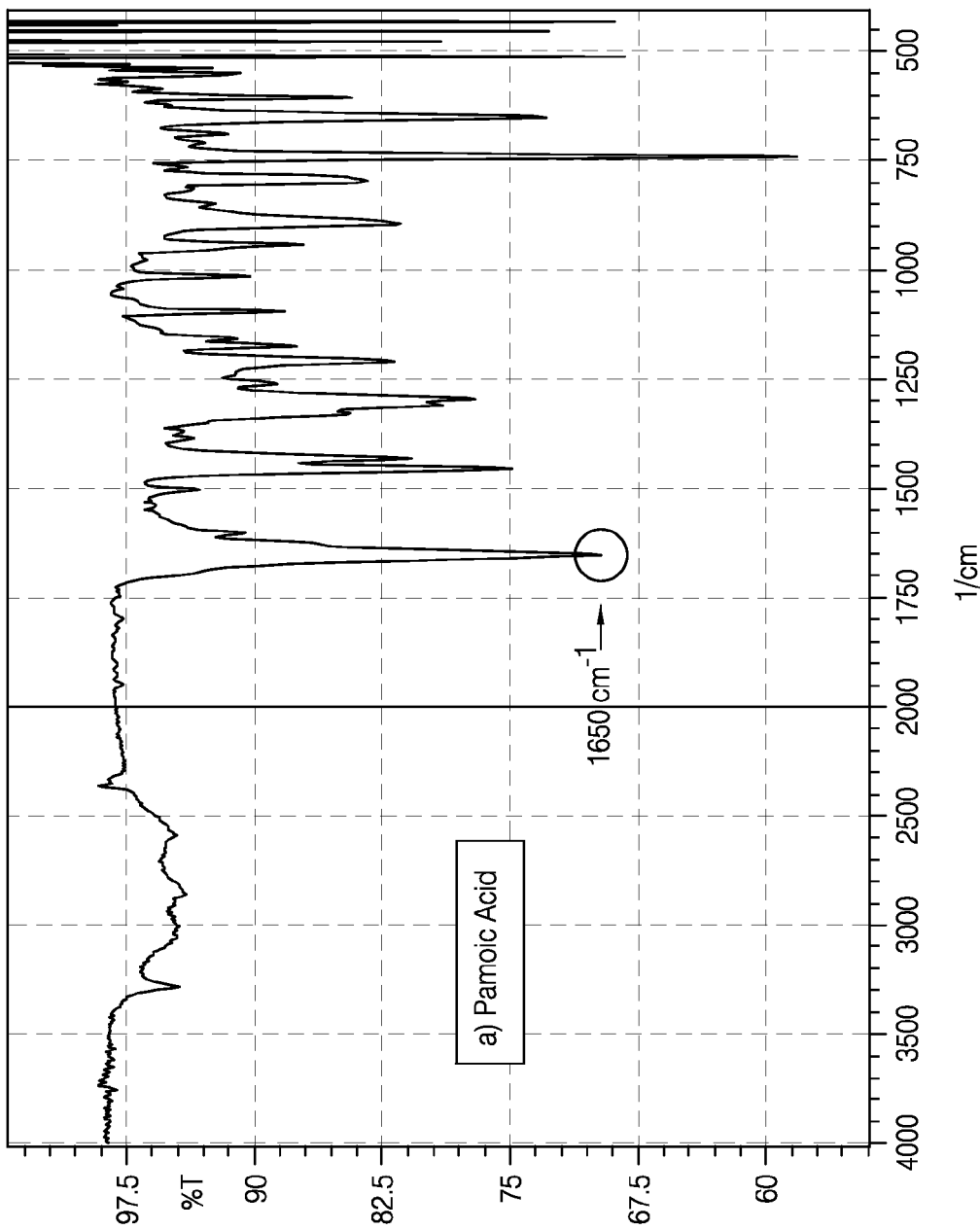
FIG. 23 depicts graphs showing FTIR spectra of pamoic acid, Levofloxacin, Levofloxacin Pamoic Acid Co-Crystallized Precipitate, and Levofloxacin-Pamoic Acid Physical Mixture.
Figure 23B:
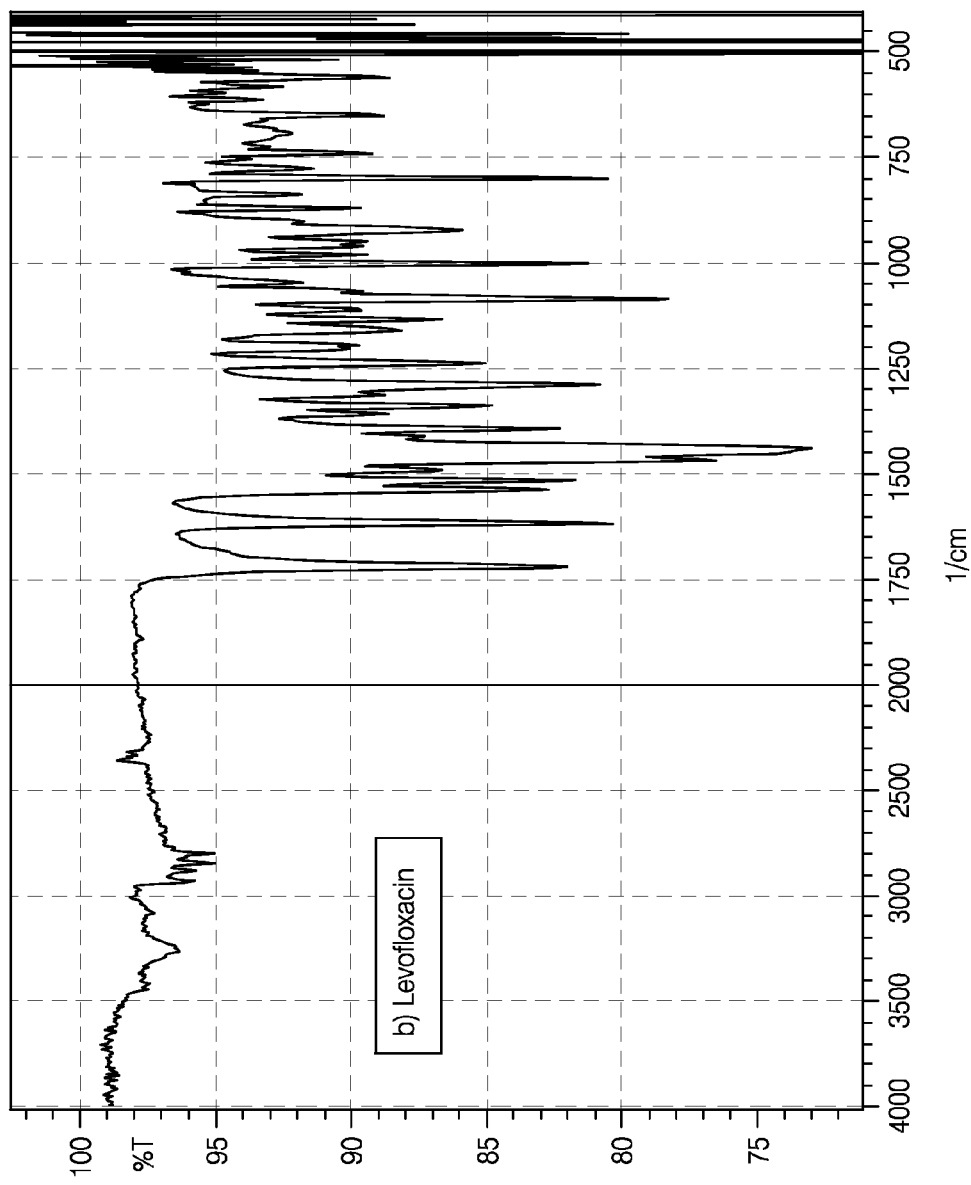
Figure 23C:
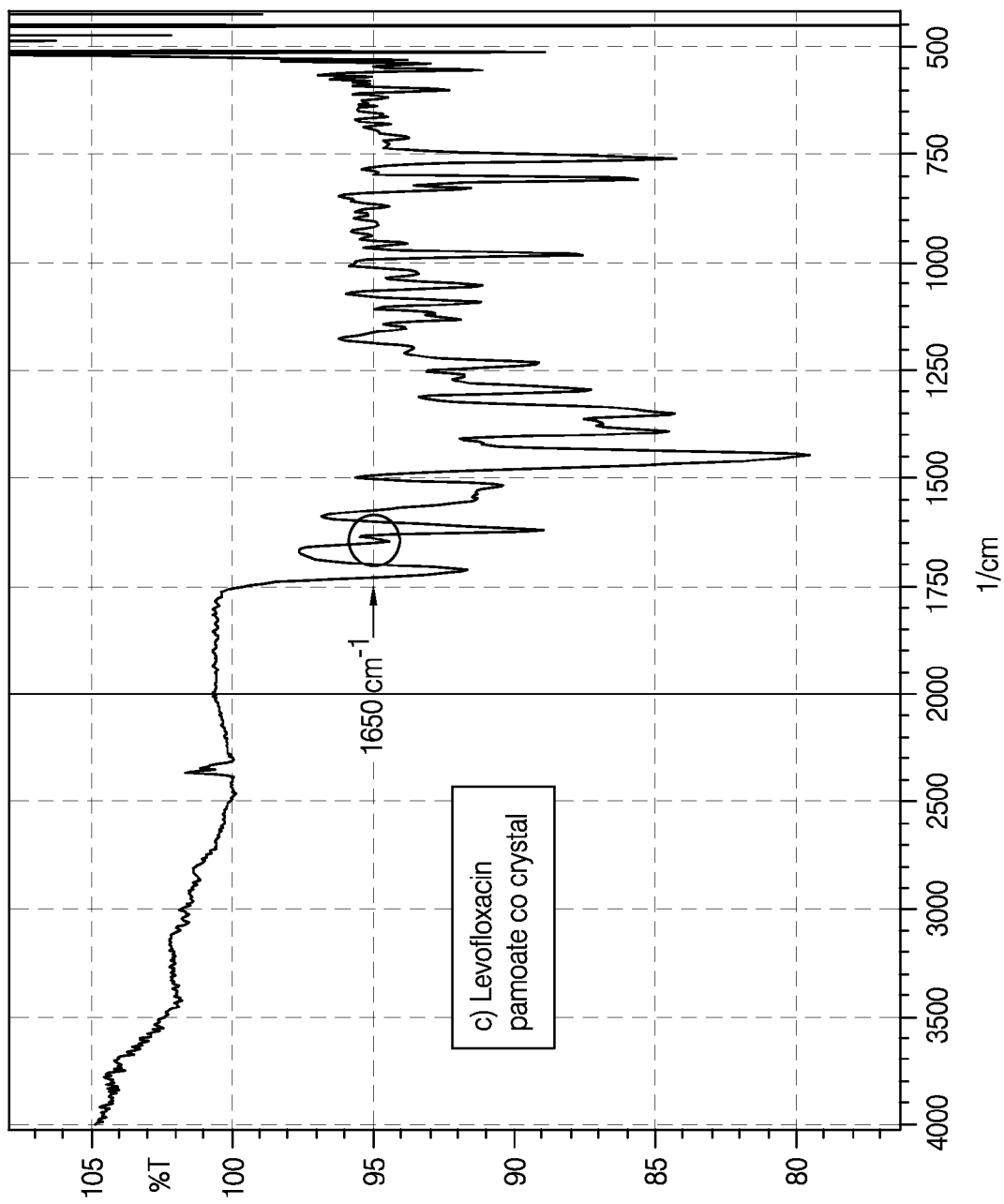
Figure 23D:
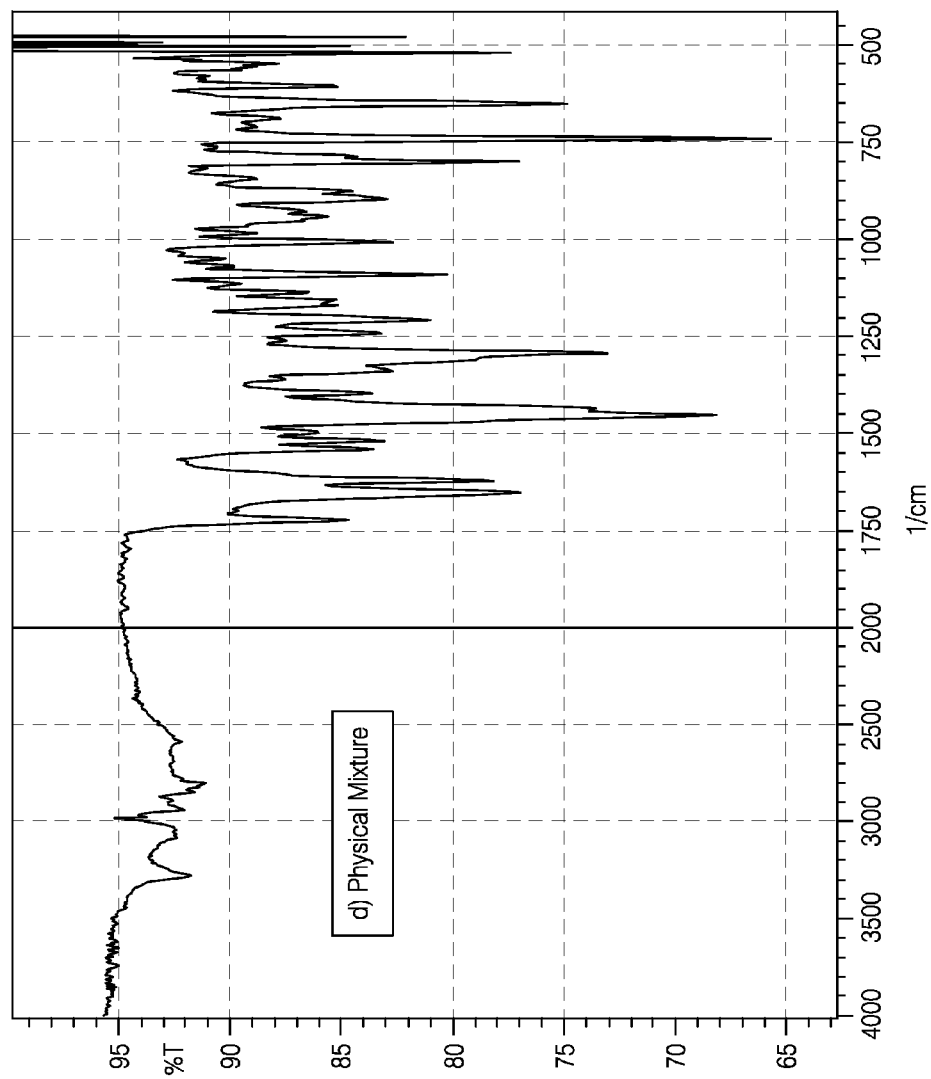

A plot of pH Vs Absorbance of the levofloxacin solution at 257 nm is shown as FIG. 21. This data was fitted into a modified Henderson Hasselbach equation:

$$Abs_{observed} = Abs_{HA}[H^+] + Abs_{A-}[H^+]Ka + [H^+]Ka + [H^+]$$

where,
$Abs_{observed}$=Absorbance of levofloxacin solution
$Abs_{HA}$=Absorbance of levofloxacin solution pH 1.2;
$Abs_{A-}$=Absorbance of levofloxacin solution at pH 7.8;
$[H^+]$=hydronium ion concentration=$10^{-pH}$ The fitted equation provided an estimate of pKa=5.91.

Example 9

Levofloxacin Salt Formation

The goal of this study was to prepare various salt forms of levofloxacin that may gain AUC shape-enhancement properties through decreased solubility and/or dissolution. These benefits may alter the pharmacodynamic properties of levofloxacin following pulmonary administration using nanoparticle suspension or dry powder inhalation. These formulations may be optimized to prolong the release of levofloxacin from decreased solubility salt forms. These properties may also be incorporated into other fluoroquinolone antibiotics including, without limitation gemifloxacin, gatifloxacin, norfloxacin, tosufloxacin, sitafloxacin sarafloxacin, prulifloxacin, and pazufloxacin. Studies are underway to characterize various salt forms and co-precipitates of gemifloxacin for taste masking, AUC shape-enhancement, nanoparticle suspension and dry powder inhalation administration. Other approaches currently being investigated include spray-dry and in situ micronization techniques.

For suspension and powder formulations, a specific salt form can provide important physical and chemical characteristics that may have impacts on the product performance. For a AUC shape-enhancing formulation, the objective of salt selection was to decrease the solubility and/or reduce the dissolution rate of levofloxacin. The acid counterions can be selected by:

Manipulation of melting point: An increase in melting point is usually accompanied by a reduction in salt solubility. Salts formed from planar, high melting aromatic acids generally yield crystalline salts of high melting point.

Manipulation of hydrophobicity: Salts formed with hydrophobic conjugate acids are hydrophobic and difficult to wet, and may ultimately lead to prolonged dissolution. Examples of acids have been selected for salt preparation are listed as follows:

a) Pamoic acid (embonic acid)
b) 2-naphthalene sulfonic acid (napsylic acid)
c) Oleic acid
d) Xinafoic acid
e) Stearic acid
f) Lauryl Sulfonate (estolate)

Other factors considered include salt surface properties, polymorph and chemical stability.

Description

The objective of the study was to prepare salt forms of levofloxacin in order to reduce its solubility and/or dissolution rate. The goal was to:

(a) make levofloxacin less soluble through salt formation with suitable excipient(s).

(b) prepare salt forms of levofloxacin that will have a lower solubility and/or dissolution rate than the free base.

To accomplish these tasks, efforts were concentrated on preparing salts at the basic site of the molecule (pKa~6.8).

Pamoic acid (mp=280° C.) and napsylic acid (mp=125° C.) possess planar, hydrophobic structures that were expected to provide hydrophobic character to the salt. The high melting point of pamoic acid may yield a high melting crystalline salt form. Oleic acid was chosen primarily because it is approved for lung delivery. It has a low melting point (4° C.) which may not satisfy the condition under (1), however it was hoped that the long aliphatic chain may impart sufficient hydrophobicity to decrease solubility. Xinafoic acid (mp=195° C.) was also selected for salt formation as it also possess planar, hydrophobic structures that is expected to provide hydrophobic character to the salt. The rationale for choosing stearic acid and lauryl sulfonate (estolate) was similar to oleic acid, only their lung toxicities are unknown. Estolate is approved for oral delivery (erythromycin estolate has approximately $\frac{1}{12}^{th}$ the solubility of the free base, and is formulated as an oral suspension).

Salt Formation

In general, levofloxacin base and the acid were dissolved in a suitable volatile, organic solvent (1:1 molar ratio), and stirred at room temperature. Any crystallized product formed was filtered, dried, and characterized. Characterization would consist of DSC, FTIR, and elemental analysis.

Formation and Characterization of Co-Crystals of Levofloxacin with Pamoic Acid

Experimental Methodology

Formation of Co-Crystals of Levofloxacin with Pamoic Acid 0.31 g (0.8 mM) of pamoic acid was dissolved by stirring in 100 ml of tetrahydrofuran (THF). To this, 0.30 g (0.8 mM) of levofloxacin was added, dissolved by stirring and the resulting solution refluxed for 2.5 hrs. The suspension formed was cooled to room temperature, filtered and the precipitate obtained was dried in vacuum at about 70° C. for 3 hours.

Characterization

Thermal analysis. Thermal analysis of (a) pamoic acid (b) levofloxacin (c) levofloxacin pamoate co-crystallized precipitate (d) physical mixture of pamoic acid and levofloxacin was performed using a Differential Scanning Calorimeter (TA Instrument DSC Q1000). 2-5 mg of each sample was weighed into pan, sealed and heated at 10° C./min from 25° C. to 300° C. under nitrogen.

Fourier transform Infrared (FT-IR) spectroscopy. FT-IR spectroscopy of (a) pamoic acid (b) levofloxacin (c) levofloxacin pamoate co-crystallized precipitate (d) physical mixture of pamoic acid and levofloxacin was carried out using a FTIR spectrometer (Model IRPrestige-21, Shimadzu).

Saturation solubility. Saturation solubility of levofloxacin and levofloxacin pamoic acid co-crystallized precipitate was determined by equilibrating excess amount of solid with water. The suspensions were adjusted to pH's 4, 5, 6 and 7 with HCL, shaken, centrifuged and the supernatant analyzed by UV spectroscopy at 288 nm.

Results

Thermal analysis. DSC scans of (a) pamoic acid (b) levofloxacin (c) levofloxacin pamoate co-crystal precipitate (d) physical mixture of pamoic acid and levofloxacin are shown as FIG. 22. Pamoic acid and levofloxacin show sharp endotherms at 330° C. and 239° C., respectively, which most likely would be due to the melting of pamoic acid and levofloxacin, respectively. The DSC profile of levofloxacin pamoate co-crystals showed one major endotherm at 210° C., while a 1:1 molar admixture of levofloxacin and pamoic acid displayed broad endotherms at 129° C. and 220° C.

FTIR. FTIR spectra obtained from (a) pamoic acid (b) levofloxacin (c) levofloxacin pamoate co-crystallized precipitate (d) physical mixture of pamoic acid and levofloxacin are displayed as FIG. 23. The high intensity absorption bands at 1650 cm$^{-1}$ in the FTIR spectra of pamoic acid, which is due to the stretching of C=0 group is greatly reduced in the co crystal.

Saturation solubility. Table 31 displays the saturation solubility data of levofloxacin and levofloxacin pamoate at different pH's. Solubility was determined in water, since buffer acids have an effect on the solubility of levofloxacin. However after shaking levofloxacin or salt solutions in water, the pH shifted, especially the levofloxacin solution at pH 5 shifted to pH 1.6. As the solution at pH 5 is between the two pKa's of levofloxacin (~1.6 and ~6), such a solution will have a lower buffer capacity and hence the pH shift. Solutions at pH's near the pKa's of the drug have a high buffer capacity and resist pH changes. Solubility of levofloxacin pamoate was considerably less than that of levofloxacin at all pH's.

TABLE 31

Saturation Solubility Data of Levofloxacin and Levofloxacin Pamoate.

| | | | | | |
|---|---|---|---|---|---|
| Levofloxacin | pH before shaking | 3.97 | 5.06 | 5.96 | |
| | pH after shaking | 4.21 | 1.63 | 5.70 | |
| | Solubility (mg/ml) | 158.28 | 225.04 | 297.20 | |
| Levofloxacin pamoate | pH before shaking | 4.06 | 4.98 | 5.98 | 7.00 |
| | pH after shaking | 5.63 | 6.30 | 6.66 | 7.32 |
| | Solubility (mg/ml) | 0.34 | 0.29 | 0.24 | 0.44 |

Interpretation

Since the co-crystallized precipitate of levofloxacin pamoate has a different melting point and FTIR spectra from that of levofloxacin, pamoic acid or their physical mixture, it is possible that the equimolar complex of the levofloxacin with pamoic acid might be the salt levofloxacin pamoate, having a considerably less solubility than levofloxacin.

Formation and Characterization of Co-Crystals of Levofloxacin with Xinafoic Acid Experimental Methodology Formation of Co-Crystals of Levofloxacin with Xinafoic Acid 1.004 g (2.7 mM) of levofloxacin was dissolved by refluxing in 80 ml ethyl acetate. To this, 0.51 g (2.7 mM) of xinafoic acid dissolved in 35 ml of ethyl acetate was added and the solution cooled overnight under stirring conditions to ambient temperature. The suspension obtained was filtered, and the precipitate dried under vacuum at 75° C. for about 3.5 hours Characterization Thermal analysis. Thermal analysis of (a) xinafoic acid (b) levofloxacin xinafoate co-crystallized precipitate was performed using a Differential Scanning Calorimeter (TA Instrument DSC Q1000). 2-5 mg of each sample was weighed into pan, sealed and heated at 10° C./min from 25° C. to 300° C. under nitrogen.

Fourier transform Infrared (FT-IR) spectroscopy. FT-IR spectroscopy of (a) xinafoic acid (b) levofloxacin xinafoate co-crystallized precipitate was carried out using a FTIR spectrometer (Model IRPrestige-21, Shimadzu).

Saturation solubility. Saturation solubility of levofloxacin xinafoic acid co-crystallized precipitate was determined by equilibrating excess amount of solid with water. The suspensions were adjusted to pH's 4, 5, 6 and 7 with HCL, shaken, centrifuged and the supernatant analyzed by UV spectroscopy at 288 nm.

Results

Figure 24A:
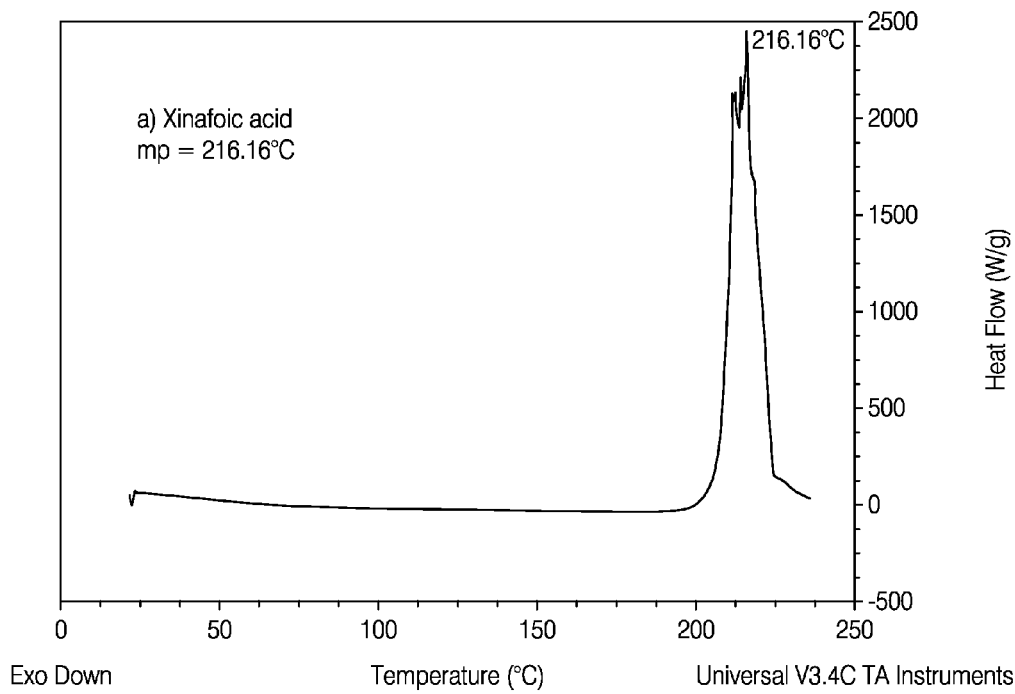
FIG. 24 depicts graphs showing DSC scans of xinafoic acid, and Levofloxacin xinafoic acid co-crystallized precipitate.
Figure 24B:
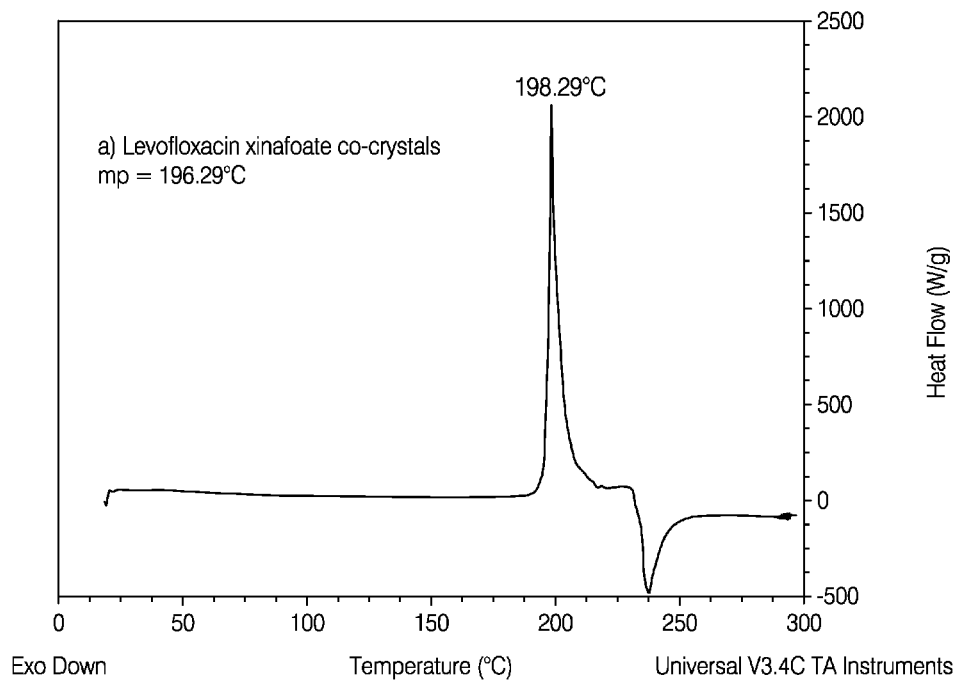

Thermal analysis. DSC profiles of (a) xinafoic acid (b) levofloxacin xinafoate co-crystallized precipitate are shown as FIG. 24. Levofloxacin xinafoate co-crystallized precipitate exhibits a melting endotherm at 196° C., which is different than that of xinafoic acid (216° C.) and levofloxacin (239° C.).

Figure 25A:
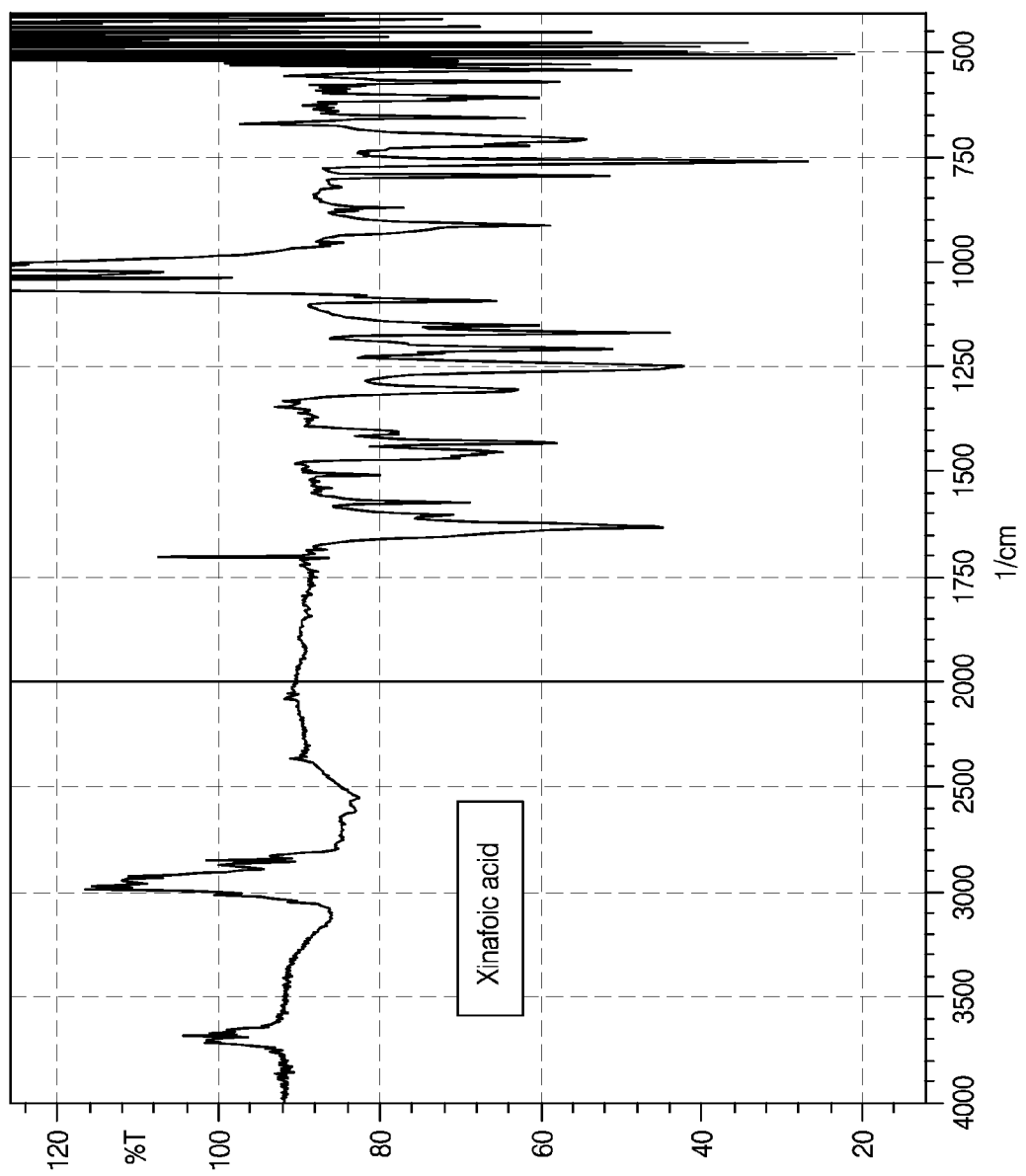
FIG. 25 depicts graphs showing FTIR spectra of xinafoic acid and Levofloxacin xinafoate co-crystals.
Figure 25B:
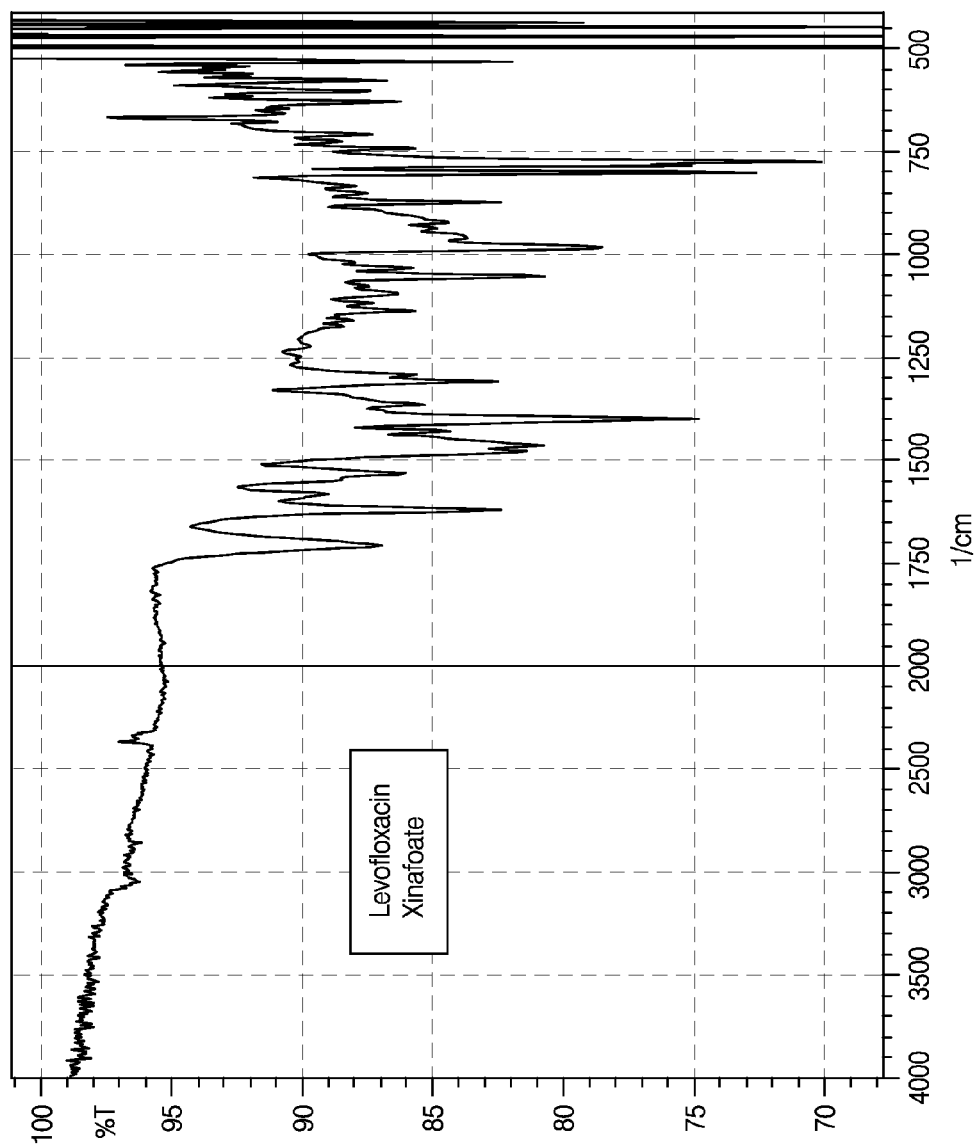

FTIR. FTIR spectra obtained from (a) xinafoic acid (b) levofloxacin xinafoate co-crystallized precipitate are displayed as FIG. 25. The FTIR spectrum of the co crystal exhibit transmittance minima's at wave numbers different from that of xinafoic acid and levofloxacin.

Saturation solubility. Table 32 shows the saturation solubility data of levofloxacin xinafoate at different pH's. Solubility of the xinafoate salt was intermediate between that of the levofloxacin base and levofloxacin pamoate co crystal.

TABLE 32

Saturation Solubility Data of Levofloxacin Xinafoate Co-Crystal.

| Levofloxacin xinafoate | pH before shaking | 4.05 | 4.94 | 6.00 | 6.95 |
|---|---|---|---|---|---|
| | pH after shaking | 4.78 | 5.37 | 6.30 | 7.17 |
| | Solubility (mg/ml) | 21.69 | 12.95 | 4.59 | 5.95 |

Interpretation

The co-crystallized precipitate of levofloxacin pamoate has a different melting point and FTIR spectra than that of levofloxacin and xinafoic acid, suggesting a possible formation of a levofloxacin xinafoate salt. This salt has intermediate solubility between levofloxacin and levofloxacin pamoate.

Formation and Characterization of Co-Crystals of Levofloxacin with Stearic Acid

Experimental Methodology

Formation of Co-Crystals of Levofloxacin with Stearic Acid 0.77 g (2.07 mM) of stearic acid was dissolved by heating and sonication in 40 ml of methanol. To this, 1.00 g (2.07 mM) of levofloxacin dissolved in 60 ml of methanol was added. The resulting solution was heated at 55° C. for about 15 minutes, followed by cooling to room temperature and then at −20° C. The suspension obtained was filtered.

Characterization

Thermal analysis. Thermal analysis of (a) stearic acid (b) levofloxacin stearate co-crystallized precipitate (c) physical mixture of stearic acid and levofloxacin was performed using a Differential Scanning Calorimeter (TA Instrument DSC Q1000). 2-5 mg of each sample was weighed into pan, sealed and heated at 10° C./min from 25° C. to 250° C. under nitrogen.

Fourier transform Infrared (FT-IR) spectroscopy. FT-IR spectroscopy of (a) stearic acid (b) levofloxacin stearic acid co-crystallized precipitate (d) physical mixture of stearic acid and levofloxacin was carried out using a FTIR spectrometer (Model IRPrestige-21, Shimadzu).

Saturation solubility. Saturation solubility of levofloxacin and levofloxacin stearic acid co-crystallized precipitate was determined by equilibrating excess amount of solid with water. The suspensions were adjusted to pH's 4, 5, 6 and 7 with HCL, shaken, centrifuged and the supernatant analyzed by UV spectroscopy at 288 nm.

Results

Figure 26A:
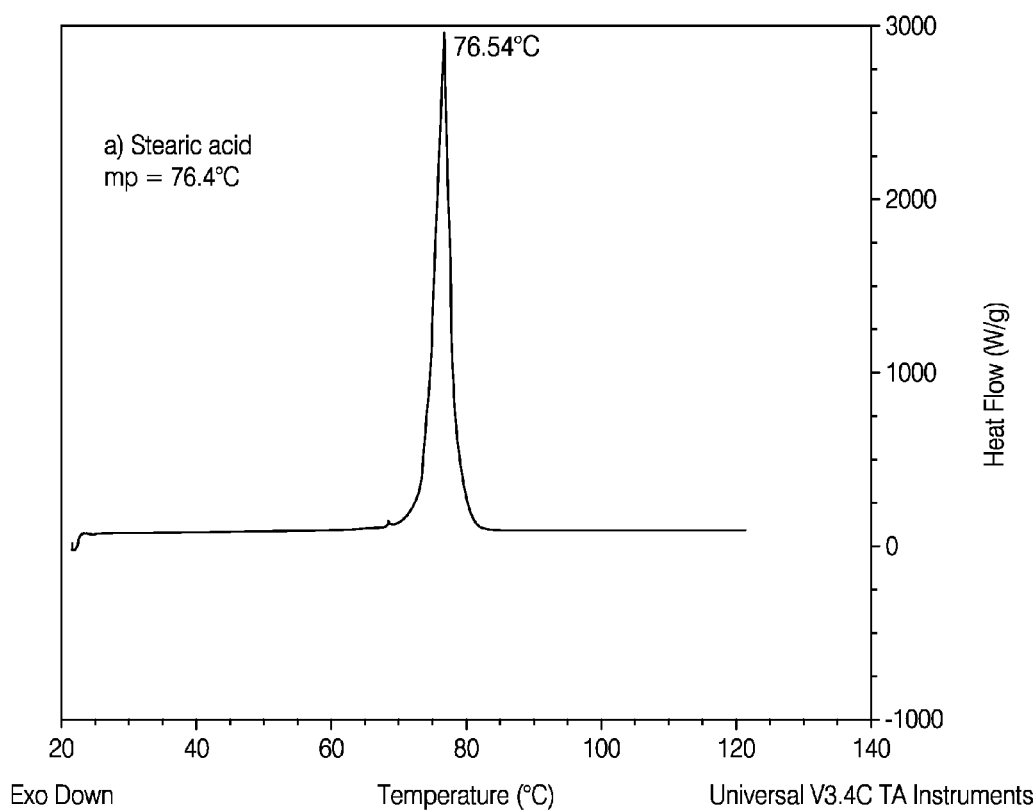
FIG. 26 depicts graphs showing DSC scans of stearic acid, Levofloxacin stearic acid co-crystallized precipitate, and a physical mixture of Levofloxacin and stearic acid.
Figure 26B:
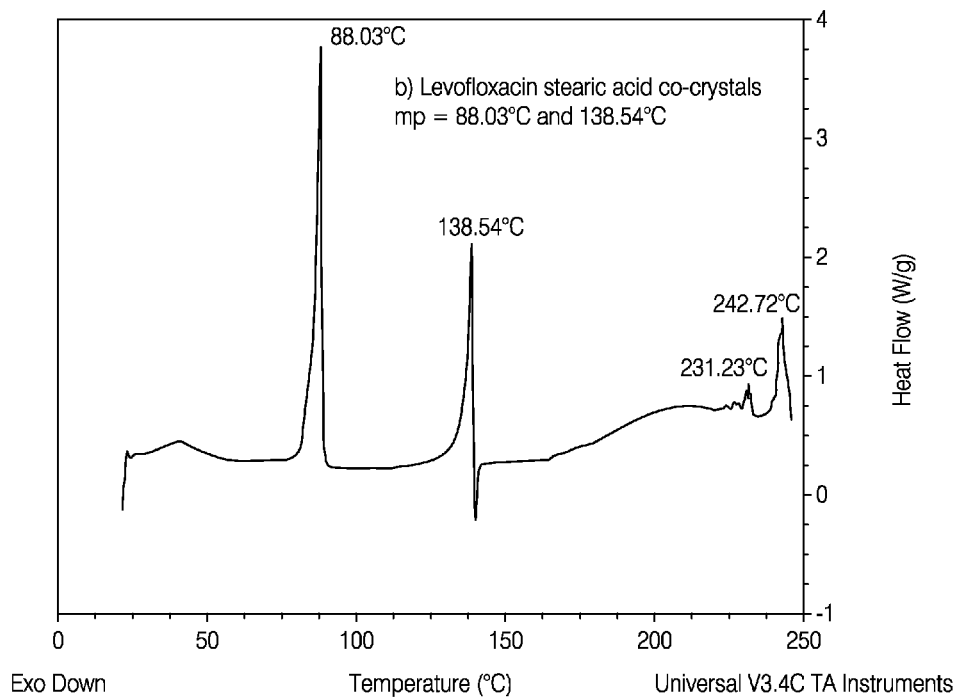
Figure 26C:
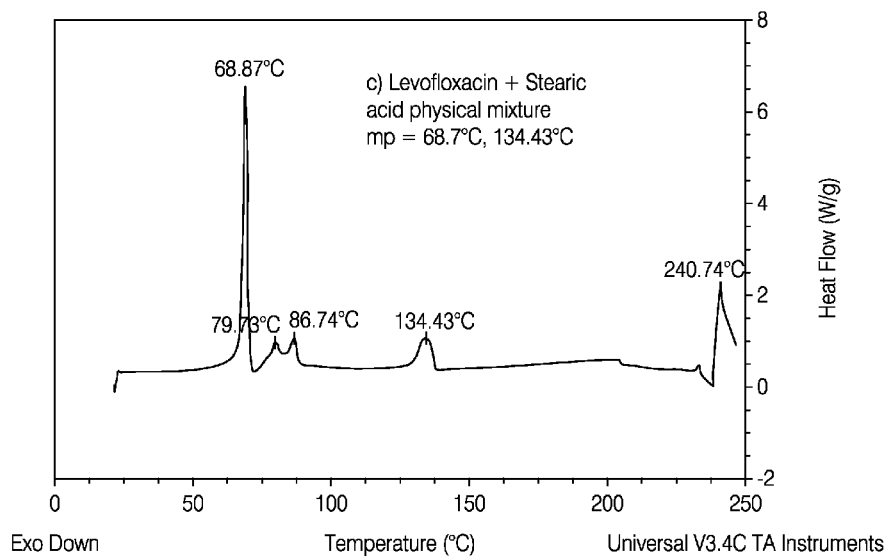

Thermal analysis. DSC scans of (a) stearic acid (b) levofloxacin stearate co-crystal precipitate (d) physical mixture of stearic acid and levofloxacin are shown as FIG. 26. Stearic acid and levofloxacin show sharp endotherms at 76.4° C. and 239° C., respectively, which most likely would be due to the melting of stearic acid and levofloxacin, respectively. The DSC profile of levofloxacin stearic acid co-crystals showed two sharp endotherms at 88.03° C. and 138.54° C. and minor endotherms at 231° C. and 242.72° C. The minor endotherms might be due to melting of trace quantities of residual levofloxacin in the original sample. A 1:1 molar admixture of levofloxacin and stearic acid displayed endotherms at 68.87° C., 134.43° C. and 240.74° C. and minor endotherms at 79.73° C. and 86.74° C.

Figure 27A:
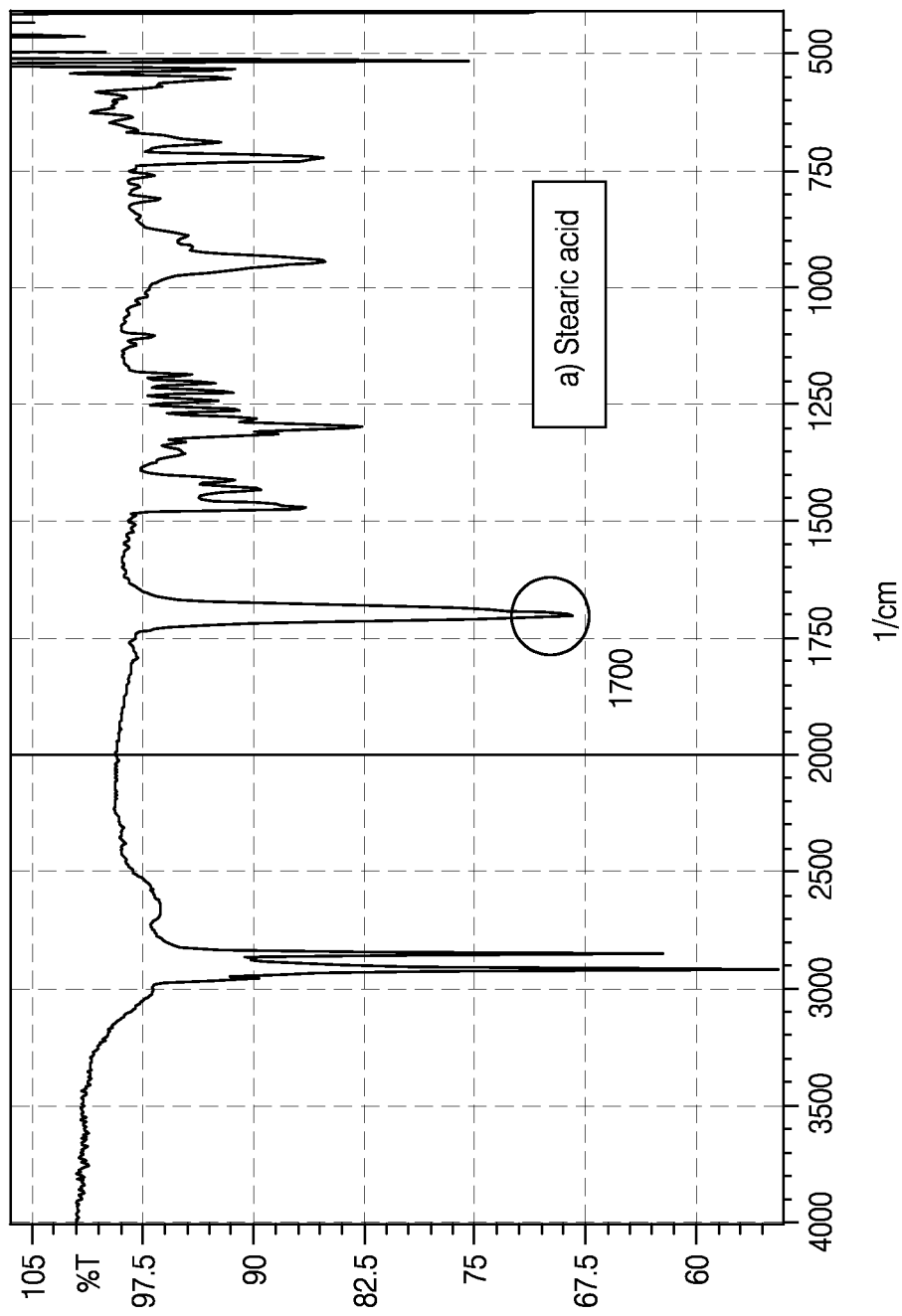
FIG. 27 depicts graphs showing FTIR spectra of stearic acid, Levofloxacin stearic acid co-crystallized precipitate, and a physical mixture of Levofloxacin and stearic acid.
Figure 27B:
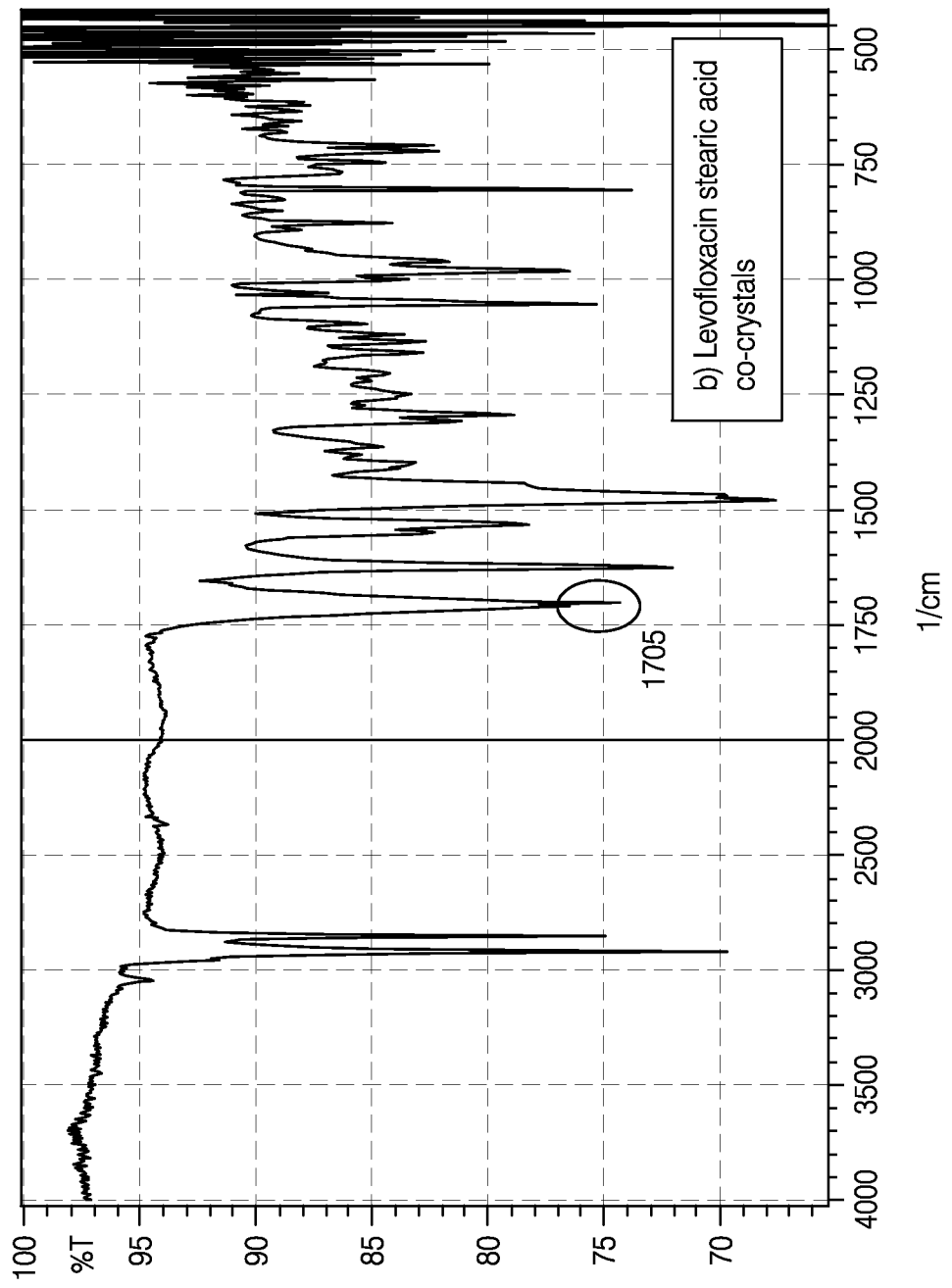
Figure 27C:
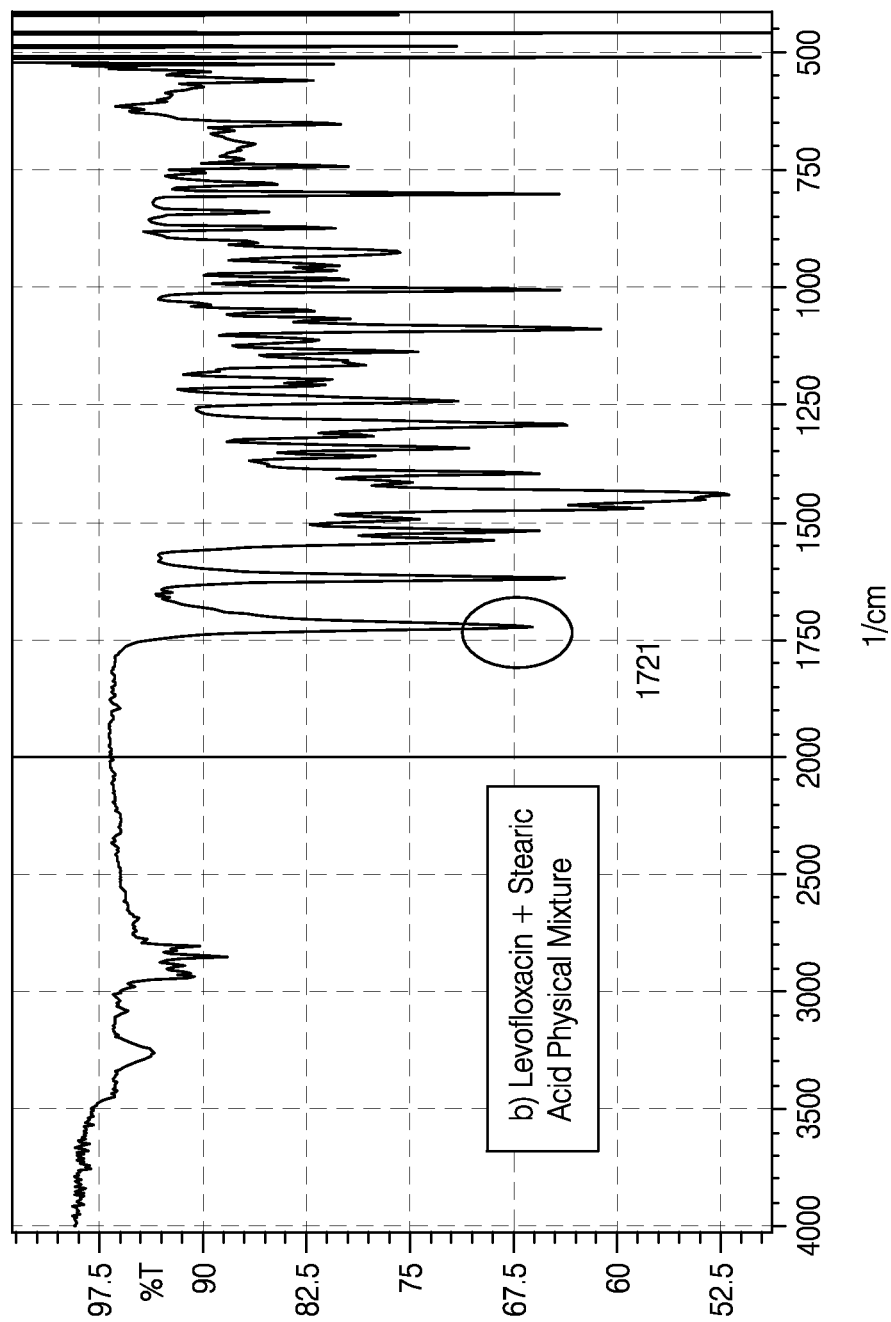
Figure 28A:
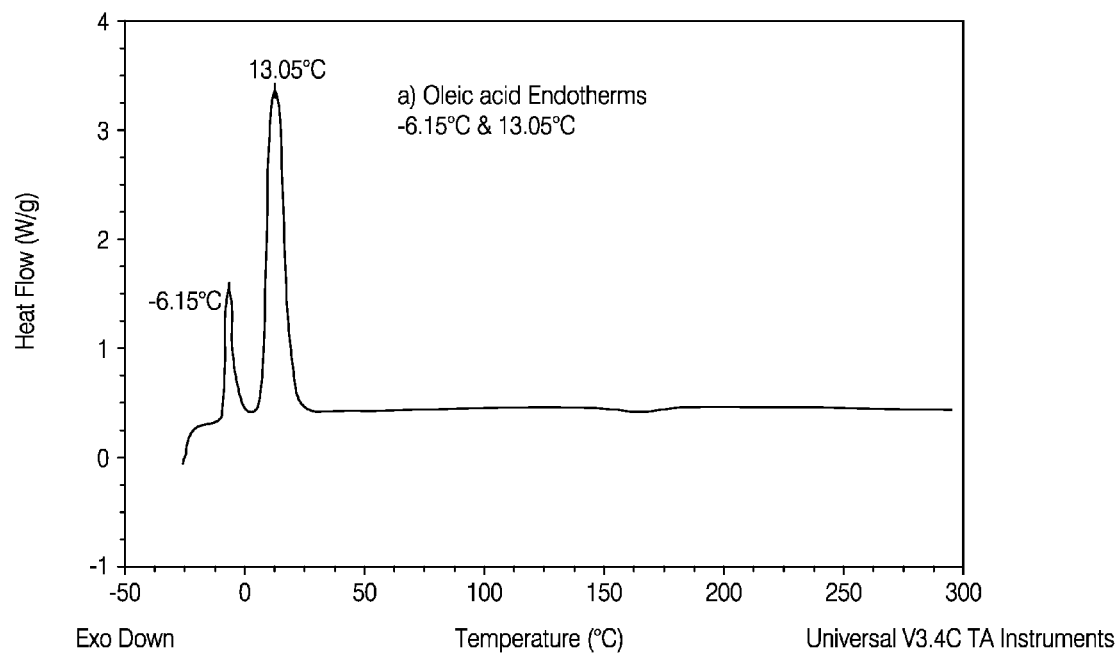
FIG. 28 depicts graphs showing DSC scans of oleic acid, Levofloxacin oleic acid co-crystallized precipitate, physical mixture of Levofloxacin and oleic acid (50:50), physical mixture of Levofloxacin and oleic acid (10:90), and physical mixture of Levofloxacin and oleic acid (90:10).
Figure 28B:
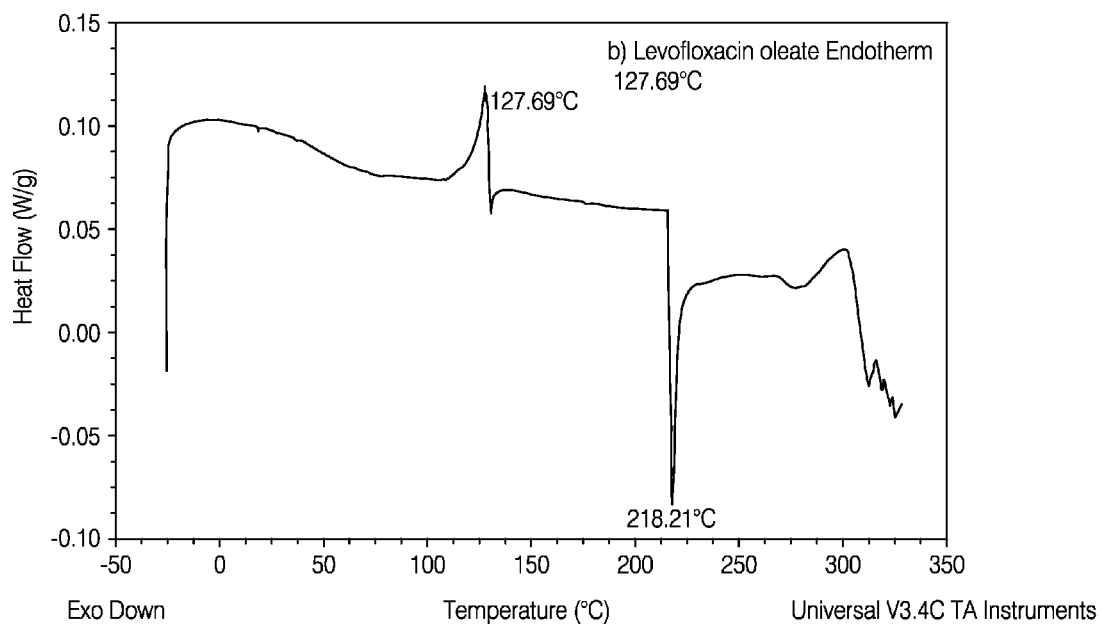
Figure 28C:
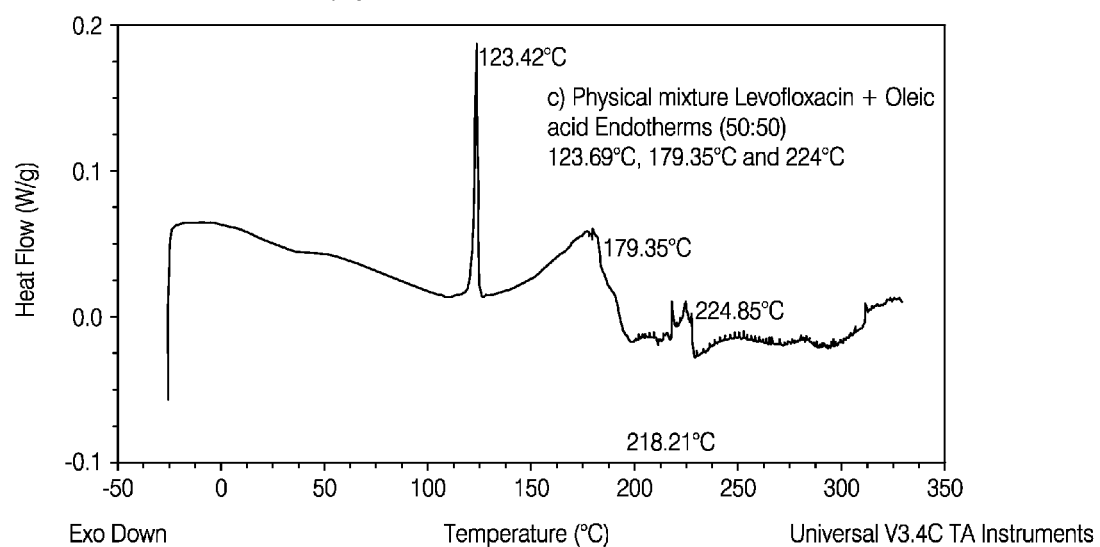
Figure 28D:
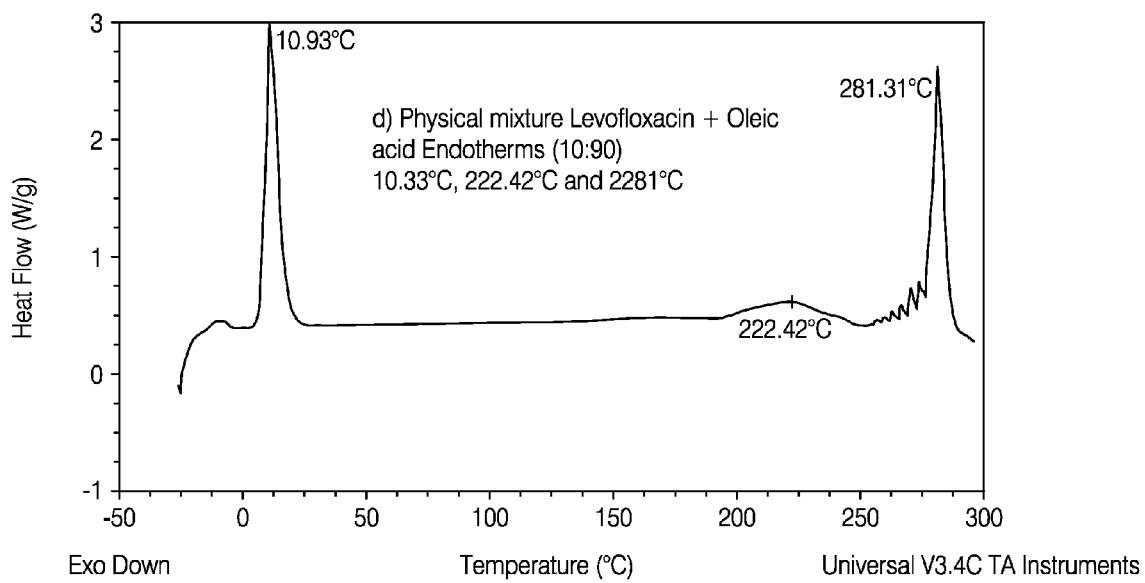
Figure 28E:
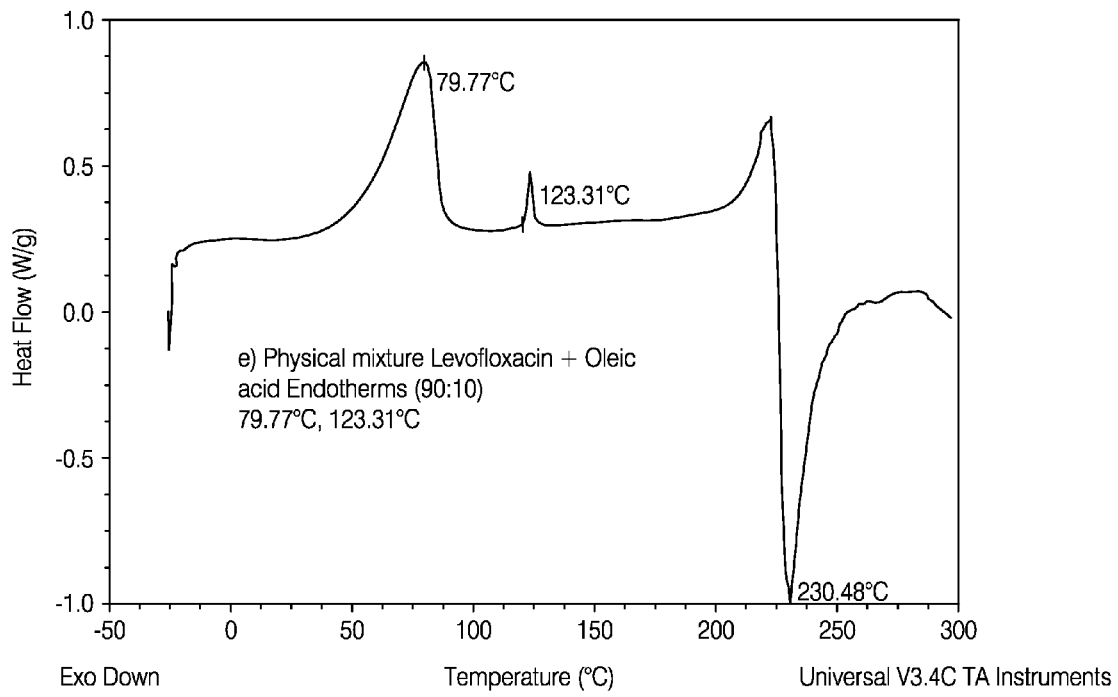

FTIR. FTIR spectra obtained from (a) stearic acid (b) levofloxacin stearic acid co-crystallized precipitate (c) physical mixture of stearic acid and levofloxacin are displayed as FIG. 27. The C=0 stretch band is seen at 1700, 1705 and 1721 cm$^{-1}$ in stearic acid, co-crystallized precipitate and physical mixture, respectively.

Saturation solubility. Table 33 shows the saturation solubility data of levofloxacin stearic acid co-crystals at different pH's.

TABLE 33

Saturation Solubility Data of Levofloxacin Stearic Acid Co-Crystals.

| Levofloxacin stearate | pH before shaking | 4.05 | 5.02 | 6.01 | 6.96 |
|---|---|---|---|---|---|
| | pH after shaking | 3.36 | 5.05 | 6.02 | 6.98 |
| | Solubility (mg/ml) | 0.86 | 1.30 | 2.20 | 1.64 |

Interpretation

The DSC profile of levofloxacin stearic acid co-crystal precipitate shows two endotherms. One of these endotherms might be due to melting of the cocrystals. The nature of the second endotherm has to be investigated. Since the levofloxacin stearic acid co-crystal precipitate has a solubility values lower than of levofloxacin, it is possible that the precipitate might be the salt, levofloxacin stearate salt.

Formation and Characterization of Co-Crystals of Levofloxacin with Oleic Acid

Experimental Methodology

Formation of Co-crystals of Levofloxacin with Oleic Acid 0.78 g (2.76 mM) of oleic acid was dissolved in 10 ml chloroform. To this, 1.025 (2.76 mM) of levofloxacin dissolved in 10 ml of chloroform was added. The resulting solution was mixed thoroughly and evaporated at 40° C.

Characterization

Thermal analysis. Thermal analysis of (a) oleic acid (b) levofloxacin oleate co-crystal precipitate (c) physical mixture of oleic acid and levofloxacin (50:50) (d) physical mixture of oleic acid and levofloxacin (10:90) and (e) physical mixture of oleic acid and levofloxacin (90:10) was performed using a Differential Scanning Calorimeter (TA Instrument DSC Q1000). 2-5 mg of each sample was weighed into pan, sealed and heated at 1° C./min or 10° C./min from 25° C. to 250° C. under nitrogen.

Fourier transform Infrared (FT-IR) spectroscopy. FT-IR spectroscopy of (a) oleic acid (b) levofloxacin oleic acid co-crystallized precipitate (d) physical mixture of oleic acid and levofloxacin was carried out using a FTIR spectrometer (Model IRPrestige-21, Shimadzu).

Kinetic solubility determination. Levofloxacin oleate co-crystallized precipitate (50 mg) was suspended in 2 ml of water. The suspension was adjusted to pH 7 with HCL and shaken. The solubility of these co-crystals was determined at various time intervals. This study was performed at room temperature and at 40° C. The kinetic solubility of an equimolar physical mixture of levofloxacin and oleic acid was also performed and compared to that of the co-crystals at 40° C.

Results

Thermal Analysis.

DSC scans of (a) oleic acid (b) levofloxacin oleate co-crystal precipitate (c) physical mixture of oleic acid and levofloxacin (50:50) (d) physical mixture of oleic acid and levofloxacin (10:90) and (e) physical mixture of oleic acid and levofloxacin (90:10) are shown as FIG. 28. Oleic acid thermogram shows endotherms at −6.15° C. and 13.05° C. The endotherm at −6.15° C. corresponds to gamma-alpha oleic acid phase transition (Crowley K. J, 1999). Levofloxacin oleate co-crystallized precipitate shows endotherm at 127.69° C., while an equimolar physical mixture of levofloxacin with oleic acid shows endotherms at 123.69° C., 179.35° C. and 224° C. The equimolar physical mixture is showing an endotherm which is close to melting point of the co-crystals, suggesting a possible reaction between oleic acid and levofloxacin in the solid state. To investigate this phenomenon, DSC on physical mixtures of levofloxacin and oleic acid (90:10) and (10:90) were performed. Physical mixture of levofloxacin and oleic acid (10:90) shows major endotherm at 10.33° C. (possible melting of oleic acid) and at 281° C. It does not show endotherm near the melting point of co-crystals. A levofloxacin oleic acid (90:10) physical mixture shows no melting endotherm at 10° C. for oleic acid. It exhibits endotherms at 79.77° C. and at 128° C. (close to the melting point of the co-crystals), suggesting a possible reaction of levofloxacin and oleic in presence of high amounts of levofloxacin.

FTIR.

The FTIR spectra of oleic acid shows a C=O stretch intense peak at 1710 cm$^{-1}$ and O—H in-plane and out-of-plane bands at 1462 and 937 cm$^{-1}$, respectively.

Figure 29A:
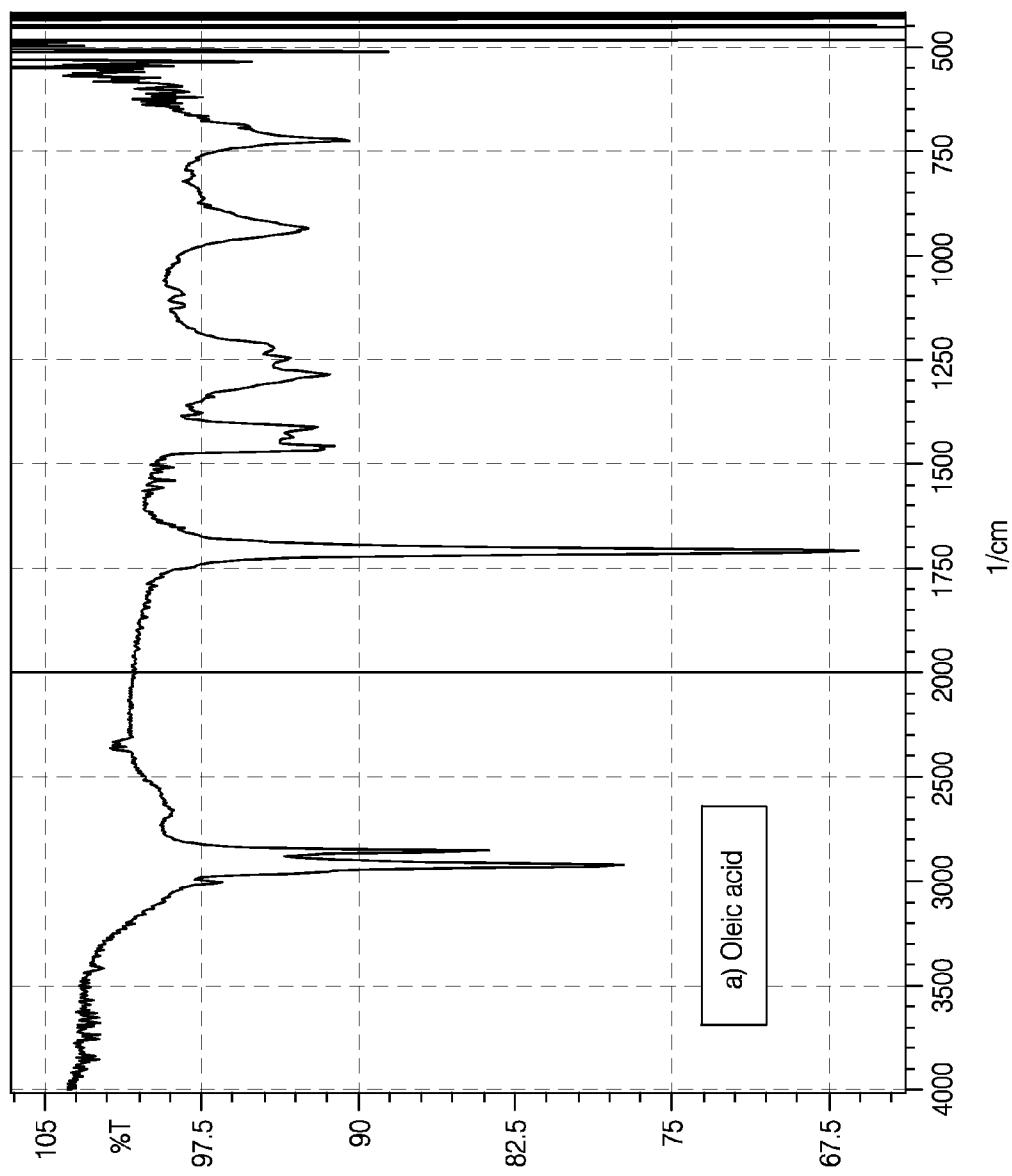
FIG. 29 depicts graphs showing FTIR spectra of oleic Acid, Levofloxacin oleic acid co-crystallized precipitate, Levofloxacin oleic acid co-crystallized precipitate as compared to an equimolar physical mixture of levofloxacin and oleic acid.
Figure 29B:
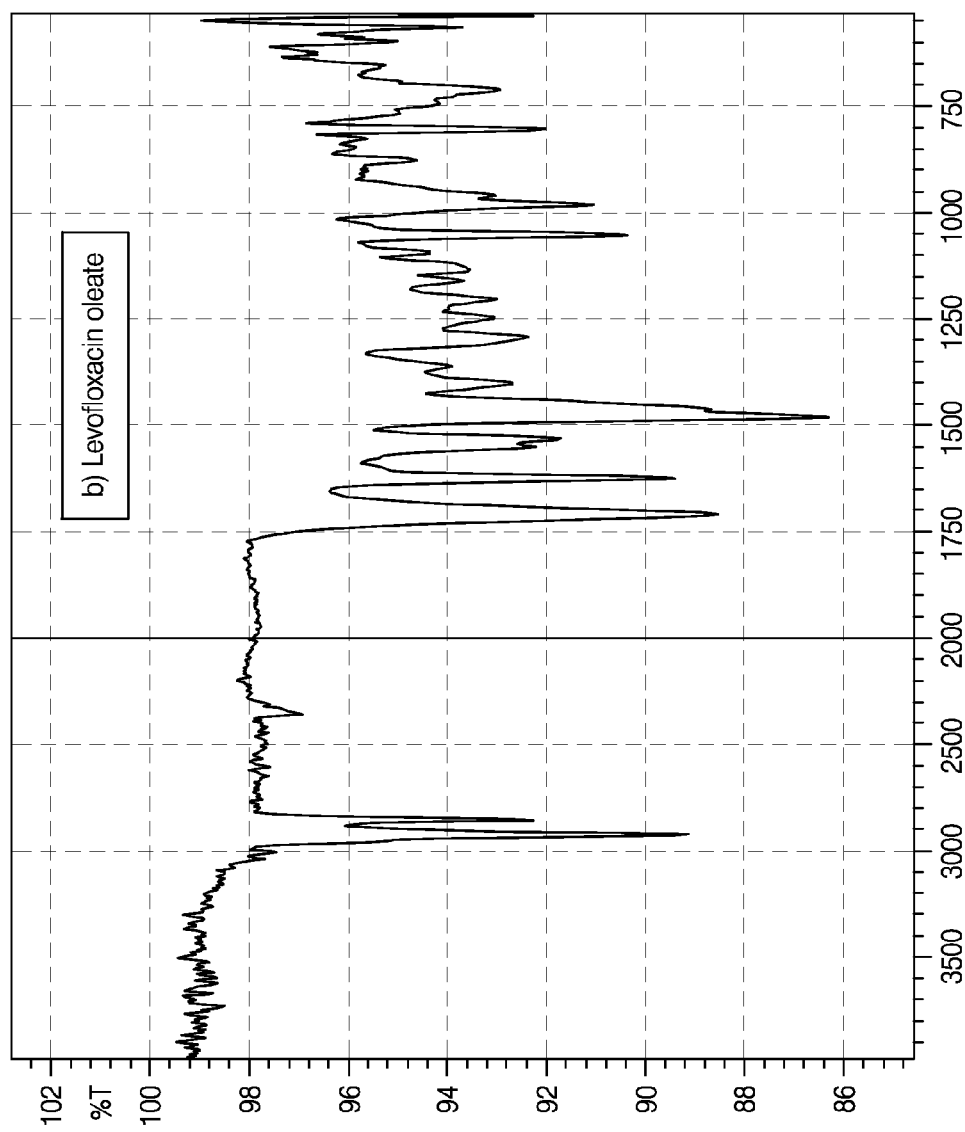
Figure 29C:
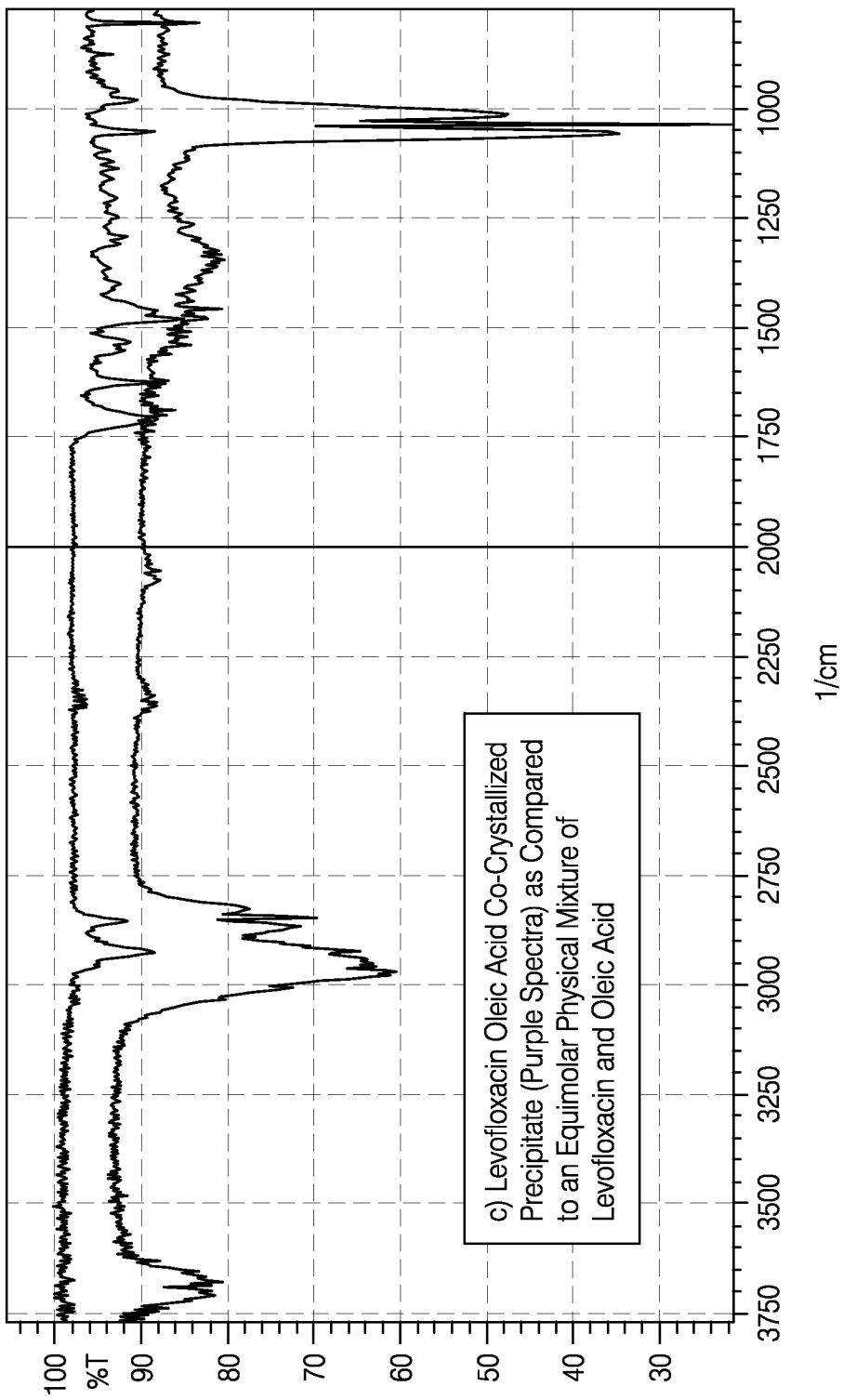

The high intensity absorption bands at 1710 cm$^{-1}$ in the FTIR spectra of oleic acid, which is due to the stretching of C=0 group is slightly reduced in the co crystal. The O—H in plane and out of plane bands at 1462 and 937 cm$^{-1}$ in the oleic acid are absent in the co-crystal. Also the FTIR spectrum of the physical mixture is different from that of the salt (FIG. 29).

Kinetic Solubility Determinations

Figure 30:
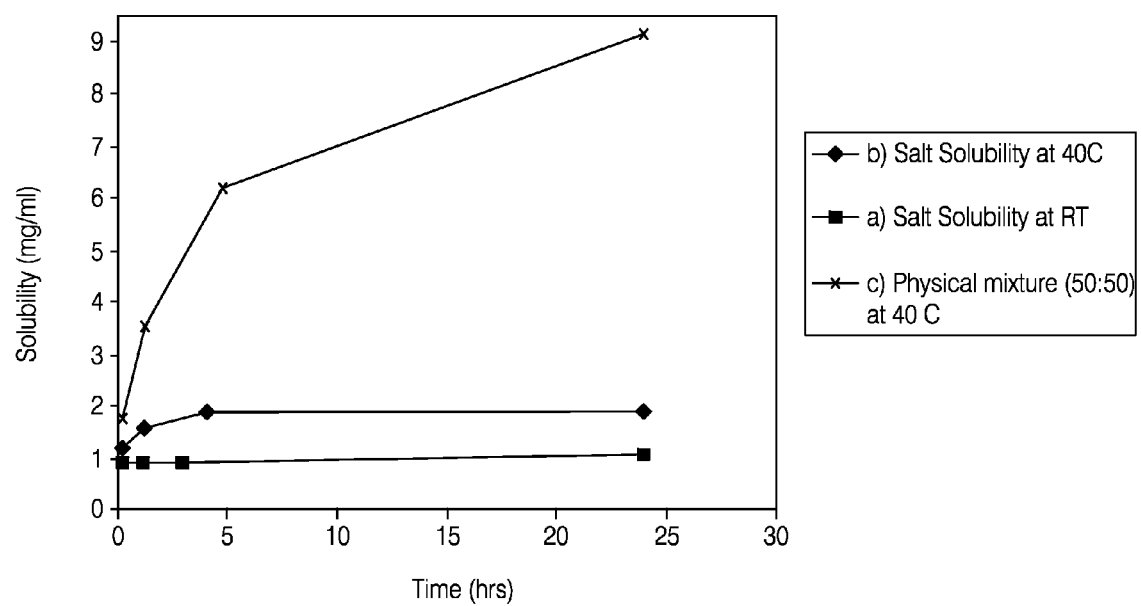
FIG. 30 is a graph showing the kinetic solubility of the co-crystallized precipitate of Levofloxacin with oleic acid at room temperature, 40° C., and equimolar physical mixture at 40° C.

FIG. 30 displays the data for the kinetic solubility experiments performed with the co-crystallized precipitate at room temperature and at 40° C. The solubility of the co-crystals at room temperature is about 0.9 mg/ml, which remains constant throughout the period of the study. At 40° C., the solubility increased from 1.17 mg/ml at 15 minutes to 1.86 mg/ml at 4 hrs which remained almost constant till 24 hrs. The solubility profile of the equimolar physical mixture at 40° C. looks different from that of the co-crystals. The physical mixture has a higher solubility (9.16 mg/ml at 24 hrs) as compared to the co-crystals (1.89 mg/ml at 24 hrs).

Interpretation

The DSC data of the equimolar physical mixture exhibits an endotherm near the melting endotherm of the co-crystallized precipitate. However the FTIR and solubility data of the co-crystals is different than that of physical mixture, with the co-crystals having a low saturation solubility. The saturation solubility of the co-crystals is 0.9 mg/ml temperature as opposed to 25 mg/ml for levofloxacin base.

However the levofloxacin oleate salt is waxy in nature which might be difficult to grind/micronize and thereby formulate. It is reported that the tacky and deformable properties of a wax-like drug fatty acid salt, propranolol oleate made particle size reduction difficult (Crowley. J., et al, International journal of Pharmaceutics, 2000, 211 (1-2): 9-17.

Dissolution Rate Studies

Levofloxacin Xinafoate

Experimental Methodology 50 mg of the levofloxacin xinafoate salt was suspended in a dissolution bath containing 500 ml of pH 7.4 Tris buffer at 37° C. and rotated by means of paddles at 100 rpm. 5 ml samples were removed at periodic time intervals and replaced with same volume of plain buffer.

Results

Figure 31:
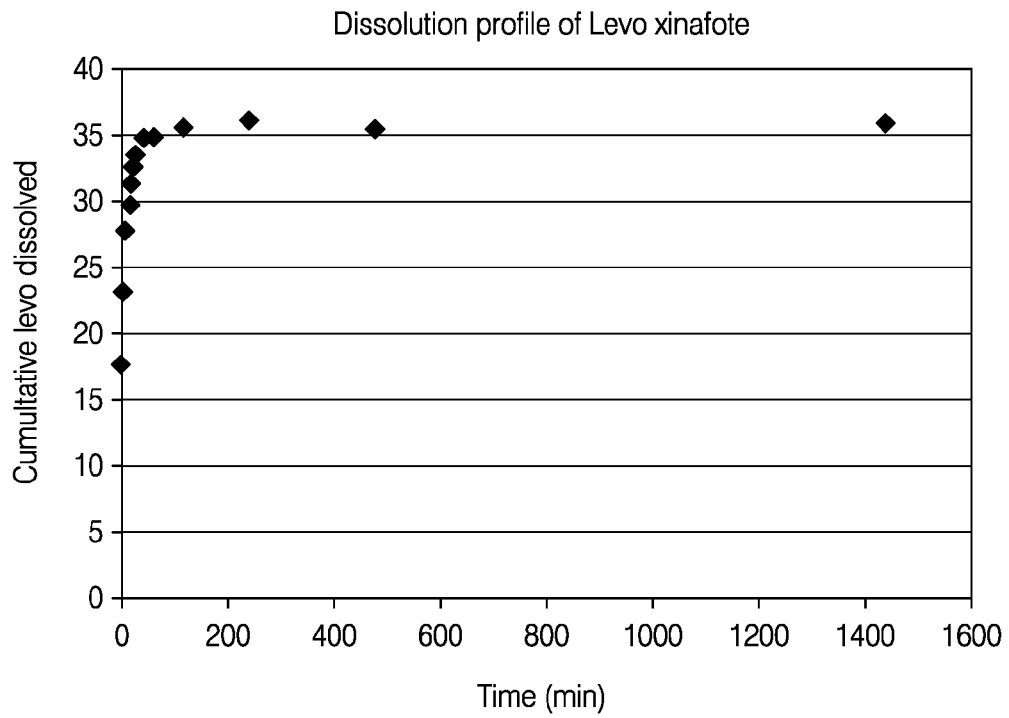
FIG. 31 is a graph showing the dissolution profile of Levofloxacin xinafoate.
Figure 32:
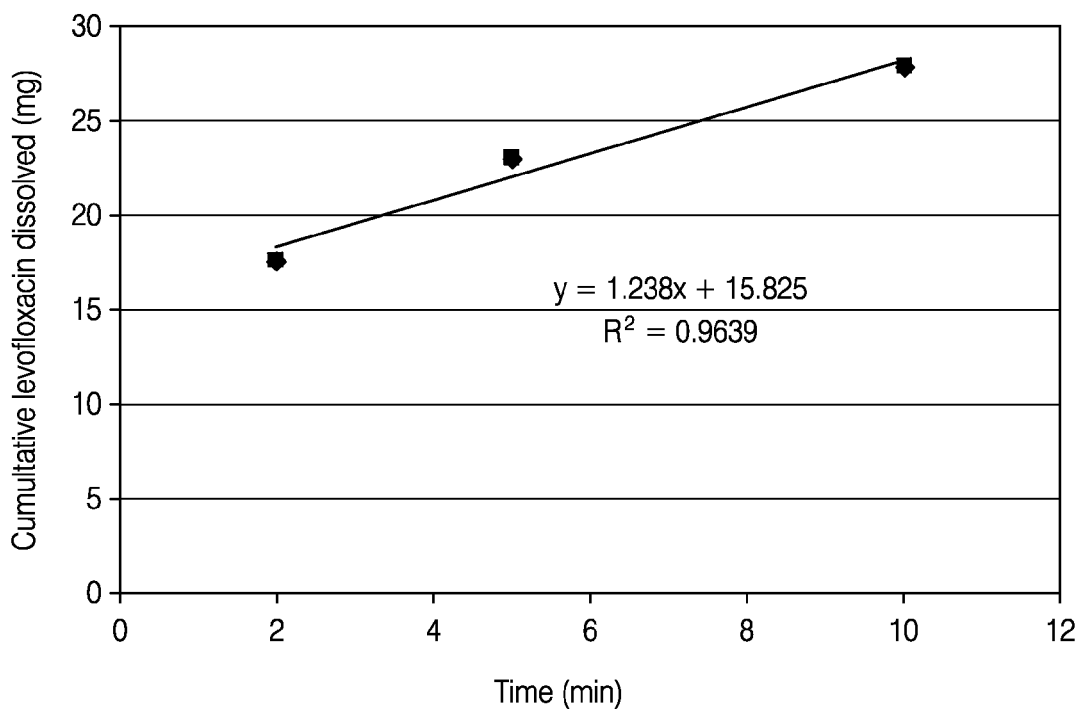
FIG. 32 is a graph showing the dissolution profile of Levofloxacin xinafoate focused on the period between two and ten minutes.
Figure 33:
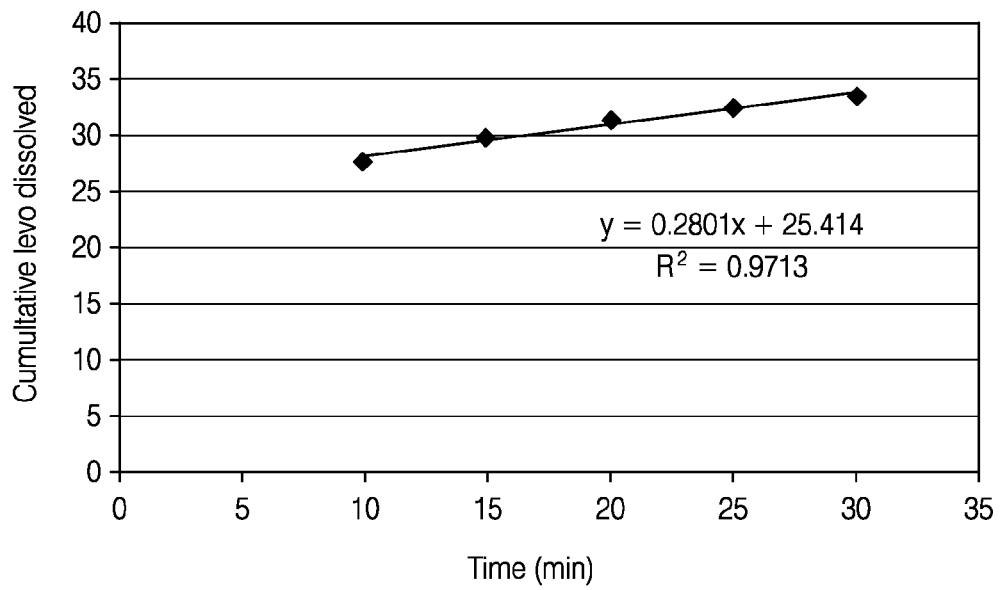
FIG. 33 is a graph showing the dissolution profile of Levofloxacin xinafoate focused on the period between ten and thirty minutes.

The dissolution profile of levofloxacin xinafoate is shown as FIG. 31. It is seen that the dissolution rate of levofloxacin xinafoate in the earlier stages of 2-10 minutes is faster than that seen from 10-30 minutes. When levofloxacin xinafoate is added to the dissolution media, it gets dispersed as a fine powder, and the dissolution from these fine particles is faster, approximately 1.24 mg/min (FIG. 32). With time, the powder gets agglomerated and moves in a vortex created by the paddle, thereby decreasing the dissolution rate to 0.28 mg/min (FIG. 33).

Levofloxacin

Experimental Methodology 200 mg of levofloxacin was suspended in a dissolution bath containing 500 ml of pH 7.4 Tris buffer at 37° C. and rotated by means of paddles at 100 rpm. 5 ml samples were removed at periodic time intervals and replaced with same volume of plain buffer.

Results

Figure 34:
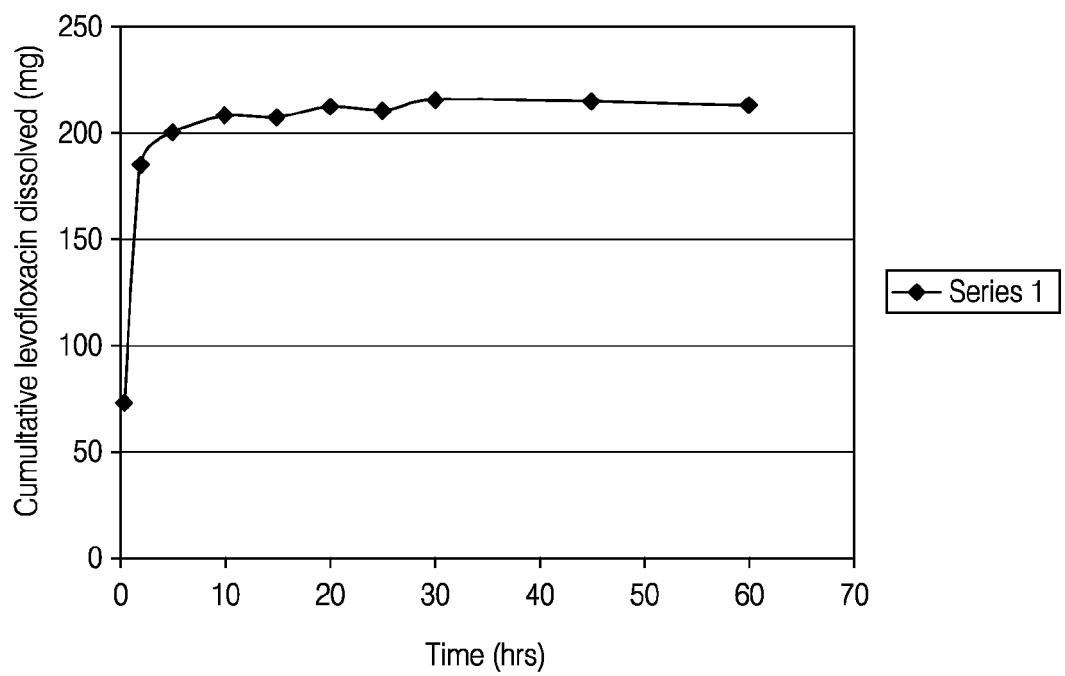
FIG. 34 is a graph showing the dissolution profile of Levofloxacin base.

The dissolution profile of levofloxacin is shown as FIG. 34. As levofloxacin has a higher solubility than the salts its dissolution rate is very fast. With levofloxacin too, the earlier dissolution was from finely dispersed particles and hence a faster dissolution rate. In the later stages the particles agglomerated and reduced its dissolution rate.

Levofloxacin Pamoate

Experimental Methodology 10 mg of the levofloxacin pamoate salt was suspended in a dissolution bath containing 500 ml of pH 7.4 Tris buffer at 37° C. and rotated by means of paddles at 100 rpm. 5 ml samples were removed at periodic time intervals (2, 5, 10, 15, 20, 25, 30, 45, 60, 120, 240, 1320 and 1440 minutes) and replaced with same volume of plain buffer. The study was performed in duplicate.

Results

Figure 35:
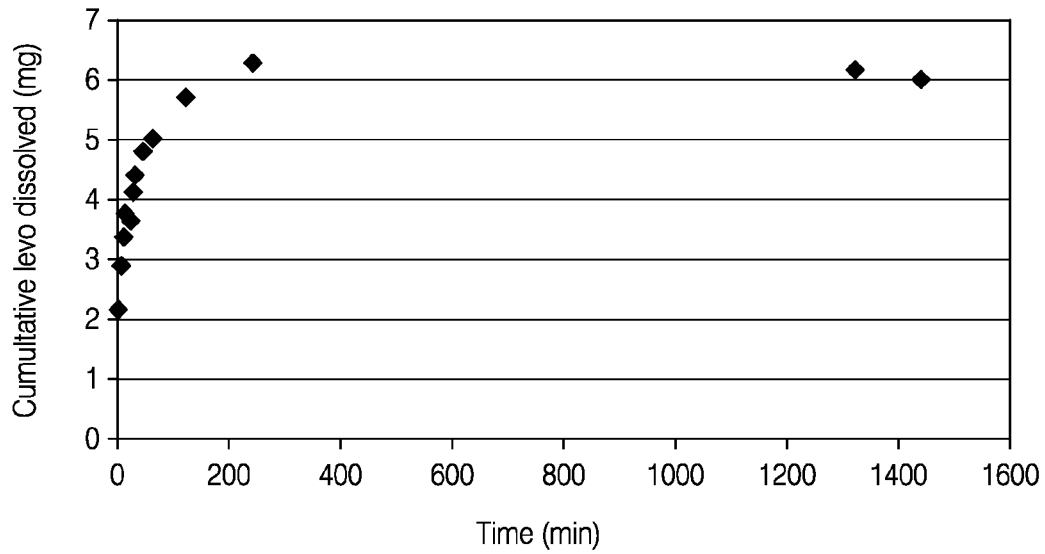
FIG. 35 is a graph showing the dissolution profile of Levofloxacin pamoate.
Figure 36:
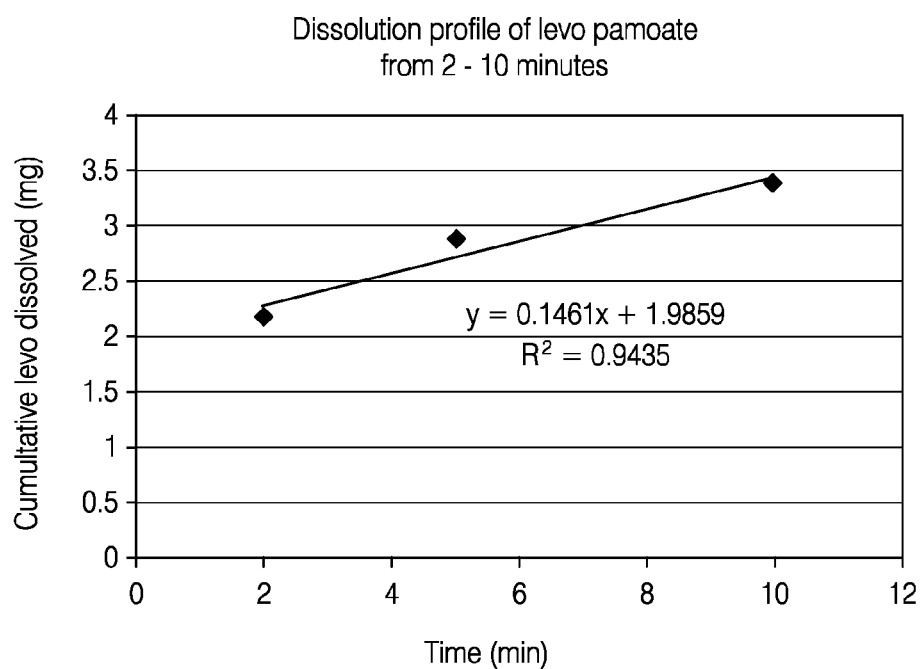
FIG. 36 is a graph showing the dissolution profile of Levofloxacin pamoate focused on the period between two and ten minutes.
Figure 37:
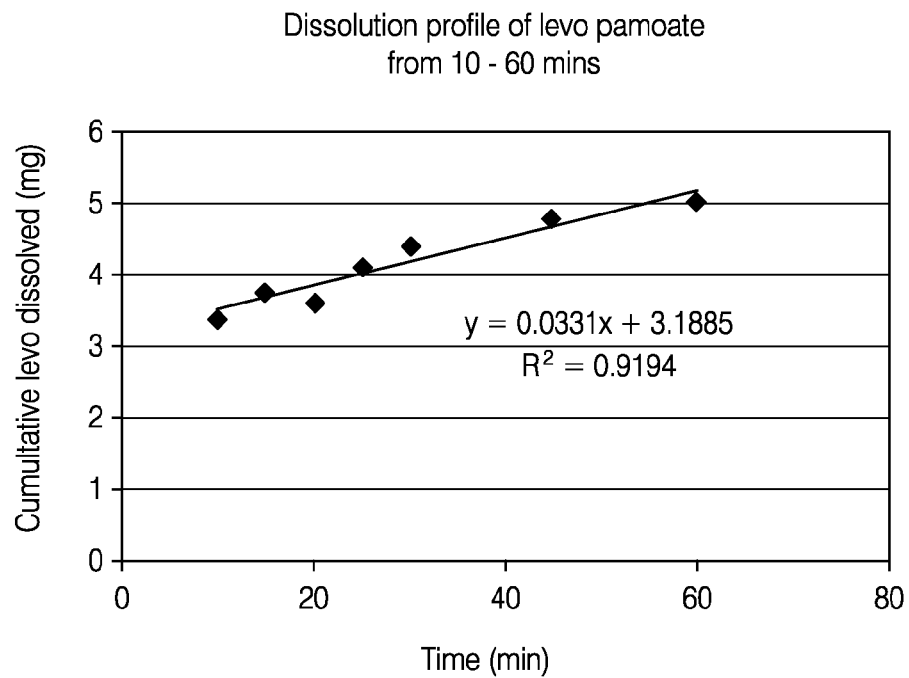
FIG. 37 is a graph showing the dissolution profile of Levofloxacin pamoate focused on the period between ten and sixty minutes.

The dissolution profile of levofloxacin pamoate is shown as FIG. 35. It is seen that the dissolution rate of levofloxacin pamoate in the earlier stages of 2-10 minutes is faster than that seen from 10-60 minutes. When levofloxacin pamoate, is added to the dissolution media, it gets dispersed as a fine powder, and the dissolution from these fine particles is faster, approximately 0.146 mg/min (FIG. 36). With time, the powder gets agglomerated and moves in a vortex created by the paddle, thereby decreasing the dissolution rate to 0.0331 mg/min (FIG. 37).

Levofloxacin Stearate

Experimental Methodology 25 mg of the levofloxacin stearate salt was suspended in a dissolution bath containing 500 ml of pH 7.4 Tris buffer at 37° C. and rotated by means of paddles at 100 rpm. 5 ml samples were removed at periodic time intervals (2, 5, 10, 15, 20, 25, 30, 45, 60, 120, 240, 1320 and 1440 minutes) and replaced with same volume of plain buffer.

Results

Figure 38:
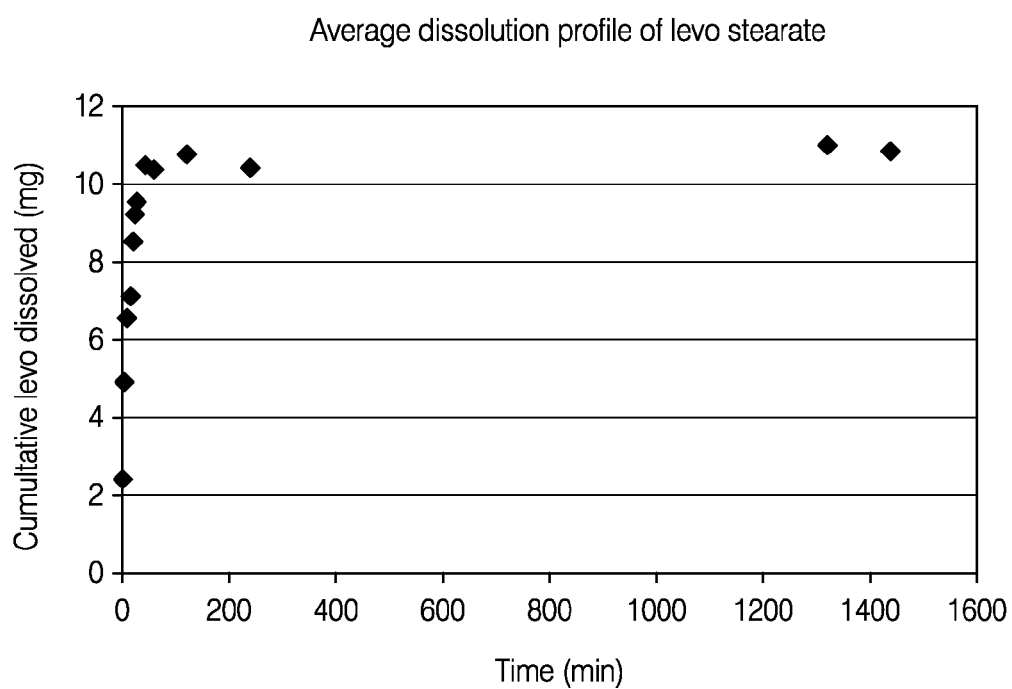
FIG. 38 is a graph showing the dissolution profile of Levofloxacin stearate.
Figure 39:
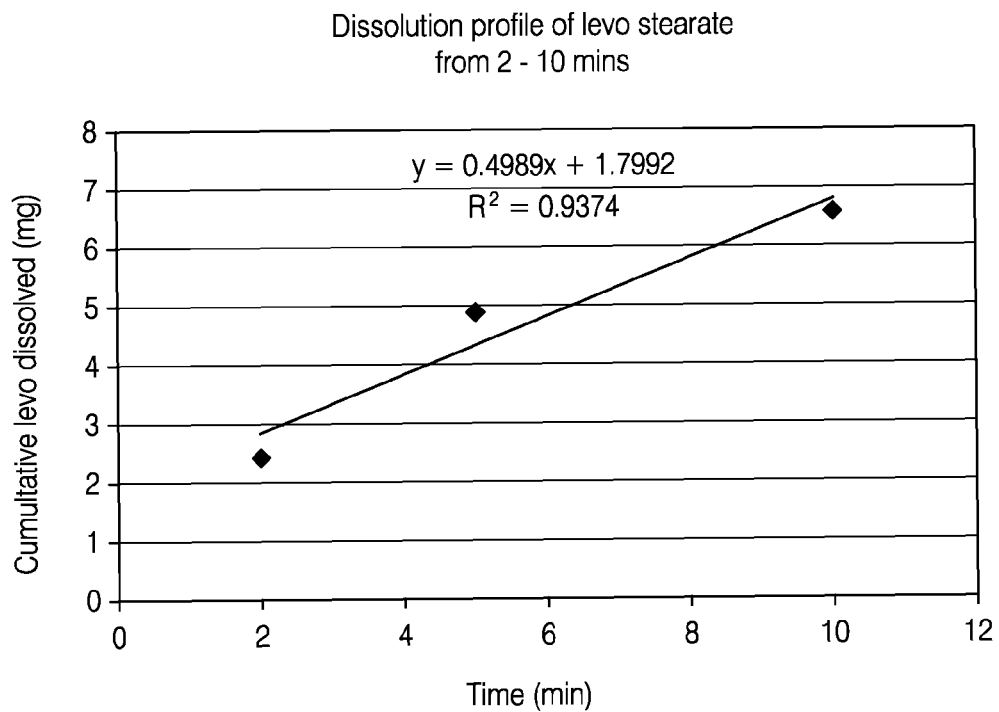
FIG. 39 is a graph showing the dissolution profile of Levofloxacin stearate focused on the period between two and ten minutes.
Figure 40:
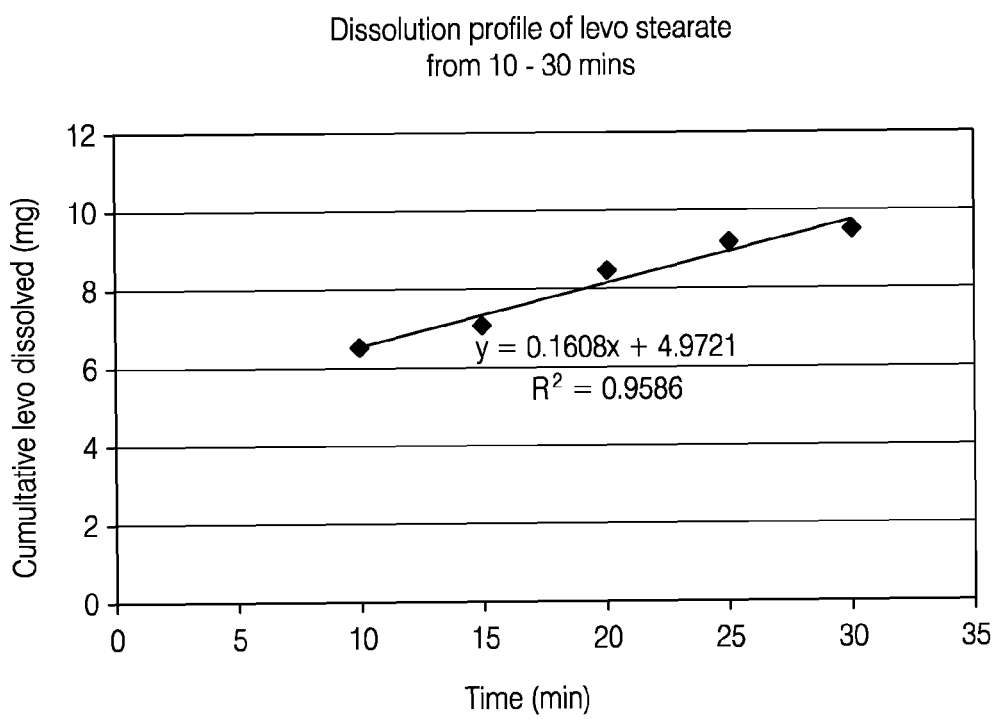
FIG. 40 is a graph showing the dissolution profile of Levofloxacin stearate focused on the period between ten and thirty minutes.

The dissolution profile of levofloxacin stearate is shown as FIG. 38. It is seen that the dissolution rate of levofloxacin stearate in the earlier stages of 2-10 minutes is 0.499 mg/min (FIG. 39) which is faster than that seen from 10-30 minutes (0.161 mg/min) (FIG. 40).

Dissolution of levofloxacin and salts was carried out with quantities such that the concentration of the dissolved solute in the dissolution bath never reached more than 10% of its saturation solubility. This was done in an attempt to maintain sink conditions.

Pending the dissolution rate of these and other salt forms and co-precipitates, these AUC shape-enhancement forms of levofloxacin, gemifloxacin and other fluoroquinolone antibiotics these forms may be best suited for nanoparticle suspension (solubilities<100 ug/ml, slow dissolution rates) or micron-size dry powders (solubilities>100 ug/ml, quicker dissolution rate than that best for nanosuspension. The nanoparticle suspensions may be administered by nebulization using jet, ultrasonic, or vibrating mesh technologies, while dry powder formulations may be administered using either active or passive dry powder inhalers.

Example 11

Levofloxacin Solid Lipid Nanoparticles

The goal of this study was to prepare solid lipid nanoparticles of levofloxacin to obtain AUC shape-enhancing properties through decreased solubility and dissolution. These benefits may enhance the pharmacodynamic properties of levofloxacin following pulmonary administration using nanoparticle suspension or dry powder inhalation formulations. These formulations are being optimized to prolong the release of levofloxacin from decreased solubility salt forms. These properties may also be incorporated into other fluoroquinolone antibiotics including, without limitation gemifloxacin, gatifloxacin, norfloxacin, tosufloxacin, sitafloxacin sarafloxacin, prulifloxacin, and pazufloxacin. Studies are also underway to characterize various lipid nanoparticle forms of gemifloxacin for taste masking, AUC shape-enhancement, nanoparticle suspension and dry powder inhalation administration. Other approaches for solid lipid nanoparticle currently being investigated include spray-dry and in situ micronization techniques.

Preformulation Studies

Partitioning of each compound (including levofloxacin salts and metal cation complexes) into 1-octanol were determined at different relevant pH values. Partitioning as a function of time may also be evaluated to determine whether dissociation of levofloxacin occurs (from both salts and complexes), and in the case of salts, also to determine if selective partitioning of the fatty acid component occurs over time. Compound(s) with significant partitioning (log P>2.0) was evaluated for their solubility in various lipid melts. Additionally, partitioning of a lipophilic fluoroquinoline (if available) is also being studied, and its solubility in different lipid melts will be evaluated. A lipid in which drug is sufficiently soluble will be selected for formulation of solid lipid nanoparticles. A prerequisite to obtain a sufficient loading capacity of the drug in solid lipid nanoparticles was a high solubility of drug in the lipid melt.

Formulation of Solid Lipid Nanoparticles

Formulation of solid lipid nanoparticles typically involves dissolving the drug in a lipid melt, followed by dispersion of the drug-containing melt in a hot aqueous surfactant solution. The coarse dispersion is homogenized using a Microfluidizer® to obtain a nanoemulsion. Cooling the nanoemulsion to room temperature will re-solidify the lipid, leading to formation of solid lipid nanoparticles. Optimization of formulation parameters (type of lipid matrix, surfactant concentration and production parameters) will be performed so as to achieve a prolonged drug delivery.

Characterization of Solid Lipid Nanoparticles

The nanoparticles are being characterized for size and zeta potential using a Dynamic Light Scattering instrument while Laser diffraction will be used for the detection of large microparticles.

Upon completion of the synthesis, differential scanning calorimetric studies will be performed to investigate any possible modifications induced in the physical form of the lipid.

In vitro drug release testing will be done using appropriate methodology."

Example 10

Levofloxacin Metal Ion Complexes

The goal of this study was to prepare levofloxacin of various chelate salt forms to obtain gain taste-masking properties, AUC shape-enhancing properties through changes in solubility, dissolution and/or bioavailability. These benefits may enhance the pharmacodynamic properties of levofloxacin following pulmonary administration using nanoparticle suspension, dry powder inhalation or simple liquid formulations. These formulations may be optimized to create AUC shape-enhancing formulations of levofloxacin from altered solubility, or slow-release or low bioavailability chelates. These properties may also be incorporated into other fluoroquinolone antibiotics including, without limitation gemifloxacin, gatifloxacin, norfloxacin, tosufloxacin, sitafloxacin sarafloxacin, prulifloxacin, and pazufloxacin. Studies are also underway to characterize various and chelate forms of gemifloxacin for taste masking, AUC shape-enhancement, nanoparticle suspension and dry powder inhalation administration.

Preparation of Levofloxacin-Metal Ion Complexes

Preliminary Studies

A mixture of levofloxacin and a salt of a given cation was solubilized in deionized water and titrated with sodium hydroxide. The titration curve was compared against one obtained for levofloxacin alone to assess formation of levofloxacin-metal complex as described in Physical Pharmacy (4th Edition) by Alfred Martin (pp 261-263). Salts of various metal cations (e.g. $Ca^{2+}$, $Mg^{2+}$, etc) were then evaluated to identify suitable candidate(s) for subsequent evaluations. Different molar ratios of cations and levofloxacin were also evaluated.

Preparation of Complexes

Levofloxacin solutions were titrated against aqueous solutions of selected metal salts. Titrations were carried out at a constant pH. Formation of complexes were monitored by different methods including titrimetry, spectrofluorometry, solubility, etc. as applicable. The end point of the complexation reaction depended on the method adopted.

Characterization of Levofloxacin Complexes

Levofloxacin-metal cation complexes were characterized for stoichiometry, formation constants and dissociation kinetics using appropriate methodology.

Goals

To formulate and characterize levofloxacin complexes with metal cations (di- and tri-valent).

Assessment of Complexation

Preliminary investigations suggested that levofloxacin forms soluble complexes with metal cations. As a result, evaluation of the complexation process by precipitation was not possible. Other approaches that were attempted are described below.

Titrimetry

This approach was based on the assumption that the carboxylic acid moiety of levofloxacin is involved in complex formation with a given metal cation and that complexation results in the release of a proton from levofloxacin. The concentration of released protons would thus be proportional to the extent of complexation (depending on the binding constant) and the stoichiometry of the complex (Physical Pharmacy: $4^{th}$ Edition by Alfred Martin; pp-261-263).

Experimental Methodology

About 0.35 mmoles of levofloxacin (in 16 mL of deionized water) were titrated with 6N NaOH in the presence and absence of salt of a metal cation (equimolar). Levofloxacin solutions were acidified to pH values less than 2.0 with 6N HCl prior to titration with NaOH. Salts of metal cations used include calcium chloride, magnesium chloride, ferrous chloride, zinc chloride, aluminum sulfate and aluminum chloride.

Results

Figure 41:
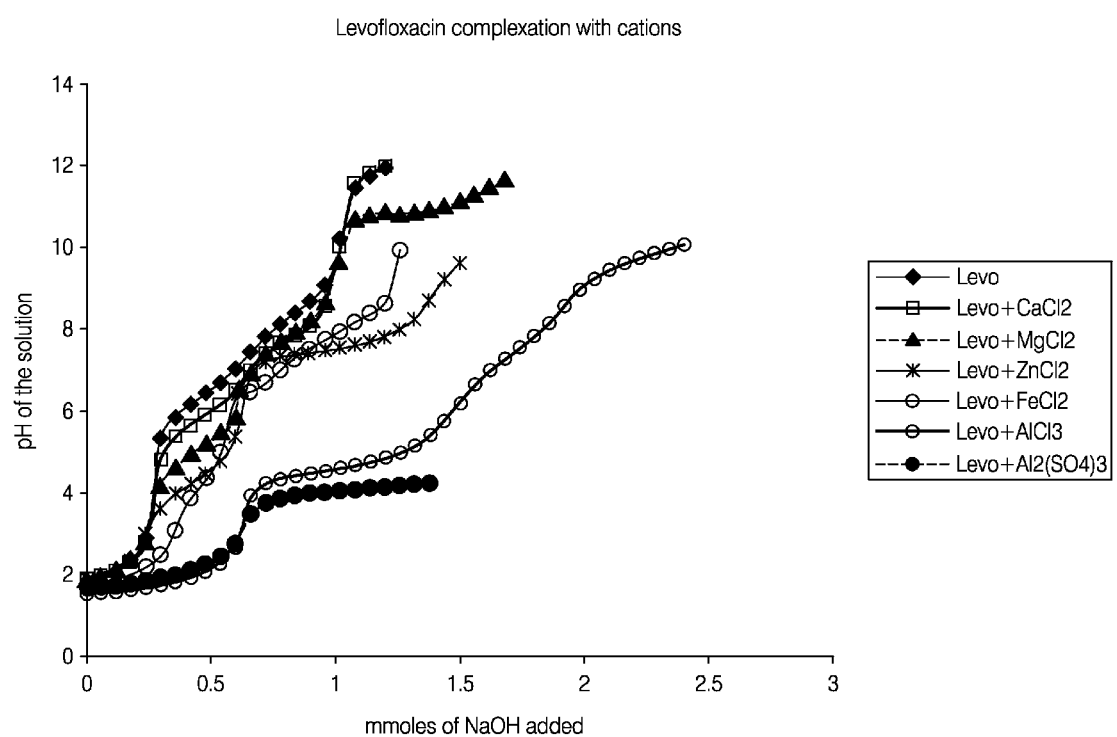
FIG. 41 is a graph showing the complexation of Levofloxacin with divalent and trivalent cations.
Figure 42:
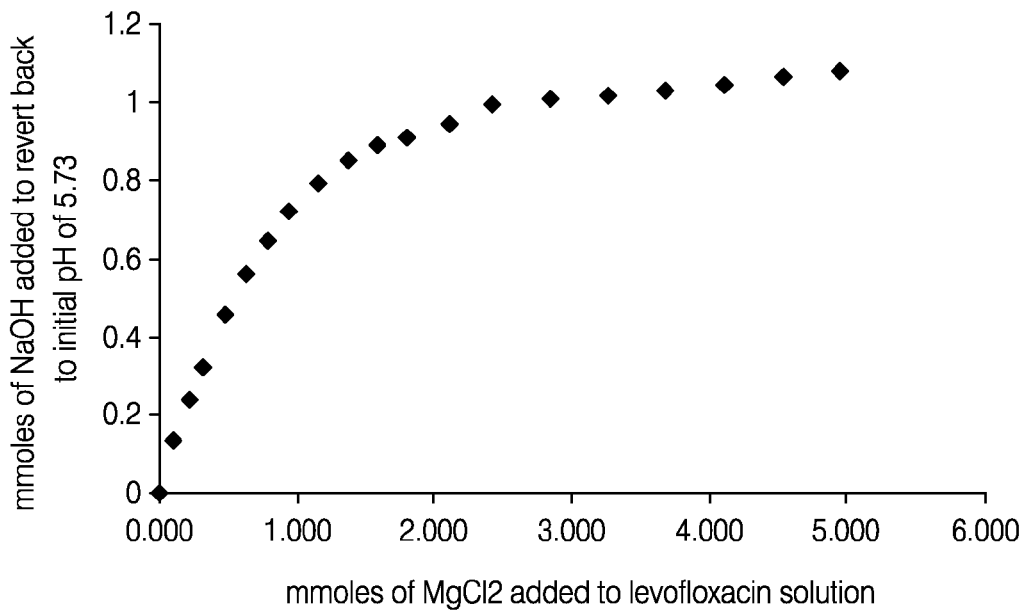
FIG. 42 is a graph showing the dual titration complexation of Levofloxacin with $Mg^{2+}$.
Figure 43:
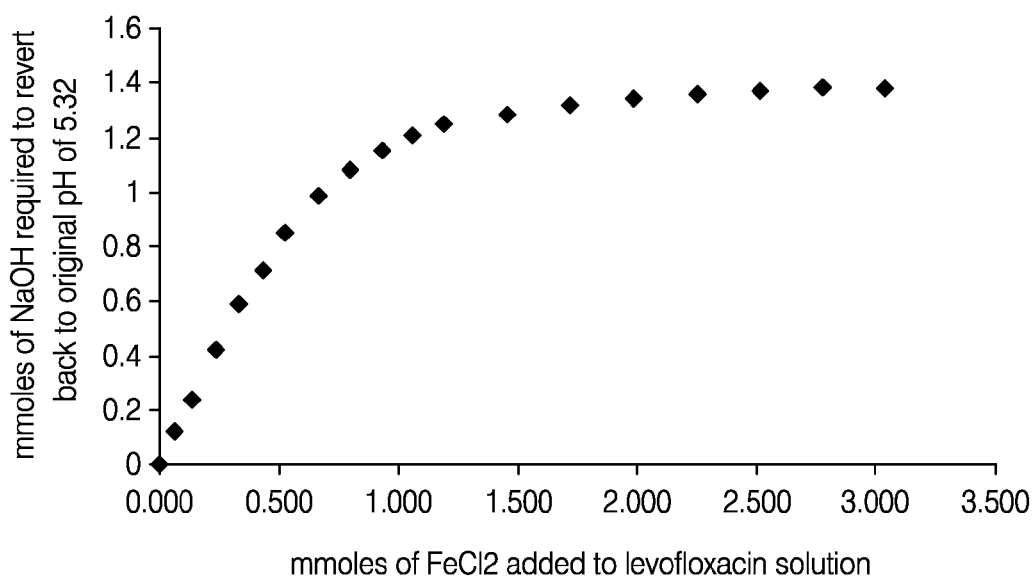
FIG. 43 is a graph showing the dual titration complexation of Levofloxacin with $Fe^{2+}$.
Figure 44:
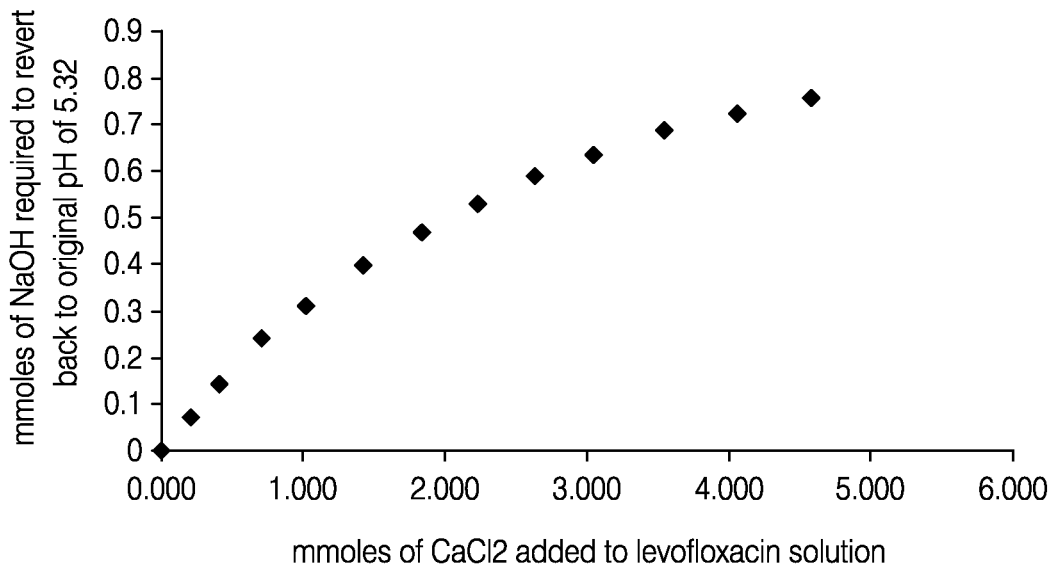
FIG. 44 is a graph showing the dual titration complexation of Levofloxacin with $Ca^{2+}$.
Figure 45:
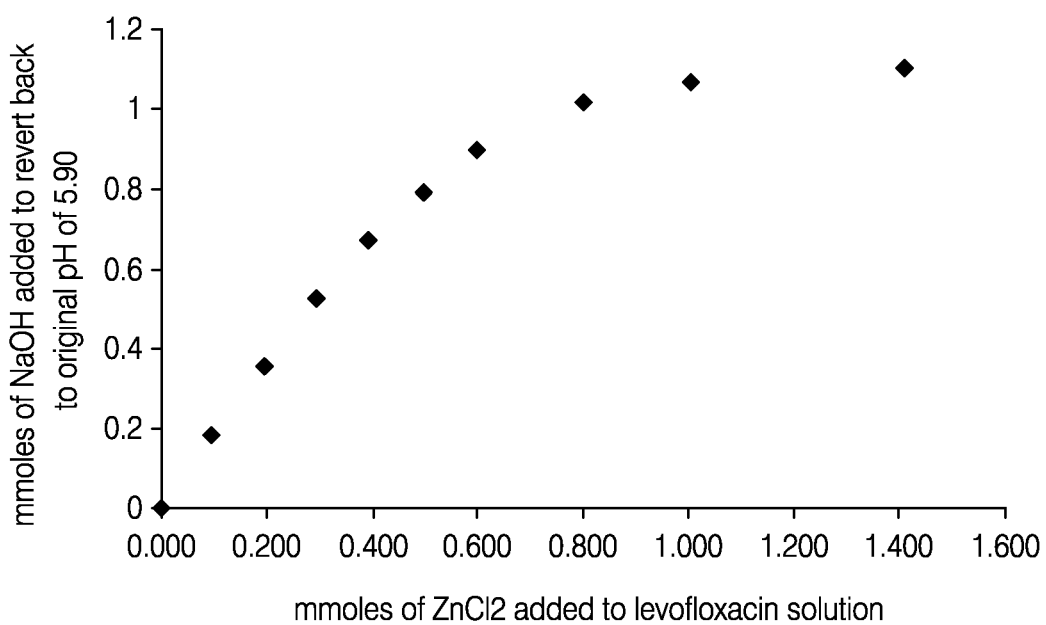
FIG. 45 is a graph showing the dual titration complexation of Levofloxacin with $Zn^{2+}$.
Figure 46A:
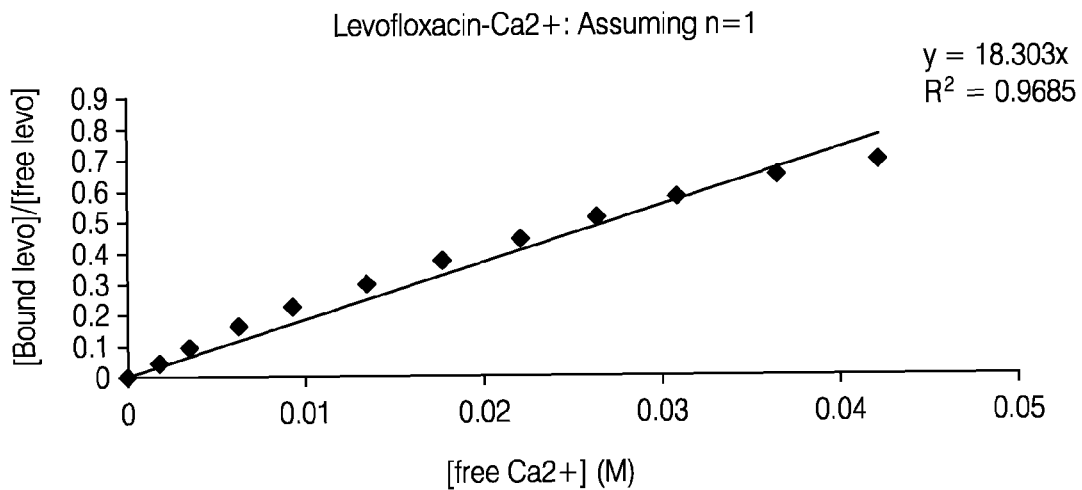
FIG. 46 is a graph showing Levofloxacin complexed with $Ca^{2+}$ vs. free Levofloxacin.
Figure 46B:
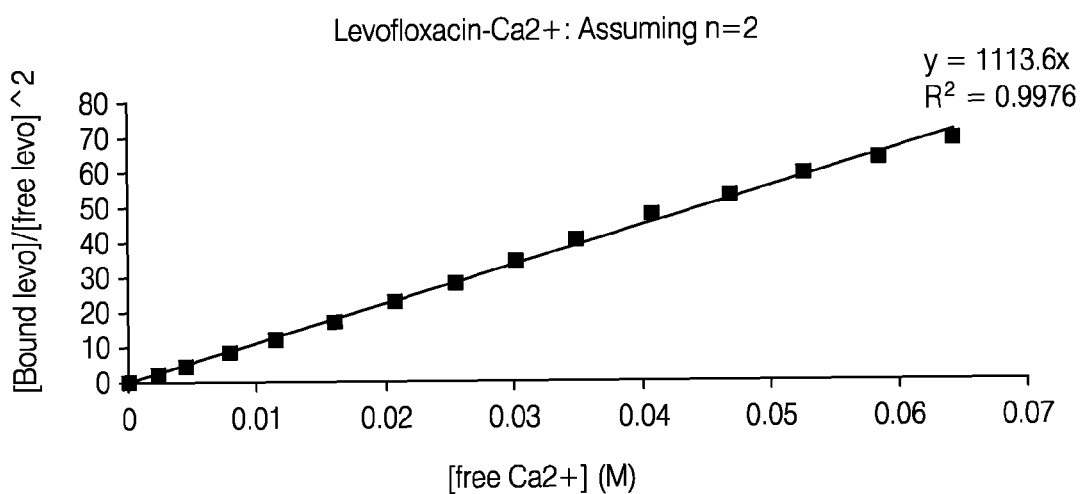
Figure 47A:
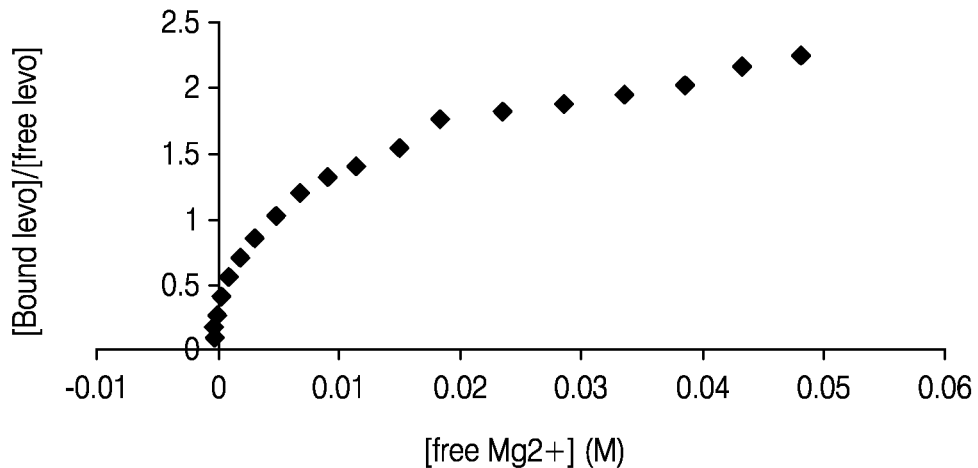
FIG. 47 is a graph showing Levofloxacin complexed with $Mg^{2+}$ vs. free Levofloxacin.
Figure 47B:
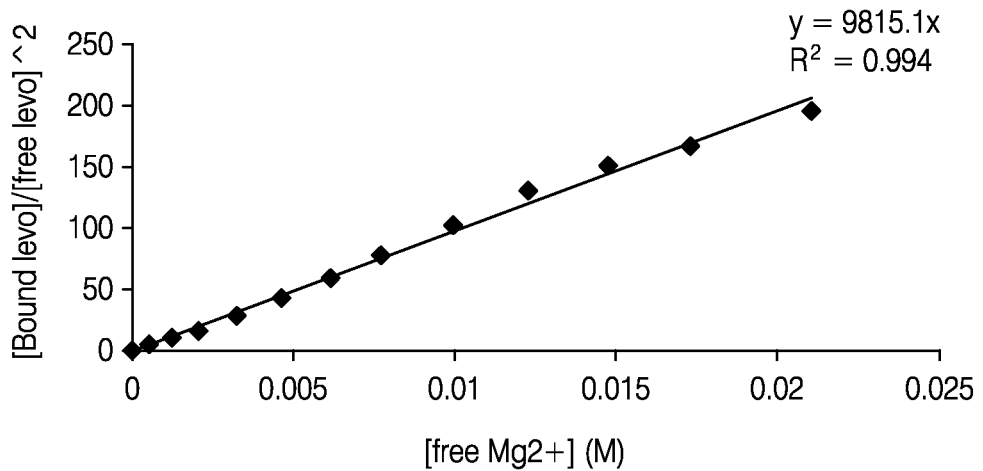
Figure 48A:
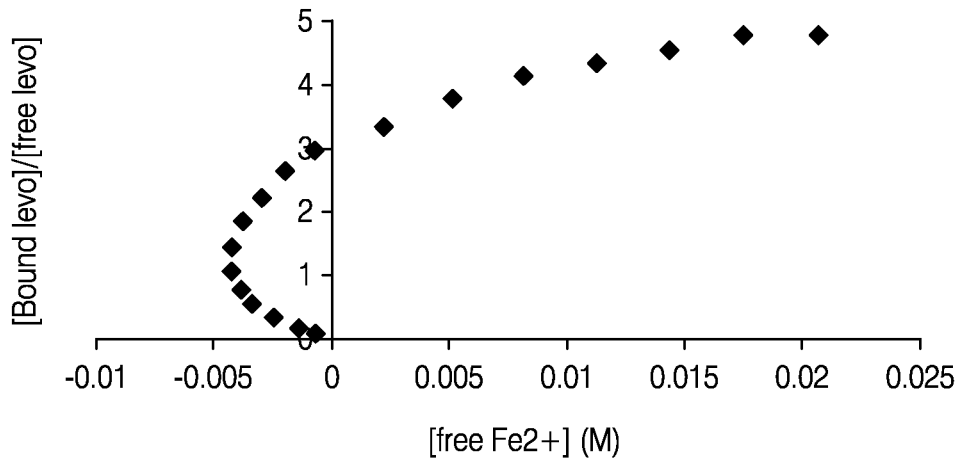
FIG. 48 is a graph showing Levofloxacin complexed with $Fe^{2+}$ vs. free Levofloxacin.
Figure 48B:
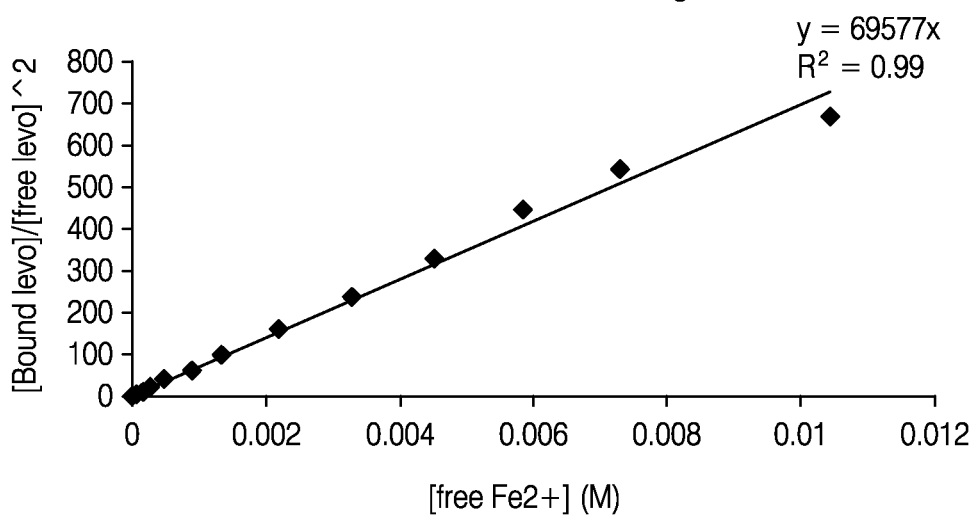
Figure 49A:
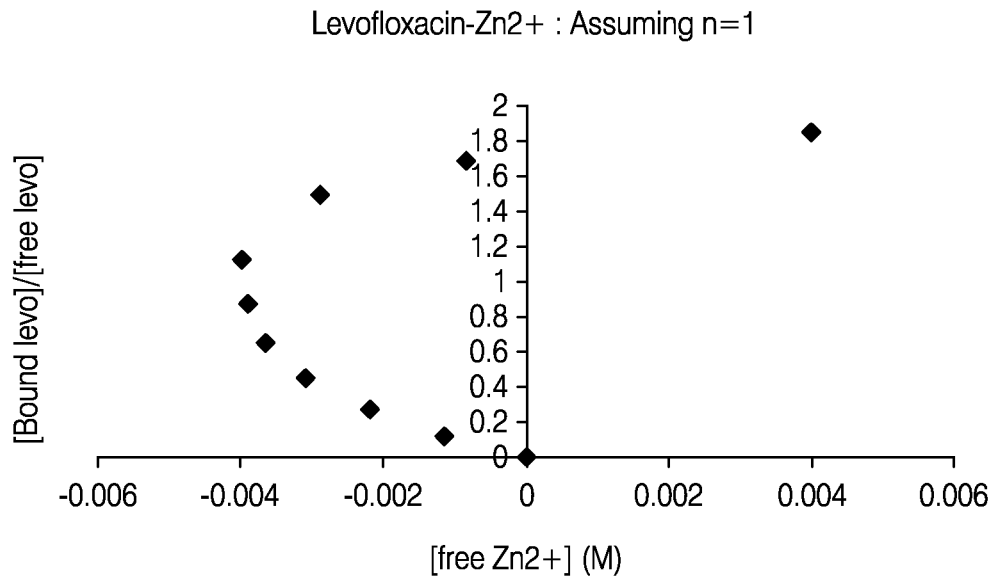
FIG. 49 is a graph showing Levofloxacin complexed with $Zn^{2+}$ vs. free Levofloxacin.
Figure 49B:
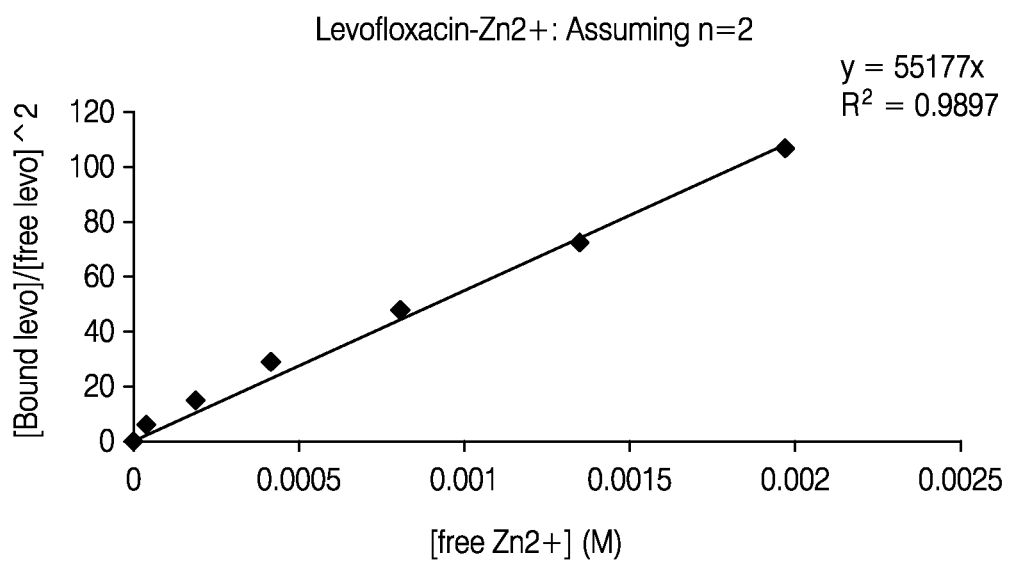

As shown in FIG. 41, titrations performed in the presence of metal cations resulted in a positive shift of the titration curves as compared to the one obtained with levofloxacin alone suggesting that additional NaOH (titrant) is required to obtain a specific pH of the solution in the presence of metal cation. The magnitude of the shift in titration curve at any point would represent moles of proton released due to complexation and hence moles of complexed levofloxacin.

Extent of complexation (binding and/or stoichiometry) appears to increase in the order $Ca^+<Mg^{2+}<Zn^{2+}=Fe^{2+}<Al^{3+}$, which is in reasonable agreement with existing literature.

Note: It was noted from the literature that aluminum chloride and aluminum sulfate have acid-like properties and would lower the pH of aqueous solutions. Consequently, the titration curves obtained with $AlCl3$ and $Al2(SO4)3$ may not provide conclusive information on complexation with levofloxacin.

Dual Titration

In this approach levofloxacin solution was titrated with a solution of a given metal cation to observe a drop in pH presumably due to release of protons through complexation. This was followed by addition of NaOH to revert back to the initial pH of the levofloxacin solution (prior to addition of solution of cation). This enables determination of the fraction of levofloxacin in the complexed form at a given pH.

Experimental Methodology

About 1.55-1.72 mmoles of levofloxacin were solubilized in deionized water and the resulting solution was acidified with 6N HCl to the desired initial pH. This acidified levofloxacin solution was titrated with a known volume of concentrated solution of a given metal cation ($Ca^{2+}$, $Mg^{2+}$, $Fe^{2+}$ and $Zn^{2+}$). The change in pH was neutralized (to the initial pH) by the addition of 6N NaOH and volume of NaOH solution added was recorded. Addition of solution of metal cation followed by neutralization with NaOH was continued until further addition of solution of metal cation failed to result in pH change of the levofloxacin solution, which would indicate endpoint of complexation. The cumulative amounts of metal cation added were plotted against cumulative amounts of NaOH required to neutralize the change in pH (FIGS. 42-45).

Results

From FIGS. 42-45, the plateau regions were extrapolated to obtain total amount of NaOH required to neutralize the change in pH due to complexation. These values also represent the amounts of levofloxacin in the complexed form (assuming that complexation of levofloxacin results in an equimolar release of protons). Amounts of levofloxacin in the complexed form with $Ca^{2+}$, $Mg^{2+}$, $Fe^{2+}$ and $Zn^{2+}$ are 0.8, 1.0, 1.3 and 1.1 mmoles, respectively. These represent 46.5, 64.5, 77.8 and 64.5% complexation for $Ca^{2+}$, $Mg^{2+}$, $Fe^{2+}$ and $Zn^{2+}$, respectively. It should be noted that % complexation would depend on the total concentrations of levofloxacin.

The binding constants as well as the stoichiometry of complexation for the levofloxacin complexes with the metal cations were determined as follows:

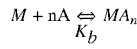

Where M, A and $MA_n$ represent the metal cation, levofloxacin and the complex, respectively. $K_b$ would be the equilibrium binding constant. The above reaction assumes that 'n' moles of levofloxacin react with one mole of metal to yield one mole of complex.

$$K_b = [MA_n]/\{[M][A]^n\} \text{ (units } M^{-n}\text{)} \quad \text{Eq. 1}$$

$[MA_n]$ is the concentration of complex formed
$[M]$ and $[A]$ are the concentrations of the unbound metal and unbound levofloxacin, respectively.

Rearranging Eq. 1, $$[MA_n]/[A]^n = K_b*[M] \quad \text{Eq.2}$$

$$[A] = [A]_{Total} - [A]_{bound} = [A]_{Total} - [NaOH]_{used}$$

$$[M] = [M]_{Total} - [M]_{bound} = [M]_{Total} - [NaOH]_{used}/n$$

$$[MA_n] = [A]_{bound}/n = [NaOH]_{used}/n$$

Note:

$[NaOH]_{used}$ is the concentration of sodium hydroxide used at any given point to neutralize the change in pH caused by the addition of metal cation (presumably due to complexation).

Eq.2 can be modified to obtain, $$[A]_{bound}/[A]^n = nK_b*[M] \quad \text{Eq.3}$$

It is inferred from Eq.3 that a plot of $[M]$ versus $[A]_{bound}/[A]^n$ would result in a straight line with a slope of $nK_b$ when, n=1, for a 1:1 complex
n=2, for a 2:1 complex
n=3, for a 3:1 complex etc.

Shown below in FIGS. 46-49 are these plots for $Ca^{2+}$, $Mg^{2+}$, $Fe^{2+}$ and $Zn^{2+}$, respectively.

As shown in FIGS. 46-49, for each of the cations evaluated a plot of [A]bound/[A]n versus $nK_b*[M]$ was linear when n=2 (for $Ca^{2+}$ n=2 resulted in a better fit than n=1). These results suggest that levofloxacin complexes with $Ca^{2+}$, $Mg^{2+}$, $Fe^{2+}$ and $Zn^{2+}$ are formed with a stoichiometry of 2 moles of drug per mole of cation (2:1).

Using n=2, the binding constants for the above complexes can be determined from the slopes of the respective linear plots.

The binding constants for 2:1 complexes represented as $\log(K_b)$ are as follows: $Ca^{2+}=2.75$, $Mg^{2+}=3.69$, $Zn^{2+}=4.44$, $Fe^{2+}=4.54$.

Solubility

This method allows for a relatively simple way of determining the stoichiometry of complexation. The approach involved evaluation of solubility of the drug (levofloxacin) in the presence of increasing concentrations of complexation agent (a given metal cation). The total solubility of the drug (complexed+uncomplexed) was expected to increase linearly owing to complexation and to reach a plateau corresponding to the saturation solubility of both the drug and the complex. Determination of the stoichiometry from such a solubility curve was explained in detail elsewhere (Physical Pharmacy: 4th Edition by Alfred Martin; pp 265).

Experimental Methodology

Excess quantities of levofloxacin (amounts were recorded) were agitated, in the presence of increasing concentrations of $MgCl_2$, with 25 mM MES buffer (pH 5.99) using a vortex mixer. The samples were then filtered and the filtrate was diluted appropriately and analyzed spectrophotometrically to determine levofloxacin concentrations (FIG. 50).

Results

Figure 50:
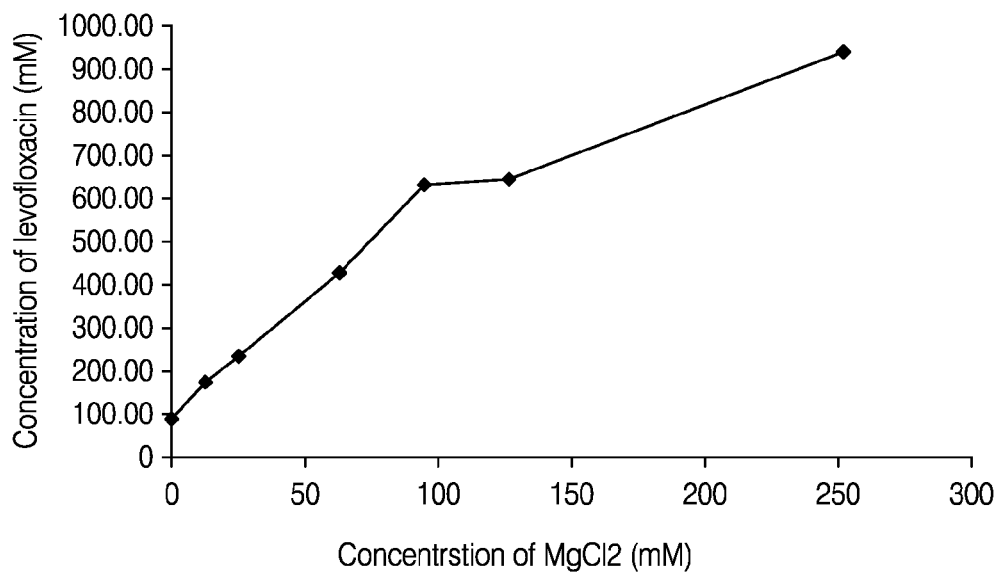
FIG. 50 is a graph showing the solubility of Levofloxacin in the presence of $Mg^{2+}$.

As shown in FIG. 50, the solubility of levofloxacin did increase with increasing MgCl2 concentrations. However, beyond the plateau solubility (~650 mM levofloxacin), further increase in solubility was observed, which is not consistent with the expected profile. This was attributed to the effect of ionic strength on levofloxacin solubility. It is important to note that the final pH of all the solutions were constant, albeit greater than 5.99 (final pH ~7.0).

Figure 51:
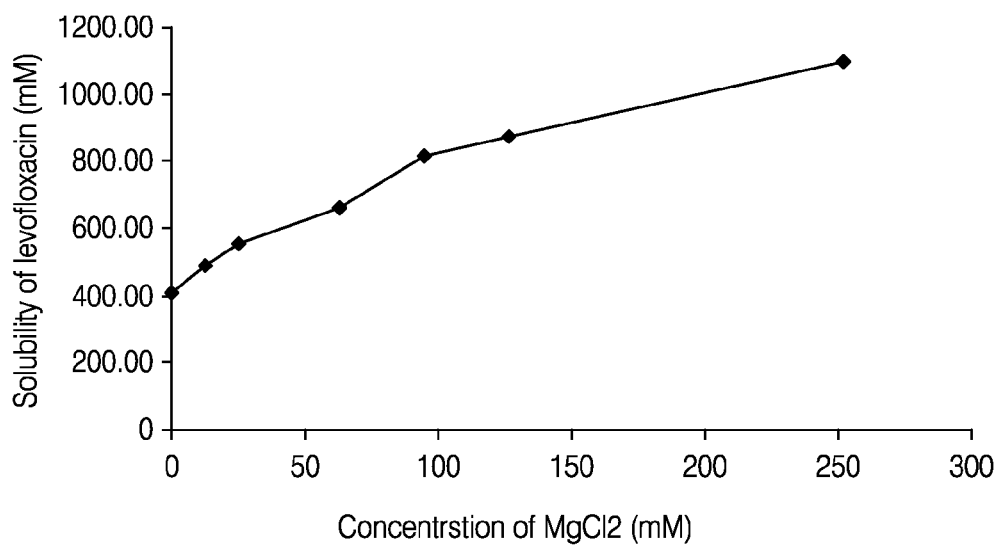
FIG. 51 is a graph showing the solubility of Levofloxacin in the presence of $Mg^{2+}$ at constant ionic strength.

Subsequently, the experiment was repeated at a constant ionic strength of ~1.0M (adjusted with NaCl) and with 0.5M MES buffer (pH 5.99) to enhance the buffer capacity of the solution (FIG. 51).

Spectrofluorometry

This approach was adopted to evaluate levofloxacin complexation based on existing literature evidence that the complexation process is associated with a change in the fluoroquinolone fluorescence properties. By monitoring the change in fluorescence emission of levofloxacin in the presence of different concentrations of a given metal cation it was possible to determine the binding constant of complexation as well as the stoichiometry.

Experimental Methodology

The fluorescence emission of levofloxacin was evaluated at excitation and emission wavelengths of 298 nm and 498 nm, respectively. Studies were conducted at two different pH values i.e. 5.0 (acetate) and 9.0 (histidine). A series of solutions containing a constant levofloxacin concentration but increasing concentrations of a given cation were analyzed for fluorescence emission due to levofloxacin. Metal salts studied included CaCl2, MgCl2, FeCl2, ZnCl2 and Al2(SO4)3.

Results

As shown in Table 34, significant data were obtained only for $Fe^{2+}$ and $Zn^{2+}$. For the remaining cations, the relative concentrations of levofloxacin and the cation need to be further optimized to observe a specific trend in change in levofloxacin fluorescence.

Figure 52:
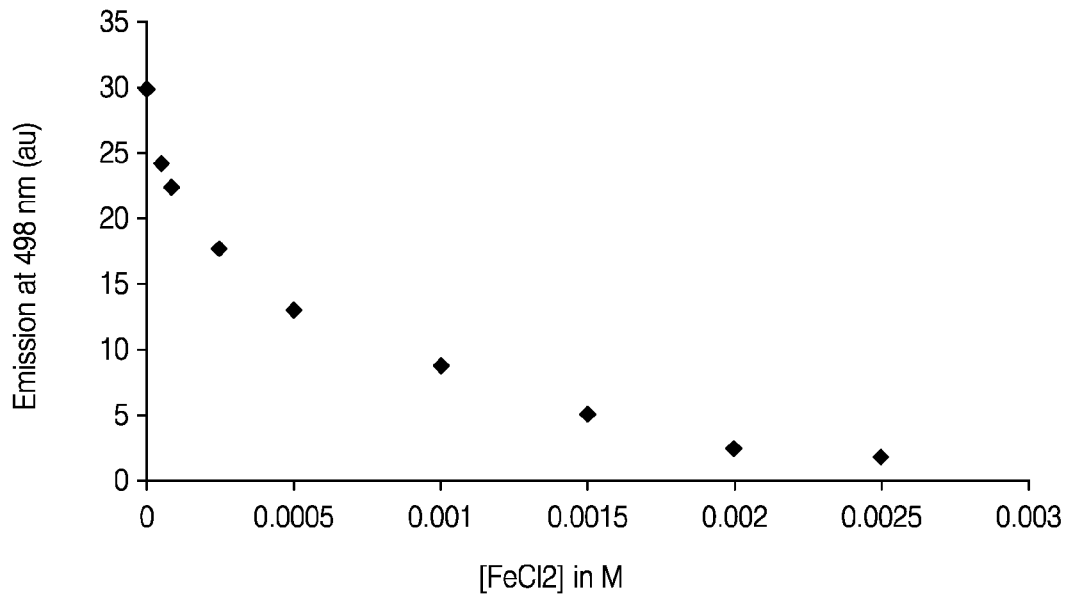
FIG. 52 is a graph showing complexation of Levofloxacin with $Fe^{2+}$ as measured by spectrofluorometry.
Figure 53:
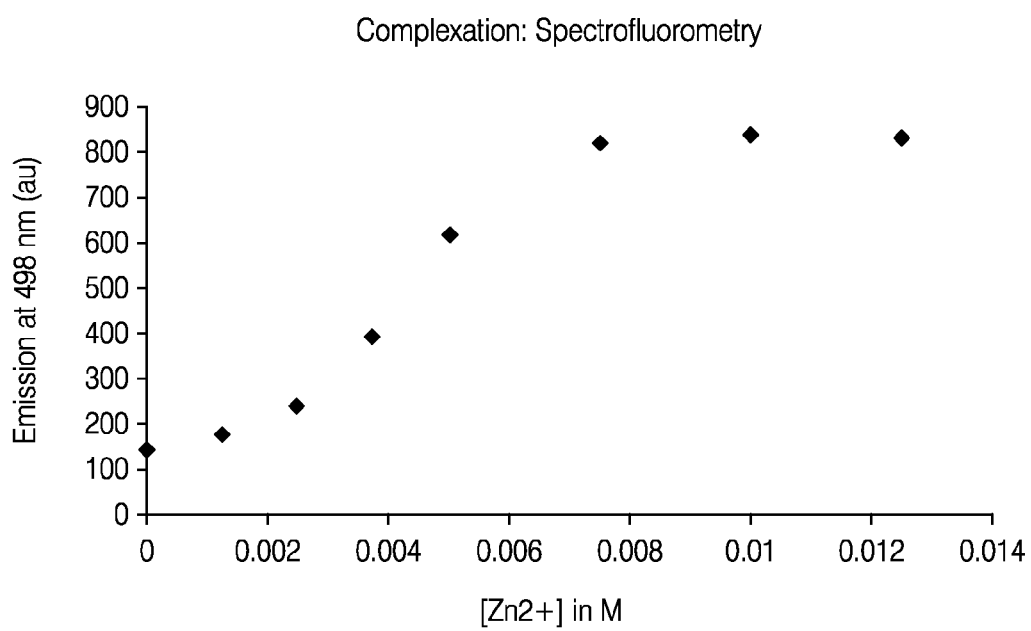
FIG. 53 is a graph showing complexation of Levofloxacin with $Zn^{2+}$ as measured by spectrofluorometry.

The influence of increasing concentrations of $Fe^{2+}$ and $Zn^{2+}$ on levofloxacin fluorescence emission are shown in FIGS. 52 and 53, respective As described above, both $Fe^{2+}$ and $Zn^{2+}$ appear to form 2:1 complexes with levofloxacin; however, their influence on levofloxacin fluorescence are dissimilar (FIGS. 52 and 53). The exact reason for this is unclear at this point.

TABLE 34

Fluorescence Characeristics of Levofloxacin in the Presence of Cations.

Figure 3:
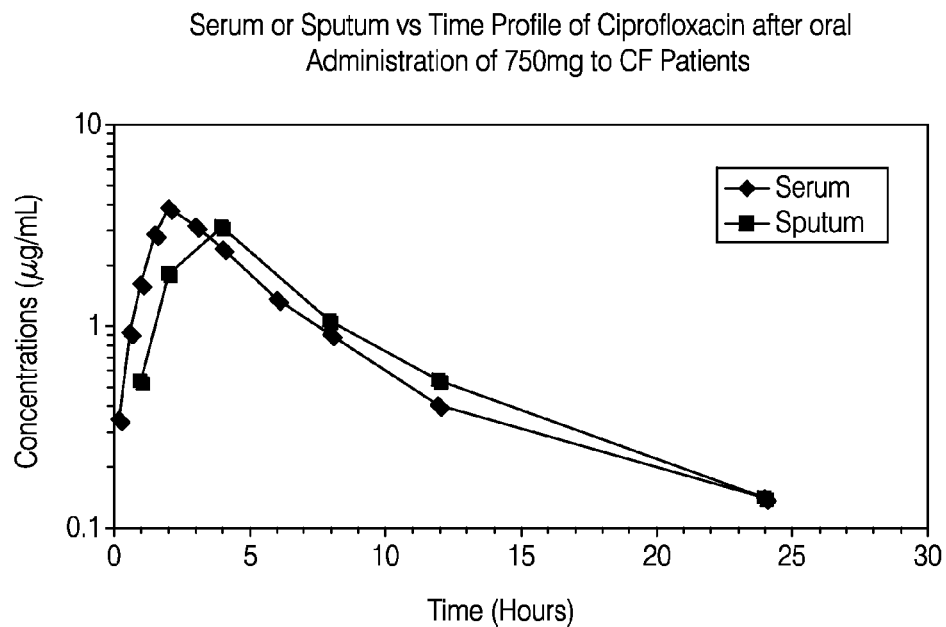
FIG. 3 is a graph showing ciprofloxacin sputum and serum concentrations following oral dosing.

| Cation | Fluorescence of levofloxacin pH 5.0 | pH 9.0 | Results | Comments |
|---|---|---|---|---|
| $Ca^{2+}$ | Change not significant | Change not significant | N/A | — |
| $Mg^{2+}$ | Change not significant | Change not significant | N/A | — |
| $Fe^{2+}$ | Decrease in emission with increasing $Fe^{2+}$ | N/A | FIG. 3.12 (pH 5.0) | $FeCl_2$ insoluble at pH 9.0 |
| $Zn^{2+}$ | Change not significant | Increase in emission with increasing $Zn^{2+}$ | FIG. 3.13 (pH 9.0) | — |
| $Al^{3+}$ | Change not significant | N/A | N/A | $Al_2(SO_4)_3$ insoluble at pH 9.0 |

Samples of Levofloxacin Complexes

Seven samples of levofloxacin complexes were evaluated in vivo for efficacy and pharmacokinetics. Details of the samples tested are shown in Table 35 below.

TABLE 35

Molar Ratios of Levofloxacin Complexes.

| Sample identifier | Cation | Molar ratio used | Total Levofloxacin (mg/mL) | Final pH of the solution |
|---|---|---|---|---|
| NB-049-001-06-066A | $Mg^{2+}$ | 1:1 | 40.2 | 6.24 |
| NB-049-001-06-066B | $Fe^{2+}$ | 1:1 | 40.1 | 6.30 |
| NB-049-001-06-066C | $Mg^{2+}$ | 1:1 | 202 | 5.98 |
| NB-049-001-06-081A | $Ca^{2+}$ | 1:1 | 40.1 | 6.53 |
| NB-049-001-06-081B | $Ca^{2+}$ | 1:1 | 201 | 6.04 |
| NB-049-001-06-081C | $Zn^{2+}$ | 1:1 | 40 | 6.33 |
| NB-049-001-06-081D | $Zn^{2+}$ | 1:1 | 200 | 5.69 |

Conclusions and Next Steps

Results obtained from our dual titration studies suggest that levofloxacin forms 2:1 complexes with all the divalent metal cations. The binding constants (log $K_b$) for complexation with $Ca^{2+}$, $Mg^{2+}$, $Fe^{2+}$ and $Zn^{2+}$ are 2.75, 3.69, 4.44 and 4.54, respectively.

Example 11

Levofloxacin and Gemifloxacin Formulations with Organic Acids

Experimental Methodology

Levofloxacin solution was prepared by dissolving either 50 or 100 mg levofloxacin base in 15-20 ml water. The initial pH of levofloxacin solution in water was about 7.3. The pH of the solution was adjusted with about 10% solution of acid prepared in water. The following acids were used to adjust the pH of the levofloxacin solution: acetic acid, ascorbic acid, citric, lactic, tartaric and propionic acid. After making up the volume of the solution to approximately 90% of the final volume, the osmolality of the solution was measured and adjusted to 300 mOsm/kg with about 20% solution of sodium chloride prepared in water After pH and osmolality adjustment, the volume of the solution was made up to about 25 ml with water and its surface tension measured. The pH and osmolality were measured after making up the volume and are reported in Table 36. (The exact quantities of levofloxacin weighed, acid required to adjust pH, sodium chloride to adjust osmolality and final volume of solutions are listed in Table 36). The content of levofloxacin in the solutions was determined by HPLC.

Results

The details about the levofloxacin formulations with organic acids are shown in Table 36. The results of HPLC are shown in Table 37.

When tartaric acid was used to adjust the pH of the 100 mg/ml levofloxacin solution, a precipitate was formed.

Note: Solutions with acetic acid, citric acid and ascorbic acid were remade for HPLC analysis and hence the theoretical concentration for these solutions in Table 36 and Table 37 are different.

Gemifloxacin Formulations with Organic Bases
Experimental Methodology and Results
Gemifloxacin Formulation with Sodium Aascorbate 50.30 mg of Gemifloxacin mesylate (equivalent to 40.37 mg Gemifloxacin) was added to 1.5 ml water. The resulting solution was cloudy. It was filtered through a 0.45 micron filter. 1.3 ml of solution was obtained after filtering having a pH of 4.28. The pH of this solution was adjusted to 5.48 with 400 uL of a 10% solution of sodium ascorbate prepared in water (Quantity of base required to adjust pH=0.04 g). The osmolality of this solution was 308 mOsm/kg, hence sodium chloride was not used to adjust osmolality. The final volume of the solution was 1.7 ml. *Theoretical concentration of gemifloxacin in this formulation would be 20.59 mg/ml.

TABLE 37

Theoretical and Measured Concentrations of Levofloxacin in the Formulations.

| Acid | Theoretical Conc. (mg/mL) | Measured Concentration (mg/ml) by HPLC |
|---|---|---|
| acetic acid | 50.05 | 51.45 |
| acetic acid | 99.9 | 102.32 |
| citric acid | 49.91 | 50.31 |
| citric acid | 99.86 | 102.99 |
| L-ascorbic acid | 49.95 | 50.01 |
| L-ascorbic acid | 100 | 102.49 |
| lactic acid | 50.05 | 50.07 |
| lactic acid | 97.54 | 95.27 |
| tartaric acid | 49.74 | 51.07 |

TABLE 36

Formulations of Levofloxacin With Organic Acids.

| Wt of Levo used (g) | 9.94% acetic acid used (ml) | Acetic acid used (g) | 19.7% NaCl used (ml) | NaCl used (g) | Measured Final Vol of solution (ml) | Levo conc (mg/ml) | Final osmolality (mOsm/kg) | Final pH | Surface tension (mN/m) |
|---|---|---|---|---|---|---|---|---|---|
| 1.253 | 1.05 | 0.104 | 0.681 | 0.134 | 25.105 | 49.9 | 312 | 6.48 | 63.2 |
| 2.501 | 2.05 | 0.204 | 0.326 | 0.064 | 25.935 | 96.4 | 300 | 6.53 | 62.5 |

| Wt of Levo used (g) | 9.99% ascorbic acid used (ml) | ascorbic acid used (g) | 19.7% NaCl used (ml) | NaCl used (g) | Measured Final Vol of solution (ml) | Levo conc (mg/ml) | Final osmolality (mOsm/kg) | Final pH | Surface tension (mN/m) |
|---|---|---|---|---|---|---|---|---|---|
| 1.253 | 3.400 | 0.339 | 0.550 | 0.108 | 25.135 | 49.8 | 297 | 6.40 | 64.4 |
| 2.505 | 7.400 | 0.739 | 0.300 | 0.059 | 25.135 | 99.7 | 298 | 6.47 | 62.5 |

| Wt of Levo used (g) | 10.05% citric acid used (ml) | citric acid used (g) | 21.54% NaCl used (ml) | NaCl used (g) | Measured Final Vol of solution (ml) | Levo conc (mg/ml) | Final osmolality (mOsm/kg) | Final pH | Surface tension (mN/m) |
|---|---|---|---|---|---|---|---|---|---|
| 1.251 | 1.25 | 0.126 | 1.005 | 0.216 | 25.12 | 49.8 | 299 | 6.54 | 61.5 |
| 2.498 | 2.6 | 0.261 | 0.918 | 0.198 | 25.82 | 96.7 | 301 | 6.53 | 61.4 |

| Wt of Levo used (g) | 10% lactic used (ml) | Lactic acid used (g) | 21.54% NaCl used (ml) | NaCl used (g) | Measured Final Vol of solution (ml) | Levo conc (mg/ml) | Final osmolality (mOsm/kg) | Final pH | Surface tension (mN/m) |
|---|---|---|---|---|---|---|---|---|---|
| 1.258 | 2.1 | 0.21 | 0.745 | 0.160 | 25.135 | 50.1 | 297 | 6.54 | 59.4 |
| 2.497 | 4.2 | 0.42 | 0.392 | 0.084 | 25.605 | 97.5 | 301 | 6.63 | 57.5 |

| Wt of Levo used (g) | 10% tartaric acid used (ml) | Tartaric acid used (g) | 21.54% NaCl used (ml) | NaCl used (g) | Measured Final Vol of solution (ml) | Levo conc (mg/ml) | Final osmolality (mOsm) | Final pH | Surface tension (mN/m) |
|---|---|---|---|---|---|---|---|---|---|
| 1.252 | 1.55 | 0.155 | 0.948 | 0.204 | 25.180 | 49.7 | 298 | 6.51 | 61.5 |

| Wt of Levo used (g) | 9.79% propionic acid used (ml) | propionic acid used(g) | 21.53% NaCl used (ml) | NaCl used (g) | Measured Final Vol of solution (ml) | Levo conc (mg/ml) | Final osmolality (mOsm) | Final pH | Surface tension (mN/m) |
|---|---|---|---|---|---|---|---|---|---|
| 1.25281 | 1.310 | 0.128 | 0.737 | 0.159 | 25.045 | 50.02 | 298 | 6.50 | 58.1 |
| 2.51342 | 2.610 | 0.256 | 0.310 | 0.067 | 25.030 | 100.42 | 297 | 6.57 | 52.0 |

*Theoretical concentration=Theoretical quantity of gemifloxacin in filtered solution (in this case 35 mg Gemifloxacin in filtered 1.3 mL)/Final volume of solution (in this case 1.7 mL).

Note: Solutions with acetic acid, citric acid and ascorbic acid were remade for HPLC analysis and hence the theoretical concentration for these solutions in Table 36 and Table 37 are different.

Gemifloxacin Formulation with Sodium Lactate 50.05 mg of Gemifloxacin mesylate (equivalent to 40.17 mg Gemifloxacin) was added to 1.8 ml water. The resulting solution was cloudy. It was filtered through a 0.45 micron filter. 1.52 ml of solution was obtained after filtering having a pH of 4.21. The pH of this solution was adjusted to 5.42 with 180 uL of a 20% solution of sodium lactate prepared in water (Quantity of base required to adjust pH=0.036 g). The osmolality of this solution was 478 mOsm/kg. The final volume of the solution was 1.7 ml. Theoretical concentration of gemifloxacin in this formulation would be 19.95 mg/ml.

Gemifloxacin Formulation with Sodium Acetate 50.47 mg of Gemifloxacin mesylate (equivalent to 40.50 mg Gemifloxacin) was added to 2.0 ml water. The resulting solution was cloudy. It was filtered through a 0.45 micron filter. 1.77 ml of solution was obtained after filtering having a pH of 4.40. The pH of this solution was adjusted to 5.40 with 50 uL of a 10% solution of sodium acetate prepared in water (Quantity of base required to adjust pH=0.005 g). The osmolality of this solution was 192 mOsm/kg. The osmolality of this solution was adjusted to 295 mOsm/kg using 28 uL of 20% solution of sodium chloride prepared in water.

Gemifloxacin Formulation with Sodium Propionate 50.00 mg of Gemifloxacin mesylate (equivalent to 40.13 mg Gemifloxacin) was added to 1.9 ml water. The resulting solution was cloudy. It was filtered through a 0.45 micron filter. 1.39 ml of solution was obtained after filtering having a pH of 4.32. The pH of this solution was adjusted to 5.50 with 30 uL of a 20% solution of sodium propionate prepared in water (Quantity of base required to adjust pH=0.006 g). The osmolality of this solution was 183 mOsm/kg. The osmolality of this solution was adjusted to 296 mOsm/kg using 25 uL of 22% solution of sodium chloride prepared in water. This solution was remade with osmolality adjustment to 237 mOsm/Kg.

Gemifloxacin Formulation with Sodium Citrate 49.92 mg of Gemifloxacin mesylate (equivalent to 40.06 mg Gemifloxacin) was added to 1.9 ml water. The resulting solution was cloudy. It was filtered through a 0.45 micron filter. 1.63 ml of solution was obtained after filtering having a pH of 4.20. The pH of this solution was adjusted to 5.39 with 15 uL of a 20% solution of sodium citrate prepared in water (Quantity of base required to adjust pH=0.003 g).

Example 12

Microspheres of Levofloxacin

The goal of this study was to prepare various microsphere forms of levofloxacin that may gain taste-masking, and AUC shape-enhancing properties through decreased solubility and/or dissolution. These benefits may enhance the pharmacodynamic properties of levofloxacin following pulmonary administration using either nanoparticle suspension or dry powder inhalation. These formulations are being optimized to prolong the release of levofloxacin from decreased solubility or dissolution forms. These properties may also be incorporated into other fluoroquinolone antibiotics including, without limitation gemifloxacin, gatifloxacin, norfloxacin, tosufloxacin, sitafloxacin sarafloxacin, prulifloxacin, and pazufloxacin. Studies are underway to characterize microspheres of gemifloxacin for taste masking, AUC shape-enhancement, nanoparticle suspension and dry powder inhalation administration. Other approaches for dry powder administration currently being investigated include spray-dry and in situ micronization techniques.

Preformulation for Levofloxacin

Preformulation Studies

Preformulation studies were performed to determine the solubility of levofloxacin and polymers in various solvents which are expected to be used during processing.

Preparation of Microspheres

A spray drying technique is being used to formulate polymer microparticles loaded with levofloxacin. Formulation of microspheres will typically involve dissolving the drug and polymer in a suitable solvent. The solution is being spray dried using a spray dryer to evaporate the solvent, thereby entrapping the drug in a polymer matrix. Optimization of formulation parameters (drug: polymer ratio, polymer solution concentration and production parameters) is being performed to achieve a desired micro particle size, optimum drug loading and in vitro drug release.

Characterization of Microspheres

The microparticles will be characterized for their morphology using SEM while microscopy or a suitable technique (Laser diffraction) will be used for estimating their size.

Drug loading will be determined by extracting the drug from the microspheres in a suitable solvent and analyzing the extract by UV/HPLC.

Drug release from the microspheres will be carried out using a USP dissolution apparatus.

Example 13

Inhalation Toxicology in Rats

In a 4 day non-GLP ascending dose study of aerosolized levofloxacin in male and female Sprague-Dawley rats, a 25 mg/ml solution of levofloxacin was administered for one hour on day one and a 50 mg/ml solution of levofloxacin was administered for two hours per day on days 2 thru 4. No clinical signs of toxicity were observed during the treatment period. Necropsy 24 hours after administration of the last dose did not show any findings.

In a GLP study of aerosolized levofloxacin in male and female Sprague-Dawley rats, aerosolized levofloxacin was administered daily with an average dose of 6.92 mg/kg/day to the males and 10.04 mg/kg/day for the females over 4 days using a nose-only aerosol delivery device. Total exposures were 29 and 42 mg/kg for males and females, respectively over the study period. Each dose was delivered over 2 hours daily. The dose for this study was chosen based on the maximum solubility of levofloxacin that could be administered in the device over 2 hours. No clinical signs of toxicity were observed, and all animals survived during the 4 day treatment period. Necropsy of animals after administration of the last dose did not show any findings.

In a 28-day GLP study in Sprague-Dawley rats, animals were randomized to 3 dose levels of aerosolized levofloxacin or saline. Additional recovery groups using the vehicle control and the highest dose were also treated and observed for a 14 day recovery period following the last dose. Average aerosolized levofloxacin doses were 1.49, 3.63, and 7.29 mg/kg/day for male rats, and 2.20, 5.35, and 11.01 mg/kg/day in female rats. The total exposures over the 28-day treatment period ranged between 41.7 and 204.1 mg/kg for males and 61.6 and 308.3 mg/kg for females. Each dose was delivered over 2 hours daily. No dose related clinical signs of toxicity were observed, and all animals survived during the 28 day treatment period. Necropsy of animals after administration of the last dose showed a dose related squamous cell hyperplasia of the larynx which declined in severity during a 14 day recovery period.

What is claimed is:

1. A kit comprising:
a sterile single use container comprising an aqueous solution of levofloxacin or ofloxacin and a divalent or trivalent cation, wherein the solution is suitable for inhalation into a lung; and
a nebulizer adapted to receive solution from the container and to aerosolize the solution for delivery to the lung through oral inhalation.

2. The kit of claim 1, wherein the nebulizer operates by ultrasonic atomization.

3. The kit of claim 1, wherein the nebulizer operates by hydraulic atomization.

4. The kit of claim 1, wherein the nebulizer operates by a vibrating mesh.

5. The kit of claim 1, wherein the nebulizer is adapted to produce particles having a mass median aerodynamic diameter from about 2 microns to about 5 microns with a geometric standard deviation less than or equal to about 2.5 microns.

6. The kit of claim 1, wherein the nebulizer is adapted to produce particles having a mass median aerodynamic diameter from about 2.8 microns to about 4.3 microns with a geometric standard deviation less than or equal to about 2 microns.

7. The kit of claim 1, wherein the nebulizer is adapted to produce particles having a mass median aerodynamic diameter from about 2.5 microns to about 4.5 microns with a geometric standard deviation less than or equal to about 1.8 microns.

8. The kit of claim 1, wherein the solution comprises levofloxacin at a concentration from about 100 mM to about 625 mM and magnesium chloride at a concentration from about 125 mM to about 250 mM, has a pH from about 5.5 to about 6.5, and an osmolality from about 350 mOsmol/kg to about 750 mOsmol/kg.

9. A system, comprising:
a reservoir comprising an aqueous solution of levofloxacin or ofloxacin and a divalent or trivalent cation, wherein the solution is suitable for inhalation into a lung; and
a nebulizer configured to aerosolize the solution for delivery to the lung through oral inhalation.

10. The system of claim 9, wherein the nebulizer operates by ultrasonic atomization.

11. The system of claim 9, wherein the nebulizer operates by hydraulic atomization.

12. The system of claim 9, wherein the nebulizer operates by a vibrating mesh.

13. The system of claim 9, wherein the nebulizer is adapted to produce particles having a mass median aerodynamic diameter from about 2 microns to about 5 microns with a geometric standard deviation less than or equal to about 2.5 microns.

14. The system of claim 9, wherein the nebulizer is adapted to produce particles having a mass median aerodynamic diameter from about 2.8 microns to about 4.3 microns with a geometric standard deviation less than or equal to about 2 microns.

15. The system of claim 9, wherein the nebulizer is adapted to produce particles having a mass median aerodynamic diameter from about 2.5 microns to about 4.5 microns with a geometric standard deviation less than or equal to about 1.8 microns.

16. The system of claim 9, wherein the solution comprises levofloxacin at a concentration from about 100 mM to about 625 mM and magnesium chloride at a concentration from about 125 mM to about 250 mM, has a pH from about 5.5 to about 6.5, and an osmolality from about 350 mOsmol/kg to about 750 mOsmol/kg.

* * * * *